US010077318B2

(12) United States Patent
Bhakta et al.

(10) Patent No.: US 10,077,318 B2
(45) Date of Patent: Sep. 18, 2018

(54) CYSTEINE ENGINEERED ANTIBODIES AND CONJUGATES

(71) Applicant: Genentech, Inc., South San Francisco, CA (US)

(72) Inventors: Sunil Bhakta, San Ramon, CA (US); Hans Erickson, South San Francisco, CA (US); Jagath R. Junutula, Fremont, CA (US); Katherine Kozak, Half Moon Bay, CA (US); Rachana Ohri, South San Francisco, CA (US); Thomas Pillow, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 154 days.

(21) Appl. No.: 14/851,348

(22) Filed: Sep. 11, 2015

(65) Prior Publication Data
US 2016/0130358 A1  May 12, 2016

Related U.S. Application Data

(60) Provisional application No. 62/050,022, filed on Sep. 12, 2014.

(51) Int. Cl.
| | |
|---|---|
| *C07K 16/00* | (2006.01) |
| *C07K 16/32* | (2006.01) |
| *C07K 16/18* | (2006.01) |
| *C07K 16/28* | (2006.01) |
| *C07K 16/30* | (2006.01) |
| *A61K 51/10* | (2006.01) |
| *C07K 16/40* | (2006.01) |
| *G01N 33/58* | (2006.01) |
| *A61K 47/68* | (2017.01) |
| *A61K 39/00* | (2006.01) |

(52) U.S. Cl.
CPC .......... *C07K 16/32* (2013.01); *A61K 47/6803* (2017.08); *A61K 47/6809* (2017.08); *A61K 47/6817* (2017.08); *A61K 47/6849* (2017.08); *A61K 47/6869* (2017.08); *A61K 51/10* (2013.01); *C07K 16/00* (2013.01); *C07K 16/18* (2013.01); *C07K 16/28* (2013.01); *C07K 16/2803* (2013.01); *C07K 16/3069* (2013.01); *C07K 16/3092* (2013.01); *C07K 16/40* (2013.01); *G01N 33/582* (2013.01); *A61K 2039/505* (2013.01); *C07K 2317/40* (2013.01); *C07K 2317/73* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,219,996 A | 6/1993 | Bodmer et al. | |
| 6,248,564 B1 | 6/2001 | Walter et al. | |
| 6,737,056 B1 | 5/2004 | Presta | |
| 6,753,165 B1 | 6/2004 | Cox et al. | |
| 7,097,840 B2 | 8/2006 | Erickson et al. | |
| 7,276,585 B2 | 10/2007 | Lazar et al. | |
| 7,332,581 B2 | 2/2008 | Presta | |
| 7,442,778 B2 | 10/2008 | Gegg et al. | |
| 7,521,541 B2 | 4/2009 | Eigenbrot et al. | |
| 7,662,936 B2 * | 2/2010 | Kadkhodayan | .... C07K 16/2866 424/178.1 |
| 7,723,485 B2 | 5/2010 | Junutula et al. | |
| 7,776,814 B2 † | 8/2010 | Domling | |
| 7,855,275 B2 † | 12/2010 | Eigenbrot | |
| 8,309,300 B2 | 11/2012 | Junutula et al. | |
| 8,394,922 B2 † | 3/2013 | Cheng | |
| 8,507,654 B2 | 8/2013 | Baker et al. | |
| 9,000,130 B2 | 4/2015 | Bhakta et al. | |
| 9,518,118 B2 * | 12/2016 | Chen | ................ A61K 47/48615 |
| 2003/0021790 A1 | 1/2003 | Hsei et al. | |
| 2004/0005324 A1 | 1/2004 | Pilkington et al. | |
| 2004/0229310 A1 | 11/2004 | Simmons | |
| 2004/0235068 A1 | 11/2004 | Levinson | |
| 2005/0048572 A1 | 3/2005 | Reilly et al. | |
| 2007/0269369 A1 | 11/2007 | Gegg et al. | |
| 2008/0050310 A1 | 2/2008 | Ebens et al. | |
| 2008/0247951 A1 | 10/2008 | Koch et al. | |
| 2008/0305044 A1 | 12/2008 | McDonagh et al. | |

(Continued)

FOREIGN PATENT DOCUMENTS

| | | |
|---|---|---|
| CN | 101037475 A | 9/2007 |
| CN | 101065151 | 10/2007 |

(Continued)

OTHER PUBLICATIONS

International Search Report for PCT/US2011/039386 dated Nov. 2, 2011, 5 pages.

(Continued)

*Primary Examiner* — Bradley Duffy

(74) *Attorney, Agent, or Firm* — McNeill Baur PLLC

(57) ABSTRACT

Cysteine engineered antibodies comprising a free cysteine amino acid in the heavy chain or light chain are prepared by mutagenizing a nucleic acid sequence of a parent antibody and replacing one or more amino acid residues by cysteine to encode the cysteine engineered antibody; expressing the cysteine engineered antibody; and isolating the cysteine engineered antibody.

41 Claims, 27 Drawing Sheets
(18 of 27 Drawing Sheet(s) Filed in Color)
Specification includes a Sequence Listing.

(56) References Cited

U.S. PATENT DOCUMENTS

| | | |
|---|---|---|
| 2008/0311134 A1 | 12/2008 | Junutula |
| 2009/0028856 A1 | 1/2009 | Chen et al. |
| 2009/0068202 A1 | 3/2009 | Chen et al. |
| 2009/0117100 A1 | 5/2009 | Mao et al. |
| 2009/0258420 A1 | 10/2009 | van Vlijmen et al. |
| 2010/0003766 A1 | 1/2010 | Eigenbrot et al. |
| 2010/0028354 A1 | 2/2010 | McKinnon et al. |
| 2010/0111856 A1 | 5/2010 | Gill et al. |
| 2010/0158909 A1 | 6/2010 | McDonagh et al. |
| 2011/0033378 A1 | 2/2011 | Dimasi et al. |
| 2011/0137017 A1 | 6/2011 | Eigenbrot et al. |
| 2011/0301334 A1 | 12/2011 | Bhakta et al. |
| 2012/0009621 A1* | 1/2012 | Yamasaki .............. C07K 16/00 435/69.6 |
| 2012/0148580 A1 | 6/2012 | Chennamsetty et al. |
| 2012/0213705 A1 | 8/2012 | Dimasi et al. |
| 2013/0066054 A1 | 3/2013 | Humphreys et al. |
| 2014/0288280 A1 | 9/2014 | Bhakta et al. |
| 2015/0017094 A1 | 1/2015 | Gill et al. |
| 2015/0017188 A1 | 1/2015 | Eigenbrot et al. |
| 2015/0165063 A1† | 6/2015 | Flygare et al. |
| 2015/0209445 A1† | 7/2015 | Maderna et al. |

FOREIGN PATENT DOCUMENTS

| | | |
|---|---|---|
| RU | 2006147264 A | 7/2008 |
| WO | 1989/01974 A1 | 3/1989 |
| WO | 1994/06474 | 3/1994 |
| WO | 2003/049704 A2 | 6/2003 |
| WO | 2003/060080 A2 | 7/2003 |
| WO | 2004/010957 A2 | 2/2004 |
| WO | WO2004010957 † | 2/2004 |
| WO | 2004/050849 A2 | 6/2004 |
| WO | 2005/117986 | 12/2005 |
| WO | 2006/034488 A2 | 3/2006 |
| WO | 2008/038024 | 4/2008 |
| WO | 2008/141044 A2 | 11/2008 |
| WO | 2009/052249 A1 | 4/2009 |
| WO | 2010/009391 A1 | 1/2010 |
| WO | 2010/108937 A2 | 9/2010 |
| WO | 2011/056983 A1 | 5/2011 |
| WO | 2011/15328 | 12/2011 |
| WO | 2012/009621 A1 | 1/2012 |
| WO | 2012/074757 A1 | 6/2012 |
| WO | 2013/093809 A1 | 6/2013 |
| WO | WO 2013/177055 A2 | 11/2013 |
| WO | 2014/011518 A1 | 1/2014 |
| WO | WO2014011518 † | 1/2014 |
| WO | 2014/022679 A2 | 2/2014 |
| WO | WO2014022679 † | 2/2014 |
| WO | WO 2014/124316 A2 | 8/2014 |
| WO | WO 2015/095212 A1 | 6/2015 |
| WO | 2015/110935 A1 | 7/2015 |
| WO | 2016/040684 A1 | 3/2016 |
| WO | WO2016040684 † | 3/2016 |

OTHER PUBLICATIONS

International Search Report and Written Opinion for PCT/US2015/049771 dated Mar. 15, 2016, 25 pages.

International Search Report for PCT/US2010/055465, dated Jan. 24, 2011, 6 pages.

Aerts et al., "Disparity between in vivo EGFR expression and 89Zr-labeled cetuximab uptake assessed with PET" J Nucl Med 50:123-131 (2009).

All drugs online. Retrieved from the internet at www.all-drugs-online.com/Drugs/Oncology/1377.aspx, retrieved on Jan. 5, 2009.

Baca et al., "Antibody humanization using monovalent phage display" J Biol Chem 272(16): 10678-10684 (1997).

Bernhard et et al., "Cysteine analogs of recombinant barley ribosome inactivating protein form antibody conjugates with enhanced stability and potency in vitro" Bioconjug Chem 5:126-132 (1994).

Better et al., "Gelonin analogs with engineered cysteine residues form antibody immunoconjugates with unique properties" J Biol Chem 269(13):9644-9650 (Apr. 1, 1994).

Bhakta et al., "Engineering THIOMABs for Site Specific Conjugation of Thiol-Reactive Linkers," Antibody-Drug Conjugates Humana Press Inc.; Methods in Molecular Biology, pp. 189-203 (2013).

Biopharma. Retrieved from the Internet >URL:http://www.biopharma.com/Samples/184.html> Retrieved on Jan. 5, 2009.

Borjesson et al., "Performance of immuno-positron emission tomography with zirconium-89-labeled chimeric monoclonal antibody U36 in the detection of lymph node metastases in head and neck cancer patients" Clin Cancer Res 12(7):2133-2140 (2006).

Boswell et al., "Impact of Drug Conjugation on Pharmacokinetics and Tissue Distribution of Anti-STEAP1 Antibody-Drug Conjugates in Rats," Bioconjugate Chemistry 22(10): 1994-2004 (2011).

Carter et al., "Humanization of an Anti-p185HER Antibody for Human Cancer Therapy" P Natl Acad Sci USA 89(10):4285-4289 (May 1992).

CellTiter-Glo Luminescent Cell Viability Assay (Technical Bulletin No. 288), Madison, WI:Promega Corp., pp. 1-11 (Feb. 2004).

Chang et al., "High-Level Secretion of Human Growth Hormone by *Escherichia coli*" Gene 55:189-196 (1987).

Chen et al., "Charge-based analysis of antibodies with engineered cysteines From multiple peaks to a single main peak" mAbs 1(6):563-571 (Nov./Dec. 2009).

Chmura et al., "Antibodies with infinite affinity" P Natl Acad Sci USA 98(15):8480-8484. (Jul. 17, 2001).

Collaborative Computational Project, No. 4, "The CCP4 Suite: Programs for Protein Crystallography" Acta Cryst D50:760-763 (1994).

Corneillie et al., "Converting Weak Binders into Infinite Binders" Bioconjugate Chem 15(6):1389-1391 (2004).

Dennis et al., "Albumin binding as a general strategy for improving the pharmacokinetics of proteins" J Biol Chem 277(38):35035-35043 (Sep. 20, 2002).

Dijkers et al., "Development and characterization of clinical-grade 89Zr-Trastuzumab for HER2/neu ImmunoPET imaging" J Nucl Med 50(6):974-981 (Jun. 2009).

Doronina et al., "Development of potent monoclonal antibody auristatin conjugates for cancer therapy" Nat Biotechnol 21(7):778-784 (Jul. 2003).

Eigenbrot et al., "X-Ray structures of the antigen-binding domains from three variants of humanized anti-p185HER2 antibody 4D5 and comparison with molecular modeling" J Mol Biol 229:969-995 (1993).

Gagnon et al., "High-throughput in vivo Screening of Targeted Molecular Imaging Agents" P Natl Acad Sci USA 106(42):17904-17909 (Oct. 2009).

Gerstner et al., "Sequence Plasticity in the Antigen-binding Site of a Therapeutic Anti-HER2 Antibody" J Mol Biol 321:851-862 (2002).

Gill et al., "A Modular Platform for the Rapid Site-Specific Radiolabeling of Proteins with 18F Exemplified by Quantitative Positron Emission Tomography of Human Epidermal Growth Factor Receptor 2" J Med Chem 52:5816-5825 (2009).

Gomez et al., "Triple Light Chain Antibodies: Factors That Influence Its Formation in Cell Culture" Biotechnology and Bioengineering 105(4):748-760 (Mar. 1, 2010).

Govindan et al., "Deferoxamine as a chelator for 67 Ga in the preparation of antibody conjugates" Nucl Med Biol 32:513-519 (Apr. 14, 2005).

Greenwood et al., "Engineering multiple-domain forms of the therapeutic antibody CAMPATH-1H: effects on complement lysis" Therapeutic Immunology 1(5):247-255 (Oct. 1994).

Hafner et al., "Noncompetitive Immunoassay of Small Analytes at the Femtomolar Level by Affinity Probe Capillary Electrophoresis: Direct Analysis of Digoxin Using a Uniform-Labeled scFv Immunoreagent" Anal Chem 72(23):5779-5786 (Dec. 1, 2000).

Hausner et al., "Use of a peptide derived from foot-and-mouth disease virus for the noninvasive imaging of human cancer: generation and evaluation of 4-[18F]fluorobenzoyl A20FMDV2 for in vivo imaging of integrin alphavbeta6 expression with positron emission tomography," Cancer Res 67(16):7833-7840 (Aug. 2007).

(56) References Cited

OTHER PUBLICATIONS

Hausner et al., "In vivo positron emission tomography (PET) imaging with an alphavbeta6 specific peptide radiolabeled using 18F-'click' chemistry: evaluation and comparison with the corresponding 4-[18F]fluorobenzoyl- and 2-[18F]fluoropropionyl-peptides" J Med Chem. 51(19):5901-4 ( 2008).
Hausner et al., "Targeted In vivo Imaging of Integrin Alphavbeta6 with an Improved Radiotracer and Its Relevance in a Pancreatic Tumor Model" Cancer Res 69(14):5843-5850 (Jul. 2009).
Ho et al., "Site-Directed Mutagenesis by Overlap Extension Using the Polymerase Chain Reaction" Gene 77(1):51-59 (1989).
Ito et al., "A general method for introducing a series of mutations into cloned DNA using the polymerase chain reaction" Gene 102(1):67-70 (Jun. 15, 1991).
Junutula et al., "ThioMabs: improving safety abd retaining efficacy of antibody drug conjugates." Proceedings of the Annual Meeting, American Association for Cancer Research 48: 220-221 (2007).
Junutula et al., "Engineered Thio-Trastuzumab-DM1 Conjugate with an Improved Therapeutic Index to Target Human Epiderman Growth Factor Receptor 2-Positive Breast Cancer" Clinical Cancer Research 16:4769-4778 (Aug. 30, 2010).
Junutula et al., "Rapid identification of reactive cysteine residues for site-specific labeling of antibody-Fabs" J Immunol Methods 332:41-52 (2008).
Junutula et al., "Site-specific conjugation of a cytotoxic drug to an antibody improves thetherapeutic index" Nat Biotechnol 26(8):925-32 (Aug. 2008).
Kabat et al. US Department of Health and Human Services, Public Health Service, NIH 4th edition,:160 and 294 (1987).
Kanno et al., "Assembling of engineered IgG-binding protein on gold surface for highly oriented antibody immobilization" J Biotechnol 76(2-3):207-214 (Jan. 21, 2000).
King et al., "Facile synthesis of maleimide bifunctional linkers" Tetrahedron Lett 43:1987-1990 (2002).
Kumaresan et al., "Evaluation of Ketone-Oxime Method for Developing Therapeutic On-Demand Cleavable Immunoconjugates" Bioconjugate Chem 19:1313-1318 (2008).
Lambert, "Drug-conjugated monoclonal antibodies for the treatment of cancer" Curr Opin Pharmacol 5(5):543-549 (Oct. 2005).
Lewis et al., "Maleimidocysteineamido-DOTA derivatives: new reagents for radiometal chelate conjugation to antibody sulfhydryl groups undergo pH-dependent cleavage reactions" Bioconjug Chem 9(1):72-86 (Jan. 1998).
Liu, "Bifunctional coupling agents for radiolabeling of biomolecules and target-specific delivery of metallic radionuclides" Adv Drug Deliver Rev 60:1347-1370 (2008).
Lowman, "Phage display of peptide libraries on protein scaffolds" Methods Molecular Biology 87:249-264 (1998).
Lund et al., "Expression and characterization of truncated forms of humanized L243 IgG1. Architectural features can influence synthesis of its oligosaccharide chains and affect superoxide production triggered through human Fcγ receptor I" Eur J Biochem 267:7246-7256 (2000).
Lyons et al., "Site-specific attachment to recombinant antibodies via introduced surface cysteine residues" Protein Engineering 3(8):703-708 (1990).
MacCallum et al., "Antibody-antigen interactions: contact analysis and binding site topography" J Mol Biol 262:732-745 (1996).
Meijs et al., "A facile method for the labeling of proteins with zirconium Isotopes" Nucl Med Biol 23:439-448 (1996).
Meijs et al., "Zirconium-labeled monoclonal antibodies and their distribution in tumor-bearing nude mice" J Nucl Med 38(1):112-118 (Jan. 1997).
Miller, "Syntheses and therapeutic potential of hydroxamic acid based siderophores and analogues" Chem Rev 89:1563-1579 (1989).
Nagengast et al., "In vivo VEGF imaging with radiolabled bevacizumab in a human ovarian tumor xenograft" J Nucl Med 48:1313-1319 (2007).
Olafsen et al., "Characterization of engineered anti-p185HER-2 (scFv-CH3)2 antibody fragments (minibodies) for tumor targeting," Protein Eng Des Sel 17(4):315-323 (2004).
Panowski et al., "Site-Specific antibody drug conjugates for cancer therapy," mAbs 6(1): 34-45 (2014).
Payne, "Progress in Immunoconjugate Cancer Therapeutics" Cancer Cell 3:207-212 (2003).
Perk et al., "(89)Zr as a PET surrogate radioisotope for scouting biodistribution of the therapeutic radiometals (90)Y and (177)Lu in tumor-bearing nude mice after coupling to the internalizing antibody cetuximab," J Nucl Med 46(11):1898-1906 (Nov. 2005).
Perk et al., "Preparation and evaluation of (89)Zr-Zevalin for monitoring of (90)Y-Zevalin biodistribution with positron emission tomography," Eur J Nucl Med Mol Imaging 33:1337-1345 ( 2006).
Perk et al., "Quantitative PET imaging of Met-expressing human cancer xenografts with 89Zr-labelled monoclonal antibody DN30," Eur J Nucl Med Mol Imaging 35:1857-1867 (2008).
Renard et al., "Deriving Topological Constraints from Functional Data for the Design of Reagentless Fluorescent Immunosensors" J Mol Biol 326:167-175 (2003).
Roitt et al., Roitt's Essential Immunology, 110-111 (2000).
Roitt et al., Roitt's Essential Immunology, 110-111 (2000), English translation (4 pages).
Roux et al., "Comparisons of the ability of human IgG3 hinge mutants, IgM, IgE, and IgA2, to form small immune complexes: a role for flexibility and geometry" J Immunol 161:4083-4090 (1998).
Rudikoff et al., "Single amino acid substitution altering antigen-binding specificity" P Natl Acad Sci USA 79:1979-1983 (Mar. 1982).
Schelte et al., "Differential Reactivity of Maleimide and Bromoacetyl Functions with Thiols: Application to the Preparation of Liposomal Diepitope Constructs" Bioconjugate Chem 11:118-123 (2000).
Senter, "Immunoconjugates comprised of drugs with impaired cellular permeability: a new approach to targeted therapy, Abstract No. 623" Proceedings of the American Association for Cancer Research, (2004).
Shen et al., "Conjugation site modulates the in vivo stability and therapeutic activity of antibody-drug conjugates" Nature Biotechnology 30(2):184-190 (Feb. 2012).
Shopes, "A Genetically Engineered Human IgG With Limited Flexibility Fully Initiates Cytolysis Via Complement" Mol Immunol 30(6):603-609 (1993).
Singh et al., "Labeling of antibodies by in situ modification of thiol groups generated from selenol-catalyzed reduction of native disulfide bonds" Anal Biochem 304(2):147-156 (May 15, 2002).
Stimmel et al., "Site-specific Conjugation on Serine—Cysteine Variant Monoclonal Antibodies" J Biol Chem 275(39):30445-50 (Sep. 29, 2000).
Sukumaran et al., "Mechanism-Based Pharmacokinetic/Pharmacodynamic Model for THIOMAV™ Drug Conjug," Pharmaceutical Research 32(6): 1884-1893 (2015).
Sun et al., "Enabling ScFvs as multi-drug carriers: a dendritic approach" Bioorg Med Chem 11:1761-1768 (2003).
Sun et al., "Syntheses of dendritic linkers containing chlorambucil residues for the preparation of antibody-multidrug immunoconjugates" Bioorg Med Chem Lett 12:2213-2215 (2002).
Tartis et al., "Dynamic MicroPET Imaging of Ultrasound Contrast Agents and Lipid Delivery" J Control Release 131:160-166 (2008).
Tinianow et al., "Site-specifically 89Zr-labeled Monoclonal Antibodies for ImmunoPET" Nucl Med Biol 37:289-297 (2010).
Trail et al., "Monoclonal Antibody Drug Immunoconjugates for Targeted Treatment of Cancer" Cancer Immunol Immunother 52:328-337 (2003).
Tu et al., "Protein footprinting at cysteines: probing ATP-modulated contacts in cysteine-substitution mutants of yeast DNA topoisomerase II" P Natl Acad Sci USA 96(9):4862-4867 (Apr. 27, 1999).
Verel et al., "Quantitative 89Zr immuno-PET for in vivo scouting of 90Y-labeled monoclonal antibodies in xenograft-bearing nude mice," J Nucl Med 44:1663-1670 (2003).
Verel et al., "89Zr immuno-PET: comprehensive procedures for the production of 89Zr-labeled monoclonal antibodies," J Nucl Med 44(8): 1271-1281 (Aug. 2003).

(56) References Cited

OTHER PUBLICATIONS

Vosjan et al., "Conjugation and Radiolabeling of Monoclonal Antibidies with Zirconium-89 for PET Imaging Using the Bifunctional Chelate p-isothiocyanatobenzyl-desferrioxamine" Nat Protoc 5(4):739-743 (2010).

Voynov et al., "Design and application of antibody cysteine variants" Bioconjug Chem 21(2):385-392 (Feb. 2010).

Wu et al., "Arming antibodies: prospects and challenges for immunoconjugates" Nat Biotechnol 23(9):1137-1146 (Sep. 23, 2005).

Wu et al., "Humanization of a Murine Monoclonal Antibody by Simultaneous Optimization of Framework and CDR Residues" J Mol Biol 294:151-162 (1999).

Xu et al., "Characterization of intact antibody-drug conjugates from plasma/serum in vivo by affinity capture capillary liquid chromatography-mass spectrometry" Analytical Biochemistry 412:56-66 (2011).

Yasuhisa et al., "Identification of Highly Reactive Cysteine Residues at Less Exposed Positions in the Fab Constant Region for Site-specific Conjugation," Bioconjugate Chemistry, 10.1021 (May 2015).

Zhang et al., "Complete disulfide bond assignment of a recombinant immunoglobulin G4 monoclonal amibody" Anal Biochem 311(1):1-9 (Dec. 1, 2002).

Ducry, L. and Stump, B., "Antibody-drug conjugates: linking cytotoxic payloads to monoclonal antibodies." Bioconjug Chem., 21(1): 5-13 (2009).

Search Report dated Feb. 27, 2018 issued in Singapore Application No. 11201701128Y, 3 Pages.

Junutula, Jagath R, Rapid identification of reactive cysteine residues for site-specific labeling of antibody-Fabs. 12 pages, Jan. 14, 2008, Journal of Immunological Methods.†

Junutula, Jagath R, Site-specific conjugation of a cytotoxic drug to an antibody improves the therapeutic index 8 pages, Jul. 20, 2008. Nature Biotechnology, vol. 26, No. 8.†

Junutula, Jagath R, Supplementary Materials for Site-specific conjugation of cytotoxic drugs to antibodies substantially improved the therapeutic window. 34 pages, Jul. 20, 2008. Nature Biotechnology, vol. 26, No. 8.†

Panowski, Siler, Site-specific antibody drug conjugates for cancer therapy. 12 pages, Jan./Feb. 2014, Landes Bioscience, vol. 6 Issue 1.†

Stimmel, Julie B, Site-specific Conjugation on Serine Cysteine Variant Monoclonal Antibodies 7 pages, Sep. 29, 2000, The Journal of Biological Chemistry, vol. 275, No. 39.†

\* cited by examiner
† cited by third party

Fig. 1A

| LC Amino Acid | GNE Seq # | LC Amino Acid | GNE Seq # | LC Amino Acid | GNE Seq # | LC Amino Acid | GNE Seq # |
|---|---|---|---|---|---|---|---|
| D | 1 | R | 66 | S | 131 | V | 196 |
| I | 2 | S | 67 | V | 132 | T | 197 |
| Q | 3 | G | 68 | V | 133 | H | 198 |
| M | 4 | T | 69 | C | 134 | Q | 199 |
| T | 5 | D | 70 | L | 135 | G | 200 |
| Q | 6 | F | 71 | L | 136 | L | 201 |
| S | 7 | T | 72 | N | 137 | S | 202 |
| P | 8 | L | 73 | N | 138 | S | 203 |
| S | 9 | T | 74 | F | 139 | P | 204 |
| S | 10 | I | 75 | Y | 140 | V | 205 |
| L | 11 | S | 76 | P | 141 | T | 206 |
| S | 12 | S | 77 | R | 142 | K | 207 |
| A | 13 | L | 78 | E | 143 | S | 208 |
| S | 14 | Q | 79 | A | 144 | F | 209 |
| V | 15 | P | 80 | K | 145 | N | 210 |
| G | 16 | E | 81 | V | 146 | R | 211 |
| D | 17 | D | 82 | Q | 147 | G | 212 |
| R | 18 | F | 83 | W | 148 | E | 213 |
| V | 19 | A | 84 | K | 149 | C | 214 |
| T | 20 | T | 85 | V | 150 | K | 190 |
| I | 21 | Y | 86 | D | 151 | V | 191 |
| T | 22 | Y | 87 | N | 152 | Y | 192 |
| C | 23 | C | 88 | A | 153 | A | 193 |
| R | 24 | Q | 89 | L | 154 | C | 194 |
| A | 25 | Q | 90 | Q | 155 | E | 195 |
| S | 26 | H | 91 | S | 156 | V | 196 |
| Q | 27 | Y | 92 | G | 157 | T | 197 |
| D | 28 | T | 93 | N | 158 | H | 198 |
| V | 29 | T | 94 | S | 159 | Q | 199 |
| N | 30 | P | 95 | Q | 160 | G | 200 |
| T | 31 | P | 96 | E | 161 | L | 201 |
| A | 32 | T | 97 | S | 162 | S | 202 |
| V | 33 | F | 98 | V | 163 | S | 203 |
| A | 34 | G | 99 | T | 164 | P | 204 |
| W | 35 | Q | 100 | E | 165 | V | 205 |
| Y | 36 | G | 101 | Q | 166 | T | 206 |
| Q | 37 | T | 102 | D | 167 | K | 207 |
| Q | 38 | K | 103 | S | 168 | S | 208 |
| K | 39 | V | 104 | K | 169 | F | 209 |
| P | 40 | E | 105 | D | 170 | N | 210 |
| G | 41 | I | 106 | S | 171 | R | 211 |
| K | 42 | K | 107 | T | 172 | G | 212 |
| A | 43 | R | 108 | Y | 173 | E | 213 |
| P | 44 | T | 109 | S | 174 | C | 214 |
| K | 45 | V | 110 | L | 175 | | |
| L | 46 | A | 111 | S | 176 | | |
| L | 47 | A | 112 | S | 177 | | |
| I | 48 | P | 113 | T | 178 | | |
| Y | 49 | S | 114 | L | 179 | | |
| S | 50 | V | 115 | T | 180 | | |
| A | 51 | F | 116 | L | 181 | | |
| S | 52 | I | 117 | S | 182 | | |
| F | 53 | F | 118 | K | 183 | | |
| L | 54 | P | 119 | A | 184 | | |
| Y | 55 | P | 120 | D | 185 | | |
| S | 56 | S | 121 | Y | 186 | | |
| G | 57 | D | 122 | E | 187 | | |
| V | 58 | E | 123 | K | 188 | | |
| P | 59 | Q | 124 | H | 189 | | |
| S | 60 | L | 125 | K | 190 | | |
| R | 61 | K | 126 | V | 191 | | |
| F | 62 | S | 127 | Y | 192 | | |
| S | 63 | G | 128 | A | 193 | | |
| G | 64 | T | 129 | C | 194 | | |
| S | 65 | A | 130 | E | 195 | | |

Fig. 1B

| HC Amino Acid | GNE Seq # | Kabat Seq # | EU Seq # |
|---|---|---|---|
| E | 1 | 1 | |
| V | 2 | 2 | |
| Q | 3 | 3 | |
| L | 4 | 4 | |
| V | 5 | 5 | 2 |
| E | 6 | 6 | 3 |
| S | 7 | 7 | 4 |
| G | 8 | 8 | 5 |
| G | 9 | 9 | 6 |
| G | 10 | 10 | 7 |
| L | 11 | 11 | 8 |
| V | 12 | 12 | 9 |
| Q | 13 | 13 | 10 |
| P | 14 | 14 | 11 |
| G | 15 | 15 | 12 |
| G | 16 | 16 | 13 |
| S | 17 | 17 | 14 |
| L | 18 | 18 | 15 |
| R | 19 | 19 | 16 |
| L | 20 | 20 | 17 |
| S | 21 | 21 | 18 |
| C | 22 | 22 | 19 |
| A | 23 | 23 | 20 |
| A | 24 | 24 | 21 |
| S | 25 | 25 | 22 |
| G | 26 | 26 | 23 |
| F | 27 | 27 | 24 |
| N | 28 | 28 | 25 |
| I | 29 | 29 | 26 |
| K | 30 | 30 | 27 |
| D | 31 | 31 | 28 |
| T | 32 | 32 | 29 |
| Y | 33 | 33 | 30 |
| I | 34 | 34 | 31 |
| H | 35 | 35 | 32 |
| W | 36 | 36 | 33 |
| V | 37 | 37 | 34 |
| R | 38 | 38 | 35 |
| Q | 39 | 39 | 36 |
| A | 40 | 40 | 37 |
| P | 41 | 41 | 38 |
| G | 42 | 42 | 39 |
| K | 43 | 43 | 40 |
| G | 44 | 44 | 41 |
| L | 45 | 45 | 42 |
| E | 46 | 46 | 43 |
| W | 47 | 47 | 44 |
| V | 48 | 48 | 45 |
| A | 49 | 49 | 46 |
| R | 50 | 50 | 47 |
| I | 51 | 51 | 48 |
| Y | 52 | 52 | 49 |
| P | 53 | 52A | 50 |
| T | 54 | 53 | 51 |
| N | 55 | 54 | 52 |
| G | 56 | 55 | 53 |
| Y | 57 | 56 | 54 |
| T | 58 | 57 | 55 |
| R | 59 | 58 | 56 |
| Y | 60 | 59 | 57 |
| A | 61 | 60 | 58 |
| D | 62 | 61 | 59 |
| S | 63 | 62 | 60 |
| V | 64 | 63 | 61 |
| K | 65 | 64 | 62 |
| G | 66 | 65 | 63 |
| R | 67 | 66 | 64 |
| F | 68 | 67 | 65 |
| T | 69 | 68 | 66 |
| I | 70 | 69 | 67 |
| S | 71 | 70 | 68 |
| A | 72 | 71 | 69 |
| D | 73 | 72 | 70 |
| T | 74 | 73 | 71 |
| S | 75 | 74 | 72 |
| K | 76 | 75 | 73 |
| N | 77 | 76 | 74 |
| T | 78 | 77 | 75 |
| A | 79 | 78 | 76 |
| Y | 80 | 79 | 77 |
| L | 81 | 80 | 78 |
| Q | 82 | 81 | 79 |
| M | 83 | 82 | 80 |
| N | 84 | 82A | 81 |
| S | 85 | 82B | 82 |
| L | 86 | 82C | 83 |
| R | 87 | 83 | 84 |
| A | 88 | 84 | 85 |
| E | 89 | 85 | 86 |
| D | 90 | 86 | 87 |
| T | 91 | 87 | 88 |
| A | 92 | 88 | 89 |
| V | 93 | 89 | 90 |
| Y | 94 | 90 | 91 |
| Y | 95 | 91 | 92 |
| C | 96 | 92 | 93 |
| S | 97 | 93 | 94 |
| R | 98 | 94 | 95 |
| W | 99 | 95 | 96 |
| G | 100 | 96 | 97 |
| G | 101 | 97 | 98 |
| D | 102 | 98 | 99 |
| G | 103 | 99 | 100 |
| F | 104 | 100 | 101 |
| Y | 105 | 100A | 102 |
| A | 106 | 100B | 103 |
| M | 107 | 100C | 104 |
| D | 108 | 101 | 105 |
| Y | 109 | 102 | 106 |
| W | 110 | 103 | 107 |
| G | 111 | 104 | 108 |
| Q | 112 | 105 | 109 |
| G | 113 | 106 | 110 |
| T | 114 | 107 | 111 |
| L | 115 | 108 | 112 |
| V | 116 | 109 | 113 |
| T | 117 | 110 | 114 |
| V | 118 | 111 | 115 |
| S | 119 | 112 | 116 |
| S | 120 | 113 | 117 |
| A | 121 | 114 | 118 |
| S | 122 | 115 | 119 |
| T | 123 | 116 | 120 |
| K | 124 | 117 | 121 |
| G | 125 | 118 | 122 |
| P | 126 | 119 | 123 |
| S | 127 | 120 | 124 |
| V | 128 | 121 | 125 |
| F | 129 | 122 | 126 |
| P | 130 | 123 | 127 |
| L | 131 | 124 | 128 |
| A | 132 | 125 | 129 |
| P | 133 | 126 | 130 |
| S | 134 | 127 | 131 |
| S | 135 | 128 | 132 |
| K | 136 | 129 | 133 |
| S | 137 | 130 | 134 |
| T | 138 | 131 | 135 |
| S | 139 | 132 | 136 |
| G | 140 | 133 | 137 |
| G | 141 | 134 | 138 |
| T | 142 | 135 | 139 |
| A | 143 | 136 | 140 |
| A | 144 | 137 | 141 |
| L | 145 | 138 | 142 |
| G | 146 | 139 | 143 |
| C | 147 | 140 | 144 |
| L | 148 | 141 | 145 |
| V | 149 | 142 | 146 |
| K | 150 | 143 | 147 |
| D | 151 | 144 | 148 |
| Y | 152 | 145 | 149 |
| F | 153 | 146 | 150 |
| P | 154 | 147 | 151 |
| E | 155 | 148 | 152 |
| P | 156 | 149 | 153 |
| V | 157 | 150 | 154 |
| T | 158 | 151 | 155 |
| V | 159 | 152 | 156 |
| S | 160 | 153 | 157 |
| W | 161 | 154 | 158 |
| N | 162 | 155 | 159 |
| S | 163 | 156 | 160 |
| G | 164 | 157 | 161 |
| A | 165 | 158 | 162 |
| L | 166 | 159 | 163 |
| T | 167 | 160 | 164 |
| S | 168 | 161 | 165 |
| G | 169 | 162 | 166 |
| V | 170 | 163 | 167 |
| H | 171 | 164 | 168 |
| T | 172 | 165 | 169 |
| F | 173 | 166 | 170 |
| P | 174 | 167 | 171 |
| A | 175 | 168 | 172 |
| V | 176 | 169 | 173 |
| L | 177 | 170 | 174 |
| Q | 178 | 171 | 175 |
| S | 179 | 172 | 176 |
| S | 180 | 173 | 177 |
| G | 181 | 174 | 178 |
| L | 182 | 175 | 179 |
| Y | 183 | 176 | 180 |
| S | 184 | 177 | 181 |
| L | 185 | 178 | 182 |
| S | 186 | 179 | 183 |
| S | 187 | 180 | 184 |
| V | 188 | 181 | 185 |
| V | 189 | 182 | 186 |
| T | 190 | 183 | 187 |
| V | 191 | 184 | 188 |
| P | 192 | 185 | 189 |
| S | 193 | 186 | 190 |
| S | 194 | 187 | 191 |
| S | 195 | 188 | 192 |

Fig. 1B (Cont.)

| HC Amino Acid | GNE Seq. # | Kabat Seq # | EU Seq # | HC Amino Acid | GNE Seq. # | Kabat Seq # | EU Seq # | HC Amino Acid | GNE Seq. # | Kabat Seq # | EU Seq # |
|---|---|---|---|---|---|---|---|---|---|---|---|
| L | 196 | 189 | 193 | E | 261 | 254 | 258 | V | 326 | 319 | 323 |
| G | 197 | 190 | 194 | V | 262 | 255 | 259 | S | 327 | 320 | 324 |
| T | 198 | 191 | 195 | T | 263 | 256 | 260 | N | 328 | 321 | 325 |
| Q | 199 | 192 | 196 | C | 264 | 257 | 261 | K | 329 | 322 | 326 |
| T | 200 | 193 | 197 | V | 265 | 258 | 262 | A | 330 | 323 | 327 |
| Y | 201 | 194 | 198 | V | 266 | 259 | 263 | L | 331 | 324 | 328 |
| I | 202 | 195 | 199 | V | 267 | 260 | 264 | P | 332 | 325 | 329 |
| C | 203 | 196 | 200 | D | 268 | 261 | 265 | A | 333 | 326 | 330 |
| N | 204 | 197 | 201 | V | 269 | 262 | 266 | P | 334 | 327 | 331 |
| V | 205 | 198 | 202 | S | 270 | 263 | 267 | I | 335 | 328 | 332 |
| N | 206 | 199 | 203 | H | 271 | 264 | 268 | E | 336 | 329 | 333 |
| H | 207 | 200 | 204 | E | 272 | 265 | 269 | K | 337 | 330 | 334 |
| K | 208 | 201 | 205 | D | 273 | 266 | 270 | T | 338 | 331 | 335 |
| P | 209 | 202 | 206 | P | 274 | 267 | 271 | I | 339 | 332 | 336 |
| S | 210 | 203 | 207 | E | 275 | 268 | 272 | S | 340 | 333 | 337 |
| N | 211 | 204 | 208 | V | 276 | 269 | 273 | K | 341 | 334 | 338 |
| T | 212 | 205 | 209 | K | 277 | 270 | 274 | A | 342 | 335 | 339 |
| K | 213 | 206 | 210 | F | 278 | 271 | 275 | K | 343 | 336 | 340 |
| V | 214 | 207 | 211 | N | 279 | 272 | 276 | G | 344 | 337 | 341 |
| D | 215 | 208 | 212 | W | 280 | 273 | 277 | Q | 345 | 338 | 342 |
| K | 216 | 209 | 213 | Y | 281 | 274 | 278 | P | 346 | 339 | 343 |
| K | 217 | 210 | 214 | V | 282 | 275 | 279 | R | 347 | 340 | 344 |
| V | 218 | 211 | 215 | D | 283 | 276 | 280 | E | 348 | 341 | 345 |
| E | 219 | 212 | 216 | G | 284 | 277 | 281 | P | 349 | 342 | 346 |
| P | 220 | 213 | 217 | V | 285 | 278 | 282 | Q | 350 | 343 | 347 |
| K | 221 | 214 | 218 | E | 286 | 279 | 283 | V | 351 | 344 | 348 |
| S | 222 | 215 | 219 | V | 287 | 280 | 284 | Y | 352 | 345 | 349 |
| C | 223 | 216 | 220 | H | 288 | 281 | 285 | T | 353 | 346 | 350 |
| D | 224 | 217 | 221 | N | 289 | 282 | 286 | L | 354 | 347 | 351 |
| K | 225 | 218 | 222 | A | 290 | 283 | 287 | P | 355 | 348 | 352 |
| T | 226 | 219 | 223 | K | 291 | 284 | 288 | P | 356 | 349 | 353 |
| H | 227 | 220 | 224 | T | 292 | 285 | 289 | S | 357 | 350 | 354 |
| T | 228 | 221 | 225 | K | 293 | 286 | 290 | R | 358 | 351 | 355 |
| C | 229 | 222 | 226 | P | 294 | 287 | 291 | D | 359 | 352 | 356 |
| P | 230 | 223 | 227 | R | 295 | 288 | 292 | E | 360 | 353 | 357 |
| P | 231 | 224 | 228 | E | 296 | 289 | 293 | L | 361 | 354 | 358 |
| C | 232 | 225 | 229 | E | 297 | 290 | 294 | T | 362 | 355 | 359 |
| P | 233 | 226 | 230 | Q | 298 | 291 | 295 | K | 363 | 356 | 360 |
| A | 234 | 227 | 231 | Y | 299 | 292 | 296 | N | 364 | 357 | 361 |
| P | 235 | 228 | 232 | N | 300 | 293 | 297 | Q | 365 | 358 | 362 |
| E | 236 | 229 | 233 | S | 301 | 294 | 298 | V | 366 | 359 | 363 |
| L | 237 | 230 | 234 | T | 302 | 295 | 299 | S | 367 | 360 | 364 |
| L | 238 | 231 | 235 | Y | 303 | 296 | 300 | L | 368 | 361 | 365 |
| G | 239 | 232 | 236 | R | 304 | 297 | 301 | T | 369 | 362 | 366 |
| G | 240 | 233 | 237 | V | 305 | 298 | 302 | C | 370 | 363 | 367 |
| P | 241 | 234 | 238 | V | 306 | 299 | 303 | L | 371 | 364 | 368 |
| S | 242 | 235 | 239 | S | 307 | 300 | 304 | V | 372 | 365 | 369 |
| V | 243 | 236 | 240 | V | 308 | 301 | 305 | K | 373 | 366 | 370 |
| F | 244 | 237 | 241 | L | 309 | 302 | 306 | G | 374 | 367 | 371 |
| L | 245 | 238 | 242 | T | 310 | 303 | 307 | F | 375 | 368 | 372 |
| F | 246 | 239 | 243 | V | 311 | 304 | 308 | Y | 376 | 369 | 373 |
| P | 247 | 240 | 244 | L | 312 | 305 | 309 | P | 377 | 370 | 374 |
| P | 248 | 241 | 245 | H | 313 | 306 | 310 | S | 378 | 371 | 375 |
| K | 249 | 242 | 246 | Q | 314 | 307 | 311 | D | 379 | 372 | 376 |
| P | 250 | 243 | 247 | D | 315 | 308 | 312 | I | 380 | 373 | 377 |
| K | 251 | 244 | 248 | W | 316 | 309 | 313 | A | 381 | 374 | 378 |
| D | 252 | 245 | 249 | L | 317 | 310 | 314 | V | 382 | 375 | 379 |
| T | 253 | 246 | 250 | N | 318 | 311 | 315 | E | 383 | 376 | 380 |
| L | 254 | 247 | 251 | G | 319 | 312 | 316 | W | 384 | 377 | 381 |
| M | 255 | 248 | 252 | K | 320 | 313 | 317 | E | 385 | 378 | 382 |
| I | 256 | 249 | 253 | E | 321 | 314 | 318 | S | 386 | 379 | 383 |
| S | 257 | 250 | 254 | Y | 322 | 315 | 319 | N | 387 | 380 | 384 |
| R | 258 | 251 | 255 | K | 323 | 316 | 320 | G | 388 | 381 | 385 |
| T | 259 | 252 | 256 | C | 324 | 317 | 321 | Q | 389 | 382 | 386 |
| P | 260 | 253 | 257 | K | 325 | 318 | 322 | P | 390 | 383 | 387 |

Fig. 1B (Cont.)

| HC Amino Acid | GNE Seq # | Kabat Seq # | EU Seq # |
|---|---|---|---|
| E | 391 | 384 | 388 |
| N | 392 | 385 | 389 |
| N | 393 | 386 | 390 |
| Y | 394 | 387 | 391 |
| K | 395 | 388 | 392 |
| T | 396 | 389 | 393 |
| T | 397 | 390 | 394 |
| P | 398 | 391 | 395 |
| P | 399 | 392 | 396 |
| V | 400 | 393 | 397 |
| L | 401 | 394 | 398 |
| D | 402 | 395 | 399 |
| S | 403 | 396 | 400 |
| D | 404 | 397 | 401 |
| G | 405 | 398 | 402 |
| S | 406 | 399 | 403 |
| F | 407 | 400 | 404 |
| F | 408 | 401 | 405 |
| L | 409 | 402 | 406 |
| Y | 410 | 403 | 407 |
| S | 411 | 404 | 408 |
| K | 412 | 405 | 409 |
| L | 413 | 406 | 410 |
| T | 414 | 407 | 411 |
| V | 415 | 408 | 412 |
| D | 416 | 409 | 413 |
| K | 417 | 410 | 414 |
| S | 418 | 411 | 415 |
| R | 419 | 412 | 416 |
| W | 420 | 413 | 417 |
| Q | 421 | 414 | 418 |
| Q | 422 | 415 | 419 |
| G | 423 | 416 | 420 |
| N | 424 | 417 | 421 |
| V | 425 | 418 | 422 |
| F | 426 | 419 | 423 |
| S | 427 | 420 | 424 |
| C | 428 | 421 | 425 |
| S | 429 | 422 | 426 |
| V | 430 | 423 | 427 |
| M | 431 | 424 | 428 |
| H | 432 | 425 | 429 |
| E | 433 | 426 | 430 |
| A | 434 | 427 | 431 |
| L | 435 | 428 | 432 |
| H | 436 | 429 | 433 |
| N | 437 | 430 | 434 |
| H | 438 | 431 | 435 |
| Y | 439 | 432 | 436 |
| T | 440 | 433 | 437 |
| Q | 441 | 434 | 438 |
| K | 442 | 435 | 439 |
| S | 443 | 436 | 440 |
| L | 444 | 437 | 441 |
| S | 445 | 438 | 442 |
| L | 446 | 439 | 443 |
| S | 447 | 440 | 444 |
| P | 448 | 441 | 445 |
| G | 449 | 442 | 446 |
| K | 450 | 443 | 447 |

Fig. 2A

EVQLVESGGGLVQPGGSLRLSCAASGFNIKDTYIHWVRQAPGKGLEWVARIYPTNGYTRY
ADSVKGRFTISADTSKNTAYLQMNSLRAEDTAVYYCSRWGGDGFYAMDYWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK

Fig. 2B

DIQMTQSPSSLSASVGDRVTITCRASQDVNTAVAWYQQKPGKAPKLLIYSASFLYSGVPS
RFSGSRSGTDFTLTISSLQPEDFATYYCQQHYTTPPTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

Thio-Her2-hu7C2-HC-A118C-disulfide-PBD and thio-Her2-hu7C2-LC-K149C-disulfide-PBD Thio-Her2-hu7C2-LC-K149C-CBI dimer Thio-Her2-hu7C2-LC-K149C-disulfide-CBI-PBD Thio-Her2-hu7C2-LC-K149C-disulfide-PNU Thio-Her2-hu7C2-HC-A118C-maleimide-PNU and thio-Her2-hu7C2-LC-K149C-maleimide-PNU Fig. 15
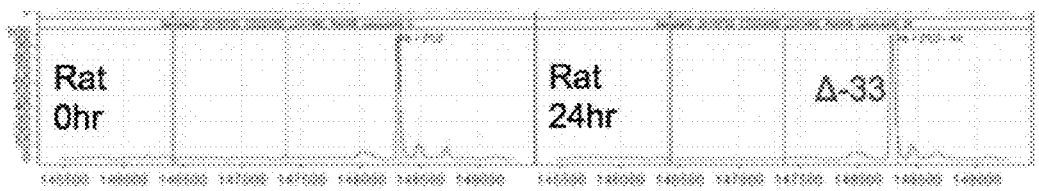
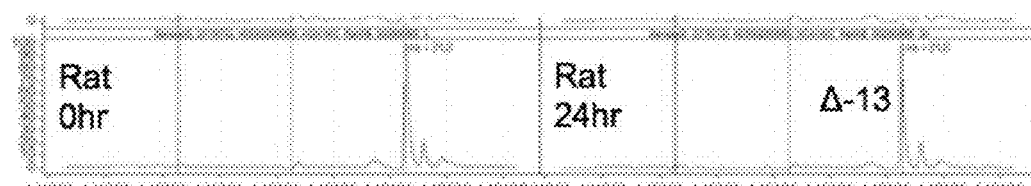
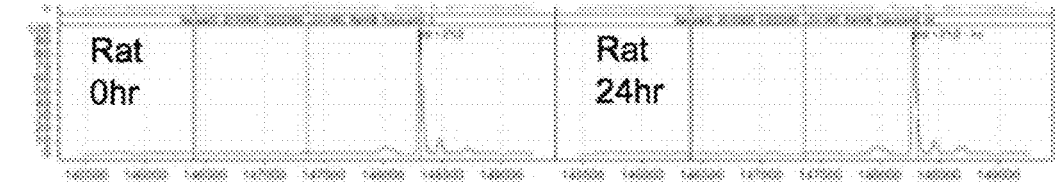
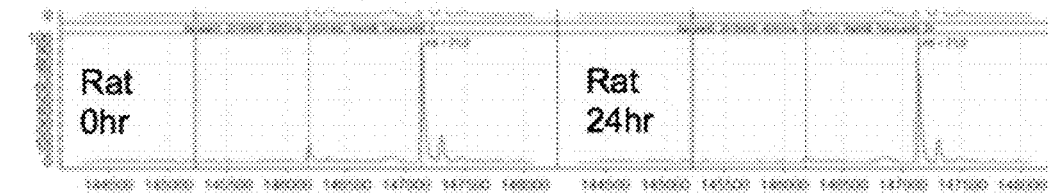

Fig. 17
LC-K149C
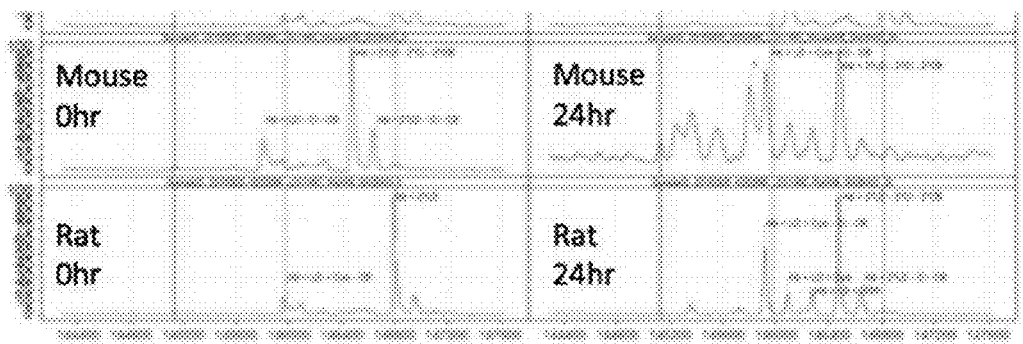
HC-A140C
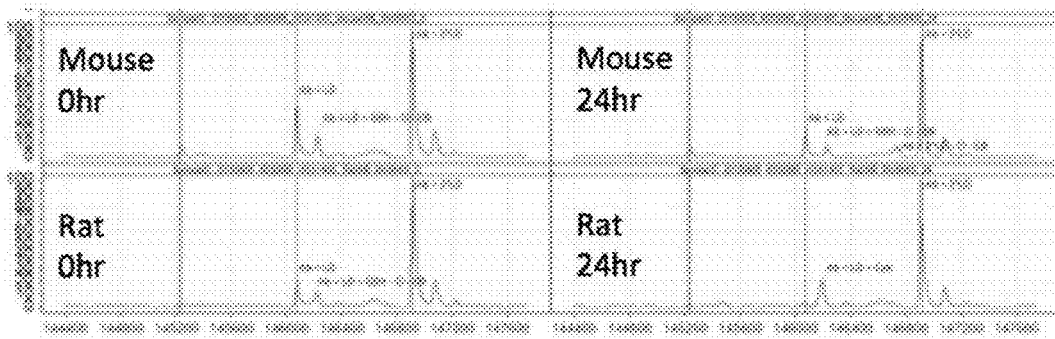

Fig. 18A
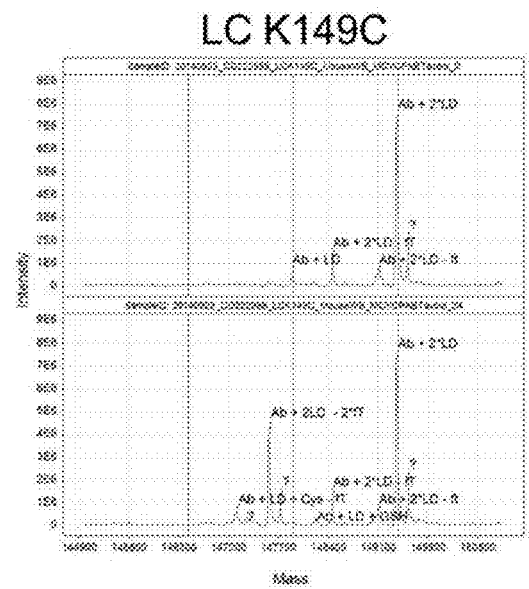 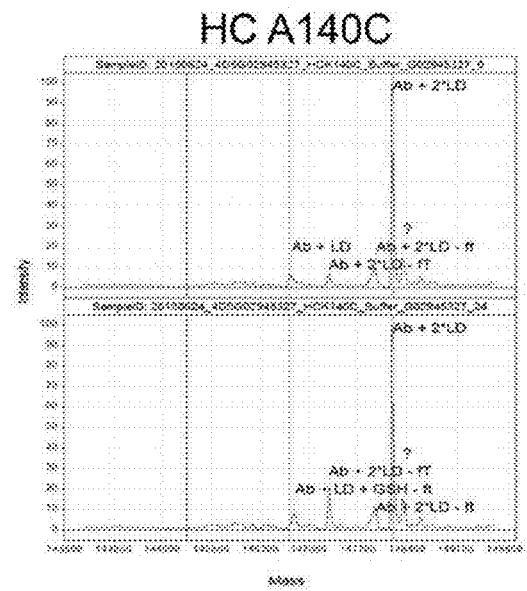
Fig. 18B
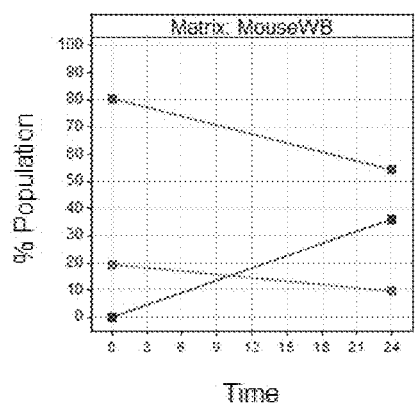
Fig. 18C
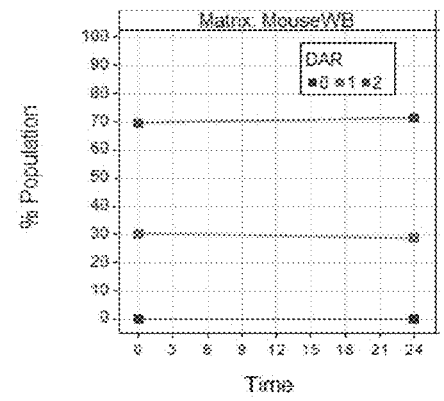

Fig. 19
LC-K149C
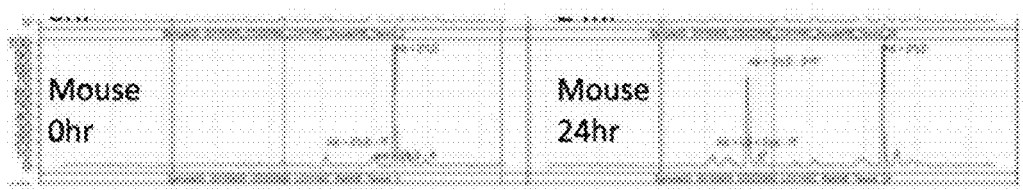
HC-A140C
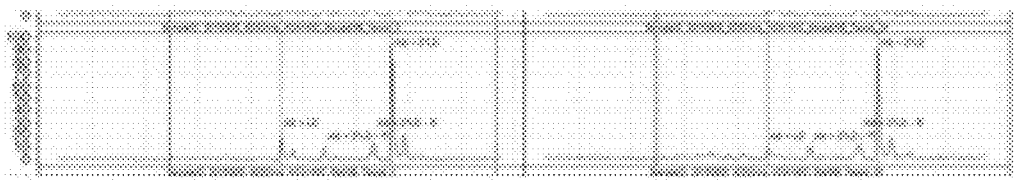

SEQUENCE LISTING

```
<160> NUMBER OF SEQ ID NOS: 199

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide:  LC-I106C

<400> SEQUENCE: 1

Gly Thr Lys Val Glu Cys Lys Arg Thr Val Ala
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide:  LC-R108C

<400> SEQUENCE: 2

Lys Val Glu Ile Lys Cys Thr Val Ala Ala Pro
1               5                   10
```

```
<210> SEQ ID NO 3
<211> LENGTH: 11
<212> TYPE: PRT
<213> ORGANISM: Artificial Sequence
<220> FEATURE:
<223> OTHER INFORMATION: Synthetic peptide: LC-R142C

<400> SEQUENCE: 3

Asn Asn Phe Tyr Pro Cys Glu Ala Lys Val Gln
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide: LC-K149C

<400> SEQUENCE: 4

Ala Lys Val Gln Trp Cys Val Asp Asn Ala Leu
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide: HC-T114C

<400> SEQUENCE: 5

Gln Gly Thr Leu Val Cys Val Ser Ser Ala Ser
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide: HC-A140C

<400> SEQUENCE: 6

Thr Ser Gly Gly Thr Cys Ala Leu Gly Cys Leu
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide: HC-L174C

<400> SEQUENCE: 7

Thr Phe Pro Ala Val Cys Gln Ser Ser Gly Leu
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide: HC-L179C

<400> SEQUENCE: 8

Leu Gln Ser Ser Gly Cys Tyr Ser Leu Ser Ser
1               5                   10
```

```
<210> SEQ ID NO 9
<211> LENGTH: 11
<212> TYPE: PRT
<213> ORGANISM: Artificial Sequence
<220> FEATURE:
<223> OTHER INFORMATION: Synthetic peptide: HC-T187C

<400> SEQUENCE: 9

Leu Ser Ser Val Val Cys Val Pro Ser Ser
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide: HC-T209C

<400> SEQUENCE: 10

His Lys Pro Ser Asn Cys Lys Val Asp Lys Lys
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide: HC-V262C

<400> SEQUENCE: 11

Pro Glu Val Thr Cys Cys Val Val Asp Val Ser
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide: HC-G371C

<400> SEQUENCE: 12

Thr Cys Leu Val Lys Cys Phe Tyr Pro Ser Asp
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide: HC-Y373C

<400> SEQUENCE: 13

Leu Val Lys Gly Phe Cys Pro Ser Asp Ile Ala
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide: HC-E382C

<400> SEQUENCE: 14

Ile Ala Val Glu Trp Cys Ser Asn Gly Gln Pro
1               5                   10
```

```
<210> SEQ ID NO 15
<211> LENGTH: 11
<212> TYPE: PRT
<213> ORGANISM: Artificial Sequence
<220> FEATURE:
<223> OTHER INFORMATION: Synthetic peptide: HC-S424C/HC-S420C

<400> SEQUENCE: 15

Gln Gly Asn Val Phe Cys Cys Ser Val Met His
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic peptide: HC-N434C

<400> SEQUENCE: 16

His Glu Ala Leu His Cys His Tyr Thr Gln Lys
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic peptide: HC-Q438C

<400> SEQUENCE: 17

His Asn His Tyr Thr Cys Lys Ser Leu Ser Leu
1               5                   10

<210> SEQ ID NO 18
<211> LENGTH: 449
<212> TYPE: PRT
<213> ORGANISM: Artificial Sequence
<220> FEATURE:
<223> OTHER INFORMATION: Synthetic polypeptide:  cysteine engineered
      antibodies

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 19
<211> LENGTH: 214
<212> TYPE: PRT
<213> ORGANISM: Artificial Sequence
<220> FEATURE:
<223> OTHER INFORMATION: Synthetic polypeptide: cysteine engineered
      antibodies

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

-continued

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide: V2C

<400> SEQUENCE: 20

Glu Cys Gln Leu Val Glu Ser Gly Gly Gly Leu
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide: L4C

<400> SEQUENCE: 21

Glu Val Gln Cys Val Glu Ser Gly Gly Gly Leu
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic peptide: V5C

<400> SEQUENCE: 22

Glu Val Gln Leu Cys Glu Ser Gly Gly Gly Leu
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic peptide: L11C

<400> SEQUENCE: 23
```

```
Glu Ser Gly Gly Gly Cys Val Gln Pro Gly Gly
1               5                   10
```

<210> SEQ ID NO 24
<211> LENGTH: 11
<212> TYPE: PRT
<213> ORGANISM: Artificial Sequence
<220> FEATURE:
<223> OTHER INFORMATION: Synthetic peptide: R19C

<400> SEQUENCE: 24

```
Pro Gly Gly Ser Leu Cys Leu Ser Cys Ala Ala
1               5                   10
```

<210> SEQ ID NO 25
<211> LENGTH: 11
<212> TYPE: PRT
<213> ORGANISM: Artificial Sequence
<220> FEATURE:
<223> OTHER INFORMATION: Synthetic peptide: F27C

<400> SEQUENCE: 25

```
Cys Ala Ala Ser Gly Cys Asn Ile Lys Asp Thr
1               5                   10
```

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide: I29C

<400> SEQUENCE: 26

```
Ala Ser Gly Phe Asn Cys Lys Asp Thr Tyr Ile
1               5                   10
```

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide: T32C

<400> SEQUENCE: 27

```
Phe Asn Ile Lys Asp Cys Tyr Ile His Trp Val
1               5                   10
```

<210> SEQ ID NO 28
<211> LENGTH: 11
<212> TYPE: PRT
<213> ORGANISM: Artificial Sequence
<220> FEATURE:
<223> OTHER INFORMATION: Synthetic peptide: Y33C

<400> SEQUENCE: 28

```
Asn Ile Lys Asp Thr Cys Ile His Trp Val Arg
1               5                   10
```

<210> SEQ ID NO 29
<211> LENGTH: 11
<212> TYPE: PRT
<213> ORGANISM: Artificial Sequence
<220> FEATURE:
<223> OTHER INFORMATION: Synthetic peptide: Q39C

<400> SEQUENCE: 29

```
Ile His Trp Val Arg Cys Ala Pro Gly Lys Gly
1               5                   10
```

<210> SEQ ID NO 30
<211> LENGTH: 11
<212> TYPE: PRT
<213> ORGANISM: Artificial Sequence
<220> FEATURE:
<223> OTHER INFORMATION: Synthetic peptide: A40C

<400> SEQUENCE: 30

His Trp Val Arg Gln Cys Pro Gly Lys Gly Leu
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic peptide: K43C

<400> SEQUENCE: 31

Arg Gln Ala Pro Gly Cys Gly Leu Glu Trp Val
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic peptide: L45C

<400> SEQUENCE: 32

Ala Pro Gly Lys Gly Cys Glu Trp Val Ala Arg
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic peptide: E46C

<400> SEQUENCE: 33

Gly Lys Gly Leu Cys Trp Val Ala Arg Ile
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic peptide: T53C

<400> SEQUENCE: 34

Ala Arg Ile Tyr Pro Cys Asn Gly Tyr Thr Arg
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic peptide: G55C

<400> SEQUENCE: 35

Ile Tyr Pro Thr Asn Cys Tyr Thr Arg Tyr Ala
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic peptide: T57C

<400> SEQUENCE: 36

Pro Thr Asn Gly Tyr Cys Arg Tyr Ala Asp Ser
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic peptide: R58C

<400> SEQUENCE: 37

Thr Asn Gly Tyr Thr Cys Tyr Ala Asp Ser Val
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic peptide: Y59C

<400> SEQUENCE: 38

Asn Gly Tyr Thr Arg Cys Ala Asp Ser Val Lys
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic peptide: A60C

<400> SEQUENCE: 39

Gly Tyr Thr Arg Tyr Cys Asp Ser Val Lys Gly
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic peptide: T68C

<400> SEQUENCE: 40

Val Lys Gly Arg Phe Cys Ile Ser Ala Asp Thr
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic peptide: N76N

<400> SEQUENCE: 41

Ala Asp Thr Ser Lys Cys Thr Ala Tyr Leu Gln
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic peptide: Y79C

<400> SEQUENCE: 42

Ser Lys Asn Thr Ala Cys Leu Gln Met Asn Ser
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic peptide: Q81C

<400> SEQUENCE: 43

Asn Thr Ala Tyr Leu Cys Met Asn Ser Leu Arg
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic peptide: W95C

<400> SEQUENCE: 44

Tyr Tyr Cys Ser Arg Cys Gly Gly Asp Gly Phe
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic peptide: G96C

<400> SEQUENCE: 45

Tyr Cys Ser Arg Trp Cys Gly Asp Gly Phe Tyr
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic peptide: D101C

<400> SEQUENCE: 46

Gly Phe Tyr Ala Met Cys Tyr Trp Gly Gln Gly
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Synthetic peptide: W103C

<400> SEQUENCE: 47

Tyr Ala Met Asp Tyr Cys Gly Gln Gly Thr Leu
1               5                   10

```
<210> SEQ ID NO 48
<211> LENGTH: 11
<212> TYPE: PRT
<213> ORGANISM: Artificial Sequence
<220> FEATURE:
<223> OTHER INFORMATION: Synthetic peptide: T116C

<400> SEQUENCE: 48

Val Ala Ser Ala Ser Cys Lys Gly Pro Ser Val
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic peptide: K117C

<400> SEQUENCE: 49

Ser Ser Ala Ser Thr Cys Gly Pro Ser Val Phe
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic peptide: T135C

<400> SEQUENCE: 50

Ser Thr Ser Gly Gly Cys Ala Ala Leu Gly Cys
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic peptide: N155C

<400> SEQUENCE: 51

Val Thr Val Ser Trp Cys Ser Gly Ala Leu Thr
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic peptide: A158C

<400> SEQUENCE: 52

Ser Trp Asn Ser Gly Cys Leu Thr Ser Gly Val
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic peptide: G162C

<400> SEQUENCE: 53

Gly Ala Leu Thr Ser Cys Val His Thr Phe Pro
1               5                   10

<210> SEQ ID NO 54
```

```
<211> LENGTH: 11
<212> TYPE: PRT
<213> ORGANISM: Artificial Sequence
<220> FEATURE:
<223> OTHER INFORMATION: Synthetic peptide: G174C

<400> SEQUENCE: 54

Val Leu Gln Ser Ser Cys Leu Tyr Ser Leu Ser
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic peptide: L175C

<400> SEQUENCE: 55

Leu Gln Ser Ser Gly Cys Tyr Ser Leu Ser Ser
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Synthetic peptide: T183C

<400> SEQUENCE: 56

Leu Ser Ser Val Val Cys Val Pro Ser Ser Ser
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic peptide: V184C

<400> SEQUENCE: 57

Ser Ser Val Val Thr Cys Pro Ser Ser Ser Leu
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic peptide: I195C

<400> SEQUENCE: 58

Gly Thr Gln Thr Tyr Cys Cys Asn Val Asn His
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic peptide: N199C

<400> SEQUENCE: 59

Tyr Ile Cys Asn Val Cys His Lys Pro Ser Asn
1               5                   10

<210> SEQ ID NO 60
<211> LENGTH: 11
```

```
<212> TYPE: PRT
<213> ORGANISM: Artificial Sequence
<220> FEATURE:
<223> OTHER INFORMATION: Synthetic peptide: S203C

<400> SEQUENCE: 60

Val Asn His Lys Pro Cys Asn Thr Lys Val Asp
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Synthetic peptide: F239C

<400> SEQUENCE: 61

Pro Ser Val Phe Leu Cys Pro Pro Lys Pro Lys
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic peptide: M248C

<400> SEQUENCE: 62

Pro Lys Asp Thr Leu Cys Ile Ser Arg Thr Pro
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic peptide: E254C

<400> SEQUENCE: 63

Ile Ser Arg Thr Pro Cys Val Thr Cys Val Val
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic peptide: V258C

<400> SEQUENCE: 64

Pro Glu Val Thr Cys Cys Val Val Asp Val Ser
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic peptide: N272C

<400> SEQUENCE: 65

Pro Glu Val Lys Phe Cys Trp Tyr Val Asp Gly
1               5                   10

<210> SEQ ID NO 66
<211> LENGTH: 11
<212> TYPE: PRT
```

```
<213> ORGANISM: Artificial Sequence
<220> FEATURE:
<223> OTHER INFORMATION: Synthetic peptide: V278C

<400> SEQUENCE: 66

Trp Tyr Val Asp Gly Cys Glu Val His Asn Ala
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic peptide: L305C

<400> SEQUENCE: 67

Ser Val Leu Thr Val Cys His Gln Asp Trp Leu
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic peptide: T331C

<400> SEQUENCE: 68

Ala Pro Ile Glu Lys Cys Ile Ser Lys Ala Lys
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Synthetic peptide: S333C

<400> SEQUENCE: 69

Ile Glu Lys Thr Ile Cys Lys Ala Lys Gly Gln
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Synthetic peptide: R340C

<400> SEQUENCE: 70

Ala Lys Gly Gln Pro Cys Glu Pro Gln Val Tyr
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic peptide: Q343C

<400> SEQUENCE: 71

Gln Pro Arg Glu Pro Cys Val Tyr Thr Leu Pro
1               5                   10

<210> SEQ ID NO 72
<211> LENGTH: 11
<212> TYPE: PRT
<213> ORGANISM: Artificial Sequence
```

```
<220> FEATURE:
<223> OTHER INFORMATION: Synthetic peptide: K356C

<400> SEQUENCE: 72

Arg Asp Glu Leu Thr Cys Asn Gln Val Ser Leu
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic peptide: E384C

<400> SEQUENCE: 73

Ser Asn Gly Gln Pro Cys Asn Asn Tyr Lys Thr
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic peptide: S399C

<400> SEQUENCE: 74

Leu Asp Ser Asp Gly Cys Phe Phe Leu Tyr Ser
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic peptide: K410C

<400> SEQUENCE: 75

Lys Leu Thr Val Asp Cys Ser Arg Trp Gln Gln
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Synthetic peptide: Q414C

<400> SEQUENCE: 76

Asp Lys Ser Arg Trp Cys Gln Gly Asn Val Phe
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Synthetic peptide: G416C

<400> SEQUENCE: 77

Ser Arg Trp Gln Gln Cys Asn Val Phe Ser Cys
1               5                   10

<210> SEQ ID NO 78
<211> LENGTH: 11
<212> TYPE: PRT
<213> ORGANISM: Artificial Sequence
<220> FEATURE:
```

```
<223> OTHER INFORMATION: Synthetic peptide: N417C

<400> SEQUENCE: 78

Arg Trp Gln Gln Gly Cys Val Phe Ser Cys Ser
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic peptide: Y432C

<400> SEQUENCE: 79

Ala Leu His Asn His Cys Thr Gln Lys Ser Leu
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthetic peptide: T433C

<400> SEQUENCE: 80

Leu His Asn His Tyr Cys Gln Lys Ser Leu Ser
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Synthetic peptide: K435C

<400> SEQUENCE: 81

Asn His Tyr Thr Gln Cys Ser Leu Ser Leu Ser
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Synthetic peptide: S438

<400> SEQUENCE: 82

Thr Gln Lys Ser Leu Cys Leu Ser Pro Gly Lys
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic peptide: L439C

<400> SEQUENCE: 83

Gln Lys Ser Leu Ser Cys Ser Pro Gly Lys
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Synthetic peptide: M100cC
```

```
<400> SEQUENCE: 84

Asp Gly Phe Tyr Ala Cys Asp Tyr Trp Gly Gln
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthetic peptide: N82aC

<400> SEQUENCE: 85

Ala Tyr Leu Gln Met Cys Ser Leu Arg Ala Glu
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthetic peptide: S12C

<400> SEQUENCE: 86

Ser Pro Ser Ser Leu Cys Ala Ser Val Gly Asp
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Synthetic peptide: S14C

<400> SEQUENCE: 87

Ser Ser Leu Ser Ala Cys Val Gly Asp Arg Val
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Synthetic peptide: G16C

<400> SEQUENCE: 88

Leu Ser Ala Ser Val Cys Asp Arg Val Thr Ile
1               5                   10

<210> SEQ ID NO 89
<211> LENGTH: 11
<212> TYPE: PRT
<213> ORGANISM: Artificial Sequence
<220> FEATURE:
<223> OTHER INFORMATION: Synthetic peptide: R18C

<400> SEQUENCE: 89

Ala Ser Val Gly Asp Cys Val Thr Ile Thr Cys
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Synthetic peptide: T22C
```

```
<400> SEQUENCE: 90

Asp Arg Val Thr Ile Cys Cys Arg Ala Ser Gln
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthetic peptide: R24C

<400> SEQUENCE: 91

Val Thr Ile Thr Cys Cys Ala Ser Gln Asp Val
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Synthetic peptide: Q27C

<400> SEQUENCE: 92

Thr Cys Arg Ala Ser Cys Asp Val Asn Thr Ala
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Synthetic peptide: T31C

<400> SEQUENCE: 93

Ser Gln Asp Val Asn Cys Ala Val Ala Trp Tyr
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Synthetic peptide: A32C

<400> SEQUENCE: 94

Gln Asp Val Asn Thr Cys Val Ala Trp Tyr Gln
1               5                   10

<210> SEQ ID NO 95
<211> LENGTH: 11
<212> TYPE: PRT
<213> ORGANISM: Artificial Sequence
<220> FEATURE:
<223> OTHER INFORMATION: Synthetic peptide: Q38C

<400> SEQUENCE: 95

Val Ala Trp Tyr Gln Cys Lys Pro Gly Lys Ala
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Synthetic peptide: K39C

<400> SEQUENCE: 96
```

```
Ala Trp Tyr Gln Gln Cys Pro Gly Lys Ala Pro
1               5                   10
```

<210> SEQ ID NO 97
<211> LENGTH: 11
<212> TYPE: PRT
<213> ORGANISM: Artificial Sequence
<220> FEATURE:
<223> OTHER INFORMATION: Synthetic peptide: G41C

<400> SEQUENCE: 97

```
Tyr Gln Gln Lys Pro Cys Lys Ala Pro Lys Leu
1               5                   10
```

<210> SEQ ID NO 98
<211> LENGTH: 11
<212> TYPE: PRT
<213> ORGANISM: Artificial Sequence
<220> FEATURE:
<223> OTHER INFORMATION: Synthetic peptide: K42C

<400> SEQUENCE: 98

```
Gln Gln Lys Pro Gly Cys Ala Pro Lys Leu Leu
1               5                   10
```

<210> SEQ ID NO 99
<211> LENGTH: 11
<212> TYPE: PRT
<213> ORGANISM: Artificial Sequence
<220> FEATURE:
<223> OTHER INFORMATION: Synthetic peptide: P44C

<400> SEQUENCE: 99

```
Lys Pro Gly Lys Ala Cys Lys Leu Leu Ile Tyr
1               5                   10
```

<210> SEQ ID NO 100
<211> LENGTH: 11
<212> TYPE: PRT
<213> ORGANISM: Artificial Sequence
<220> FEATURE:
<223> OTHER INFORMATION: Synthetic peptide: Y49C

<400> SEQUENCE: 100

```
Pro Lys Leu Leu Ile Cys Ser Ala Ser Phe Leu
1               5                   10
```

<210> SEQ ID NO 101
<211> LENGTH: 11
<212> TYPE: PRT
<213> ORGANISM: Artificial Sequence
<220> FEATURE:
<223> OTHER INFORMATION: Synthetic peptide: S50C

<400> SEQUENCE: 101

```
Lys Leu Leu Ile Tyr Cys Ala Ser Phe Leu Tyr
1               5                   10
```

<210> SEQ ID NO 102
<211> LENGTH: 11
<212> TYPE: PRT
<213> ORGANISM: Artificial Sequence
<220> FEATURE:
<223> OTHER INFORMATION: Synthetic peptide: S52C

<400> SEQUENCE: 102

```
Leu Ile Tyr Ser Ala Cys Phe Leu Tyr Ser Gly
1               5                   10
```

<210> SEQ ID NO 103
<211> LENGTH: 11
<212> TYPE: PRT
<213> ORGANISM: Artificial Sequence
<220> FEATURE:
<223> OTHER INFORMATION: Synthetic peptide: F53C

<400> SEQUENCE: 103

```
Ile Tyr Ser Ala Ser Cys Leu Tyr Ser Gly Val
1               5                   10
```

<210> SEQ ID NO 104
<211> LENGTH: 11
<212> TYPE: PRT
<213> ORGANISM: Artificial Sequence
<220> FEATURE:
<223> OTHER INFORMATION: Synthetic peptide: L54C

<400> SEQUENCE: 104

```
Tyr Ser Ala Ser Phe Cys Tyr Ser Gly Val Pro
1               5                   10
```

<210> SEQ ID NO 105
<211> LENGTH: 11
<212> TYPE: PRT
<213> ORGANISM: Artificial Sequence
<220> FEATURE:
<223> OTHER INFORMATION: Synthetic peptide: Y55C

<400> SEQUENCE: 105

```
Ser Ala Ser Phe Leu Cys Ser Gly Val Pro Ser
1               5                   10
```

<210> SEQ ID NO 106
<211> LENGTH: 11
<212> TYPE: PRT
<213> ORGANISM: Artificial Sequence
<220> FEATURE:
<223> OTHER INFORMATION: Synthetic peptide: S63C

<400> SEQUENCE: 106

```
Val Pro Ser Arg Phe Cys Gly Ser Arg Ser Gly
1               5                   10
```

<210> SEQ ID NO 107
<211> LENGTH: 11
<212> TYPE: PRT
<213> ORGANISM: Artificial Sequence
<220> FEATURE:
<223> OTHER INFORMATION: Synthetic peptide: G64C

<400> SEQUENCE: 107

```
Pro Ser Arg Phe Ser Cys Ser Arg Ser Gly Thr
1               5                   10
```

<210> SEQ ID NO 108
<211> LENGTH: 11
<212> TYPE: PRT
<213> ORGANISM: Artificial Sequence
<220> FEATURE:
<223> OTHER INFORMATION: Synthetic peptide: R66C

<400> SEQUENCE: 108

```
Arg Phe Ser Gly Ser Cys Ser Gly Thr Asp Phe
```

<210> SEQ ID NO 109
<211> LENGTH: 11
<212> TYPE: PRT
<213> ORGANISM: Artificial Sequence
<220> FEATURE:
<223> OTHER INFORMATION: Synthetic peptide: D70C

<400> SEQUENCE: 109

Ser Arg Ser Gly Thr Cys Phe Thr Leu Thr Ile
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic peptide: T72C

<400> SEQUENCE: 110

Ser Gly Thr Asp Phe Cys Leu Thr Ile Ser Ser
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Synthetic peptide: T74C

<400> SEQUENCE: 111

Thr Asp Phe Thr Leu Cys Ile Ser Ser Leu Gln
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Synthetic peptide: S76C

<400> SEQUENCE: 112

Phe Thr Leu Thr Ile Cys Ser Leu Gln Pro Glu
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Synthetic peptide: Q79C

<400> SEQUENCE: 113

Thr Ile Ser Ser Leu Cys Pro Glu Asp Phe Ala
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Synthetic peptide: T85C

<400> SEQUENCE: 114

Pro Glu Asp Phe Ala Cys Tyr Tyr Cys Gln Gln
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Synthetic peptide: H91C

<400> SEQUENCE: 115

Tyr Tyr Cys Gln Gln Cys Tyr Thr Thr Pro Pro
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Synthetic peptide: Y92C

<400> SEQUENCE: 116

Tyr Cys Gln Gln His Cys Thr Thr Pro Pro Thr
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Synthetic peptide: P95C

<400> SEQUENCE: 117

Gln His Tyr Thr Thr Cys Pro Thr Phe Gly Gln
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Synthetic peptide: T97C

<400> SEQUENCE: 118

Tyr Thr Thr Pro Pro Cys Phe Gly Gln Gly Thr
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Synthetic peptide: F98C

<400> SEQUENCE: 119

Thr Thr Pro Pro Thr Cys Gly Gln Gly Thr Lys
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Synthetic peptide: K103C

<400> SEQUENCE: 120

Phe Gly Gln Gly Thr Cys Val Glu Ile Lys Arg
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Synthetic peptide: E105C

<400> SEQUENCE: 121

Gln Gly Thr Lys Val Cys Ile Lys Arg Thr Val
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Synthetic peptide: K107C

<400> SEQUENCE: 122

Thr Lys Val Glu Ile Cys Arg Thr Val Ala Ala
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Synthetic peptide: P119C

<400> SEQUENCE: 123

Ser Val Phe Ile Phe Cys Pro Ser Asp Glu Gln
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Synthetic peptide: K126C

<400> SEQUENCE: 124

Ser Asp Glu Gln Leu Cys Ser Gly Thr Ala Ser
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Synthetic peptide: T129C

<400> SEQUENCE: 125

Gln Leu Lys Ser Gly Cys Ala Ser Val Val Cys
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Synthetic peptide: S131C

<400> SEQUENCE: 126

Lys Ser Gly Thr Ala Cys Val Val Cys Leu Leu
1               5                   10

```
<210> SEQ ID NO 127
<211> LENGTH: 11
<212> TYPE: PRT
<213> ORGANISM: Artificial Sequence
<220> FEATURE:
<223> OTHER INFORMATION: Synthetic peptide: Q147C

<400> SEQUENCE: 127

Arg Glu Ala Lys Val Cys Trp Lys Val Asp Asn
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Synthetic peptide: W148C

<400> SEQUENCE: 128

Glu Ala Lys Val Gln Cys Lys Val Asp Asn Ala
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Synthetic peptide: A153C

<400> SEQUENCE: 129

Trp Lys Val Asp Asn Cys Leu Gln Ser Gly Asn
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Synthetic peptide: Q155C

<400> SEQUENCE: 130

Val Asp Asn Ala Leu Cys Ser Gly Asn Ser Gln
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Synthetic peptide: S156C

<400> SEQUENCE: 131

Asp Asn Ala Leu Gln Cys Gly Asn Ser Gln Glu
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Synthetic peptide: S159C

<400> SEQUENCE: 132

Leu Gln Ser Gly Asn Cys Gln Glu Ser Val Thr
1               5                   10

<210> SEQ ID NO 133
```

-continued

```
<211> LENGTH: 11
<212> TYPE: PRT
<213> ORGANISM: Artificial Sequence
<220> FEATURE:
<223> OTHER INFORMATION: Synthetic peptide: Q160C

<400> SEQUENCE: 133

Gln Ser Gly Asn Ser Cys Glu Ser Val Thr Glu
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Synthetic peptide: S162C

<400> SEQUENCE: 134

Gly Asn Ser Gln Glu Cys Val Thr Glu Gln Asp
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Synthetic peptide: Q166C

<400> SEQUENCE: 135

Glu Ser Val Thr Glu Cys Asp Ser Lys Asp Ser
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Synthetic peptide: T172C

<400> SEQUENCE: 136

Asp Ser Lys Asp Ser Cys Tyr Ser Leu Ser Ser
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Synthetic peptide: T180C

<400> SEQUENCE: 137

Leu Ser Ser Thr Leu Cys Leu Ser Lys Ala Asp
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Synthetic peptide: V191C

<400> SEQUENCE: 138

Tyr Glu Lys His Lys Cys Tyr Ala Cys Glu Val
1               5                   10

<210> SEQ ID NO 139
<211> LENGTH: 11
```

```
<212> TYPE: PRT
<213> ORGANISM: Artificial Sequence
<220> FEATURE:
<223> OTHER INFORMATION: Synthetic peptide: A193C

<400> SEQUENCE: 139

Lys His Lys Val Tyr Cys Cys Glu Val Thr His
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Synthetic peptide: E195C

<400> SEQUENCE: 140

Lys Val Tyr Ala Cys Cys Val Thr His Gln Gly
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Synthetic peptide: V205C

<400> SEQUENCE: 141

Gly Leu Ser Ser Pro Cys Thr Lys Ser Phe Asn
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Synthetic peptide: T206C

<400> SEQUENCE: 142

Leu Ser Ser Pro Val Cys Lys Ser Phe Asn Arg
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Synthetic peptide: N210C

<400> SEQUENCE: 143

Pro Val Thr Lys Ser Phe Cys Arg Gly Glu Cys
1               5                   10

<210> SEQ ID NO 144
<211> LENGTH: 30
<212> TYPE: PRT
<213> ORGANISM: Artificial Sequence
<220> FEATURE:
<223> OTHER INFORMATION: Synthetic peptide: albumin-binding peptide

<400> SEQUENCE: 144

Cys Asp Lys Thr His Thr Gly Gly Gly Ser Gln Arg Leu Met Glu Asp
1               5                   10                  15

Ile Cys Leu Pro Arg Trp Gly Cys Leu Trp Glu Asp Asp Phe
            20                  25                  30
```

```
<210> SEQ ID NO 145
<211> LENGTH: 20
<212> TYPE: PRT
<213> ORGANISM: Artificial Sequence
<220> FEATURE:
<223> OTHER INFORMATION: Synthetic peptide: albumin-binding peptide

<400> SEQUENCE: 145

Gln Arg Leu Met Glu Asp Ile Cys Leu Pro Arg Trp Gly Cys Leu Trp
1               5                   10                  15

Glu Asp Asp Phe
            20

<210> SEQ ID NO 146
<211> LENGTH: 20
<212> TYPE: PRT
<213> ORGANISM: Artificial Sequence
<220> FEATURE:
<223> OTHER INFORMATION: Synthetic peptide: albumin-binding peptide

<400> SEQUENCE: 146

Gln Arg Leu Ile Glu Asp Ile Cys Leu Pro Arg Trp Gly Cys Leu Trp
1               5                   10                  15

Glu Asp Asp Phe
            20

<210> SEQ ID NO 147
<211> LENGTH: 18
<212> TYPE: PRT
<213> ORGANISM: Artificial Sequence
<220> FEATURE:
<223> OTHER INFORMATION: Synthetic peptide: albumin-binding peptide

<400> SEQUENCE: 147

Arg Leu Ile Glu Asp Ile Cys Leu Pro Arg Trp Gly Cys Leu Trp Glu
1               5                   10                  15

Asp Asp

<210> SEQ ID NO 148
<211> LENGTH: 11
<212> TYPE: PRT
<213> ORGANISM: Artificial Sequence
<220> FEATURE:
<223> OTHER INFORMATION: Synthetic peptide: albumin-binding peptide

<400> SEQUENCE: 148

Asp Ile Cys Leu Pro Arg Trp Gly Cys Leu Trp
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Synthetic peptide: Anti-Muc16 antibody HVR-L1

<400> SEQUENCE: 149

Lys Ala Ser Asp Leu Ile His Asn Trp Leu Ala
1               5                   10

<210> SEQ ID NO 150
<211> LENGTH: 8
<212> TYPE: PRT
<213> ORGANISM: Artificial Sequence
<220> FEATURE:
<223> OTHER INFORMATION: Synthetic peptide: Anti-Muc16 antibody HVR-L2
```

<400> SEQUENCE: 150

Tyr Gly Ala Thr Ser Leu Glu Thr
1               5

<210> SEQ ID NO 151
<211> LENGTH: 9
<212> TYPE: PRT
<213> ORGANISM: Artificial Sequence
<220> FEATURE:
<223> OTHER INFORMATION: Synthetic peptide:  Anti-Muc16 antibody HVR-L3

<400> SEQUENCE: 151

Gln Gln Tyr Trp Thr Thr Pro Phe Thr
1               5

<210> SEQ ID NO 152
<211> LENGTH: 11
<212> TYPE: PRT
<213> ORGANISM: Artificial Sequence
<220> FEATURE:
<223> OTHER INFORMATION: Synthetic peptide:  Anti-Muc16 antibody HVR-H1

<400> SEQUENCE: 152

Gly Tyr Ser Ile Thr Asn Asp Tyr Ala Trp Asn
1               5                   10

<210> SEQ ID NO 153
<211> LENGTH: 17
<212> TYPE: PRT
<213> ORGANISM: Artificial Sequence
<220> FEATURE:
<223> OTHER INFORMATION: Synthetic peptide:  Anti-Muc16 antibody HVR-H2

<400> SEQUENCE: 153

Gly Tyr Ile Ser Tyr Ser Gly Tyr Thr Thr Tyr Asn Pro Ser Leu Lys
1               5                   10                  15

Ser

<210> SEQ ID NO 154
<211> LENGTH: 9
<212> TYPE: PRT
<213> ORGANISM: Artificial Sequence
<220> FEATURE:
<223> OTHER INFORMATION: Synthetic peptide:  Anti-Muc16 antibody HVR-H3

<400> SEQUENCE: 154

Ala Arg Trp Ala Ser Gly Leu Asp Tyr
1               5

<210> SEQ ID NO 155
<211> LENGTH: 108
<212> TYPE: PRT
<213> ORGANISM: Artificial Sequence
<220> FEATURE:
<223> OTHER INFORMATION: Synthetic polypeptide:  Anti-Muc16 antibody
      light chain variable region

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
        35                  40                  45

```
Tyr Gly Ala Thr Ser Leu Glu Thr Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Trp Thr Thr Pro Phe
                85                  90                  95

Thr Phe Gly Gln Gly Thr Lys Val Glu Ile Lys Arg
            100                 105

<210> SEQ ID NO 156
<211> LENGTH: 116
<212> TYPE: PRT
<213> ORGANISM: Artificial Sequence
<220> FEATURE:
<223> OTHER INFORMATION: Synthetic polypeptide:  Anti-Muc16 antibody
      heavy chain variable region

<400> SEQUENCE: 156

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Ser Tyr Ser Gly Tyr Thr Thr Tyr Asn Pro Ser Leu
 50                  55                  60

Lys Ser Arg Phe Thr Ile Ser Arg Asp Thr Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Trp Ala Ser Gly Leu Asp Tyr Trp Gly Gln Gly Thr Leu Val
            100                 105                 110

Thr Val Ser Ser
        115

<210> SEQ ID NO 157
<211> LENGTH: 11
<212> TYPE: PRT
<213> ORGANISM: Artificial Sequence
<220> FEATURE:
<223> OTHER INFORMATION: Synthetic peptide:  Anti-STEAP-1 HVR-H1

<400> SEQUENCE: 157

Gly Tyr Ser Ile Thr Ser Asp Tyr Ala Trp Asn
 1               5                  10

<210> SEQ ID NO 158
<211> LENGTH: 17
<212> TYPE: PRT
<213> ORGANISM: Artificial Sequence
<220> FEATURE:
<223> OTHER INFORMATION: Synthetic peptide:  Anti-STEAP-1 HVR-H2

<400> SEQUENCE: 158

Gly Tyr Ile Ser Asn Ser Gly Ser Thr Ser Tyr Asn Pro Ser Leu Lys
 1               5                  10                  15

Ser

<210> SEQ ID NO 159
<211> LENGTH: 15
```

```
<212> TYPE: PRT
<213> ORGANISM: Artificial Sequence
<220> FEATURE:
<223> OTHER INFORMATION: Synthetic peptide: Anti-STEAP-1 HVR-H3

<400> SEQUENCE: 159

Glu Arg Asn Tyr Asp Tyr Asp Asp Tyr Tyr Ala Met Asp Tyr
1               5                   10                  15

<210> SEQ ID NO 160
<211> LENGTH: 17
<212> TYPE: PRT
<213> ORGANISM: Artificial Sequence
<220> FEATURE:
<223> OTHER INFORMATION: Synthetic peptide: Anti-STEAP-1 HVR-L1

<400> SEQUENCE: 160

Lys Ser Ser Gln Ser Leu Leu Tyr Arg Ser Asn Gln Lys Asn Tyr Leu
1               5                   10                  15

Ala

<210> SEQ ID NO 161
<211> LENGTH: 7
<212> TYPE: PRT
<213> ORGANISM: Artificial Sequence
<220> FEATURE:
<223> OTHER INFORMATION: Synthetic peptide: Anti-STEAP-1 HVR-L2

<400> SEQUENCE: 161

Trp Ala Ser Thr Arg Glu Ser
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic peptide: Anti-STEAP-1 HVR-L3

<400> SEQUENCE: 162

Gln Gln Tyr Tyr Asn Tyr Pro Arg Thr
1               5

<210> SEQ ID NO 163
<211> LENGTH: 124
<212> TYPE: PRT
<213> ORGANISM: Artificial Sequence
<220> FEATURE:
<223> OTHER INFORMATION: Synthetic polypeptide: Anti-STEAP1 heavy chain
      variable region

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Val Gly Tyr Ile Ser Asn Ser Gly Ser Thr Ser Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Glu Arg Asn Tyr Asp Tyr Asp Asp Tyr Tyr Tyr Ala Met Asp
            100                 105                 110

Tyr Trp Gly Gln Gly Thr Leu Val Thr Val Ser Ser
        115                 120
```

<210> SEQ ID NO 164
<211> LENGTH: 113
<212> TYPE: PRT
<213> ORGANISM: Artificial Sequence
<220> FEATURE:
<223> OTHER INFORMATION: Synthetic polypeptide: Anti-STEAP1 light chain variable region

<400> SEQUENCE: 164

```
Asp Ile Gln Met Thr Gln Ser Pro Ser Leu Ser Ala Ser Val Gly
1               5                   10                  15

Asp Arg Val Thr Ile Thr Cys Lys Ser Ser Gln Ser Leu Leu Tyr Arg
            20                  25                  30

Ser Asn Gln Lys Asn Tyr Leu Ala Trp Tyr Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65              70                  75                  80

Ile Ser Ser Leu Gln Pro Glu Asp Phe Ala Thr Tyr Tyr Cys Gln Gln
                85                  90                  95

Tyr Tyr Asn Tyr Pro Arg Thr Phe Gly Gln Gly Thr Lys Val Glu Ile
            100                 105                 110

Lys
```

<210> SEQ ID NO 165
<211> LENGTH: 10
<212> TYPE: PRT
<213> ORGANISM: Artificial Sequence
<220> FEATURE:
<223> OTHER INFORMATION: Synthetic peptide: Anti-NaPi2b HVR-H1

<400> SEQUENCE: 165

```
Gly Phe Ser Phe Ser Asp Phe Ala Met Ser
1               5                   10
```

<210> SEQ ID NO 166

<400> SEQUENCE: 166

000

<210> SEQ ID NO 167
<211> LENGTH: 18
<212> TYPE: PRT
<213> ORGANISM: Artificial Sequence
<220> FEATURE:
<223> OTHER INFORMATION: Synthetic peptide: Anti- NaPi2b HVR-H2

<400> SEQUENCE: 167

```
Ala Thr Ile Gly Arg Val Ala Phe His Thr Tyr Tyr Pro Asp Ser Met
1               5                   10                  15

Lys Gly
```

<210> SEQ ID NO 168
<211> LENGTH: 13

```
<212> TYPE: PRT
<213> ORGANISM: Artificial Sequence
<220> FEATURE:
<223> OTHER INFORMATION: Synthetic peptide:  Anti- NaPi2b HVR-H3

<400> SEQUENCE: 168

Ala Arg His Arg Gly Phe Asp Val Gly His Phe Asp Phe
1               5                   10

<210> SEQ ID NO 169
<211> LENGTH: 16
<212> TYPE: PRT
<213> ORGANISM: Artificial Sequence
<220> FEATURE:
<223> OTHER INFORMATION: Synthetic peptide:  Anti- NaPi2b HVR-L1

<400> SEQUENCE: 169

Arg Ser Ser Glu Thr Leu Val His Ser Ser Gly Asn Thr Tyr Leu Glu
1               5                   10                  15

<210> SEQ ID NO 170
<211> LENGTH: 7
<212> TYPE: PRT
<213> ORGANISM: Artificial Sequence
<220> FEATURE:
<223> OTHER INFORMATION: Synthetic peptide:  Anti- NaPi2b HVR-L2

<400> SEQUENCE: 170

Arg Val Ser Asn Arg Phe Ser
1               5

<210> SEQ ID NO 171
<211> LENGTH: 9
<212> TYPE: PRT
<213> ORGANISM: Artificial Sequence
<220> FEATURE:
<223> OTHER INFORMATION: Synthetic peptide:  Anti- NaPi2b HVR-L3

<400> SEQUENCE: 171

Phe Gln Gly Ser Phe Asn Pro Leu Thr
1               5

<210> SEQ ID NO 172
<211> LENGTH: 120
<212> TYPE: PRT
<213> ORGANISM: Artificial Sequence
<220> FEATURE:
<223> OTHER INFORMATION: Synthetic polypeptide:  Anti- NaPi2b heavy
      chain variable region

<400> SEQUENCE: 172

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
                20                  25                  30

Ala Met Ser Trp Val Arg Gln Ala Pro Gly Lys Gly Leu Glu Trp Val
            35                  40                  45

Ala Thr Ile Gly Arg Val Ala Phe His Thr Tyr Tyr Pro Asp Ser Met
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Phe Asp Val Gly His Phe Asp Phe Trp Gly Gln
```

```
                100             105             110
Gly Thr Leu Val Thr Val Ser Ser
        115                 120

<210> SEQ ID NO 173
<211> LENGTH: 113
<212> TYPE: PRT
<213> ORGANISM: Artificial Sequence
<220> FEATURE:
<223> OTHER INFORMATION: Synthetic polypeptide:  Anti- NaPi2b light
      chain variable region

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Thr Leu Val His Ser
            20                  25                  30

Ser Gly Asn Thr Tyr Leu Glu Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Gly
                85                  90                  95

Ser Phe Asn Pro Leu Thr Phe Gly Gln Gly Thr Lys Val Glu Ile Lys
            100                 105                 110

Arg

<210> SEQ ID NO 174
<211> LENGTH: 107
<212> TYPE: PRT
<213> ORGANISM: Artificial Sequence
<220> FEATURE:
<223> OTHER INFORMATION: Synthetic polypeptide:  anti-Ly6E antibody
      hu9B12 v12 light chain variable region

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys
            100                 105

<210> SEQ ID NO 175
<211> LENGTH: 120
<212> TYPE: PRT
<213> ORGANISM: Artificial Sequence
<220> FEATURE:
<223> OTHER INFORMATION: Synthetic polypeptide:  anti-Ly6E antibody
      hu9B12 v12 heavy chain variable region
```

<400> SEQUENCE: 175

Glu Val Gln Leu Val Glu Ser Gly Pro Ala Leu Val Lys Pro Thr Gln
1               5                   10                  15

Thr Leu Thr Leu Thr Cys Thr Val Ser Gly Phe Ser Leu Thr Gly Tyr
            20                  25                  30

Ser Val Asn Trp Ile Arg Gln Pro Pro Gly Lys Ala Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Arg Asp Tyr Tyr Phe Asn Tyr Ala Ser Trp Phe Ala Tyr Trp Gly Gln
            100                 105                 110

Gly Thr Leu Val Thr Val Ser Ser
        115                 120

<210> SEQ ID NO 176
<211> LENGTH: 11
<212> TYPE: PRT
<213> ORGANISM: Artificial Sequence
<220> FEATURE:
<223> OTHER INFORMATION: Synthetic peptide: anti-Ly6E antibody hu9B12
      v12 HVR-L1

<400> SEQUENCE: 176

Ser Ala Ser Gln Gly Ile Ser Asn Tyr Leu Asn
1               5                   10

<210> SEQ ID NO 177
<211> LENGTH: 7
<212> TYPE: PRT
<213> ORGANISM: Artificial Sequence
<220> FEATURE:
<223> OTHER INFORMATION: Synthetic peptide: anti-Ly6E antibody hu9B12
      v12 HVR-L2

<400> SEQUENCE: 177

Tyr Thr Ser Asn Leu His Ser
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic peptide: anti-Ly6E antibody hu9B12
      v12 HVR-L3

<400> SEQUENCE: 178

Gln Gln Tyr Ser Glu Leu Pro Trp Thr
1               5

<210> SEQ ID NO 179
<211> LENGTH: 10
<212> TYPE: PRT
<213> ORGANISM: Artificial Sequence
<220> FEATURE:
<223> OTHER INFORMATION: Synthetic peptide: anti-Ly6E antibody hu9B12
      v12 HVR-H1

<400> SEQUENCE: 179

```
Gly Phe Ser Leu Thr Gly Tyr Ser Val Asn
1               5                   10
```

<210> SEQ ID NO 180
<211> LENGTH: 16
<212> TYPE: PRT
<213> ORGANISM: Artificial Sequence
<220> FEATURE:
<223> OTHER INFORMATION: Synthetic peptide: anti-Ly6E antibody hu9B12
      v12 HVR-H2

<400> SEQUENCE: 180

```
Met Ile Trp Gly Asp Gly Ser Thr Asp Tyr Asn Ser Ala Leu Lys Ser
1               5                   10                  15
```

<210> SEQ ID NO 181
<211> LENGTH: 12
<212> TYPE: PRT
<213> ORGANISM: Artificial Sequence
<220> FEATURE:
<223> OTHER INFORMATION: Synthetic peptide: anti-Ly6E antibody hu9B12
      v12 HVR-H3

<400> SEQUENCE: 181

```
Asp Tyr Tyr Val Asn Tyr Ala Ser Trp Phe Ala Tyr
1               5                   10
```

<210> SEQ ID NO 182
<211> LENGTH: 214
<212> TYPE: PRT
<213> ORGANISM: Artificial Sequence
<220> FEATURE:
<223> OTHER INFORMATION: Synthetic polypeptide: anti-Ly6E antibody
      hu9B12 v12 K149C kappa light chain

<400> SEQUENCE: 182

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
                20                  25                  30

Leu Asn Trp Tyr Gln Gln Lys Pro Gly Lys Thr Val Lys Leu Leu Ile
            35                  40                  45

Tyr Tyr Thr Ser Asn Leu His Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Cys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
        195                 200                 205

Phe Asn Arg Gly Glu Cys
    210

<210> SEQ ID NO 183
<211> LENGTH: 450
<212> TYPE: PRT
<213> ORGANISM: Artificial Sequence
<220> FEATURE:
<223> OTHER INFORMATION: Synthetic polypeptide: anti-Ly6E antibody
      hu9B12 v12 IgG1 heavy chain

<400> SEQUENCE: 183

Glu Val Gln Leu Val Glu Ser Gly Pro Ala Leu Val Lys Pro Thr Gln
1               5                   10                  15

Thr Leu Thr Leu Thr Cys Thr Val Ser Gly Phe Ser Leu Thr Gly Tyr
            20                  25                  30

Ser Val Asn Trp Ile Arg Gln Pro Pro Gly Lys Ala Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Arg Asp Tyr Tyr Phe Asn Tyr Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

```
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 184
<211> LENGTH: 117
<212> TYPE: PRT
<213> ORGANISM: Artificial Sequence
<220> FEATURE:
<223> OTHER INFORMATION: Synthetic polypeptide:  huMA79bv28 heavy chain
      variable region

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser
        115

<210> SEQ ID NO 185
<211> LENGTH: 112
<212> TYPE: PRT
<213> ORGANISM: Artificial Sequence
<220> FEATURE:
<223> OTHER INFORMATION: Synthetic polypeptide:  huMA79bv28 light chain
      variable region

<400> SEQUENCE: 185

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45
```

Lys Leu Leu Ile Tyr Ala Ala Ser Asn Leu Glu Ser Gly Val Pro Ser
            50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Leu Thr Phe Gly Gln Gly Thr Lys Val Glu Ile Lys Arg
            100                 105                 110

<210> SEQ ID NO 186
<211> LENGTH: 10
<212> TYPE: PRT
<213> ORGANISM: Artificial Sequence
<220> FEATURE:
<223> OTHER INFORMATION: Synthetic peptide: huMA79bv28 HVR H1

<400> SEQUENCE: 186

Gly Tyr Thr Phe Ser Ser Tyr Trp Ile Glu
1               5                   10

<210> SEQ ID NO 187
<211> LENGTH: 18
<212> TYPE: PRT
<213> ORGANISM: Artificial Sequence
<220> FEATURE:
<223> OTHER INFORMATION: Synthetic peptide: huMA79bv28 HVR H2

<400> SEQUENCE: 187

Gly Glu Ile Leu Pro Gly Gly Gly Asp Thr Asn Tyr Asn Glu Ile Phe
1               5                   10                  15

Lys Gly

<210> SEQ ID NO 188
<211> LENGTH: 10
<212> TYPE: PRT
<213> ORGANISM: Artificial Sequence
<220> FEATURE:
<223> OTHER INFORMATION: Synthetic peptide: huMA79bv28 HVR H3

<400> SEQUENCE: 188

Thr Arg Arg Val Pro Ile Arg Leu Asp Tyr
1               5                   10

<210> SEQ ID NO 189
<211> LENGTH: 15
<212> TYPE: PRT
<213> ORGANISM: Artificial Sequence
<220> FEATURE:
<223> OTHER INFORMATION: Synthetic peptide: huMA79bv28 HVR L1

<400> SEQUENCE: 189

Lys Ala Ser Gln Ser Val Asp Tyr Glu Gly Asp Ser Phe Leu Asn
1               5                   10                  15

<210> SEQ ID NO 190
<211> LENGTH: 7
<212> TYPE: PRT
<213> ORGANISM: Artificial Sequence
<220> FEATURE:
<223> OTHER INFORMATION: Synthetic peptide: huMA79bv28 HVR L2

<400> SEQUENCE: 190

Ala Ala Ser Asn Leu Glu Ser
1               5

<210> SEQ ID NO 191
<211> LENGTH: 9
<212> TYPE: PRT
<213> ORGANISM: Artificial Sequence
<220> FEATURE:
<223> OTHER INFORMATION: Synthetic peptide: huMA79bv28 HVR L3

<400> SEQUENCE: 191

Gln Gln Ser Asn Glu Asp Pro Leu Thr
1               5

<210> SEQ ID NO 192
<211> LENGTH: 10
<212> TYPE: PRT
<213> ORGANISM: Artificial Sequence
<220> FEATURE:
<223> OTHER INFORMATION: Synthetic peptide:  Anti-CD22 HVR-H1

<400> SEQUENCE: 192

Gly Tyr Glu Phe Ser Arg Ser Trp Met Asn
1               5                   10

<210> SEQ ID NO 193
<211> LENGTH: 18
<212> TYPE: PRT
<213> ORGANISM: Artificial Sequence
<220> FEATURE:
<223> OTHER INFORMATION: Synthetic peptide:  Anti- CD22 HVR-H2

<400> SEQUENCE: 193

Gly Arg Ile Tyr Pro Gly Asp Gly Asp Thr Asn Tyr Ser Gly Lys Phe
1               5                   10                  15

Lys Gly

<210> SEQ ID NO 194
<211> LENGTH: 11
<212> TYPE: PRT
<213> ORGANISM: Artificial Sequence
<220> FEATURE:
<223> OTHER INFORMATION: Synthetic peptide:  Anti- CD22 HVR-H3

<400> SEQUENCE: 194

Asp Gly Ser Ser Trp Asp Trp Tyr Phe Asp Val
1               5                   10

<210> SEQ ID NO 195
<211> LENGTH: 16
<212> TYPE: PRT
<213> ORGANISM: Artificial Sequence
<220> FEATURE:
<223> OTHER INFORMATION: Synthetic peptide:  Anti- CD22 HVR-L1

<400> SEQUENCE: 195

Arg Ser Ser Gln Ser Ile Val His Ser Val Gly Asn Thr Phe Leu Glu
1               5                   10                  15

<210> SEQ ID NO 196
<211> LENGTH: 7
<212> TYPE: PRT
<213> ORGANISM: Artificial Sequence
<220> FEATURE:
<223> OTHER INFORMATION: Synthetic peptide:  Anti- CD22 HVR-L2

<400> SEQUENCE: 196

Lys Val Ser Asn Arg Phe Ser

```
<210> SEQ ID NO 197
<211> LENGTH: 10
<212> TYPE: PRT
<213> ORGANISM: Artificial Sequence
<220> FEATURE:
<223> OTHER INFORMATION: Synthetic peptide:  Anti- CD22 HVR-L3

<400> SEQUENCE: 197

Gly Tyr Glu Phe Ser Arg Ser Trp Met Asn
1               5                   10

<210> SEQ ID NO 198
<211> LENGTH: 450
<212> TYPE: PRT
<213> ORGANISM: Artificial Sequence
<220> FEATURE:
<223> OTHER INFORMATION: Synthetic polypeptide:  Fig. 2A - cysteine
      mutagenesis in the heavy chain

<400> SEQUENCE: 198

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 199
<211> LENGTH: 214
<212> TYPE: PRT
<213> ORGANISM: Artificial Sequence
<220> FEATURE:
<223> OTHER INFORMATION: Synthetic polypeptide:  Fig. 2B - cysteine
      mutagenesis in the light chain

<400> SEQUENCE: 199

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
                180             185             190
Ala Cys Glu Val Thr His Gln Gly Leu Ser Ser Pro Val Thr Lys Ser
        195                     200                     205

Phe Asn Arg Gly Glu Cys
    210
```

CYSTEINE ENGINEERED ANTIBODIES AND CONJUGATES

REFERENCE TO RELATED APPLICATIONS

This application claims the benefit of priority of provisional U.S. Application No. 62/050,022 filed Sep. 12, 2014, which is herein incorporated by reference in its entirety.

INCORPORATION OF SEQUENCE LISTING

The present application contains a Sequence Listing in electronic format. The Sequence Listing is provided as a file entitled "2015-11-11_01146-0052-00US_ST25.txt" created on Nov. 11, 2015, which is 70,685 bytes in size. The information in the electronic format of the sequence listing is incorporated herein by reference in its entirety.

FIELD OF THE INVENTION

The invention relates generally to antibodies engineered with reactive cysteine residues and more specifically to antibodies with therapeutic or diagnostic applications. The cysteine engineered antibodies may be conjugated with chemotherapeutic drugs, toxins, affinity ligands such as biotin, and detection labels such as fluorophores. The invention also relates to methods of using antibodies and antibody-drug conjugate compounds for in vitro, in situ, and in vivo diagnosis or treatment of mammalian cells, or associated pathological conditions.

BACKGROUND OF THE INVENTION

Antibody drug conjugates (ADC) are attractive targeted chemo-therapeutic molecules as they combine ideal properties of both antibodies and cytotoxic drugs by targeting potent cytotoxic drugs to the antigen-expressing tumor cells, thereby enhancing their antitumor activity. The successful ADC development for a given target antigen depends on optimization of antibody selection, linker stability, cytotoxic drug potency and mode of linker-drug conjugation to the antibody.

Conventional means of attaching, i.e. linking through covalent bonds, a drug moiety to an antibody generally leads to a heterogeneous mixture of molecules where the drug moieties are attached at a number of sites on the antibody. For example, cytotoxic drugs have typically been conjugated to antibodies through the often-numerous lysine residues of an antibody, generating a heterogeneous antibody-drug conjugate mixture. Depending on reaction conditions, the heterogeneous mixture typically contains a distribution of antibodies with from 0 to about 8, or more, attached drug moieties. In addition, within each subgroup of conjugates with a particular integer ratio of drug moieties to antibody, is a potentially heterogeneous mixture where the drug moiety is attached at various sites on the antibody. Analytical and preparative methods are inadequate to separate and characterize the antibody-drug conjugate species molecules within the heterogeneous mixture resulting from a conjugation reaction. Antibodies are large, complex and structurally diverse biomolecules, often with many reactive functional groups. Their reactivities with linker reagents and drug-linker intermediates are dependent on factors such as pH, concentration, salt concentration, and co-solvents. Furthermore, the multistep conjugation process may be nonreproducible due to difficulties in controlling the reaction conditions and characterizing reactants and intermediates.

Cysteine thiols are reactive at neutral pH, unlike most amines which are protonated and less nucleophilic near pH 7. Since free thiol (RSH, sulfhydryl) groups are relatively reactive, proteins with cysteine residues often exist in their oxidized form as disulfide-linked oligomers or have internally bridged disulfide groups. Antibody cysteine thiol groups are generally more reactive, i.e. more nucleophilic, towards electrophilic conjugation reagents than antibody amine or hydroxyl groups. Engineering in cysteine thiol groups by the mutation of various amino acid residues of a protein to cysteine amino acids is potentially problematic, particularly in the case of unpaired (free Cys) residues or those which are relatively accessible for reaction or oxidation. In concentrated solutions of the protein, whether in the periplasm of E. coli, culture supernatants, or partially or completely purified protein, unpaired Cys residues on the surface of the protein can pair and oxidize to form intermolecular disulfides, and hence protein dimers or multimers. Disulfide dimer formation renders the new Cys unreactive for conjugation to a drug, ligand, or other label. Furthermore, if the protein oxidatively forms an intramolecular disulfide bond between the newly engineered Cys and an existing Cys residue, both Cys groups are unavailable for active site participation and interactions. Furthermore, the protein may be rendered inactive or non-specific, by misfolding or loss of tertiary structure (Zhang et al (2002) Anal. Biochem. 311:1-9).

Antibodies with cysteine substitutions (THIOMAB™ antibodies) at sites where the engineered cysteines are available for conjugation but do not perturb immunoglobulin folding and assembly or alter antigen binding and effector functions (Junutula, et al., 2008b Nature Biotech., 26(8): 925-932; Dornan et al (2009) Blood 114(13):2721-2729; U.S. Pat. No. 7,521,541; U.S. Pat. No. 7,723,485; WO2009/052249). These THIOMAB™ antibodies can then be conjugated to cytotoxic drugs through the engineered cysteine thiol groups to obtain THIOMAB™ antibody drug conjugates (TDC) with uniform stoichiometry (e.g., up to 2 drugs per antibody in an antibody that has a single engineered cysteine site). Studies with multiple antibodies against different antigens have shown that TDCs are as efficacious as conventional ADC in xenograft models and are tolerated at higher doses in relevant preclinical models. THIOMAB™ antibodies have been engineered for drug attachment at different locations of the antibody (e.g., specific amino acid positions (i.e., sites) within the light chain-Fab, heavy chain-Fab and heavy chain-Fc). The in vitro & in vivo stability, efficacy and PK properties of THIOMAB™ antibodies provide a unique advantage over conventional ADCs due to their homogeneity and site-specific conjugation to cytotoxic drugs.

SUMMARY

This application includes disclosure of novel, isolated cysteine engineered antibodies comprising a free cysteine amino acid in the heavy chain or light chain (THIOMAB™ antibodies).

An aspect of the invention is a process to prepare the isolated cysteine engineered antibodies (THIOMAB™ antibodies) by mutagenizing a nucleic acid sequence of a parent antibody by replacing one or more amino acid residues by cysteine to encode the cysteine engineered antibody; expressing the cysteine engineered antibody; and isolating the cysteine engineered antibody.

Another aspect of the invention are conjugates of isolated cysteine engineered antibodies (THIOMAB™ antibodies) wherein the antibody is covalently attached to a capture label, a detection label, a drug moiety, or a solid support.

In certain embodiments, the invention is a cysteine engineered antibody comprising a cysteine mutation selected from the cysteine mutations identified in any of Tables 1-4 and preferably in either Table 1 or 2. In specific embodiments, the cysteine mutation is a free cysteine amino acid. In certain embodiments, the cysteine mutation in the heavy chain selected from the cysteine mutations identified in Tables 2 or 3. In certain embodiments, the cysteine mutation in the in the light chain selected from the cysteine mutations identified in Tables 1 or 4. In certain embodiments, the cysteine mutation is selected from the group consisting of HC-I195C, HC-S420C, HC-Y432C, and LC-G64C (according to Kabat numbering). In certain embodiments, the cysteine mutation is selected from the group consisting of HC-Y432C and LC-G64C (according to Kabat numbering). In certain embodiments, the cysteine mutation is a heavy chain mutation and is selected from the group consisting of Y33C, G162C, V184C, I195C, S420C, Y432C, and Q434C (according to Kabat numbering). In certain embodiments, the cysteine mutation is a heavy chain mutation and is selected from the group consisting of R19C, E46C, T57C, Y59C, A60C, M100cC, W103C, G162C, I195C, V258C, S420C, H425C, and N430C (according to Kabat numbering). In certain embodiments, the cysteine mutation is a heavy chain mutation and is selected from the group consisting of Y33C, G162C, V184C, and I195C (according to Kabat numbering). In certain embodiments, the cysteine mutation is a heavy chain mutation and is selected from the group consisting of R19C, E46C, Y59C, A60C, M100cC, W103C, V258C, H425C, and N430C (according to Kabat numbering).

In certain embodiments, the cysteine mutation is a light chain mutation and is selected from the group consisting of Y55C, G64C, T85C, and T180C, and N430C (according to Kabat numbering). In certain embodiments, the cysteine mutation is a light chain mutation and is selected from the group consisting of T31C, S52C, G64C, R66C, A193C, and N430C (according to Kabat numbering). In certain embodiments, the cysteine mutation is a light chain mutation and is selected from the group consisting of G64C, T85C, and T180C, and N430C (according to Kabat numbering). In certain embodiments, the cysteine mutation is a light chain mutation and is selected from the group consisting of S52C, G64C, R66C, and A193C N430C (according to Kabat numbering). In specific embodiments, the cysteine mutation in the light chain is selected from the group of cysteine mutations comprising LC-I106C, LC-R108C, LC-R142C, and LC-K149C according to Kabat numbering (see FIG. 1a; Table 1). In a preferred embodiment, the cysteine mutation in the in the light chain is LC-K149C according to Kabat numbering (see FIG. 1a).

TABLE 1

Exemplary light chain cysteine mutations

| Residue | Sequence (+/-5 Residues) | SEQ ID No. | EU Numbering | Kabat Numbering |
|---|---|---|---|---|
| I | GTKVECKRTVA | 1 | 106 | 106 |
| R | KVEIKCTVAAP | 2 | 108 | 108 |
| R | NNFYPCEAKVQ | 3 | 142 | 142 |
| K | AKVQWCVDNAL | 4 | 149 | 149 |

In preferred embodiments, the cysteine mutation in the heavy chain is selected from the group of cysteine mutations comprising HC-T114C, HC-A140C, HC-L174C, HC-L179C, HC-T187C, HC-T209C, HC-V262C, HC-G371C, HC-Y373C, HC-E382C, HC-S424C, HC-N434C, and HC-Q438C according to EU numbering (see FIG. 1b; Table 2). In a preferred embodiment, the cysteine mutation in the in the heavy chain is HC-A143C according to Kabat numbering (i.e., HC-A140C according to EU numbering) (see FIGS. 1b and 21; Table 2). In a preferred embodiment, the cysteine mutation in the in the heavy chain is HC-A174C according to EU numbering (see FIGS. 1b and 21; Table 2).

TABLE 2

Exemplary heavy chain cysteine mutations

| Residue | Sequence (+/−5 Residues) | SEQ ID No. | EU Numbering | Kabat Numbering |
|---|---|---|---|---|
| T | QGTLVCVSSAS | 5 | 114 | 110 |
| A | TSGGTCALGCL | 6 | 140 | 136 |
| L | TFPAVCQSSGL | 7 | 174 | 170 |
| L | LQSSGCYSLSS | 8 | 179 | 175 |
| T | LSSVVCVPSSS | 9 | 187 | 183 |
| T | HKPSNCKVDKK | 10 | 209 | 205 |
| V | PEVTCCVVDVS | 11 | 262 | 258 |
| G | TCLVKCFYPSD | 12 | 371 | 367 |
| Y | LVKGFCPSDIA | 13 | 373 | 369 |
| E | IAVEWCSNGQP | 14 | 382 | 378 |
| S | QGNVFCCSVMH | 15 | 424 | 420 |
| N | HEALHCHYTQK | 16 | 434 | 430 |
| Q | HNHYTCKSLSL | 17 | 438 | 434 |

In certain embodiments, a cysteine engineered antibody as described herein is prepared by a process comprising:

(i) mutagenizing a nucleic acid sequence of a parent antibody by replacing one or more amino acid residues by cysteine to encode the cysteine engineered antibody;

(ii) expressing the cysteine engineered antibody; and (iii) isolating the cysteine engineered antibody.

In certain embodiments, a cysteine engineered antibody as described herein is a fusion protein comprising the albumin-binding peptide (ABP). In specific embodiments, the ABP comprises a sequence selected from:

a)
(SEQ ID NO: 144)
CDKTHTGGGSQRLMEDICLPRWGCLWEDDF, b)
(SEQ ID NO: 145)
QRLMEDICLPRWGCLWEDDF, c)
(SEQ ID NO: 146)
QRLIEDICLPRWGCLWEDDF, d)
(SEQ ID NO: 147)
RLIEDICLPRWGCLWEDD,
or e)
(SEQ ID NO: 148)
DICLPRWGCLW.

In certain embodiments, a cysteine engineered antibody as described herein is selected from a monoclonal antibody, an antibody fragment, a bispecific antibody, a chimeric antibody, a human antibody, and a humanized antibody. In specific embodiments, the antibody fragment is a Fab fragment.

In certain embodiments, a cysteine engineered antibody as described herein is an anti-HER2 antibody. In certain embodiments, a cysteine engineered antibody as described herein is an anti-MUC16 antibody. In certain embodiments, a cysteine engineered antibody as described herein is an anti-STEAP1 antibody. In certain embodiments, a cysteine engineered antibody as described herein is an anti-CD79b antibody. In certain embodiments, a cysteine engineered antibody as described herein is an anti-CD22 antibody. In certain embodiments, a cysteine engineered antibody as described herein is an anti-B7H4 antibody. In certain embodiments, a cysteine engineered antibody as described herein is an anti-Ly6E antibody. In certain embodiments, a cysteine engineered antibody as described herein is an anti-NaPi2b antibody.

In certain embodiments, a cysteine engineered antibody as described herein binds to one or more of receptors (1)-(53):

(1) BMPR1B (bone morphogenetic protein receptor-type IB);

(2) E16 (LAT1, SLC7A5);

(3) STEAP1 (six transmembrane epithelial antigen of prostate);

(4) 0772P (CA125, MUC16);

(5) MPF (MPF, MSLN, SMR, megakaryocyte potentiating factor, mesothelin);

(6) Napi3b (also known as NaPi2b) (NAPI-3B, NPTIIb, SLC34A2, solute carrier family 34 (sodium phosphate), member 2, type II sodium-dependent phosphate transporter 3b);

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);

(8) PSCA hlg (2700050C12Rik, C530008O16Rik, RIKEN cDNA 2700050C12, RIKEN cDNA 2700050C12 gene);

(9) ETBR (Endothelin type B receptor);

(10) MSG783 (RNF124, hypothetical protein FLJ20315);

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);

(12) TrpM4 (BR22450, FLJ20041, TRPM4, TRPM4B, transient receptor potential cation channel, subfamily M, member 4);

(13) CRIPTO (CR, CR1, CRGF, CRIPTO, TDGF1, teratocarcinoma-derived growth factor);

(14) CD21 (CR2 (Complement receptor 2) or C3DR (C3d/Epstein Barr virus receptor) or Hs.73792);

(15) CD79b (CD79B, CD79β, IGb (immunoglobulin-associated beta), B29);

(16) FcRH2 (IFGP4, IRTA4, SPAP1A (SH2 domain containing phosphatase anchor protein 1a), SPAP1B, SPAP1C);

(17) HER2;

(18) NCA;

(19) MDP;

(20) IL20Rα;

(21) Brevican;

(22) EphB2R;

(23) ASLG659;

(24) PSCA;

(25) GEDA;

(26) BAFF-R (B cell-activating factor receptor, BLyS receptor 3, BR3;

(27) CD22 (B-cell receptor CD22-B isoform);

(28) CD79a (CD79A, CD79α, immunoglobulin-associated alpha, a B cell-specific protein);

(29) CXCR5 (Burkitt's lymphoma receptor 1, a G protein-coupled receptor);

(30) HLA-DOB (Beta subunit of MHC class II molecule (Ia antigen);

(31) P2X5 (Purinergic receptor P2X ligand-gated ion channel 5);

(32) CD72 (B-cell differentiation antigen CD72, Lyb-2);

(33) LY64 (Lymphocyte antigen 64 (RP105), type I membrane protein of the leucine rich repeat (LRR) family);

(34) FcRH1 (Fc receptor-like protein 1);

(35) IRTA2 (Immunoglobulin superfamily receptor translocation associated 2);

(36) TENB2 (putative transmembrane proteoglycan);

(37) PMEL17 (silver homolog; SILV; D12S53E; PMEL17; SI; SIL);

(38) TMEFF1 (transmembrane protein with EGF-like and two follistatin-like domains 1; Tomoregulin-1);

(39) GDNF-Ra1 (GDNF family receptor alpha 1; GFRA1; GDNFR; GDNFRA; RETL1; TRNR1; RET1L; GDNFR-alpha1; GFR-ALPHA-1);

(40) Ly6E (lymphocyte antigen 6 complex, locus E; Ly67, RIG-E, SCA-2, TSA-1)

(41) TMEM46 (shisa homolog 2);

(42) Ly6G6D (lymphocyte antigen 6 complex, locus G6D; Ly6-D, MEGT1);

(43) LGR5 (leucine-rich repeat-containing G protein-coupled receptor 5; GPR49, GPR67);

(44) RET (ret proto-oncogene; MEN2A; HSCR1; MEN2B; MTC1; PTC; CDHF12; Hs.168114; RET51; RET-ELE1);

(45) LY6K (lymphocyte antigen 6 complex, locus K; LY6K; HSJ001348; FLJ35226);

(46) GPR19 (G protein-coupled receptor 19; Mm.4787);

(47) GPR54 (KISS1 receptor; KISS1R; GPR54; HOT7T175; AXOR12);

(48) ASPHD1 (aspartate beta-hydroxylase domain containing 1; LOC253982);

(49) Tyrosinase (TYR; OCAIA; OCA1A; tyrosinase; SHEP3);

(50) TMEM118 (ring finger protein, transmembrane 2; RNFT2; FLJ14627);

(51) GPR172A (G protein-coupled receptor 172A; GPCR41; FLJ11856; D15Ertd747e);

(52) CD33; and

(53) CLL-1 (CLEC12A, MICL, and DCAL2).

In certain embodiments, a cysteine engineered antibody as described herein is covalently attached to a capture label, a detection label, a drug moiety, or a solid support. In specific embodiments the antibody is covalently attached to a biotin capture label. In specific embodiments the antibody is covalently attached to a fluorescent dye detection label. In specific embodiments the fluorescent dye is selected from a fluorescein type, a rhodamine type, dansyl, Lissamine, a cyanine, a phycoerythrin, Texas Red, and an analog thereof. In specific embodiments, the antibody is covalently attached to a radionuclide detection label selected from $^{3}$H, $^{11}$C, $^{14}$C, $^{18}$F, $^{32}$F, $^{35}$S, $^{64}$Cu, $^{68}$Ga, $^{86}$Y, $^{89}$Zr, $^{99}$Tc, $^{111}$In, $^{123}$I, $^{124}$I, $^{125}$I, $^{131}$I, $^{133}$Xe, $^{177}$Lu, $^{211}$At, and $^{213}$Bi. In specific embodiments the antibody is covalently attached to a detection label by a chelating ligand. In specific embodiments the chelating ligand is selected from DOTA, DOTP, DOTMA, DTPA and TETA.

In certain embodiments, a cysteine engineered antibody as described herein is covalently attached to a drug moiety selected from a maytansinoid, an auristatin, a dolastatin, a trichothecene, CC1065, a calicheamicin, enediyne antibiotics, a taxane, and an anthracycline to form an antibody-drug conjugate having Formula I (i.e., Ab-(L-D)$_p$) where Ab is the antibody, L is a linker, D is the drug moiety, and p is 1, 2, 3, or 4. In specific embodiments the antibody-drug conjugate has the structure:

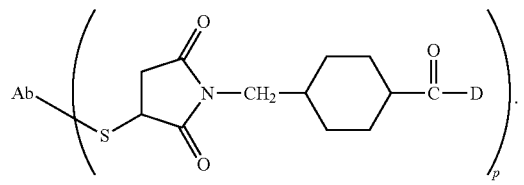

In specific embodiments, the drug (D) of Formula I of that is conjugated to a cysteine engineered antibody as described herein is a maytansinoid having the structure:

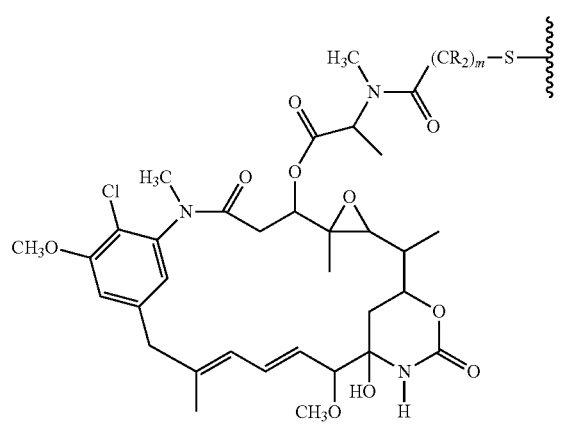

wherein the wavy line indicates the covalent attachment of the sulfur atom of D to the linker; R is independently selected from H, methyl, ethyl, 1-propyl, 2-propyl, 1-butyl, 2-methyl-1-propyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl; and m is 1, 2, or 3.

In specific embodiments, the drug (D) of Formula I of that is conjugated to a cysteine engineered antibody as described herein is selected from the structures:

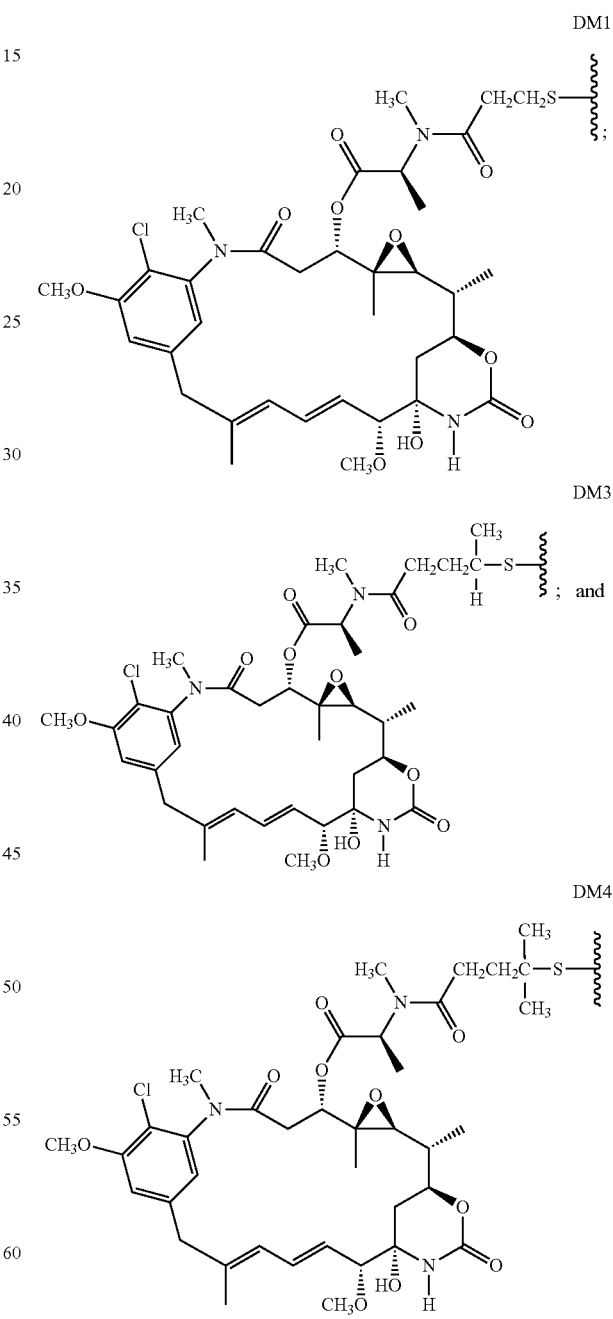

In specific embodiments, the drug (D) of Formula I of that is conjugated to a cysteine engineered antibody as described herein has the following structure:

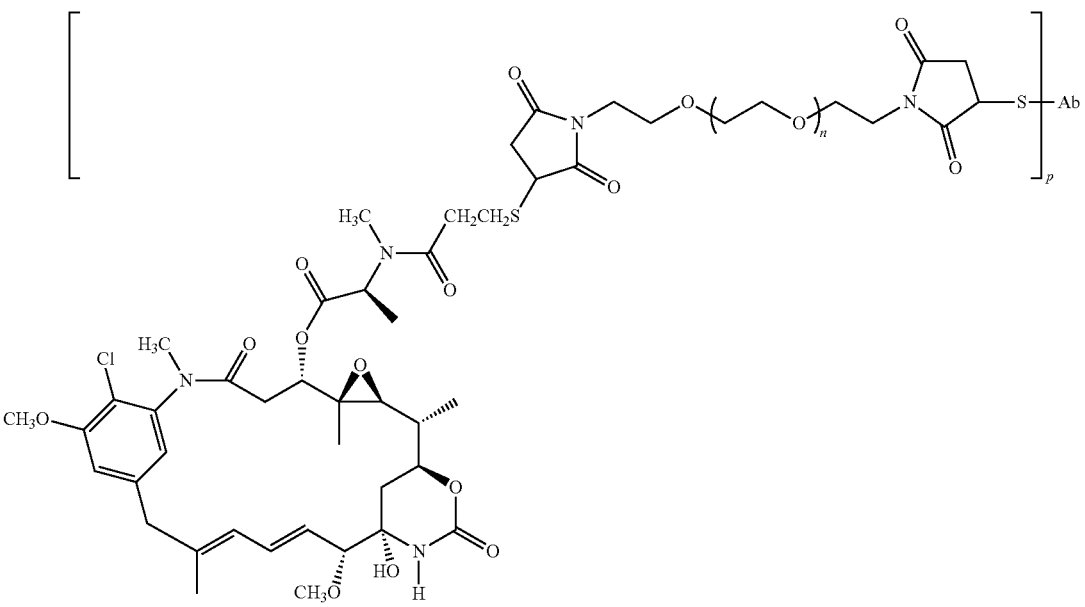

wherein n is 0, 1, or 2.

In specific embodiments, the drug (D) of Formula I of that is conjugated to a cysteine engineered antibody as described herein is a monomethylauristatin drug moiety MMAE or MMAF having the structures:

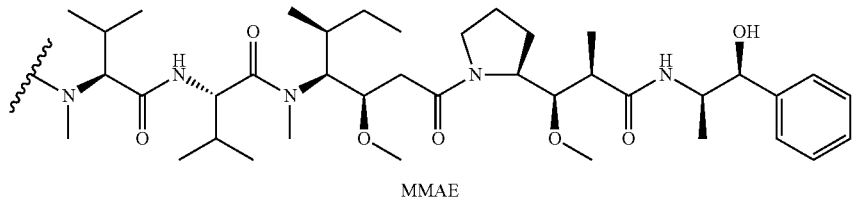

MMAE

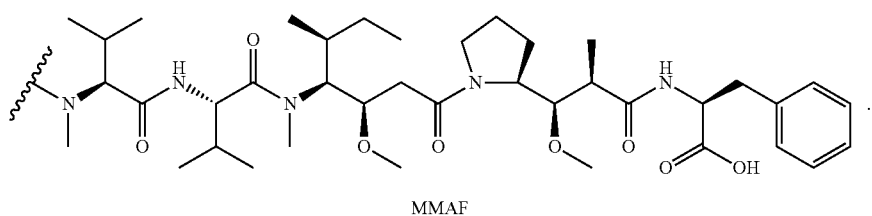

MMAF

In certain embodiments of the invention, a cysteine engineered antibody as described herein has one of the following structures:

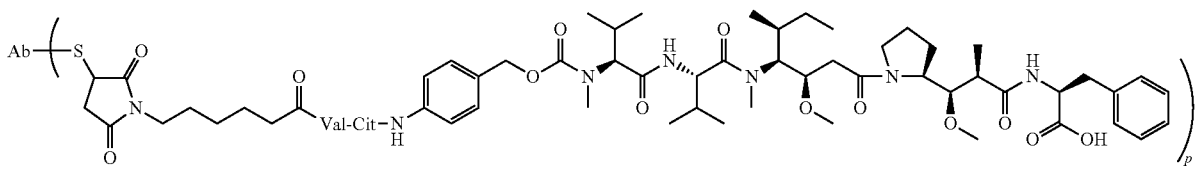

Ab-MC-vc-PAB-MMAF

-continued

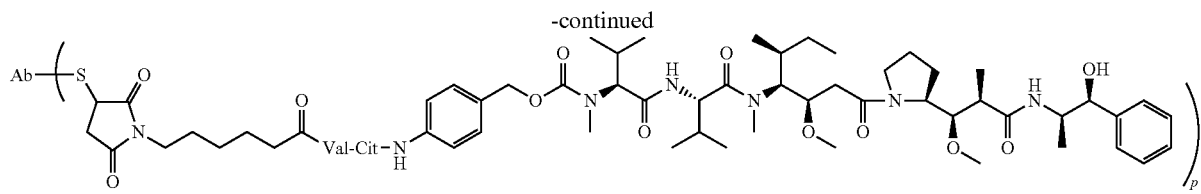

Ab-MC-vc-PAB-MMAE

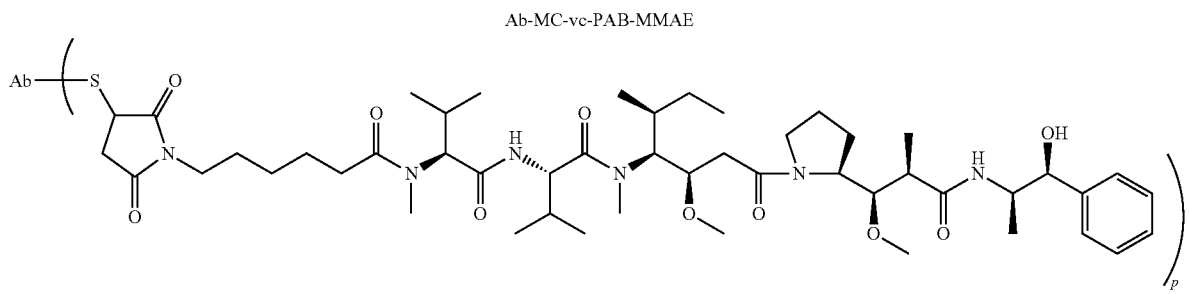

Ab-MC-MMAE

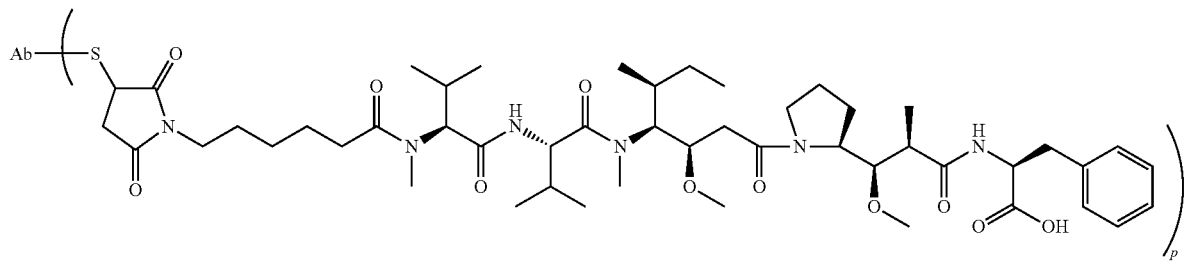

Ab-MC-MMAF where Val is valine; Cit is citrulline; and p is 1, 2, 3, or 4.
In certain embodiments of the invention, a cysteine engineered antibody as described herein has the following structures:

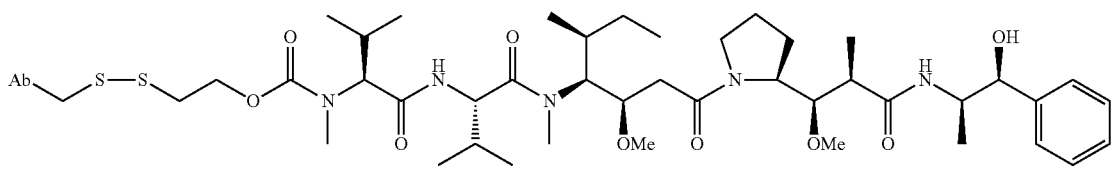

In certain embodiments, a cysteine engineered antibody as described herein is conjugated to a drug that falls into one of the following classes, that is described in further detail in a later section of this specification: auristatins, dolastatins, trichothecenes, CC1065, calicheamicins, enediyne antibiotics, taxanes, pyrrolobenzodiazepines (PBDs), 1-(Chloromethyl)-2,3-dihydro-1H-benzo[e]indole (CBI) dimers, CBI-PBD heterodimers, and anthracyclines.

In certain embodiments, the linker (L) of a cysteine engineered antibody as described herein comprises a thiol-reactive agent. In specific embodiments, the linker (L) is selected from the group consisting of a maleimide, an iodoacetamide, and a pyridyl disulfide. In specific embodiments, the linker (L) is a pyridyl disulfide. In specific embodiments, the linker (L) is a pyridyl disulfide and the drug (D) is MMAE.

In certain embodiments, this invention comprises a method of preparing an antibody-drug conjugate comprising reacting at least one free cysteine of a cysteine engineered antibody (Ab) with a linker-drug (L-D) reagent to form an antibody-drug conjugate having Formula (i.e., Ab-(L-D)$_p$) wherein Ab is the cysteine engineered antibody, L is a linker, D is a drug moiety, and p is 1, 2, 3, or 4; and wherein the cysteine engineered antibody comprises one or more free cysteine amino acids, wherein at least one free cysteine amino acid is selected from the cysteine mutations identified in any of Tables 1 or 2 or alternatively is selected from an alternate stable cysteine mutation identified in Tables 3 or 4.

In certain embodiments, this invention comprises a method of preparing an antibody-drug conjugate comprising reacting at least one free cysteine of a cysteine engineered antibody (Ab) with a linker-drug (L-D) reagent to form an antibody-drug conjugate having Formula (i.e., Ab-(L-D)$_p$) wherein Ab is the cysteine engineered antibody, L is a linker, D is a drug moiety, and p is 1, 2, 3, or 4; and wherein the cysteine engineered antibody comprises one or more free cysteine amino acids, wherein at least one free cysteine amino acid is preferably selected from the cysteine mutations identified in Tables 1 and 2 or alternatively is selected from an alternate stable cysteine mutation identified in Tables 3 or 4.

In specific embodiments, the methods can be used to make a cysteine engineered antibody, wherein the in the cysteine mutation is in the heavy chain and is selected from the cysteine mutations identified in Tables 2 or 3. In specific embodiments, the methods can be used to make a cysteine engineered antibody, wherein the in the cysteine mutation is in the light chain and is selected from the cysteine mutations identified in Tables 1 and 4. In a preferred embodiment, the methods can be used to make a cysteine engineered antibody, wherein the in the cysteine mutation is selected from the cysteine mutations identified in FIG. 21. In other embodiments, the methods can be used to make a cysteine engineered antibody, wherein the in the cysteine mutation is selected from the cysteine mutations identified in Table 5. In certain embodiments, the methods can be used to make a cysteine engineered antibody, wherein the in the cysteine mutation is selected from the group consisting of HC-I195C, HC-S420C, HC-Y432C, and LC-G64C (according to Kabat numbering). In certain embodiments, the methods can be used to make a cysteine engineered antibody, wherein the in the cysteine mutation is selected from the group consisting of HC-Y432C and LC-G64C (according to Kabat numbering). In certain embodiments, the methods can be used to make a cysteine engineered antibody, wherein the in the cysteine mutation is a heavy chain mutation and is selected from the group consisting of Y33C, G162C, V184C, I195C, S420C, Y432C, and Q434C (according to Kabat numbering). In certain embodiments, the methods can be used to make a cysteine engineered antibody, wherein the in the cysteine mutation is a heavy chain mutation and is selected from the group consisting of R19C, E46C, T57C, Y59C, A60C, M100cC, W103C, G162C, I195C, V258C, S420C, H425C, and N430C (according to Kabat numbering). In certain embodiments, the methods can be used to make a cysteine engineered antibody, wherein the in the cysteine mutation is a heavy chain mutation and is selected from the group consisting of Y33C, G162C, V184C, and I195C (according to Kabat numbering). In certain embodiments, the methods can be used to make a cysteine engineered antibody, wherein the in the cysteine mutation is a heavy chain mutation and is selected from the group consisting of R19C, E46C, Y59C, A60C, M100cC, W103C, V258C, H425C, and N430C (according to Kabat numbering). In certain embodiments, the methods can be used to make a cysteine engineered antibody, wherein the in the cysteine mutation is in the light chain and is selected from the group consisting of Y55C, G64C, T85C, and T180C (according to Kabat numbering). In certain embodiments, the methods can be used to make a cysteine engineered antibody, wherein the in the cysteine mutation is in the light chain and is selected from the group consisting of T31C, S52C, G64C, R66C, A193C (according to Kabat numbering). In certain embodiments, the methods can be used to make a cysteine engineered antibody, wherein the in the cysteine mutation is in the light chain and selected from the group consisting of G64C, T85C, and T180C (according to Kabat numbering). In certain embodiments, the methods can be used to make a cysteine engineered antibody, wherein the in the cysteine mutation is in the light chain and is selected from the group consisting of S52C, G64C, R66C, and A193C (according to Kabat numbering).

In preferred embodiments, the methods can be used to make a cysteine engineered antibody, wherein the in the cysteine mutation in the light chain is selected from the group of cysteine mutations comprising LC-I106C, LC-R108C, LC-R142C, and LC-K149C according to Kabat numbering (see FIGS. 1a and 21). In preferred embodiments, the methods can be used to make a cysteine engineered antibody, wherein the in the cysteine mutation in the in the light chain is LC-K149C according to Kabat numbering (see FIGS. 1a and 21 and Table 1).

In preferred embodiments, the methods can be used to make a cysteine engineered antibody, wherein the in the cysteine mutation in the heavy chain is selected from the group of cysteine mutations comprising HC-T114C, HC-A140C, HC-L174C, HC-L179C, HC-T187C, HC-T209C, HC-V262C, HC-G371C, HC-Y373C, HC-E382C, HC-S424C, HC-N434C, and HC-Q438C according to EU numbering (see FIGS. 1b and 21 and Table 2). In preferred embodiments, the methods can be used to make a cysteine engineered antibody, wherein the in the cysteine mutation in the in the heavy chain is HC-A140C according to EU numbering (i.e., HC-A136C according to Kabat numbering) (see FIGS. 1b and 21 and Table 2). In preferred embodiments, the methods can be used to make a cysteine engineered antibody, wherein the in the cysteine mutation in the in the heavy chain is HC-L174C according to EU numbering (see FIGS. 1b and 21 and Table 2).

In certain embodiments, the methods can be used to make a cysteine engineered antibody as described herein, wherein the in the cysteine engineered antibody is prepared by a process comprising:
  mutagenizing a nucleic acid sequence of a parent antibody by replacing one or more amino acid residues by cysteine to encode the cysteine engineered antibody;
  (ii) expressing the cysteine engineered antibody; and
  (iii) isolating the cysteine engineered antibody.

In certain embodiments, the methods can be used to make a cysteine engineered antibody, wherein the cysteine engineered antibody is a fusion protein comprising the albumin-binding peptide (ABP). In specific embodiments, the ABP comprises a sequence selected from:

a)
(SEQ ID NO: 144)
CDKTHTGGGSQRLMEDICLPRWGCLWEDDF, b)
(SEQ ID NO: 145)
QRLMEDICLPRWGCLWEDDF, c)
(SEQ ID NO: 146)
QRLIEDICLPRWGCLWEDDF, d)
(SEQ ID NO: 147)
RLIEDICLPRWGCLWEDD,
or e)
(SEQ ID NO: 148)
DICLPRWGCLW.

In certain embodiments, the methods can be used to make a cysteine engineered antibody, wherein the cysteine engineered antibody is selected from a monoclonal antibody, an antibody fragment, a bispecific antibody, a chimeric antibody, a human antibody, and a humanized antibody. In specific embodiments, the antibody fragment is a Fab fragment.

In certain embodiments, the methods can be used to make a cysteine engineered antibody, wherein the cysteine engineered antibody is an anti-HER2 antibody. In certain embodiments, a cysteine engineered antibody as described herein is an anti-MUC16 antibody. In certain embodiments, a cysteine engineered antibody as described herein is an anti-STEAP1 antibody. In certain embodiments, a cysteine engineered antibody as described herein is an anti-CD79b antibody. In certain embodiments, a cysteine engineered antibody as described herein is an anti-CD22 antibody. In certain embodiments, a cysteine engineered antibody as described herein is an anti-B7H4 antibody. In certain embodiments, a cysteine engineered antibody as described herein is an anti-Ly6E antibody. In certain embodiments, a cysteine engineered antibody as described herein is an anti-NaPi2b antibody.

In certain embodiments, the methods can be used to make a cysteine engineered antibody, wherein the cysteine engineered antibody binds to one or more of receptors (1)-(53):

(1) BMPR1B (bone morphogenetic protein receptor-type IB);
(2) E16 (LAT1, SLC7A5);
(3) STEAP1 (six transmembrane epithelial antigen of prostate);
(4) 0772P (CA125, MUC16);
(5) MPF (MPF, MSLN, SMR, megakaryocyte potentiating factor, mesothelin);
(6) Napi3b (also known as NaPi2b) (NAPI-3B, NPTIIb, SLC34A2, solute carrier family 34 (sodium phosphate), member 2, type II sodium-dependent phosphate transporter 3b);
(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);
(8) PSCA hlg (2700050C12Rik, C530008O16Rik, RIKEN cDNA 2700050C12, RIKEN cDNA 2700050C12 gene);
(9) ETBR (Endothelin type B receptor);
(10) MSG783 (RNF124, hypothetical protein FLJ20315);
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);
(12) TrpM4 (BR22450, FLJ20041, TRPM4, TRPM4B, transient receptor potential cation channel, subfamily M, member 4);
(13) CRIPTO (CR, CR1, CRGF, CRIPTO, TDGF1, teratocarcinoma-derived growth factor);
(14) CD21 (CR2 (Complement receptor 2) or C3DR (C3d/Epstein Barr virus receptor) or Hs.73792);
(15) CD79b (CD79B, CD79β, IGb (immunoglobulin-associated beta), B29);
(16) FcRH2 (IFGP4, IRTA4, SPAP1A (SH2 domain containing phosphatase anchor protein 1a), SPAP1B, SPAP1C);
(17) HER2;
(18) NCA;
(19) MDP;
(20) IL20Rα;
(21) Brevican;
(22) EphB2R;
(23) ASLG659;
(24) PSCA;
(25) GEDA;
(26) BAFF-R (B cell-activating factor receptor, BLyS receptor 3, BR3;
(27) CD22 (B-cell receptor CD22-B isoform);
(28) CD79a (CD79A, CD79α, immunoglobulin-associated alpha, a B cell-specific protein);
(29) CXCR5 (Burkitt's lymphoma receptor 1, a G protein-coupled receptor);
(30) HLA-DOB (Beta subunit of MHC class II molecule (Ia antigen);
(31) P2X5 (Purinergic receptor P2X ligand-gated ion channel 5);
(32) CD72 (B-cell differentiation antigen CD72, Lyb-2);
(33) LY64 (Lymphocyte antigen 64 (RP105), type I membrane protein of the leucine rich repeat (LRR) family);
(34) FcRH1 (Fc receptor-like protein 1);
(35) IRTA2 (Immunoglobulin superfamily receptor translocation associated 2);
(36) TENB2 (putative transmembrane proteoglycan);
(37) PMEL17 (silver homolog; SILV; D12S53E; PMEL17; SI; SIL);
(38) TMEFF1 (transmembrane protein with EGF-like and two follistatin-like domains 1; Tomoregulin-1);
(39) GDNF-Ra1 (GDNF family receptor alpha 1; GFRA1; GDNFR; GDNFRA; RETL1; TRNR1; RET1L; GDNFR-alpha1; GFR-ALPHA-1);
(40) Ly6E (lymphocyte antigen 6 complex, locus E; Ly67, RIG-E, SCA-2, TSA-1)
(41) TMEM46 (shisa homolog 2);
(42) Ly6G6D (lymphocyte antigen 6 complex, locus G6D; Ly6-D, MEGT1);
(43) LGR5 (leucine-rich repeat-containing G protein-coupled receptor 5; GPR49, GPR67);
(44) RET (ret proto-oncogene; MEN2A; HSCR1; MEN2B; MTC1; PTC; CDHF12; Hs.168114; RET51; RET-ELE1);
(45) LY6K (lymphocyte antigen 6 complex, locus K; LY6K; HSJ001348; FLJ35226);
(46) GPR19 (G protein-coupled receptor 19; Mm.4787);
(47) GPR54 (KISS1 receptor; KISS1R; GPR54; HOT7T175; AXOR12);
(48) ASPHD1 (aspartate beta-hydroxylase domain containing 1; LOC253982);
(49) Tyrosinase (TYR; OCAIA; OCA1A; tyrosinase; SHEP3);
(50) TMEM118 (ring finger protein, transmembrane 2; RNFT2; FLJ14627);
(51) GPR172A (G protein-coupled receptor 172A; GPCR41; FLJ11856; D15Ertd747e);
(52) CD33; and
(53) CLL-1 (CLEC12A, MICL, and DCAL2).

In certain embodiments, the methods can be used to make a cysteine engineered antibody, wherein the cysteine engineered antibody is covalently attached to a capture label, a detection label, a drug moiety, or a solid support. In specific embodiments, the antibody is covalently attached to a biotin capture label. In certain embodiments, the antibody is covalently attached to a fluorescent dye detection label. In certain embodiments the fluorescent dye is selected from a fluorescein type, a rhodamine type, dansyl, Lissamine, a cyanine, a phycoerythrin, Texas Red, and an analog thereof. In certain embodiments, the antibody is covalently attached to a radionuclide detection label selected from $^{3}H$, $^{11}C$, $^{14}C$, $^{18}F$, $^{32}P$, $^{35}S$, $^{64}Cu$, $^{68}Ga$, $^{86}Y$, $^{89}Zr$, $^{99}Tc$, $^{111}In$, $^{123}I$, $^{124}I$, $^{125}I$, $^{131}I$, $^{133}Xe$, $^{177}Lu$, $^{211}At$, and $^{213}Bi$. In specific embodiments, the antibody is covalently attached to a detection label by a chelating ligand. In specific embodiments, the chelating ligand is selected from DOTA, DOTP, DOTMA, DTPA and TETA.

In certain embodiments, the methods can be used to make a cysteine engineered antibody, wherein the cysteine engineered antibody is covalently attached to a drug moiety selected from a maytansinoid, an auristatin, a dolastatin, a trichothecene, CC1065, a calicheamicin, enediyne antibiotics, a taxane, and an anthracycline to form an antibody-drug conjugate having Formula I (i.e., Ab-(L-D)$_p$) where Ab is the antibody, L is a linker, D is the drug moiety, and p is 1, 2, 3, or 4.

In specific embodiments, the methods can be used to make a cysteine engineered antibody, wherein the cysteine engineered antibody has the structure:

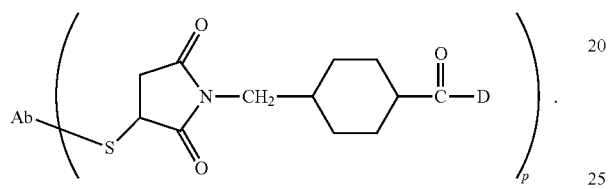

In specific embodiments, the methods can be used to make a cysteine engineered antibody, wherein the drug (D) of the cysteine engineered antibody is a maytansinoid having the structure:

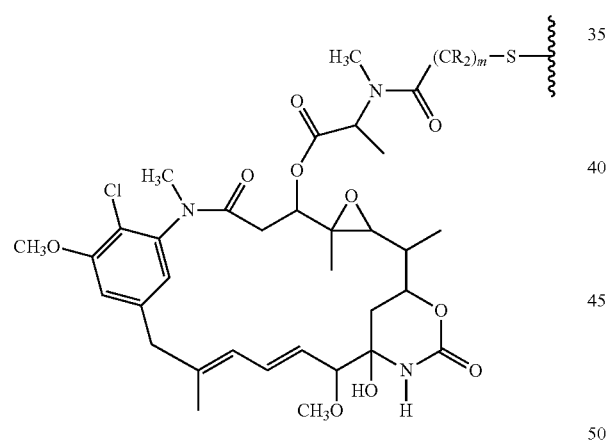

wherein the wavy line indicates the covalent attachment of the sulfur atom of D to the linker; R is independently selected from H, methyl, ethyl, 1-propyl, 2-propyl, 1-butyl, 2-methyl-1-propyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl; and m is 1, 2, or 3.

In specific embodiments, the methods can be used to make a cysteine engineered antibody, wherein the drug (D) is selected from the structures:

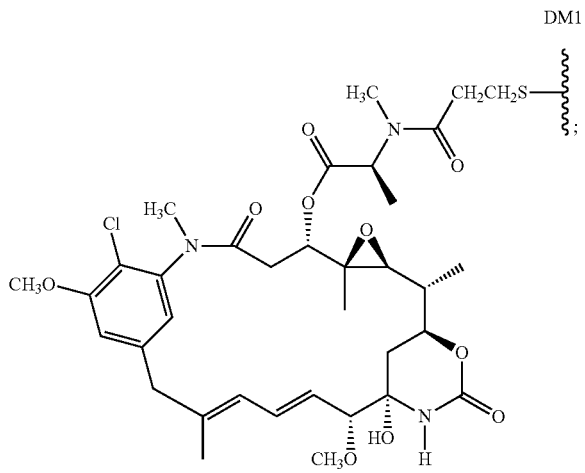

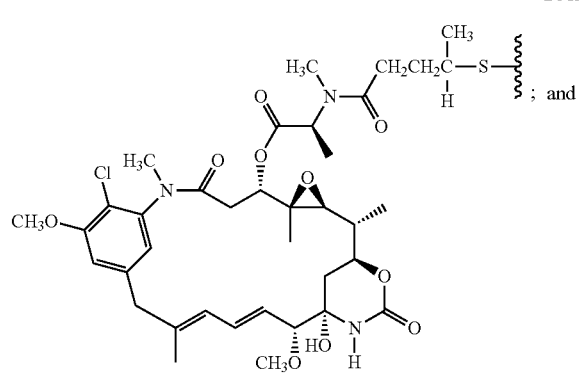

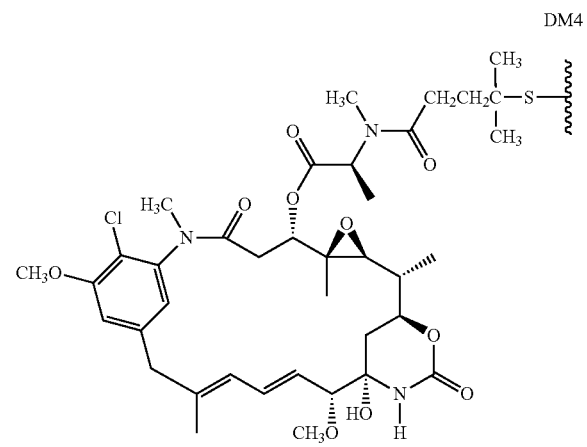

In specific embodiments, the methods can be used to make a cysteine engineered antibody that has the structure:

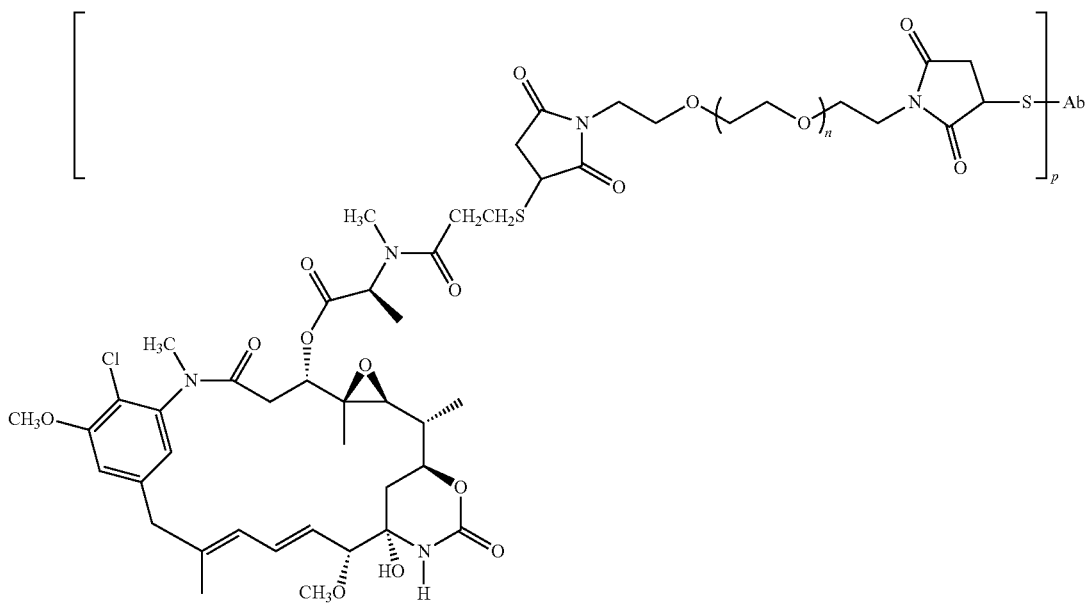
wherein n is 0, 1, or 2
or
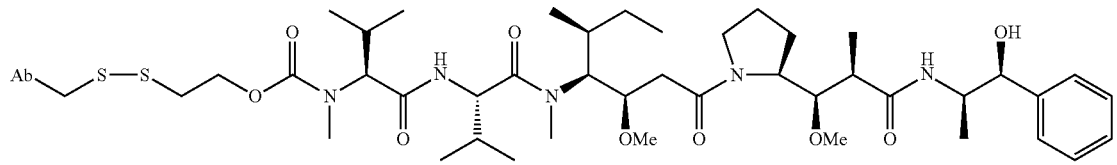
In specific embodiments, the methods can be used to make a cysteine engineered antibody wherein D is a monomethylauristatin drug moiety MMAE or MMAF having the structures:
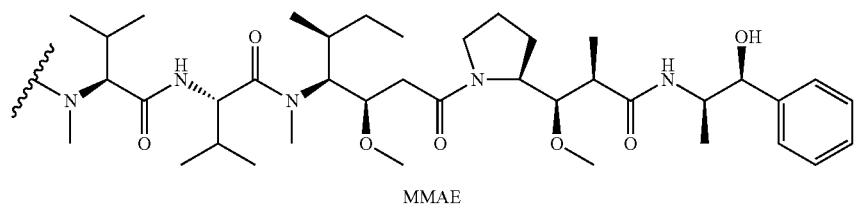
MMAE
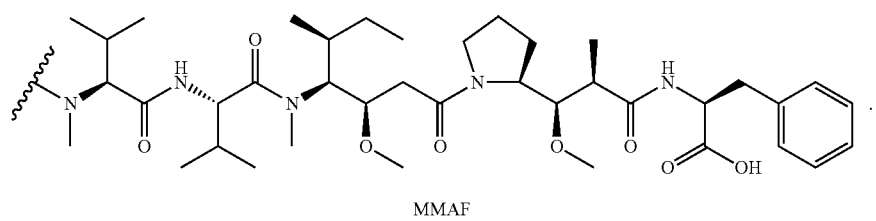
MMAF In specific embodiments, the methods can be used to make a cysteine engineered antibody that is selected from the structures:

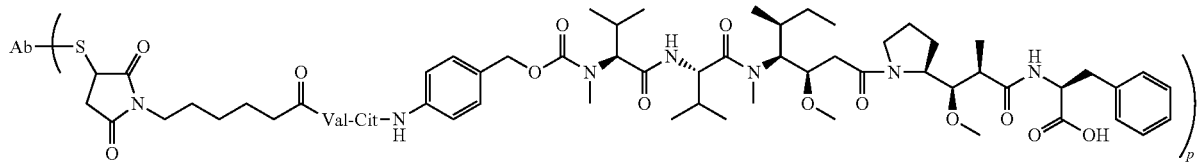

Ab-MC-vc-PAB-MMAF

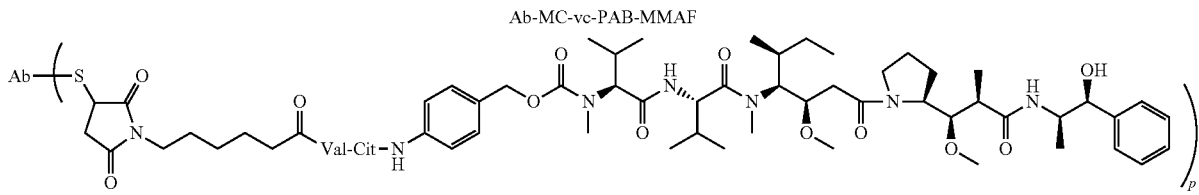

Ab-MC-vc-PAB-MMAE

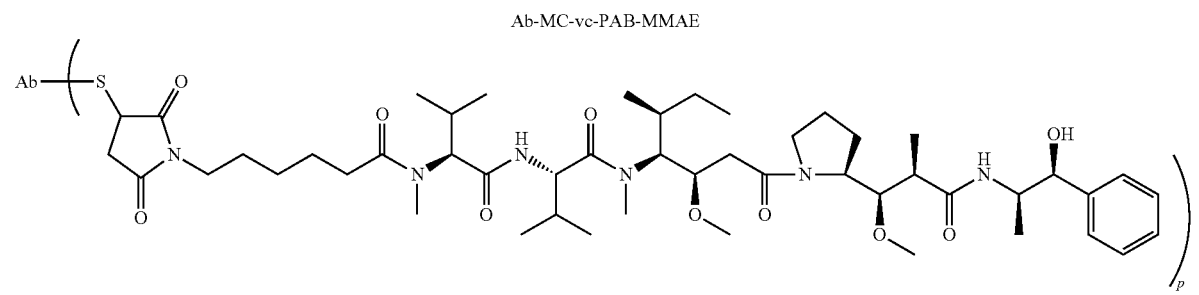

Ab-MC-MMAE

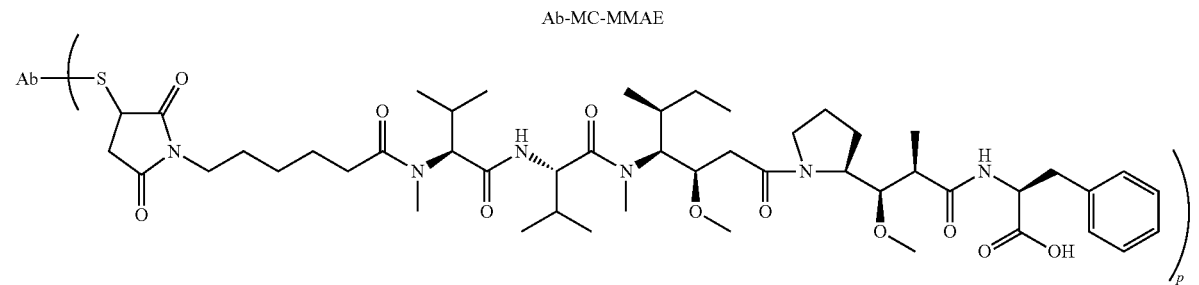

Ab-MC-MMAF where Val is valine; Cit is citrulline; and p is 1, 2, 3, or 4.

In specific embodiments, the methods can be used to make a cysteine engineered antibody that is conjugated to a drug into one of the following classes and that is described in further detail in later sections of this specification: auristatins, dolastatins, trichothecenes, CC1065, calicheamicins, enediyne antibiotics, taxanes, pyrrolobenzodiazepines (PBDs), 1-(Chloromethyl)-2,3-dihydro-1H-benzo[e]indole (CBI) dimers, CBI-PBD heterodimers, and anthracyclines.

In specific embodiments, the methods can be used to make a cysteine engineered antibody wherein the linker (L) comprises a thiol-reactive agent. In specific embodiments the, linker (L) is selected from the group consisting of a maleimide, an iodoacetamide, and a pyridyl disulfide. In specific embodiments, the linker (L) is a pyridyl disulfide. In specific embodiments, the linker (L) is a pyridyl disulfide and the drug (D) is MMAE.

In certain embodiments, the methods can be used to make a cysteine engineered antibody wherein the cysteine engineered antibody is an isolated cysteine engineered antibody. In certain embodiments, the methods can be used to make an isolated cysteine engineered antibody, wherein the in the isolated cysteine mutation in the light chain is selected from the group of cysteine mutations comprising LC-1106C, LC-R108C, LC-R142C, and LC-K149C according to Kabat numbering (see FIG. 1a and FIG. 21). In certain embodiments, the methods can be used to make an isolated cysteine engineered antibody, wherein the in the isolated cysteine mutation in the in the light chain is LC-K149C according to Kabat numbering (see FIGS. 1a and 21 and Table 1). In certain embodiments, the methods can be used to make an isolated cysteine engineered antibody, wherein the in the isolated cysteine mutation in the heavy chain is selected from the group of cysteine mutations comprising HC-T114C, HC-A140C, HC-L174C, HC-L179C, HC-T187C, HC-T209C, HC-V262C, HC-G371C, HC-Y373C, HC-E382C, HC-S424C, HC-N434C, and HC-Q438C according to EU numbering (see FIGS. 1b and 21 and Table 2). In certain embodiments, the methods can be used to make an isolated cysteine engineered antibody, wherein the in the isolated cysteine mutation in the in the heavy chain is HC-A140C according to EU numbering (i.e., HC-A136C according to Kabat numbering) (see FIGS. 1b and 21 and Table 2).

In a preferred embodiment, any cysteine engineered antibody as described herein has one of the following cysteine mutations: LC-K149C according to Kabat numbering and HC-A140C according to EU numbering (see Tables 1 and 2 and FIGS. 1a and 1b).

In certain embodiments of the invention, any cysteine engineered antibody as described herein has a thiol reactivity value of 0.8-1.0. In certain embodiments of the invention, any cysteine engineered antibody as described herein has a thiol reactivity value of 0.9-1.0. In certain embodiments of the invention, any cysteine engineered antibody as described herein has a thiol reactivity value of 0.6-0.9. In certain embodiments of the invention, any cysteine engineered antibody as described herein has a thiol reactivity value of 0.5-0.7. In certain embodiments of the invention, any cysteine engineered antibody as described herein has a thiol reactivity value of 0.4-0.6. In certain embodiments of the invention, any cysteine engineered antibody as described herein has a thiol reactivity value of 0.3-0.5. In certain embodiments of the invention, any cysteine engineered antibody as described herein has a thiol reactivity value of 0.2-0.4.

In certain embodiments, the invention is a pharmaceutical composition comprising any cysteine engineered antibody as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows the Kabat numbering scheme for the 4D5 light chain. FIG. 1B shows a sequential numbering scheme (left row) starting at the N-terminus in comparison with the Kabat numbering scheme (middle row) and EU numbering scheme (right row) for the 4D5 antibody.

FIGS. 2A-B show exemplary sites for cysteine mutagenesis and drug conjugation in an antibody. The bold and underlined residues are exemplary sites for cysteine mutagenesis. The underlined residues are additional exemplary sites for cysteine mutagenesis. FIG. 2A (SEQ ID NO: 198) shows the exemplary and additional exemplary residues for cysteine mutagenesis in the heavy chain. FIG. 2B (SEQ ID NO: 199) shows the exemplary and additional exemplary residues for cysteine mutagenesis in the light chain. The preferred sites for cysteine mutagenesis are shaded in grey and include HC-T114C, HC-A140C, HC-L174C, HC-L179C, HC-T187C, HC-T209C, HC-V262C, HC-G371C, HC-Y373C, HC-E382C, HC-S424C, HC-N434C, and HC-Q438C according to EU numbering (FIG. 2A) and LC-I106C, LC-R108C, LC-R142C, and LC-K149C according to Kabat numbering (FIG. 2B). The preferred HC-A140C according to EU numbering (HC-A136C according to Kabat numbering) and LC-K149C according to Kabat numbering are boxed and highlighted in a large font.

FIG. 4A shows the conjugation peak detected by UV280 LC/MS. FIG. 4B shows DAR0 (naked antibody), DAR1, and DAR2 conjugation peaks.

FIG. 6A shows representative stability graphs of the PDS-MMAE LC-R142C THIOMAB™ antibodies using LC/MS analysis at 0 hr, 48 hrs, and 96 hrs. FIG. 6B shows representative stability graphs of the MC-vc-MMAE LC-R142C THIOMAB™ antibodies using LC/MS analysis at 0 hr, 48 hrs, and 96 hrs.

FIG. 10A shows the structure of thio-Her2-hu7C2-HC-A118C-disulfide-PBD and thio-Her2-hu7C2-LC-K149C-disulfide-PBD THIOMAB™ antibody. FIG. 10B shows the structure for thio-Her2-hu7C2-LC-K149C-CBI dimer. FIG. 10C shows the structure for thio-Her2-hu7C2-LC-K149C-disulfide-CBI-PBD. FIG. 10D shows the structure for thio-Her2-hu7C2-LC-K149C-disulfide-PNU. FIG. 10E shows the structure for thio-Her2-hu7C2-HC-A118C-maleimide-PNU and thio-Her2-hu7C2-LC-K149C-maleimide-PNU.

FIG. 15 shows the acetyl loss was drastically reduced at HC-A140C compared to LC-K149C using multiple rounds of WB assays. It was confirmed that HC-A140C rescues acetyl loss modification

FIG. 17 shows that HC-A140C was more stable than LC-K149C using the novel whole blood assay described herein.

FIG. 18A shows that HC-A140C provides protection from modification of taxoids. Specifically, it was shown using LCMS that there is less degradation of the drug using HC-A140C as the site of attachment than LC-K149C after 24 hrs of incubation. FIGS. 18B and 18C show that HC-A140C was more stable than LC-K149C after 24 hrs of incubation using a novel whole blood assay.

FIG. 19 shows that HC-A140C was more stable (e.g., in terms of protecting taxoid drug loss) than LC-K149C using the novel whole blood assay.

DETAILED DESCRIPTION OF EXEMPLARY EMBODIMENTS

Figure 3:
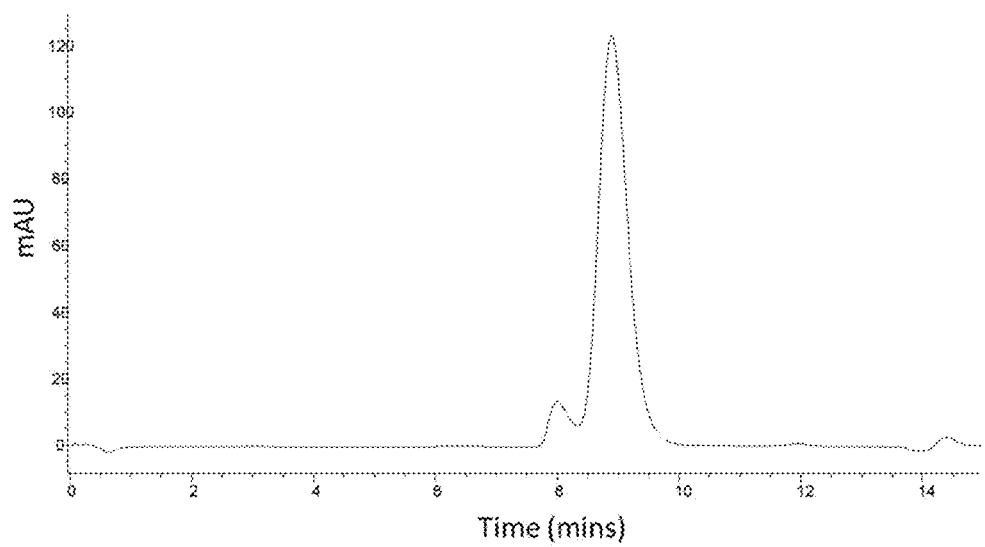
FIG. 3 shows a representative plot of aggregate and monomer peaks used for the aggregation analysis and calculations. The large peak between 8 and 10 minutes is the monomer peak and the small peak at 8 minutes is the aggregate peak.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

Unless defined otherwise, technical and scientific terms used herein have the same meaning as commonly understood by one of ordinary skill in the art to which this invention belongs, and are consistent with: Singleton et al (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

Definitions

Unless stated otherwise, the following terms and phrases as used herein are intended to have the following meanings:

When trade names are used herein, applicants intend to independently include the trade name product formulation, the generic drug, and the active pharmaceutical ingredient(s) of the trade name product.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; minibodies (Olafsen et al (2004) Protein Eng. Design & Sel. 17(4):315-323), fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

In certain embodiments, an antibody provided herein is a multispecific antibody, e.g. a bispecific antibody. The term "multispecific antibody" as used herein refers to an antibody comprising an antigen-binding domain that has polyepitopic specificity (i.e., is capable of binding to two, or more, different epitopes on one molecule or is capable of binding to epitopes on two, or more, different molecules).

In some embodiments, multispecific antibodies are monoclonal antibodies that have binding specificities for at least two different antigen binding sites (such as a bispecific antibody). In some embodiments, the first antigen-binding domain and the second antigen-binding domain of the multispecific antibody may bind the two epitopes within one and the same molecule (intramolecular binding). For example, the first antigen-binding domain and the second antigen-binding domain of the multispecific antibody may bind to two different epitopes on the same molecule. In certain embodiments, the two different epitopes that a multispecific antibody binds are epitopes that are not normally bound at the same time by one monospecific antibody, such as e.g. a conventional antibody or one immunoglobulin single variable domain. In some embodiments, the first antigen-binding domain and the second antigen-binding domain of the multispecific antibody may bind epitopes located within two distinct molecules (intermolecular binding). For example, the first antigen-binding domain of the multispecific antibody may bind to one epitope on one molecule, whereas the second antigen-binding domain of the multispecific antibody may bind to another epitope on a different molecule, thereby cross-linking the two molecules.

In some embodiments, the antigen-binding domain of a multispecific antibody (such as a bispecific antibody) comprises two VH/VL units, wherein a first VH/VL unit binds to a first epitope and a second VH/VL unit binds to a second epitope, wherein each VH/VL unit comprises a heavy chain variable domain (VH) and a light chain variable domain (VL). Such multispecific antibodies include, but are not limited to, full length antibodies, antibodies having two or more VL and VH domains, and antibody fragments (such as Fab, Fv, dsFv, scFv, diabodies, bispecific diabodies and triabodies, antibody fragments that have been linked covalently or non-covalently). A VH/VL unit that further comprises at least a portion of a heavy chain variable region and/or at least a portion of a light chain variable region may also be referred to as an "arm" or "hemimer" or "half antibody." In some embodiments, a hemimer comprises a sufficient portion of a heavy chain variable region to allow intramolecular disulfide bonds to be formed with a second hemimer. In some embodiments, a hemimer comprises a knob mutation or a hole mutation, for example, to allow heterodimerization with a second hemimer or half antibody that comprises a complementary hole mutation or knob mutation. Knob mutations and hole mutations are discussed further below.

In certain embodiments, a multispecific antibody provided herein may be a bispecific antibody. The term "bispecific antibody" as used herein refers to a multispecific antibody comprising an antigen-binding domain that is capable of binding to two different epitopes on one molecule or is capable of binding to epitopes on two different molecules. A bispecific antibody may also be referred to herein as having "dual specificity" or as being "dual specific." Exemplary bispecific antibodies may bind both the molecule and any other antigen. In certain embodiments, one of the binding specificities is for the molecule and the other is for CD3. See, e.g., U.S. Pat. No. 5,821,337. In certain embodiments, bispecific antibodies may bind to two different epitopes of the same molecule. In certain embodiments, bispecific antibodies may bind to two different epitopes on two different molecules. Bispecific antibodies may also be used to localize cytotoxic agents to cells which express the molecule of interest. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983), WO 93/08829, and Traunecker et al., *EMBO J.* 10: 3655 (1991)), and "knob-in-hole" engineering (see, e.g., U.S. Pat. No. 5,731,168, WO2009/089004, US2009/0182127, US2011/0287009, Marvin and Zhu, Acta Pharmacol. Sin. (2005) 26(6):649-658, and Kontermann (2005) Acta Pharmacol. Sin., 26:1-9). The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (see, e.g., US 2011/0287009, US2007/0178552, WO 96/027011, WO 98/050431, Zhu et al., 1997, *Protein Science* 6:781-788, and WO2012/106587). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation.

The term "hole mutation" as used herein refers to a mutation that introduces a cavity (hole) into a polypeptide at an interface in which the polypeptide interacts with another polypeptide. In some embodiments, the other polypeptide has a knob mutation. A brief nonlimiting discussion is provided below.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g., by altering nucleic acid encoding the interface). In some embodiments, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US2011/0287009. A mutation to introduce a "protuberance" may be referred to as a "knob mutation."

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T) and valine (V). In some embodiments, an import residue is serine, alanine or threonine. In some embodiments, the original residue for the formation of the cavity has a large side chain volume, such as tyrosine, arginine, phenylalanine or tryptophan. A mutation to introduce a "cavity" may be referred to as a "hole mutation."

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely accepted techniques in the art.

In some embodiments, a knob mutation in an IgG1 constant region is T366W (EU numbering). In some embodiments, a hole mutation in an IgG1 constant region comprises one or more mutations selected from T366S, L368A and Y407V (EU numbering). In some embodiments, a hole mutation in an IgG1 constant region comprises T366S, L368A and Y407V (EU numbering).

In some embodiments, a knob mutation in an IgG4 constant region is T366W (EU numbering). In some embodiments, a hole mutation in an IgG4 constant region comprises one or more mutations selected from T366S, L368A, and Y407V (EU numbering). In some embodiments, a hole mutation in an IgG4 constant region comprises T366S, L368A, and Y407V (EU numbering).

Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies" or "dual-variable domain immunoglobulins" (DVDs) are also included herein (see, e.g., US 2006/0025576A1, and Wu et al. *Nature Biotechnology* (2007)).). The antibody or fragment herein also includes a "Dual Acting FAb" or "DAF" comprising an antigen binding site that binds to the molecule as well as another, different antigen (see, US 2008/0069820, for example).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see for example: U.S. Pat. No. 4,816,567; U.S. Pat. No. 5,807,715). The monoclonal antibodies may also be isolated from phage antibody libraries using the techniques described in Clackson et al (1991) Nature, 352: 624-628; Marks et al (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape etc) and human constant region sequences.

An "intact antibody" herein is one comprising a VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l Immunol.* 18(12):1759-1769 (2006)).

In some embodiments, one or more amino acid modifications may be introduced into the Fc portion of the antibody provided herein in order to increase IgG binding to the neonatal Fc receptor. In certain embodiments, the antibody comprises the following three mutations according to EU numbering: M252Y, S254T, and T256E (the "YTE mutation") (U.S. Pat. No. 8,697,650; see also Dall'Acqua et al., Journal of Biological Chemistry 281(33):23514-23524 (2006). In certain embodiments, the YTE mutation does not affect the ability of the antibody to bind to its cognate antigen. In certain embodiments, the YTE mutation increases the antibody's serum half-life compared to the native (i.e., non-YTE mutant) antibody. In some embodiments, the YTE mutation increases the serum half-life of the antibody by 3-fold compared to the native (i.e., non-YTE mutant) antibody. In some embodiments, the YTE mutation increases the serum half-life of the antibody by 2-fold compared to the native (i.e., non-YTE mutant) antibody. In some embodiments, the YTE mutation increases the serum half-life of the antibody by 4-fold compared to the native (i.e., non-YTE mutant) antibody. In some embodiments, the YTE mutation increases the serum half-life of the antibody by at least 5-fold compared to the native (i.e., non-YTE mutant) antibody. In some embodiments, the YTE mutation increases the serum half-life of the antibody by at least 10-fold compared to the native (i.e., non-YTE mutant) antibody. See, e.g., U.S. Pat. No. 8,697,650; see also Dall'Acqua et al., Journal of Biological Chemistry 281(33): 23514-23524 (2006).

In certain embodiments, the YTE mutant provides a means to modulate antibody-dependent cell-mediated cytotoxicity (ADCC) activity of the antibody. In certain embodiments, the YTEO mutant provides a means to modulate ADCC activity of a humanized IgG antibody directed against a human antigen. See, e.g., U.S. Pat. No. 8,697,650; see also Dall'Acqua et al., Journal of Biological Chemistry 281(33):23514-23524 (2006).

In certain embodiments, the YTE mutant allows the simultaneous modulation of serum half-life, tissue distribution, and antibody activity (e.g., the ADCC activity of an IgG antibody). See, e.g., U.S. Pat. No. 8,697,650; see also Dall'Acqua et al., Journal of Biological Chemistry 281(33): 23514-23524 (2006).

Antibodies with reduced effector function include those with substitution of one or more of Fc region residues 238, 265, 269, 270, 297, 327 and 329 according to EU numbering (U.S. Pat. No. 6,737,056). Such Fc mutants include Fc mutants with substitutions at two or more of amino acid positions 265, 269, 270, 297 and 327 according to EU numbering, including the so-called "DANA" Fc mutant with substitution of residues 265 and 297 to alanine according to EU numbering (i.e., D265A and N297A according to EU numbering) (U.S. Pat. No. 7,332,581). In certain embodiments the Fc mutant comprises the following two amino acid substitutions: D265A and N297A. In certain embodiments the Fc mutant consists of the following two amino acid substitutions: D265A and N297A.

In certain embodiments, the proline at position329 (EU numbering) (P329) of a wild-type human Fc region is substituted with glycine or arginine or an amino acid residue large enough to destroy the proline sandwich within the Fc/Fcγ receptor interface, that is formed between the P329 of the Fc and tryptophan residues W87 and W110 of FcgRIII (Sondermann et al.: Nature 406, 267-273 (20 Jul. 2000)). In a further embodiment, at least one further amino acid substitution in the Fc variant is S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region, all according to EU numbering (U.S. Pat. No. 8,969,526 which is incorporated by reference in its entirety).

In certain embodiments, a polypeptide comprises the Fc variant of a wild-type human IgG Fc region wherein the polypeptide has P329 of the human IgG Fc region substituted with glycine and wherein the Fc variant comprises at least two further amino acid substitutions at L234A and L235A of the human IgG1 Fc region or S228P and L235E of the human IgG4 Fc region, and wherein the residues are numbered according to the EU numbering (U.S. Pat. No. 8,969,526 which is incorporated by reference in its entirety). In certain embodiments, the polypeptide comprising the P329G, L234A and L235A (EU numbering) substitutions exhibit a reduced affinity to the human FcγRIIIA and FcγRIIA, for down-modulation of ADCC to at least 20% of the ADCC induced by the polypeptide comprising the wild type human IgG Fc region, and/or for down-modulation of ADCP (U.S. Pat. No. 8,969,526 which is incorporated by reference in its entirety).

In a specific embodiment the polypeptide comprising an Fc variant of a wild type human Fc polypeptide comprises a triple mutation: an amino acid substitution at position Pro329, a L234A and a L235A mutation according to EU numbering (P329/LALA) (U.S. Pat. No. 8,969,526 which is incorporated by reference in its entirety). In specific embodiments, the polypeptide comprises the following amino acid substitutions: P329G, L234A, and L235A according to EU numbering.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826) according to EU numbering. See also Duncan & Winter, *Nature* 322:738-40 (1988); U.S. Pat. No. 5,648,260; U.S. Pat. No. 5,624,821; and WO 94/29351 concerning other examples of Fc region variants.

Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and µ, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) Eur. J. Biochem. 267: 7246-7256; US 2005/0048572; US 2004/0229310).

A "cysteine engineered antibody" or "cysteine engineered antibody variant" is an antibody in which one or more residues of an antibody are substituted with cysteine residues. The thiol group(s) of the cysteine engineered antibodies can be conjugated to a drug moiety (e.g., via a linker) to form a THIOMAB™ antibody (i.e., a THIOMAB™ antibody drug conjugate (TDC)). In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. For example, a THIOMAB™ antibody may be an antibody with a single mutation of a non-cysteine native residue to a cysteine in the light chain (e.g., G64C, I106C, R108C, K149C or R142C according to Kabat numbering) or in the heavy chain (e.g., HC-D101C, HC-V184C, or HC-T205C according to Kabat numbering, or HC-T114C, HC-A140C, HC-L174C, HC-L179C, HC-T187C, HC-T209C, HC-V262C, HC-G371C, HC-Y373C, HC-E382C, HC-S424C, HC-N434C, and HC-Q438C according to EU numbering (i.e., HC-A136C according to Kabat numbering is HC-A140C according to EU numbering) (see FIG. 1*b*)). In specific examples, a THIOMAB™ antibody has a single cysteine mutation in either the heavy or light chain such that each full-length antibody (i.e., an antibody with two heavy chains and two light chains) has two engineered cysteine residues.

An "ErbB receptor" is a receptor protein tyrosine kinase which belongs to the ErbB receptor family whose members are important mediators of cell growth, differentiation and survival. The ErbB receptor family includes four distinct members including epidermal growth factor receptor (EGFR, ErbB1, HER1), HER2 (ErbB2 or p185neu), HER3 (ErbB3) and HER4 (ErbB4 or tyro2). A panel of anti-ErbB2 antibodies has been characterized using the human breast tumor cell line SKBR3 (Hudziak et al (1989) Mol. Cell. Biol. 9(3):1165-1172. Maximum inhibition was obtained with the antibody called 4D5 which inhibited cellular proliferation by 56%. Other antibodies in the panel reduced cellular proliferation to a lesser extent in this assay. The antibody 4D5 was further found to sensitize ErbB2-overexpressing breast tumor cell lines to the cytotoxic effects of TNF-α (U.S. Pat. No. 5,677,171). The anti-ErbB2 antibodies discussed in Hudziak et al. are further characterized in Fendly et al (1990) Cancer Research 50:1550-1558; Kotts et al. (1990) In Vitro 26(3):59A; Sarup et al. (1991) Growth Regulation 1:72-82; Shepard et al. J. (1991) Clin. Immunol. 11(3):117-127; Kumar et al. (1991) Mol. Cell. Biol. 11(2): 979-986; Lewis et al. (1993) Cancer Immunol. Immunother. 37:255-263; Pietras et al. (1994) Oncogene 9:1829-1838; Vitetta et al. (1994) Cancer Research 54:5301-5309; Sliwkowski et al. (1994) J. Biol. Chem. 269(20):14661-14665; Scott et al. (1991) J. Biol. Chem. 266:14300-5; D'souza et al. Proc. Natl. Acad. Sci. (1994) 91:7202-7206; Lewis et al. (1996) Cancer Research 56:1457-1465; and Schaefer et al. (1997) Oncogene 15:1385-1394. The ErbB receptor will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a "native sequence" ErbB receptor or an "amino acid sequence variant" thereof. Preferably, the ErbB receptor is native sequence human ErbB receptor. Accordingly, a "member of the ErbB receptor family" includes EGFR (ErbB1), ErbB2, ErbB3, ErbB4.

The term "amino acid sequence variant" refers to polypeptides having amino acid sequences that differ to some extent from a native sequence polypeptide. The amino acid sequence variants possess substitutions, deletions, and/or insertions at certain positions within the amino acid sequence of the native amino acid sequence. Amino acids are designated by the conventional names, one-letter and three-letter codes.

For example, in certain embodiments an amino acid sequence variant will possess at least about 70% sequence identity with at least one receptor binding domain of a native ErbB ligand or with at least one ligand binding domain of a native ErbB receptor, and preferably, it will be at least about 80%, more preferably, at least about 90% homologous by sequence with such receptor or ligand binding domains.

"Sequence identity" is defined as the percentage of residues in the amino acid sequence variant that are identical after aligning the sequences and introducing gaps, if necessary, to achieve the maximum percent sequence identity. Methods and computer programs for the alignment are well known in the art. One such computer program is "Align 2," authored by Genentech, Inc., which was filed with user documentation in the United States Copyright Office, Washington, D.C. 20559, on Dec. 10, 1991.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, Md.). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (H3) in the heavy chain variable domain; Kabat et al supra) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk (1987) J. Mol. Biol., 196:901-917). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the VH and VL domains which enables the scFv to form the desired structure for antigen binding. For a review of scFv, see Plückthun in The Pharmacology of Monoclonal Antibodies, vol. 113, Rosenburg and Moore eds., Springer-Verlag, New York, pp. 269-315 (1994). Anti-ErbB2 antibody scFv fragments are described in WO 93/16185; U.S. Pat. No. 5,571,894; and U.S. Pat. No. 5,587,458.

"Humanized" forms of non-human (e.g., rodent) antibodies are chimeric antibodies that contain minimal sequence derived from non-human immunoglobulin. Humanization is a method to transfer the murine antigen binding information to a non-immunogenic human antibody acceptor, and has resulted in many therapeutically useful drugs. The method of humanization generally begins by transferring all six murine complementarity determining regions (CDRs) onto a human antibody framework (Jones et al, (1986) Nature 321:522-525). These CDR-grafted antibodies generally do not retain their original affinity for antigen binding, and in fact, affinity is often severely impaired. Besides the CDRs, select non-human antibody framework residues must also be incorporated to maintain proper CDR conformation (Chothia et al (1989) Nature 342:877). The transfer of key mouse framework residues to the human acceptor in order to support the structural conformation of the grafted CDRs has been shown to restore antigen binding and affinity (Riechmann et al (1992) J. Mol. Biol. 224, 487-499; Foote and Winter, (1992) J. Mol. Biol. 224:487-499; Presta et al (1993) J. Immunol. 151, 2623-2632; Werther et al (1996) J. Immunol. Methods 157:4986-4995; and Presta et al (2001) Thromb. Haemost. 85:379-389). For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see U.S. Pat. No. 6,407,213; Jones et al (1986) Nature, 321:522-525; Riechmann et al (1988) Nature 332:323-329; and Presta, (1992) Curr. Op. Struct. Biol., 2:593-596.

A "free cysteine amino acid" refers to a cysteine amino acid residue which has been engineered into a parent antibody, has a thiol functional group (—SH), and is not paired as an intramolecular or intermolecular disulfide bridge.

The term "thiol reactivity value" is a quantitative characterization of the reactivity of free cysteine amino acids. The thiol reactivity value is the percentage of a free cysteine amino acid in a cysteine engineered antibody which reacts with a thiol-reactive reagent, and converted to a maximum value of 1. For example, a free cysteine amino acid on a cysteine engineered antibody which reacts in 100% yield with a thiol-reactive reagent, such as a biotin-maleimide reagent, to form a biotin-labelled antibody has a thiol reactivity value of 1.0. Another cysteine amino acid engineered into the same or different parent antibody which reacts in 90% yield with a thiol-reactive reagent has a thiol reactivity value of about 0.9. Another cysteine amino acid engineered into the same or different parent antibody which reacts in 80% yield with a thiol-reactive reagent has a thiol reactivity value of about 0.8. Another cysteine amino acid engineered into the same or different parent antibody which reacts in 70% yield with a thiol-reactive reagent has a thiol reactivity value of about 0.7. Another cysteine amino acid engineered into the same or different parent antibody which reacts in 60% yield with a thiol-reactive reagent has a thiol reactivity value of about 0.6. Another cysteine amino acid engineered into the same or different parent antibody which reacts in 50% yield with a thiol-reactive reagent has a thiol reactivity value of about 0.5. Another cysteine amino acid engineered into the same or different parent antibody which reacts in 40% yield with a thiol-reactive reagent has a thiol reactivity value of about 0.4. Another cysteine amino acid engineered into the same or different parent antibody which reacts in 30% yield with a thiol-reactive reagent has a thiol reactivity value of about 0.3. Another cysteine amino acid engineered into the same or different parent antibody which reacts in 20% yield with a thiol-reactive reagent has a thiol reactivity value of about 0.2. Another cysteine amino acid engineered into the same or different parent antibody which reacts in 10% yield with a thiol-reactive reagent has a thiol reactivity value of about 0.1. Another cysteine amino acid engineered into the same or different parent antibody which fails totally to react with a thiol-reactive reagent has a thiol reactivity value of 0. Determination of the thiol reactivity value of a particular cysteine may be conducted by ELISA assay, mass spectroscopy, liquid chromatography, autoradiography, or other quantitative analytical tests.

A "parent antibody" is an antibody comprising an amino acid sequence from which one or more amino acid residues are replaced by one or more cysteine residues. The parent antibody may comprise a native or wild type sequence. The parent antibody may have pre-existing amino acid sequence modifications (such as additions, deletions and/or substitutions) relative to other native, wild type, or modified forms of an antibody. A parent antibody may be directed against a target antigen of interest, e.g. a biologically important polypeptide. Antibodies directed against nonpolypeptide antigens (such as tumor-associated glycolipid antigens; see U.S. Pat. No. 5,091,178) are also contemplated.

Exemplary parent antibodies include antibodies having affinity and selectivity for cell surface and transmembrane receptors and tumor-associated antigens (TAA).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody "which binds" a molecular target or an antigen of interest, e.g., ErbB2 antigen, is one capable of binding that antigen with sufficient affinity such that the antibody is useful in targeting a cell expressing the antigen. Where the antibody is one which binds ErbB2, it will usually preferentially bind ErbB2 as opposed to other ErbB receptors, and may be one which does not significantly cross-react with other proteins such as EGFR, ErbB3 or ErbB4. In such embodiments, the extent of binding of the antibody to these non-ErbB2 proteins (e.g., cell surface binding to endogenous receptor) will be less than 10% as determined by fluorescence activated cell sorting (FACS) analysis or radioimmunoprecipitation (RIA). Sometimes, the anti-ErbB2 antibody will not significantly cross-react with the rat neu protein, e.g., as described in Schecter et al. (1984) Nature 312:513 and Drebin et al (1984) Nature 312:545-548.

Molecular targets for antibodies encompassed by the present invention include CD proteins and their ligands, such as, but not limited to: (i) CD3, CD4, CD8, CD19, CD20, CD22, CD34, CD40, CD79α (CD79a), and CD79β (CD79b); (ii) members of the ErbB receptor family such as the EGF receptor, HER2, HER3 or HER4 receptor; (iii) cell adhesion molecules such as LFA-1, Mac1, p150,95, VLA-4, ICAM-1, VCAM and Alpha-v/Beta-3 integrin, including either alpha or beta subunits thereof (e.g. anti-CD11a, anti-CD18 or anti-CD11b antibodies); (iv) growth factors such as VEGF; IgE; blood group antigens; flk2/flt3 receptor; obesity (OB) receptor; mpl receptor; CTLA-4; protein C, BR3, c-met, tissue factor, etc; and (v) cell surface and transmembrane tumor-associated antigens (TAA).

The terms "anti-Ly6E antibody" and "an antibody that binds to Ly6E" refer to an antibody that is capable of binding Ly6E with sufficient affinity such that the antibody is useful as a diagnostic and/or therapeutic agent in targeting Ly6E. In one embodiment, the extent of binding of an anti-Ly6E antibody to an unrelated, non-Ly6E protein is less than about 10% of the binding of the antibody to Ly6E as measured, e.g., by a radioimmunoassay (RIA). In certain embodiments, an antibody that binds to Ly6E has a dissociation constant (Kd) of ≤1 μM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$ M or less, e.g. from $10^{-8}$ M to $10^{-13}$M, e.g., from $10^{-9}$M to $10^{-13}$ M). In certain embodiments, an anti-Ly6E antibody binds to an epitope of Ly6E that is conserved among Ly6E from different species.

The terms "anti-STEAP1 antibody" and "an antibody that binds to STEAP1" refer to an antibody that is capable of binding STEAP1 with sufficient affinity such that the antibody is useful as a diagnostic and/or therapeutic agent in targeting STEAP1. In one embodiment, the extent of binding of an anti-STEAP1 antibody to an unrelated, non-STEAP1 protein is less than about 10% of the binding of the antibody to STEAP1 as measured, e.g., by a radioimmunoassay (RIA). In certain embodiments, an antibody that binds to STEAP1 has a dissociation constant (Kd) of ≤1 μM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$M or less, e.g. from $10^{-8}$M to $10^{-13}$M, e.g., from $10^{-9}$M to $10^{-13}$M). In certain embodiments, an anti-STEAP1 antibody binds to an epitope of STEAP1 that is conserved among STEAP1 from different species.

The terms "anti-CD79b antibody" and "an antibody that binds to CD79b" refer to an antibody that is capable of binding CD79b with sufficient affinity such that the antibody is useful as a diagnostic and/or therapeutic agent in targeting CD79b. In one embodiment, the extent of binding of an anti-CD79b antibody to an unrelated, non-CD79b protein is less than about 10% of the binding of the antibody to CD79b as measured, e.g., by a radioimmunoassay (RIA). In certain embodiments, an antibody that binds to CD79b has a dissociation constant (Kd) of ≤1 μM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$ M or less, e.g. from $10^{-8}$ M to $10^{-13}$M, e.g., from $10^{-9}$M to $10^{-13}$ M). In certain embodiments, an anti-CD79b antibody binds to an epitope of CD79b that is conserved among CD79b from different species.

The terms "anti-MUC16 antibody" and "an antibody that binds to MUC16" refer to an antibody that is capable of binding MUC16 with sufficient affinity such that the antibody is useful as a diagnostic and/or therapeutic agent in targeting MUC16. In one embodiment, the extent of binding of an anti-MUC16 antibody to an unrelated, non-MUC16 protein is less than about 10% of the binding of the antibody to MUC16 as measured, e.g., by a radioimmunoassay (RIA). In certain embodiments, an antibody that binds to MUC16 has a dissociation constant (Kd) of ≤1 μM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$M or less, e.g. from $10^{-8}$M to $10^{-13}$M, e.g., from $10^{-9}$M to $10^{-13}$M). In certain embodiments, an anti-MUC16 antibody binds to an epitope of MUC16 that is conserved among MUC16 from different species.

The terms "anti-HER2 antibody" and "an antibody that binds to HER2" refer to an antibody that is capable of binding HER2 with sufficient affinity such that the antibody is useful as a diagnostic and/or therapeutic agent in targeting HER2. In one embodiment, the extent of binding of an anti-HER2 antibody to an unrelated, non-HER2 protein is less than about 10% of the binding of the antibody to HER2 as measured, e.g., by a radioimmunoassay (RIA). In certain embodiments, an antibody that binds to HER2 has a dissociation constant (Kd) of ≤1 μM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$ M or less, e.g. from $10^{-8}$ M to $10^{-13}$M, e.g., from $10^{-9}$M to $10^{-13}$ M). In certain embodiments, an anti-HER2 antibody binds to an epitope of HER2 that is conserved among HER2 from different species.

The terms "CD22 antibody" and "an antibody that binds to CD22" refer to an antibody that is capable of binding CD22 with sufficient affinity such that the antibody is useful as a diagnostic and/or therapeutic agent in targeting CD22. In one embodiment, the extent of binding of an anti-CD22 antibody to an unrelated, non-CD22 protein is less than about 10% of the binding of the antibody to CD22 as measured, e.g., by a radioimmunoassay (RIA). In certain embodiments, an antibody that binds to CD22 has a dissociation constant (Kd) of ≤1 μM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$M or less, e.g. from $10^{-8}$M to $10^{-13}$M, e.g., from $10^{-9}$M to $10^{-13}$ M). In certain embodiments, an anti-CD22 antibody binds to an epitope of CD22 that is conserved among CD22 from different species.

The terms "anti-CD79b antibody" and "an antibody that binds to CD79b" refer to an antibody that is capable of binding CD79b with sufficient affinity such that the antibody is useful as a diagnostic and/or therapeutic agent in targeting CD79b. In one embodiment, the extent of binding of an anti-CD79b antibody to an unrelated, non-CD79b protein is less than about 10% of the binding of the antibody to CD79b as measured, e.g., by a radioimmunoassay (RIA). In certain embodiments, an antibody that binds to CD79b has a dissociation constant (Kd) of ≤1 μM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$M or less, e.g. from $10^{-8}$M to $10^{-13}$M, e.g., from $10^{-9}$M to $10^{-13}$ M). In certain embodiments, an anti-CD79b antibody binds to an epitope of CD79b that is conserved among CD79b from different species.

The terms "anti-NaPi2b antibody" and "an antibody that binds to NaPi2b" refer to an antibody that is capable of binding NaPi2b with sufficient affinity such that the antibody is useful as a diagnostic and/or therapeutic agent in targeting NaPi2b. In one embodiment, the extent of binding of an anti-NaPi2b antibody to an unrelated, non-NaPi2b protein is less than about 10% of the binding of the antibody to NaPi2b as measured, e.g., by a radioimmunoassay (RIA). In certain embodiments, an antibody that binds to NaPi2b has a dissociation constant (Kd) of ≤1 μM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$ M or less, e.g. from $10^{-8}$M to $10^{-13}$M, e.g., from $10^{-9}$M to $10^{-13}$ M). In certain embodiments, an anti-NaPi2b antibody binds to an epitope of *NaPi*2b that is conserved among NaPi2b from different species.

Unless indicated otherwise, the term "monoclonal antibody 4D5" refers to an antibody that has antigen binding residues of, or derived from, the murine 4D5 antibody (ATCC CRL 10463). For example, the monoclonal antibody 4D5 may be murine monoclonal antibody 4D5 or a variant thereof, such as a humanized 4D5. Exemplary humanized 4D5 antibodies include huMAb4D5-1, huMAb4D5-2, huMAb4D5-3, huMAb4D5-4, huMAb4D5-5, huMAb4D5-6, huMAb4D5-7 and huMAb4D5-8 (trastuzumab, HERCEPTIN®) as in U.S. Pat. No. 5,821,337.

Unless indicated otherwise, the term "monoclonal antibody 7C2" or "7C2" refers to an antibody that has antigen biding residues of, or derived from the 7C2.v2.2.LA antibody. The 7C2 antibody is an anti-HER2 antibody.

A "hu7C2.v.2.2.LA antibody-drug conjugate" (hu7C2 ADC) refers to a humanized 7C2 antibody conjugated to a drug. In specific embodiments, the humanized 7C2 antibody conjugated to a drug via an engineered cysteine and linker. In specific embodiments, the humanized 7C2 ADC is co-administered with one or more additional therapeutic agents selected from trastuzumab (Herceptin®), T-DM1 (Kadcyla®) and pertuzumab (Perjeta®). In some embodiments, a hu7C2 ADC is co-administered with trastuzumab. In some embodiments, a hu7C2 ADC is co-administered with T-DM1. In some embodiments, a hu7C2 ADC is co-administered with pertuzumab. In some embodiments, a hu7C2 ADC is co-administered with trastuzumab and pertuzumab. In some embodiments, a hu7C2 ADC is co-administered with T-DM1 and pertuzumab.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

An "ErbB-expressing cancer" is one comprising cells which have ErbB protein present at their cell surface. An "ErbB2-expressing cancer" is one which produces sufficient levels of ErbB2 at the surface of cells thereof, such that an anti-ErbB2 antibody can bind thereto and have a therapeutic effect with respect to the cancer.

A cancer which "overexpresses" an antigenic receptor is one which has significantly higher levels of the receptor, such as ErbB2, at the cell surface thereof, compared to a noncancerous cell of the same tissue type. Such overexpression may be caused by gene amplification or by increased transcription or translation. Receptor overexpression may be determined in a diagnostic or prognostic assay by evaluating increased levels of the receptor protein present on the surface of a cell (e.g., via an immunohistochemistry assay; IHC). Alternatively, or additionally, one may measure levels of receptor-encoding nucleic acid in the cell, e.g., via fluorescent in situ hybridization (FISH; see WO 98/45479), southern blotting, or polymerase chain reaction (PCR) techniques, such as real time quantitative PCR (RT-PCR).

A "chemotherapy" is use of a chemotherapeutic agent useful in the treatment of cancer.

A "chemotherapeutic agent" is a chemical compound useful in the treatment of cancer, regardless of mechanism of action. As used herein, the term "drug" or "drug moiety" are examples of chemotherapeutic agents. Accordingly, a wherein the THIOMAB™ antibodies described herein comprise a cysteine engineered antibody, a linker, and a drug, the drug may be any of the chemotherapeutic agents described herein.

Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafamib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammaI1, calicheamicin omegaI1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (T-2 toxin, verracurin A, roridin A and anguidine); urethan; vindesine; dacarbazine; mannomustine; mitobronitol; mitolactol; pipobroman; gacytosine; arabinoside (Ara-C); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

The term "cytotoxic agent" as used herein refers to a substance that inhibits or prevents the function of cells and/or causes destruction of cells. A chemotherapeutic agent (i.e., a "drug" or "drug moiety") is can be a cytotoxic agent. Accordingly, a wherein the THIOMAB™ antibodies described herein comprise a cysteine engineered antibody, a linker, and a drug, the drug may be any of the cytotoxic agents described herein The term is intended to include radioactive isotopes (e.g., $^{211}At$, $^{131}I$, $^{125}I$ $^{90}Y$, $^{186}Re$, $^{188}Re$, $^{153}Sm$, $^{212}Bi$, $^{32}P$, $^{60}C$, and radioactive isotopes of Lu), chemotherapeutic agents, and toxins such as small molecule toxins or enzymatically active toxins of bacterial, fungal, plant or animal origin, including synthetic analogs and derivatives thereof.

"Phage display" is a technique by which variant polypeptides are displayed as fusion proteins to a coat protein on the surface of phage, e.g., filamentous phage, particles. One utility of phage display lies in the fact that large libraries of randomized protein variants can be rapidly and efficiently sorted for those sequences that bind to a target molecule with high affinity. Display of peptide and protein libraries on phage has been used for screening millions of polypeptides for ones with specific binding properties. Polyvalent phage display methods have been used for displaying small random peptides and small proteins, typically through fusions to either pIII or pVIII of filamentous phage (Wells and Lowman, (1992) Curr. Opin. Struct. Biol., 3:355-362, and references cited therein). In monovalent phage display, a protein or peptide library is fused to a phage coat protein or a portion thereof, and expressed at low levels in the presence of wild type protein. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology*, 3:205-0216 (1991). Phage display includes techniques for producing antibody-like molecules (Janeway, C., Travers, P., Walport, M., Shlomchik (2001) *Immunobiology*, 5th Ed., Garland Publishing, New York, p627-628; Lee et al).

A "phagemid" is a plasmid vector having a bacterial origin of replication, e.g., ColE1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

"Linker", "Linker Unit", or "link" means a chemical moiety comprising a covalent bond or a chain of atoms that covalently attaches an antibody to a drug moiety. In various embodiments, a linker is specified as L. Linkers include a divalent radical such as an alkyldiyl, an arylene, a heteroarylene, moieties such as: —$(CR_2)_nO(CR_2)_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

The term "label" means any moiety which can be covalently attached to an antibody and that functions to: (i)

provide a detectable signal; (ii) interact with a second label to modify the detectable signal provided by the first or second label, e.g. FRET (fluorescence resonance energy transfer); (iii) stabilize interactions or increase affinity of binding, with antigen or ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The phrase "pharmaceutically acceptable salt," as used herein, refers to pharmaceutically acceptable organic or inorganic salts of an ADC. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" refers to an association of one or more solvent molecules and an ADC. Examples of solvents that form pharmaceutically acceptable solvates include, but are not limited to, water, isopropanol, ethanol, methanol, DMSO, ethyl acetate, acetic acid, and ethanolamine.

Cysteine Engineered Antibodies

The compounds of the invention include cysteine engineered antibodies where one or more amino acids of a wild-type or parent antibody are replaced (i.e., "substituted" or "mutated") with a cysteine amino acid (i.e., and "engineered cysteine"). Any form of antibody may be so engineered, i.e. mutated. For example, a parent monoclonal antibody may be engineered to form a "THIOMAB™ antibody." One example of a THIOMAB™ antibody is an antibody fragment (i.e., a Fab) that has an engineered cysteine. This Fab THIOMAB™ antibody can be referred to as "ThioFab." It should be noted that a single site mutation yields a single engineered cysteine residue in a ThioFab, while a single site mutation yields two engineered cysteine residues in a THIOMAB™ antibody, due to the dimeric nature of the IgG antibody. Mutants with engineered cysteine (Cys) residues were evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies of the invention are in the range of 0.0 to 1.0. Specifically, the thiol reactivity values of cysteine engineered antibodies of the invention are in the range of 0.1 to 1.0. In certain embodiments, the thiol reactivity values of cysteine engineered antibodies of the invention are in the ranges of 0.0 to 0.1, 0.1 to 0.5, 0.1 to 0.6, 0.1 to 0.7, 0.1 to 0.8, 0.1 to 0.9, or 0.1 to 1.0. In certain embodiments, the thiol reactivity values of cysteine engineered antibodies of the invention are in the ranges of 0.2 to 1.0, 0.3 to 1.0, 0.4 to 1.0, 0.5 to 1.0, 0.6 to 1.0, 0.7 to 1.0, or 0.8 to 1.0. In certain embodiments, the thiol reactivity values of cysteine engineered antibodies of the invention are in the range of 0.6 to 1.0. In certain embodiments, the thiol reactivity values of cysteine engineered antibodies of the invention are in the ranges of 0.7 to 1.0. In certain embodiments, the thiol reactivity values of cysteine engineered antibodies of the invention are in the ranges of 0.8 to 10. In certain embodiments, the thiol reactivity values of cysteine engineered antibodies of the invention are in the ranges of 0.5 to 0.8. In certain embodiments, the thiol reactivity values of cysteine engineered antibodies of the invention are in the ranges of 0.5 to 0.9. In certain embodiments, the thiol reactivity values of cysteine engineered antibodies of the invention are in the ranges of 0.5 to 0.7. In certain embodiments, the thiol reactivity values of cysteine engineered antibodies of the invention are in the ranges of 0.5 to 1.0.

The design, selection, and preparation methods of the invention enable cysteine engineered antibodies which are reactive with electrophilic functionality. These methods further enable antibody conjugate compounds such as antibody-drug conjugate (ADC) compounds with drug molecules at designated, designed, selective sites. Reactive cysteine residues on an antibody surface allow specifically conjugating a drug moiety through a thiol reactive group such as maleimide or haloacetyl. The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in iodoacetyl and maleimide reagents may react with amine groups, but higher pH (>9.0) and longer reaction times are required (Garman, 1997, Non-Radioactive Labelling: A Practical Approach, Academic Press, London).

Cysteine engineered antibodies of the invention preferably retain the antigen binding capability of their wild type, parent antibody counterparts. Thus, cysteine engineered antibodies are capable of binding, preferably specifically, to antigens. Such antigens include, for example, tumor-associated antigens (TAA), cell surface receptor proteins and other cell surface molecules, transmembrane proteins, signalling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which a cysteine engineered antibody is capable of binding may be a member of a subset of one of the above-mentioned categories, wherein the other subset(s) of said category comprise other molecules/antigens that have a distinct characteristic (with respect to the antigen of interest).

The parent antibody may also be a humanized antibody selected from huMAb4D5-1, huMAb4D5-2, huMAb4D5-3, huMAb4D5-4, huMAb4D5-5, huMAb4D5-6, huMAb4D5-7 and huMAb4D5-8 (Trastuzumab, HERCEPTIN®) as described in Table 3 of U.S. Pat. No. 5,821,337, expressly incorporated herein by reference; humanized 520C9 (WO 93/21319) and humanized 2C4 antibodies as described herein.

Cysteine engineered antibodies of the invention may be site-specifically and efficiently coupled with a thiol-reactive reagent. The thiol-reactive reagent may be a multifunctional linker reagent, a capture, i.e. affinity, label reagent (e.g. a biotin-linker reagent), a detection label (e.g. a fluorophore reagent), a solid phase immobilization reagent (e.g. SEPHAROSE™, polystyrene, or glass), or a drug-linker intermediate. One example of a thiol-reactive reagent is N-ethyl maleimide (NEM). In an exemplary embodiment, reaction of a THIOMAB™ antibody with a biotin-linker reagent provides a biotinylated THIOMAB™ antibody by which the presence and reactivity of the engineered cysteine residue may be detected and measured. Reaction of a THIOMAB™ antibody with a multifunctional linker reagent provides a THIOMAB™ antibody with a functionalized linker which may be further reacted with a drug moiety reagent or other label. Reaction of a THIOMAB™ antibody with a drug-linker intermediate provides a THIOMAB™ antibody drug conjugate. In certain embodiments, the THIOMAB™ antibody is a ThioFab.

The exemplary methods described here may be applied generally to the identification and production of antibodies, and more generally, to other proteins through application of the design and screening steps described herein.

Such an approach may be applied to the conjugation of other thiol-reactive agents in which the reactive group is, for example, a maleimide, an iodoacetamide, a pyridyl disulfide, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671). The partner may be a cytotoxic agent (e.g. a toxin such as doxorubicin or pertussis toxin), a fluorophore such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent.

The sites identified on the exemplary antibody, hu4D5, herein are primarily in the constant domain of an antibody which is well conserved across all species of antibodies. These sites should be broadly applicable to other antibodies, without further need of structural design or knowledge of specific antibody structures, and without interference in the antigen binding properties inherent to the variable domains of the antibody.

Cysteine engineered antibodies which may be useful in the treatment of cancer include, but are not limited to, antibodies against cell surface receptors and tumor-associated antigens (TAA). Such antibodies may be used as naked antibodies (unconjugated to a drug or label moiety) or as Formula I antibody-drug conjugates (ADC). Tumor-associated antigens are known in the art, and can prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to, TAA (1)-(53) listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to TAA (1)-(53) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Tumor-Associated Antigens (1)-(53):

(1) BMPR1B (bone morphogenetic protein receptor-type IB, Genbank accession no. NM_001203) ten Dijke, P., et al Science 264 (5155):101-104 (1994), Oncogene 14 (11): 1377-1382 (1997)); WO2004063362 (Claim 2); WO2003042661 (Claim 12); US2003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377 (Page 349-350); WO200230268 (Claim 27; Page 376); WO200148204 (Example; FIG. 4); NP_001194 bone morphogenetic protein receptor, type IB/pid=NP_001194.1. Cross-references: MIM:603248; NP_001194.1; AY065994

(2) E16 (LAT1, SLC7A5, Genbank accession no. NM 003486) Biochem. Biophys. Res. Commun. 255 (2), 283-288 (1999), Nature 395 (6699):288-291 (1998), Gaugitsch, H. W., et al (1992) J. Biol. Chem. 267 (16):11267-11273;

WO2004048938 (Example 2); WO2004032842 (Example IV); WO2003042661 (Claim 12); WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150); NP_003477 solute carrier family 7 (cationic amino acid transporter, y+system), member 5/pid=NP_003477.3—Homo sapiens; Cross-references: MIM:600182; NP_003477.3; NM_015923; NM_003486_1

Figure 13:
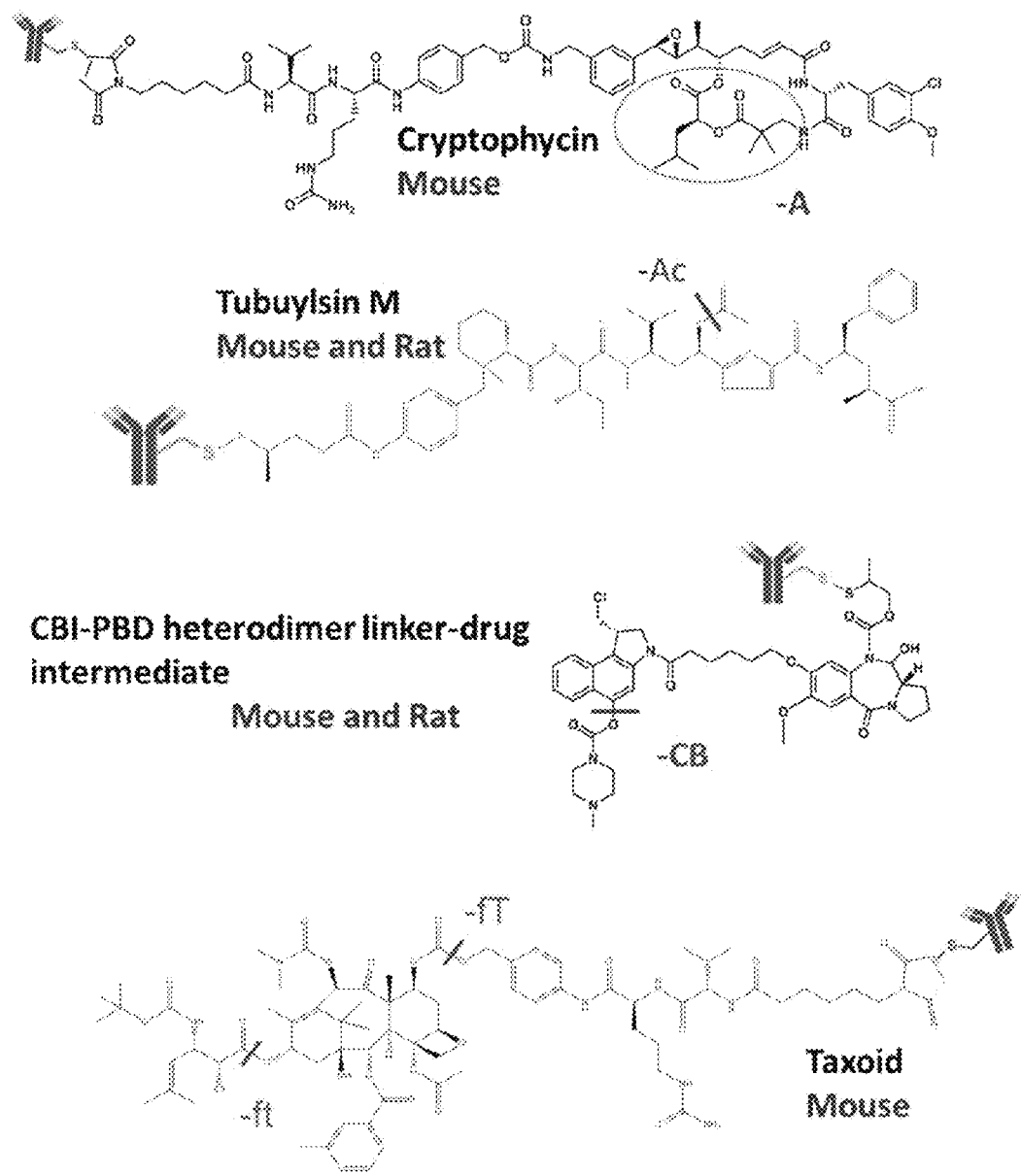
FIG. 13 shows diagrams of the enzymatic modifications of certain drugs conjugated to a LC-K149C cysteine engineered antibody. The modifications are as follows: cryptophycin was subject to an amide cleavage, Tubulysin was subject to an acetyl loss (i.e., deacetylation), a CBI-PBD heterodimer linker-drug intermediate was subject to a carbamate loss, and Taxoids were unstable and showed multiple enzymatic cleavages.

(3) STEAP1 (six transmembrane epithelial antigen of prostate, Genbank accession no. NM 012449); Cancer Res. 61 (15), 5857-5860 (2001), Hubert, R. S., et al (1999) Proc. Natl. Acad. Sci. U.S.A. 96 (25):14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A); NP_036581 six transmembrane epithelial antigen of the prostate
Cross-references: MIM:604415; NP_036581.1; NM_012449_1

Figure 12:
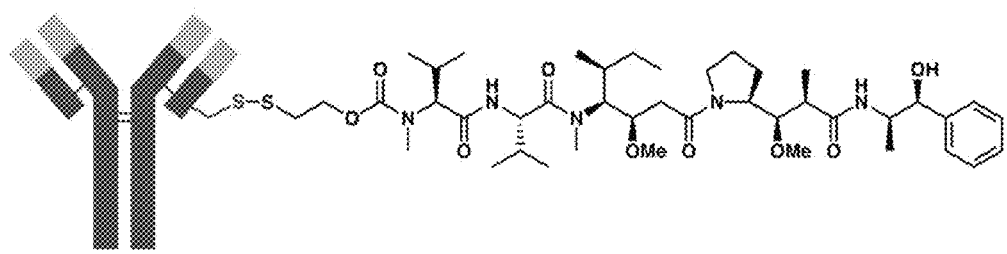
FIG. 12 shows a drawing (not to scale) of a PDS-MMAE THIOMAB™ antibody.

(4) 0772P (CA125, MUC16, Genbank accession no. AF361486); J. Biol. Chem. 276 (29):27371-27375 (2001)); WO2004045553 (Claim 14); WO200292836 (Claim 6; FIG. 12); WO200283866 (Claim 15; Page 116-121); US2003124140 (Example 16); Cross-references: GI:34501467; AAK74120.3; AF361486_1

(5) MPF (MPF, MSLN, SMR, megakaryocyte potentiating factor, mesothelin, Genbank accession no. NM_005823) Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (Claim 14); (WO2002102235 (Claim 13; Page 287-288); WO2002101075 (Claim 4; Page 308-309); WO200271928 (Page 320-321); WO9410312 (Page 52-57); Cross-references: MIM:601051; NP_005814.2; NM_005823_1

(6) Napi3b (also known as NaPi2b) (NAPI-3B, NPTIIb, SLC34A2, solute carrier family 34 (sodium phosphate), member 2, type II sodium-dependent phosphate transporter 3b, Genbank accession no. NM_006424) J. Biol. Chem. 277 (22):19665-19672 (2002), Genomics 62 (2):281-284 (1999), Feild, J. A., et al (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV); WO200175177 (Claim 24; Page 139-140); Cross-references: MIM:604217; NP_006415.1; NM_006424_1

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878); Nagase T., et al (2000) DNA Res. 7 (2):143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11); Accession: Q9P283; EMBL; AB040878; BAA95969.1. Genew; HGNC:10737

(8) PSCA hlg (2700050C12Rik, C530008O16Rik, RIKEN cDNA 2700050C12, RIKEN cDNA 2700050C12 gene, Genbank accession no. AY358628); Ross et al (2002) Cancer Res. 62:2546-2553; US2003129192 (Claim 2); US2004044180 (Claim 12); US2004044179 (Claim 11); US2003096961 (Claim 11); US2003232056 (Example 5); WO2003105758 (Claim 12); US2003206918 (Example 5); EP1347046 (Claim 1); WO2003025148 (Claim 20); Cross-references: GI:37182378; AAQ88991.1; AY358628_1

Figure 6A:
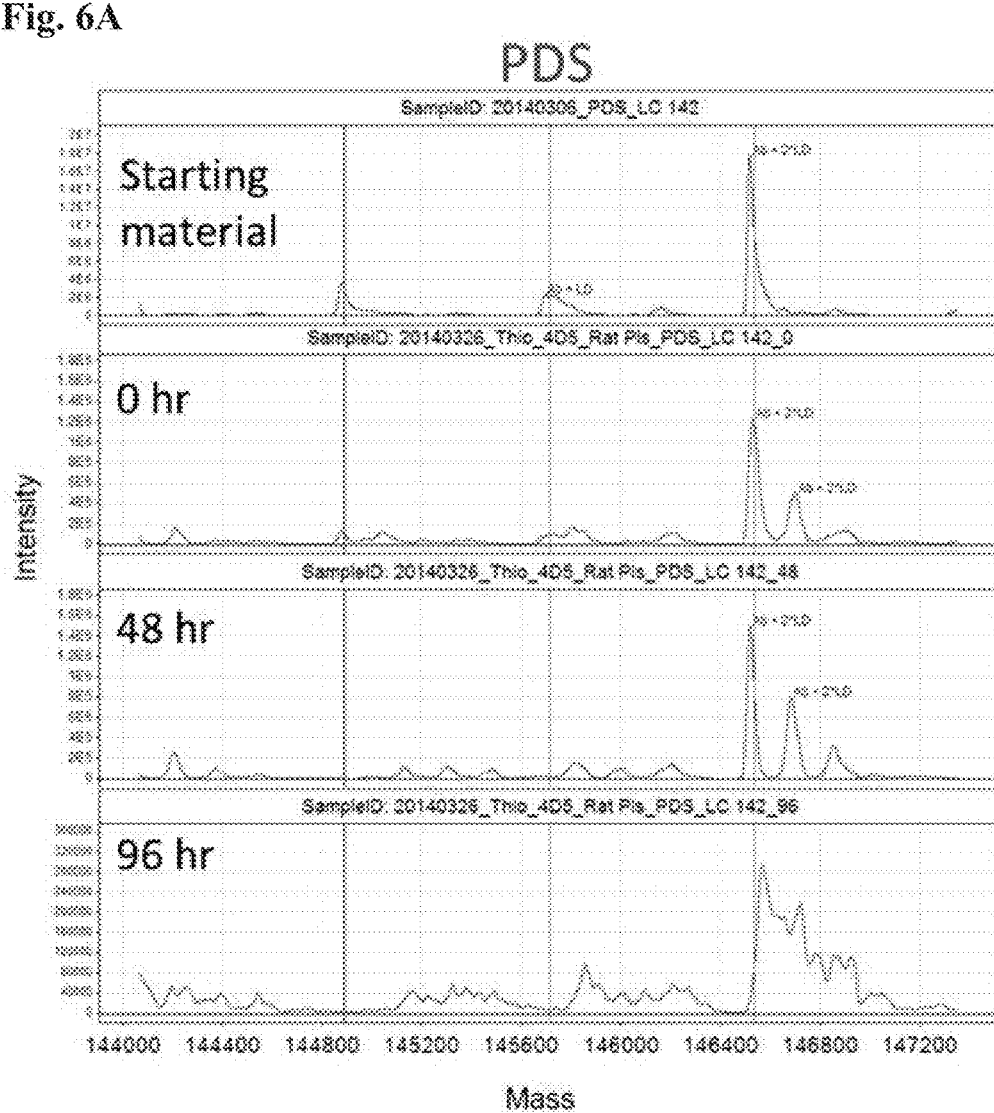
FIGS. 6A-B show representative stability graphs of MC-vc-MMAE and PDS-MMAE conjugates.

(9) ETBR (Endothelin type B receptor, Genbank accession no. AY275463); Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (Claim 1); WO2004048938 (Example 2); WO2004040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; U.S. Pat. No. 6,518,404 (FIG. 3); U.S. Pat. No. 5,773,223 (Claim 1a; Col 31-34); WO2004001004

(10) MSG783 (RNF124, hypothetical protein FLJ20315, Genbank accession no. NM_017763); WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6); Cross-references: LocusID:54894; NP_060233.2; NM_017763_1

Figure 4A:
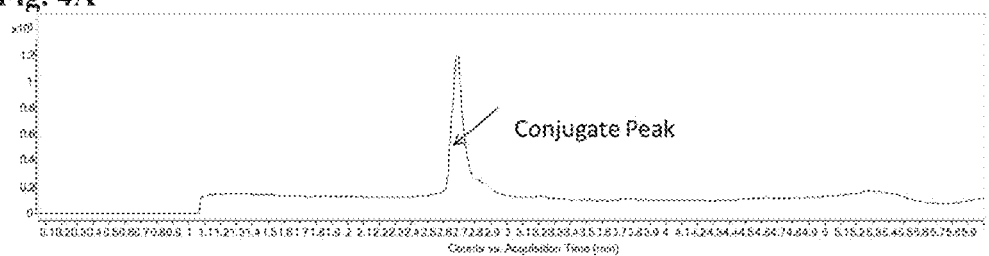
FIGS. 4A-B show UV280 LC/MS chromatographs of THIOMAB™ antibodies.
Figure 4B:
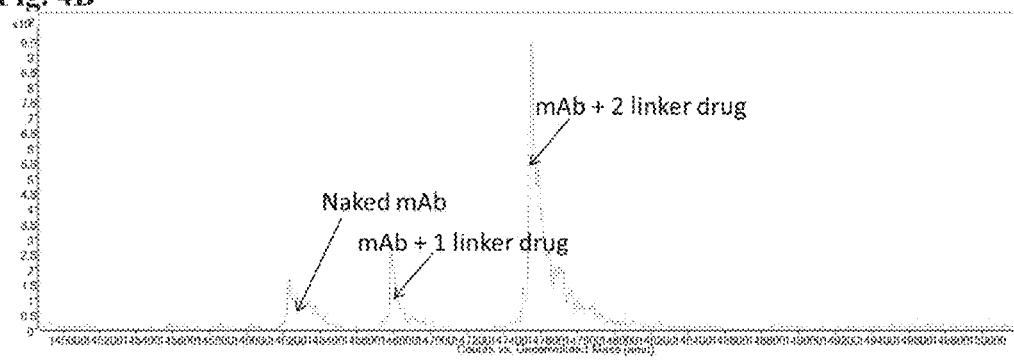

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138); Lab. Invest. 82 (11):1573-1582 (2002)); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10); Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636); Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806

(Claim 4); WO200162794 (Claim 14; FIG. 1A-D); Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212); Ciccodicola, A., et al EMBO J. 8 (7):1987-1991 (1989), Am. J. Hum. Genet. 49 (3):555-565 (1991)); US2003224411 (Claim 1); WO2003083041 (Example 1); WO2003034984 (Claim 12); WO200288170 (Claim 2; Page 52-53); WO2003024392 (Claim 2; FIG. 58); WO200216413 (Claim 1; Page 94-95, 105); WO200222808 (Claim 2; FIG. 1); U.S. Pat. No. 5,854,399 (Example 2; Col 17-18); U.S. Pat. No. 5,792,616 (FIG. 2); Cross-references: MIM:187395; NP_003203.1; NM_003212_1

Figure 9:
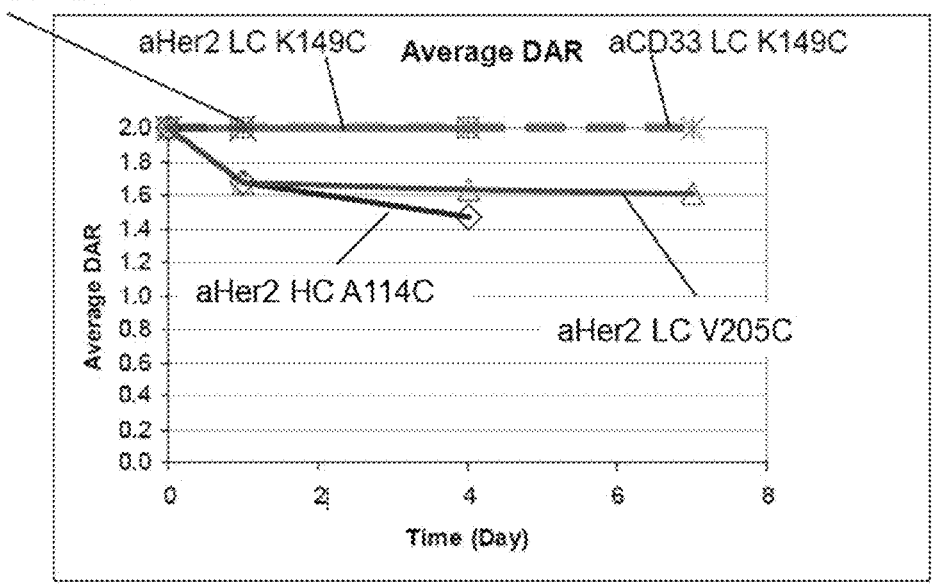
FIG. 9 shows a graph of the Average DAR over time of LC-K149C, LC-V205C, and HC-A114C THIOMAB™ anti-HER2 and anti-CD33 antibodies.

(14) CD21 (CR2 (Complement receptor 2) or C3DR (C3d/Epstein Barr virus receptor) or Hs.73792 Genbank accession no. M26004); Fujisaku et al (1989) J. Biol. Chem. 264 (4):2118-2125; Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (Claim 9); WO2004045520 (Example 4); WO9102536 (FIGS. 9.1-9.9); WO2004020595 (Claim 1); Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674); Proc. Natl. Acad. Sci. U.S.A. (2003) 100 (7):4126-4131, Blood (2002) 100 (9):3068-3076, Muller et al (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146); Cross-references: MIM:147245; NP_000617.1; NM_000626_1

(16) FcRH2 (IFGP4, IRTA4, SPAP1A (SH2 domain containing phosphatase anchor protein 1a), SPAP1B, SPAP1C, Genbank accession no. NM_030764, AY358130); Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (Claim 2); WO2003077836; WO200138490 (Claim 5; FIG. 18D-1-18D-2); WO2003097803 (Claim 12); WO2003089624 (Claim 25); Cross-references: MIM:606509; NP_110391.2; NM_030764_1

Figure 5:
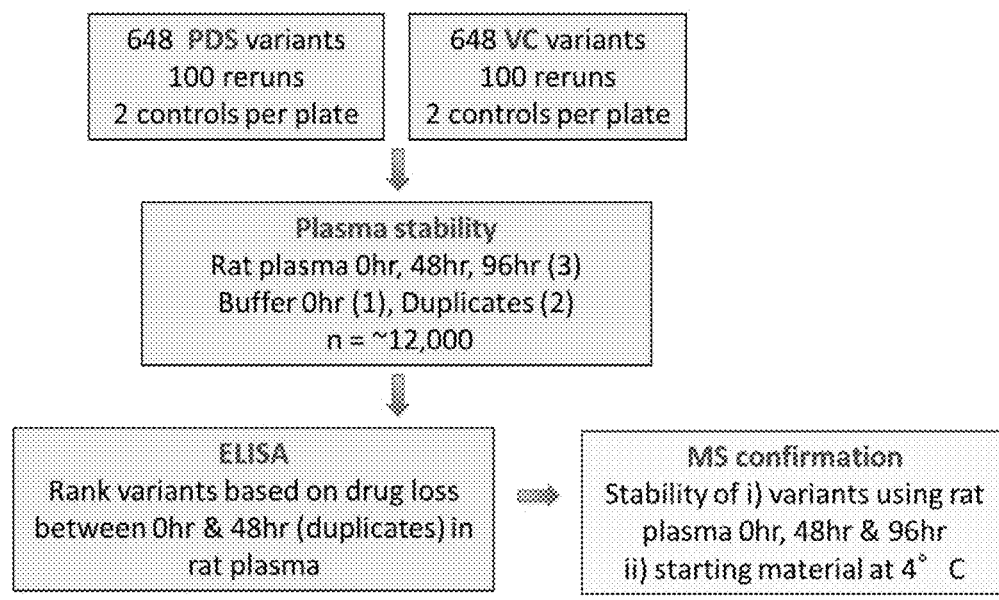
FIG. 5 shows the protocol for performing the full antibody cysteine screen. Full antibody screens were performed on PDS-MMAE and MC-vc-MMAE conjugates. Accordingly, 648 PDS-MMAE and 648 MC-vc-MMAE (total of 1296) THIOMAB™ antibodies were made and tested.
Figure 7:
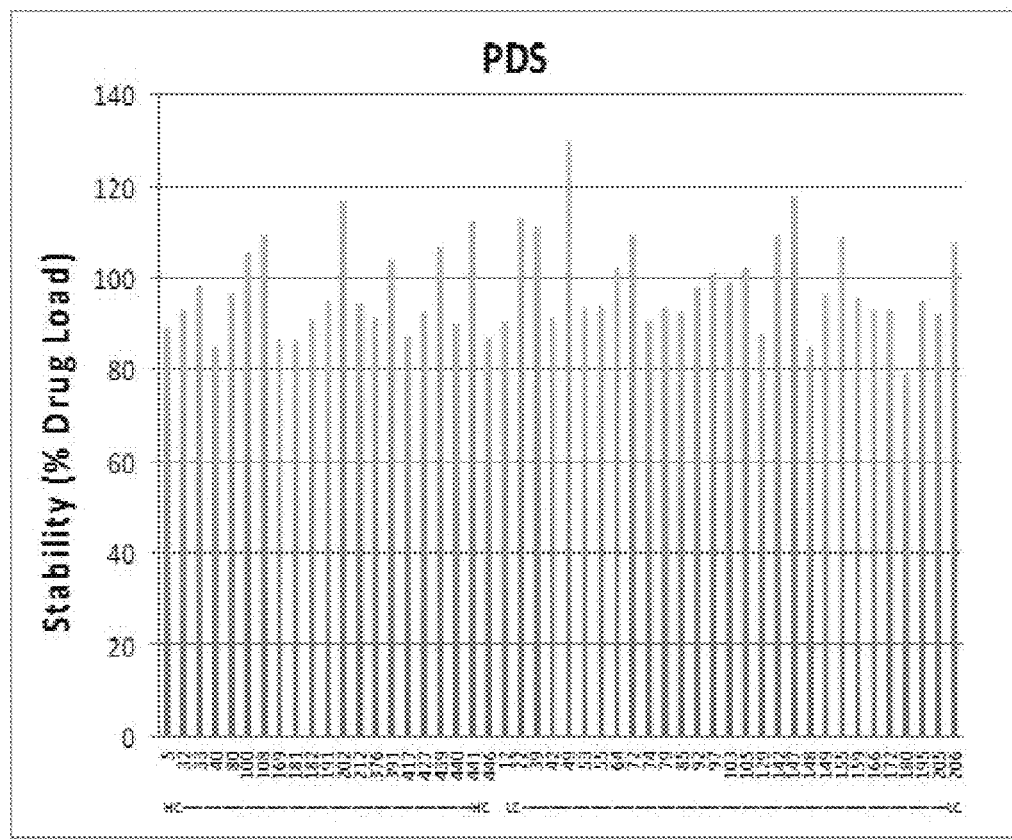
FIG. 7 shows a graph of the stabilities of different PDS-MMAE THIOMAB™ antibodies as assessed by the percent drug load.

(17) HER2 (ErbB2, Genbank accession no. M11730); Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 1I); WO2004009622; WO2003081210; WO2003089904 (Claim 9); WO2003016475 (Claim 1); US2003118592; WO2003008537 (Claim 1); WO2003055439 (Claim 29; FIG. 1A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7); WO2004022709; WO200100244 (Example 3; FIG. 4); Accession: P04626; EMBL; M11767; AAA35808.1. EMBL; M11761; AAA35808.1

(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (Claim 7); WO2004044178 (Example 4); WO2004031238; WO2003042661 (Claim 12); WO200278524 (Example 2); WO200286443 (Claim 27; Page 427); WO200260317 (Claim 2); Accession: P40199; Q14920; EMBL; M29541; AAA59915.1. EMBL; M18728

Figure 8:
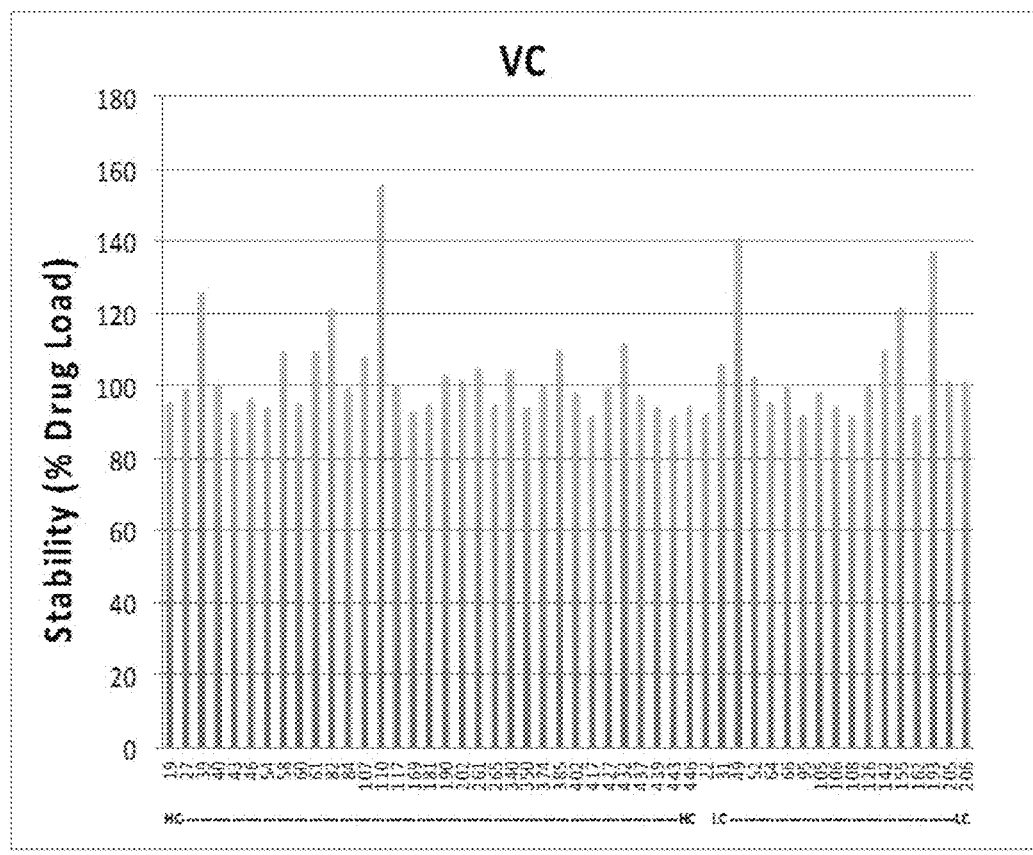
FIG. 8 shows a graph of the stabilities of different MC-vc-MMAE THIOMAB™ antibodies as assessed by the percent drug load.

(19) MDP (DPEP1, Genbank accession no. BC017023); Proc. Natl. Acad. Sci. U.S.A. 99 (26):16899-16903 (2002)); WO2003016475 (Claim 1); WO200264798 (Claim 33; Page 85-87); JP05003790 (FIG. 6-8); WO9946284 (FIG. 9); Cross-references: MIM:179780; AAH17023.1; BC017023_1

(20) IL20Rα (IL20Ra, ZCYTOR7, Genbank accession no. AF184971); Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (Claim 2; Page 63); WO200222153 (Page 45-47); US2002042366 (Page 20-21); WO200146261 (Page 57-59); WO200146232 (Page 63-65); WO9837193 (Claim 1; Page 55-59); Accession: Q9UHF4; Q6UWA9; Q96SH8; EMBL; AF184971; AAF01320.1.

(21) Brevican (BCAN, BEHAB, Genbank accession no. AF229053); Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1)

(22) EphB2R (DRT, ERK, Hek5, EPHT3, Tyro5, Genbank accession no. NM_004442); Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42); Cross-references: MIM:600997; NP_004433.2; NM_004442_1

(23) ASLG659 (B7h, Genbank accession no. AX092328); US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46);

WO200206317 (Example 2; Page 320-321, Claim 34; Page 321-322); WO200271928 (Page 468-469); WO200202587 (Example 1; FIG. 1); WO200140269 (Example 3; Pages 190-192); WO200036107 (Example 2; Page 205-207); WO200405379 (Claim 12); WO2003004989 (Claim 1); WO200271928 (Page 233-234, 452-453); WO 0116318

(24) PSCA (Prostate stem cell antigen precursor, Genbank accession no. AJ297436); Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10; Page 94); WO9840403 (Claim 2; FIG. 1B); Accession: 043653; EMBL; AF043498; AAC39607.1

(25) GEDA (Genbank accession No. AY260763); AAP14954 lipoma HMGIC fusion-partner-like protein/pid=AAP14954.1—Homo sapiens (human); WO2003054152 (Claim 20); WO2003000842 (Claim 1); WO2003023013 (Example 3, Claim 20); US2003194704 (Claim 45); Cross-references: GI:30102449; AAP14954.1; AY260763_1

Figure 6B:
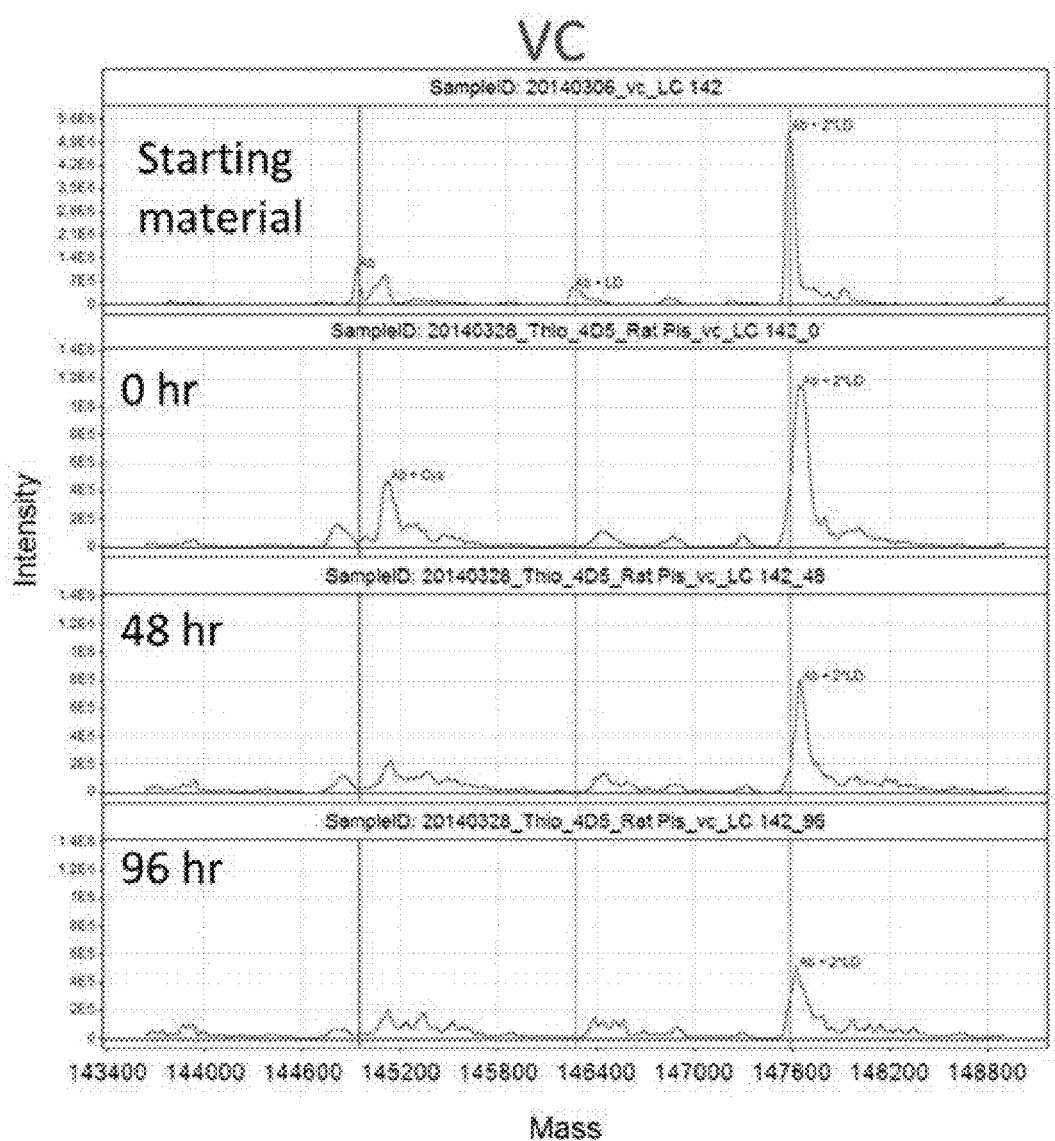

(26) BAFF-R (B cell-activating factor receptor, BLyS receptor 3, BR3, Genbank accession No. AF116456); BAFF receptor/pid=NP_443177.1—Homo sapiens: Thompson, J. S., et al Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO200294852 (Col 136-137); WO200238766 (Claim 3; Page 133); WO200224909 (Example 3; FIG. 3); Cross-references: MIM:606269; NP_443177.1; NM_052945_1; AF132600

(27) CD22 (B-cell receptor CD22-B isoform, BL-CAM, Lyb-8, Lyb8, SIGLEC-2, FLJ22814, Genbank accession No. AK026467); Wilson et al (1991) J. Exp. Med. 173:137-146; WO2003072036 (Claim 1; FIG. 1); Cross-references: MIM: 107266; NP_001762.1; NM_001771_1

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10); WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11): 3457-3464

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1); WO2004040000; WO2004015426; US2003105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) Eur. J. Immunol. 22:2795-2799; Barella et al (1995) Biochem. J. 309:773-779

(30) HLA-DOB (Beta subunit of MHC class II molecule (Ia antigen) that binds peptides and presents them to CD4+ T lymphocytes); 273 aa, pI: 6.56, MW: 30820.TM: 1 [P] Gene Chromosome: 6p21.3, Genbank accession No. NP_002111.1); Tonnelle et al (1985) EMBO J. 4(11):2839-2847; Jonsson et al (1989) Immunogenetics 29(6):411-413; Beck et al (1992) J. Mol. Biol. 228:433-441; Strausberg et al (2002) Proc. Natl. Acad. Sci USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) Immunogenetics 30(1):66-68; Larhammar et al (1985) J. Biol. Chem. 260(26):14111-14119

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, Genbank accession No. NP_002552.2); Le et al (1997) FEBS Lett. 418(1-2):195-199; WO2004047749; WO2003072035 (claim 10); Touchman et al (2000) Genome Res. 10:165-173; WO200222660 (claim 20); WO2003093444 (claim 1); WO2003087768 (claim 1); WO2003029277 (page 82)

(32) CD72 (B-cell differentiation antigen CD72, Lyb-2); 359 aa, pI: 8.66, MW: 40225, TM: 1 [P] Gene Chromosome: 9p13.3, Genbank accession No. NP_001773.1); WO2004042346 (claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci USA 99:16899-16903.

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1); US2002193567; WO9707198 (claim 11, pages 39-42); Miura et al (1996) Genomics 38(3):299-304; Miura et al (1998) Blood 92:2815-2822; WO2003083047; WO9744452 (claim 8, pages 57-61); WO200012130 (pages 24-26)

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1); WO2003077836; WO200138490 (claim 6, FIG. 18E-1-18-E-2); Davis et al (2001) Proc. Natl. Acad. Sci USA 98(17):9772-9777; WO2003089624 (claim 8); EP1347046 (claim 1); WO2003089624 (claim 7)

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88, MW: 106468, TM: 1 [P] Gene Chromosome: 1q21, Genbank accession No. Human:

AF343662, AF343663, AF343664, AF343665, AF369794, AF397453, AK090423, AK090475, AL834187, AY358085; Mouse: AK089756, AY158090, AY506558; NP_112571.1; WO2003024392 (claim 2, FIG. 97); Nakayama et al (2000) Biochem. Biophys. Res. Commun. 277(1):124-127; WO2003077836; WO200138490 (claim 3, FIG. 18B-1-18B-2)

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436; WO2004074320; JP2004113151; WO2003042661; WO2003009814; EP1295944 (pages 69-70); WO200230268 (page 329); WO200190304; US2004249130; US2004022727; WO2004063355; US2004197325; US2003232350; US2004005563; US2003124579; Hone et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94(2): 178-84. (37) PMEL17 (silver homolog; SILV; D12S53E; PMEL17; SI; SIL); ME20; gp100) BC001414; BT007202; M32295; M77348; NM_006928; McGlinchey, R. P. et al (2009) Proc. Natl. Acad. Sci. U.S.A. 106 (33), 13731-13736; Kummer, M. P. et al (2009) J. Biol. Chem. 284 (4), 2296-2306;

(38) TMEFF1 (transmembrane protein with EGF-like and two follistatin-like domains 1; Tomoregulin-1); H7365; C9orf2; C9ORF2; U19878; X83961; NM_080655; NM_003692; Harms, P. W. (2003) Genes Dev. 17 (21), 2624-2629; Gery, S. et al (2003) Oncogene 22 (18):2723-2727;

(39) GDNF-Ra1 (GDNF family receptor alpha 1; GFRA1; GDNFR; GDNFRA; RETL1; TRNR1; RET1L; GDNFR-alpha1; GFR-ALPHA-1); U95847; BC014962; NM_145793 NM_005264; Kim, M. H. et al (2009) Mol. Cell. Biol. 29 (8), 2264-2277; Treanor, J. J. et al (1996) Nature 382 (6586):80-83;

(40) Ly6E (lymphocyte antigen 6 complex; locus E; Ly67, RIG-E, SCA-2, TSA-1); NP_002337.1; NM_002346.2; de Nooij-van Dalen, A. G. et al (2003) Int. J. Cancer 103 (6), 768-774; Zammit, D. J. et al (2002) Mol. Cell. Biol. 22 (3):946-952;

(41) TMEM46 (shisa homolog 2 (*Xenopus laevis*); SHISA2); NP_001007539.1; NM_001007538.1; Furushima, K. et al (2007) Dev. Biol. 306 (2), 480-492; Clark, H. F. et al (2003) Genome Res. 13 (10):2265-2270;

(42) Ly6G6D (lymphocyte antigen 6 complex, locus G6D; Ly6-D, MEGT1); NP_067079.2; NM_021246.2; Mallya, M. et al (2002) Genomics 80 (1):113-123; Ribas, G. et al (1999) J. Immunol. 163 (1):278-287;

(43) LGR5 (leucine-rich repeat-containing G protein-coupled receptor 5; GPR49, GPR67); NP_003658.1; NM_003667.2; Salanti, G. et al (2009) Am. J. Epidemiol. 170 (5):537-545; Yamamoto, Y. et al (2003) Hepatology 37 (3):528-533;

(44) RET (ret proto-oncogene; MEN2A; HSCR1; MEN2B; MTC1; PTC; CDHF12; Hs.168114; RET51; RET-ELE1); NP 066124.1; NM 020975.4; Tsukamoto, H. et al (2009) Cancer Sci. 100 (10):1895-1901; Narita, N. et al (2009) Oncogene 28 (34):3058-3068;

(45) LY6K (lymphocyte antigen 6 complex, locus K; LY6K; HSJ001348; FLJ35226); NP_059997.3; NM_017527.3; Ishikawa, N. et al (2007) Cancer Res. 67 (24):11601-11611; de Nooij-van Dalen, A. G. et al (2003) Int. J. Cancer 103 (6):768-774;

(46) GPR19 (G protein-coupled receptor 19; Mm.4787); NP_006134.1; NM_006143.2; Montpetit, A. and Sinnett, D. (1999) Hum. Genet. 105 (1-2):162-164; O'Dowd, B. F. et al (1996) FEBS Lett. 394 (3):325-329;

(47) GPR54 (KISS1 receptor: KISS1R; GPR54; HOT7T175; AXOR12); NP_115940.2; NM_032551.4; Navenot, J. M. et al (2009) Mol. Pharmacol. 75 (6):1300-1306; Hata, K. et al (2009) Anticancer Res. 29 (2):617-623;

(48) ASPHD1 (aspartate beta-hydroxylase domain containing 1; LOC253982); NP_859069.2; NM_181718.3; Gerhard, D. S. et al (2004) Genome Res. 14 (10B):2121-2127;

(49) Tyrosinase (TYR; OCAIA; OCA1A; tyrosinase; SHEP3); NP_000363.1; NM_000372.4; Bishop, D. T. et al (2009) Nat. Genet. 41 (8):920-925; Nan, H. et al (2009) Int. J. Cancer 125 (4):909-917;

(50) TMEM118 (ring finger protein, transmembrane 2; RNFT2; FLJ14627); NP_001103373.1; NM_001109903.1; Clark, H. F. et al (2003) Genome Res. 13 (10):2265-2270; Scherer, S. E. et al (2006) Nature 440 (7082):346-351

(51) GPR172A (G protein-coupled receptor 172A; GPCR41; FLJ11856; D15Ertd747e); NP_078807.1; NM_024531.3; Ericsson, T. A. et al (2003) Proc. Natl. Acad. Sci. U.S.A. 100 (11):6759-6764; Takeda, S. et al (2002) FEBS Lett. 520 (1-3):97-101.

(52) CD33, a member of the sialic acid binding, immunoglobulin-like lectin family, is a 67-kDa glycosylated transmembrane protein. CD33 is expressed on most myeloid and monocytic leukemia cells in addition to committed myelomonocytic and erythroid progenitor cells. It is not seen on the earliest pluripotent stem cells, mature granulocytes, lymphoid cells, or nonhematopoietic cells (Sabbath et al., (1985) *J. Clin. Invest.* 75:756-56; Andrews et al., (1986) *Blood* 68:1030-5). CD33 contains two tyrosine residues on its cytoplasmic tail, each of which is followed by hydrophobic residues similar to the immunoreceptor tyrosine-based inhibitory motif (ITIM) seen in many inhibitory receptors.

(53) CLL-1 (CLEC12A, MICL, and DCAL2), encodes a member of the C-type lectin/C-type lectin-like domain (CTL/CTLD) superfamily. Members of this family share a common protein fold and have diverse functions, such as cell adhesion, cell-cell signalling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer K (1999) Curr. Opin. Struct. Biol. 9 (5):585-90; van Rhenen A, et al., (2007) Blood 110 (7):2659-66; Chen C H, et al. (2006) Blood 107 (4):1459-67; Marshall A S, et al. (2006) Eur. J. Immunol. 36 (8):2159-69; Bakker A B, et al (2005) Cancer Res. 64 (22):8443-50; Marshall A S, et al (2004) J. Biol. Chem. 279 (15):14792-802). CLL-1 has been shown to be a type II transmembrane receptor comprising a single C-type lectin-like domain (which is not predicted to bind either calcium or sugar), a stalk region, a transmembrane domain and a short cytoplasmic tail containing an ITIM motif The parent antibody may also be a fusion protein comprising an albumin-binding peptide (ABP) sequence (Dennis et al. (2002) "Albumin Binding As A General Strategy For Improving The Pharmacokinetics Of Proteins" J Biol Chem. 277:35035-35043; WO 01/45746). Antibodies of the invention include fusion proteins with ABP sequences taught by: (i) Dennis et al (2002) J Biol Chem. 277:35035-35043 at Tables III and IV, page 35038; (ii) US 20040001827 at [0076]; and (iii) WO 01/45746 at pages 12-13, and all of which are incorporated herein by reference.

Mutagenesis

DNA encoding an amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies. General guidance can be found in Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993.

Site-directed mutagenesis is one method for preparing substitution variants, i.e. mutant proteins. This technique is well known in the art (see for example, Carter (1985) et al Nucleic Acids Res. 13:4431-4443; Ho et al (1989) Gene (Amst.) 77:51-59; and Kunkel et al (1987) Proc. Natl. Acad. Sci. USA 82:488). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA. Site-directed mutagenesis may be carried out within the gene expressing the protein to be mutagenized in an expression plasmid and the resulting plasmid may be sequenced to confirm the introduction of the desired cysteine replacement mutations (Liu et al (1998) J. Biol. Chem. 273:20252-20260). Site-directed of protocols and formats, including those commercially available, e.g. QuikChange® Multi Site-Directed Mutagenesis Kit (Stratagene, La Jolla, Calif.).

PCR mutagenesis is also suitable for making amino acid sequence variants of the starting polypeptide. See Higuchi, (1990) in PCR Protocols, pp. 177-183, Academic Press; Ito et al (1991) Gene 102:67-70; Bernhard et al (1994) Bioconjugate Chem. 5:126-132; and Vallette et al (1989) Nuc. Acids Res. 17:723-733. Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al (1985) Gene 34:315-323. The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. Oligonucleotides are prepared by the phosphoramidite synthesis method (U.S. Pat. No. 4,415,732; U.S. Pat. No. 4,458,066; Beaucage, S. and Iyer, R. (1992) "Advances in the synthesis of oligonucleotides by the phosphoramidite approach", Tetrahedron 48:2223-2311). This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence. Mutant DNA containing the encoded cysteine replacements can be confirmed by DNA sequencing.

Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition; Zoller et al (1983) Methods Enzymol. 100:468-500; Zoller, M. J. and Smith, M. (1982) Nucl. Acids Res. 10:6487-6500).

In the present invention, hu4D5 displayed on M13 phage (Gerstner et al (2002) "Sequence Plasticity In The Antigen-Binding Site Of A Therapeutic Anti-HER2 Antibody", J Mol Biol. 321:851-62) was used for experiments as a model system. Cysteine mutations were introduced in hu4D5-phage, hu4D5, and ABP-hu4D5 constructs. The hu4D5-THIOMAB™ antibody-Phage preps were carried out using the polyethylene glycol (PEG) precipitation method as described earlier (Lowman, Henry B. (1998) Methods in Molecular Biology (Totowa, N.J.) 87 (Combinatorial Peptide Library Protocols) 249-264).

Pheselector Assay

The PHESELECTOR (Phage ELISA for Selection of Reactive Thiols) assay allows for detection of reactive cysteine groups in antibodies in an ELISA phage format. See U.S. Pat. No. 7,521,541 and U.S. Pat. Pub. No. 20110301334 which are incorporated by reference in their entirety. Specifically, the PHESESLECTOR assay includes the process of coating the protein (e.g. antibody) of interest on well surfaces, followed incubation with phage particles and then HRP labeled secondary antibody with absorbance detection. Mutant proteins displayed on phage may be screened in a rapid, robust, and high-throughput manner. Libraries of cysteine engineered antibodies can be produced and subjected to binding selection using the same approach to identify appropriately reactive sites of free Cys incorporation from random protein-phage libraries of antibodies or other proteins. This technique includes reacting cysteine mutant proteins displayed on phage with an affinity reagent or reporter group which is also thiol-reactive.

In certain embodiments, the PHESELECTOR assay includes the following steps: 1) bovine serum albumin (BSA), a portion or entirety of a target protein (e.g., an erbB2 extracellular domain (HER2)), and streptavidin (100 µl of 2 µg/ml) are separately coated on Maxisorp 96 well plates; 2) After blocking with 0.5% Tween-20 (in PBS), biotinylated and non-biotinylated THIOMAB™ antibody-Phage ($2 \times 10^{10}$ phage particles) are incubated for 1 hour at room temperature (e.g., if the target protein is an erbB2 extracellular domain (HER2) then the hu4D5-THIOMAB™ antibody-Phage); 3) the incubation with the Phage is followed by incubation with horseradish peroxidase (HRP) labeled secondary antibody (anti-M13 phage coat protein, pVIII protein antibody); 4) standard HRP reaction are carried out and the absorbance is measured at 450 nm; 5) thiol reactivity is measured by calculating the ratio between $OD_{450}$ for streptavidin/$OD_{450}$ for the target protein (e.g., HER2) such that a thiol reactivity value of 1 indicates complete biotinylation of the cysteine thiol.

Protein Expression and Purification

DNA encoding the cysteine engineered antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as E. coli cells, simian COS cells, Chinese Hamster Ovary (CHO) cells, HEK293T cells, or other mammalian host cells, such as myeloma cells (U.S. Pat. No. 5,807,715; US 2005/0048572; US 2004/0229310) that do not otherwise produce the antibody protein, to obtain the synthesis of monoclonal antibodies in the recombinant host cells. In most cases, the yields of the cysteine engineered antibodies were similar to wild type antibodies. Review articles on recombinant expression in bacteria of DNA encoding the antibody include Skerra et al (1993) Curr. Opinion in Immunol. 5:256-262 and Plückthun (1992) Immunol. Revs. 130:151-188.

After design and selection, cysteine engineered antibodies, e.g. THIOMAB™ antibodies, with highly reactive unpaired Cys residues, may be produced by: (i) expression in a bacterial, e.g. E. coli, system or a mammalian cell culture system (WO 01/00245), e.g. Chinese Hamster Ovary cells (CHO) or HEK293 cells (e.g., HEK293T cells); and (ii) purification using common protein purification techniques (Lowman et al (1991) J. Biol. Chem. 266(17):10982-10988). In specific embodiments of this invention, the THIOMAB™ antibodies were expressed in a mammalian cell expression system. In specific embodiments, the mammalian cell expression system is HEK293T cells.

THIOMAB™ antibodies are full length antibodies that include native cysteine residues that form disulfide bonds within the antibody. Accordingly, these native cysteine residues do not have any reactive thiol groups to conjugate with drug-maleimide (unless treated with a reducing agent). Hence, the newly engineered Cys residue, can remain unpaired, and able to react with, i.e. conjugate to, an electrophilic linker reagent or drug-linker intermediate, such as a drug-maleimide.

The structure positions of the engineered Cys residues of the heavy and light chains are numbered according to a sequential numbering system. This sequential numbering system is correlated to the Kabat numbering system (Kabat et al., (1991) Sequences of Proteins of Immunological Interest, 5th Ed. Public Health Service, National Institutes of Health, Bethesda, Md.) for the 4D5 antibody. Using the Kabat numbering system, the actual linear amino acid sequence of the may contain fewer or additional amino acids corresponding to a shortening of, or insertion into, a FR or CDR of the variable domain. The cysteine engineered heavy chain variant sites and light chain variant sites are identified by the sequential numbering and Kabat numbering in FIGS. 1A and 1B.

Thiol reactivity may also be generalized to certain domains of an antibody, such as the light chain constant domain (CL) and heavy chain constant domains, CH1, CH2 and CH3. Cysteine replacements resulting in thiol reactivity values of about 0.1, 0.2, 0.3, 0.4, 0.5, 0.6, 0.7, 0.8, 0.9, and 0.95 and higher may be made in the heavy chain constant domains α, δ, ε, γ, and μ of intact antibodies: IgA, IgD, IgE, IgG, and IgM, respectively, including the IgG subclasses: IgG1, IgG2, IgG3, IgG4, IgA, and IgA2.

Labelled Cysteine Engineered Antibodies

The cysteine engineered antibodies of the invention may be conjugated with any label moiety which can be covalently attached to the antibody through a reactive cysteine thiol group (Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The attached label may function to: (i) provide a detectable signal; (ii) interact with a second label to modify the detectable signal provided by the first or second label, e.g. to give FRET (fluorescence resonance energy transfer); (iii) stabilize interactions or increase affinity of binding, with antigen or ligand; (iv) affect mobility, e.g. electrophoretic mobility or cell-permeability, by charge, hydrophobicity, shape, or other physical parameters, or (v) provide a capture moiety, to modulate ligand affinity, antibody/antigen binding, or ionic complexation.

Labelled cysteine engineered antibodies may be useful in diagnostic assays, e.g., for detecting expression of an antigen of interest in specific cells, tissues, or serum. For diagnostic applications, the antibody will typically be labeled with a detectable moiety. Numerous labels are available which can be generally grouped into the following categories:

(a) Radioisotopes (radionuclides), such as $^3H$, $^{11}C$, $^{14}C$, $^{18}F$, $^{32}F$, $^{35}S$, $^{64}Cu$, $^{68}Ga$, $^{86}Y$, $^{89}Zr$, $^{99}TC$, $^{111}In$, $^{123}I$, $^{124}I$, $^{125}I$, $^{131}I$, $^{133}Xe$, $^{177}Lu$, $^{211}At$, or $^{213}Bi$. Radioisotope labelled antibodies are useful in receptor targeted imaging experiments. The antibody can be labeled with ligand reagents that bind, chelate or otherwise complex a radioisotope metal where the reagent is reactive with the engineered cysteine thiol of the antibody, using the techniques described in Current Protocols in Immunology, (1991) Volumes 1 and 2, Coligen et al, Ed. Wiley-Interscience, New York, N.Y., Pubs. Chelating ligands which may complex a metal ion include DOTA, DOTP, DOTMA, DTPA and TETA (Macrocyclics, Dallas, Tex.). Radionuclides can be targeted via complexation with the antibody-drug conjugates of the invention (Wu et al (2005) Nature Biotechnology 23(9): 1137-1146). DOTA-maleimide reagents react with the free cysteine amino acids of the cysteine engineered antibodies and provide a metal complexing ligand on the antibody (Lewis et al (1998) Bioconj. Chem. 9:72-86). Chelating linker labelling reagents such as DOTA-NHS (1,4,7,10-tetraazacyclododecane-1,4,7,10-tetraacetic acid mono (N-hydroxysuccinimide ester) are commercially available (Macrocyclics, Dallas, Tex.). Receptor target imaging with radionuclide labelled antibodies can provide a marker of pathway activation by detection and quantitation of progressive accumulation of antibodies in tumor tissue (Albert et al (1998) Bioorg. Med. Chem. Lett. 8:1207-1210).

Metal-chelate complexes suitable as antibody labels for imaging experiments (US 2010/0111856; U.S. Pat. No. 5,342,606; U.S. Pat. No. 5,428,155; U.S. Pat. No. 5,316,757; U.S. Pat. No. 5,480,990; U.S. Pat. No. 5,462,725; U.S. Pat. No. 5,428,139; U.S. Pat. No. 5,385,893; U.S. Pat. No. 5,739,294; U.S. Pat. No. 5,750,660; U.S. Pat. No. 5,834,456; Hnatowich et al (1983) J. Immunol. Methods 65:147-157; Meares et al (1984) Anal. Biochem. 142:68-78; Mirzadeh et al (1990) Bioconjugate Chem. 1:59-65; Meares et al (1990)

J. Cancer 1990, Suppl. 10:21-26; Izard et al (1992) Bioconjugate Chem. 3:346-350; Nikula et al (1995) Nucl. Med. Biol. 22:387-90; Camera et al (1993) Nucl. Med. Biol. 20:955-62; Kukis et al (1998) J. Nucl. Med. 39:2105-2110; Verel et al (2003) J. Nucl. Med. 44:1663-1670; Camera et al (1994) J. Nucl. Med. 21:640-646; Ruegg et al (1990) Cancer Res. 50:4221-4226; Verel et al (2003) J. Nucl. Med. 44:1663-1670; Lee et al (2001) Cancer Res. 61:4474-4482; Mitchell, et al (2003) J. Nucl. Med. 44:1105-1112; Kobayashi et al (1999) Bioconjugate Chem. 10:103-111; Miederer et al (2004) J. Nucl. Med. 45:129-137; DeNardo et al (1998) Clinical Cancer Research 4:2483-90; Blend et al (2003) Cancer Biotherapy & Radiopharmaceuticals 18:355-363; Nikula et al (1999) J. Nucl. Med. 40:166-76; Kobayashi et al (1998) J. Nucl. Med. 39:829-36; Mardirossian et al (1993) Nucl. Med. Biol. 20:65-74; Roselli et al (1999) Cancer Biotherapy & Radiopharmaceuticals, 14:209-20).

(b) Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to antibodies using the techniques disclosed in *Current Protocols in Immunology*, supra, for example. Fluorescent dyes and fluorescent label reagents include those which are commercially available from Invitrogen/Molecular Probes (Eugene, Oreg.) and Pierce Biotechnology, Inc. (Rockford, Ill.).

Detection labels such as fluorescent dyes and chemiluminescent dyes (Briggs et al (1997) "Synthesis of Functionalised Fluorescent Dyes and Their Coupling to Amines and Amino Acids," J. Chem. Soc., Perkin-Trans. 1:1051-1058) provide a detectable signal and are generally applicable for labelling antibodies, preferably with the following properties: (i) the labelled antibody should produce a very high signal with low background so that small quantities of antibodies can be sensitively detected in both cell-free and cell-based assays; and (ii) the labelled antibody should be photostable so that the fluorescent signal may be observed, monitored and recorded without significant photo bleaching. For applications involving cell surface binding of labelled antibody to membranes or cell surfaces, especially live cells, the labels preferably (iii) have good water-solubility to achieve effective conjugate concentration and detection sensitivity and (iv) are non-toxic to living cells so as not to disrupt the normal metabolic processes of the cells or cause premature cell death.

(c) Various enzyme-substrate labels are available or disclosed (U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al (1981) "Methods for the Preparation of Enzyme-Antibody Conjugates for use in Enzyme Immunoassay", in *Methods in Enzym*. (ed J. Langone & H. Van Vunakis), Academic Press, New York, 73:147-166.

Examples of enzyme-substrate combinations (U.S. Pat. Nos. 4,275,149 and 4,318,980) include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

A label may be indirectly conjugated with a cysteine engineered antibody. For example, the antibody can be conjugated with biotin and any of the three broad categories of labels mentioned above can be conjugated with avidin or streptavidin, or vice versa. Biotin binds selectively to streptavidin and thus, the label can be conjugated with the antibody in this indirect manner. Alternatively, to achieve indirect conjugation of the label with the polypeptide variant, the polypeptide variant is conjugated with a small hapten (e.g., digoxin) and one of the different types of labels mentioned above is conjugated with an anti-hapten polypeptide variant (e.g., anti-digoxin antibody). Thus, indirect conjugation of the label with the polypeptide variant can be achieved (Hermanson, G. (1996) in *Bioconjugate Techniques* Academic Press, San Diego).

The polypeptide variant of the present invention may be employed in any known assay method, such as ELISA, competitive binding assays, direct and indirect sandwich assays, and immunoprecipitation assays (Zola, (1987) *Monoclonal Antibodies: A Manual of Techniques*, pp. 147-158, CRC Press, Inc.).

A detection label may be useful for localizing, visualizing, and quantitating a binding or recognition event. The labelled antibodies of the invention can detect cell-surface receptors. Another use for detectably labelled antibodies is a method of bead-based immunocapture comprising conjugating a bead with a fluorescent labelled antibody and detecting a fluorescence signal upon binding of a ligand. Similar binding detection methodologies utilize the surface plasmon resonance (SPR) effect to measure and detect antibody-antigen interactions.

Labelled cysteine engineered antibodies of the invention are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Tinianow, J. et al (2010) Nuclear Medicine and Biology, 37(3):289-297; Chen et al (2004) Bioconjugate Chem. 15:41-49; US 2010/0111856 (v) bioluminescence; (vi) fluorescence; and (vii) ultrasound. Immunoscintigraphy is an imaging procedure in which antibodies labeled with radioactive substances are administered to an animal or human patient and a picture is taken of sites in the body where the antibody localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Peptide labelling methods are well known. See Haugland, 2003, *Molecular Probes Handbook of Fluorescent Probes and Research Chemicals*, Molecular Probes, Inc.; Brinkley, 1992, Bioconjugate Chem. 3:2; Garman, (1997) *Non-Radioactive Labelling: A Practical Approach*, Academic Press, London; Means (1990) Bioconjugate Chem. 1:2; Glazer et al (1975) *Chemical Modification of Proteins. Laboratory Techniques in Biochemistry and Molecular Biology* (T. S. Work and E. Work, Eds.) American Elsevier Publishing Co., New York; Lundblad, R. L. and Noyes, C. M. (1984) *Chemical Reagents for Protein Modification*, Vols. I and II, CRC Press, New York; Pfleiderer, G. (1985) "Chemical Modification of Proteins", *Modern Methods in Protein Chemistry*, H. Tscheshe, Ed., Walter DeGryter, Berlin and New York; and Wong (1991) *Chemistry of Protein Conjugation and Cross-linking*, CRC Press, Boca Raton, Fla.); De Leon-Rodriguez et al (2004) Chem. Eur. J. 10:1149-1155; Lewis et al (2001) Bioconjugate Chem. 12:320-324; Li et al (2002) Bioconjugate Chem. 13:110-115; Mier et al (2005) Bioconjugate Chem. 16:240-237.

Peptides and proteins labelled with two moieties, a fluorescent reporter and quencher in sufficient proximity undergo fluorescence resonance energy transfer (FRET). Reporter groups are typically fluorescent dyes that are excited by light at a certain wavelength and transfer energy to an acceptor, or quencher, group, with the appropriate Stokes shift for emission at maximal brightness. Fluorescent dyes include molecules with extended aromaticity, such as fluorescein and rhodamine, and their derivatives. The fluorescent reporter may be partially or significantly quenched by the quencher moiety in an intact peptide. Upon cleavage of the peptide by a peptidase or protease, a detectable increase in fluorescence may be measured (Knight, C. (1995) "Fluorimetric Assays of Proteolytic Enzymes", Methods in Enzymology, Academic Press, 248:18-34).

The labelled antibodies of the invention may also be used as an affinity purification agent. In this process, the labelled antibody is immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized polypeptide variant. Finally, the support is washed with another suitable solvent, such as glycine buffer at pH 5.0 that will release the antigen from the polypeptide variant.

Labelling reagents typically bear reactive functionality which may react (i) directly with a cysteine thiol of a cysteine engineered antibody to form the labelled antibody, (ii) with a linker reagent to form a linker-label intermediate, or (iii) with a linker antibody to form the labelled antibody. Reactive functionality of labelling reagents include: maleimide, haloacetyl, iodoacetamide succinimidyl ester (e.g. NHS, N-hydroxysuccinimide), isothiocyanate, sulfonyl chloride, 2,6-dichlorotriazinyl, pentafluorophenyl ester, and phosphoramidite, although other functional groups can also be used.

Conjugation of Linker Drugs to THIOMAB™ Antibodies

The THIOMAB™ antibodies described herein were conjugated to two different linker drugs to demonstrate the conjugation efficiency of engineered cysteines at every site within the heavy and light chains.

A cysteine residue was engineered at every position of the representative antibody Hu Anti-Her2 4D5 (the "4D5 antibody") to produce THIOMAB™ antibodies. Each THIOMAB™ antibody was separately conjugated to two linker drugs (MC-vc-PAB-MMAE and PDS-MMAE). Conjugations were performed in 96 well filter plates (volume 2 ml, PolyProplyene 0.45 um filter from EK Scientific). The plates allow aqueous buffer to flow through only upon centrifugation at 500×g for 2 min. 450 µl of MabSelect SuRe resin as 50% slurry in 20% ethanol (GE Healthcare) was added to each well. The resin was washed 3 times and equilibrated in 50 mM Tris pH 8.0, 150 mM NaCl, 2 mM EDTA (buffer A).

Each THIOMAB™ antibody (1.5 mgs) was added to each well and allowed to bind to resin for 30 min on a plate shaker at 600 RPM at RT. After 30 min the plates were centrifuged to remove excess buffer. The THIOMAB™ antibodies were reduced in the presence of 0.9 ml of 2 mM dithiothreitol in buffer A overnight with agitation at room temperature (RT). The reducing agent and any cysteine or glutathione blocks were purified away by washing with buffer A 2 times. The plates were washed 3 times with 1 ml of 1 mM dehydroascorbic acid (DHAA) in buffer A to saturate the plates with oxidizing agent. After the last addition of 0.9 ml of 1 mM DHAA in buffer A the THIOMAB™ antibodies were allow to reoxidize for 3 hrs on a plate shaker at RT.

The oxidizing agent was removed by centrifugation. A two-fold molar excess (over available thiol groups) of the linker drug (either MC-vc-PAB-MMAE or PDS-MMAE) dissolved in 10% DMA in buffer A was added to each well and incubated for 2 hrs on a plate shaker at RT with the THIOMAB™ antibodies. The excess linker drug was purified away by washing the plates 6 times with equilibration buffer. The conjugated THIOMAB™ antibodies were eluted with 0.1 M glycine buffer, pH 2.7 for 30 min on a plate shaker at RT. The THIOMAB™ antibodies were neutralized immediately with 15% of 0.5M Tris, pH 8.0. The number of drugs conjugated per mAb was quantified by LC/MS analysis. Aggregation of the conjugate was assessed by size exclusion chromatography.

Mass Spectroscopy Analysis

Liquid chromatography electrospray ionization mass spectrometric (LC-ESI-MS) analysis was employed for the accurate molecular weight determination of the conjugated THIOMAB™ antibodies (Cole, R. B. Electro Spray Ionization Mass Spectrometry: Fundamentals, Instrumentation And Applications. (1997) Wiley, New York).

LC/MS analysis was performed on a 6224 Mass Time-of-Flight (TOF) LC/MS (Agilent Technologies). Samples were chromatographed on a PRLP-S column, 1000 Å, 8 µm (50 mm×2.1 mm, Agilent Technologies) heated to 80° C. A linear gradient from 34-42% B in 3 minutes at 0.7 ml/min flow rate (solvent A, 0.05% TFA in water; solvent B, 0.04% TFA in acetonitrile) was used and the eluent was directly ionized using the electrospray source. Data was collected and deconvoluted using the Agilent Mass Hunter qualitative analysis software. The drug to antibody ratio (DAR) was calculated using the abundance of the deconvoluted peaks present in LC/MS chromatogram.

Aggregation Analysis of the THIOMAB™ Antibodies

Size exclusion chromatography was performed on 1100 series HPLC (Agilent Technologies). Samples were chromatographed on a Shodex KW 802.5 column. An isocratic method using mobile phase of 0.2M potassium phosphate, 0.25 potassium chloride, pH 6.2, at 0.75 ml/min for 15 min was used to elute the conjugate. Percent aggregation was calculated from integrated areas of aggregate and monomeric peaks from the UV 280 nm chromatogram.

Engineering of Thio IgG Variants of Trastuzumab

Cysteines were introduced into the full-length monoclonal antibody, trastuzumab (HERCEPTIN®, Genentech Inc.) at every residue in the heavy and light chains (each native, non-cysteine residue of SEQ ID NO.:1 (the 4D5 Heavy Chain) and SEQ ID NO.:2 (the 4D5 Light Chain) was mutated to a cysteine). A heavy chain of the representative 4D5 antibody has 450 amino acids: 12 cysteine residues and 438 non-cysteine residues. A light chain of the representative 4D5 antibody has 214 amino acids: 6 cysteine residues and 208 non-cysteine residues. Specifically, a single residue was mutated from its native amino acid to a cysteine, thereby resulting in a full length antibody with two engineered cysteine residues. Each cysteine mutation was conjugated to a PDS-MMAE and a MC-vc-MMAE. This resulted in a total of 648 THIOMAB™ antibodies: 648 PDS-MMAE THIOMAB™ antibodies and 648 MC-vc-MMAE THIOMAB™ antibodies. These cysteine engineered antibodies (THIOMAB™ antibodies) were expressed in HEK293T cells in media.

```
                                                  SEQ ID NO: 18
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

SEQ ID NO: 19
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

In a preferred embodiment, the THIOMAB™ antibodies comprise one or more of the heavy chain mutations according to Kabat numbering in Table 2. In a preferred embodiment, the THIOMAB™ antibodies comprise an engineered cysteine at the equivalent position as those listed in Table 2 according to the 4D5 sequence. In a preferred embodiment, the engineered cysteines identified in Table 2, or the positional equivalent engineered cysteine, in the THIOMAB™ antibodies is a free cysteine. In a preferred embodiment, the THIOMAB™ antibody comprises an engineered cysteine at position HC-A136C according to Kabat numbering (i.e., HC-A140C according to EU numbering) (see Example 11).

Figure 21:
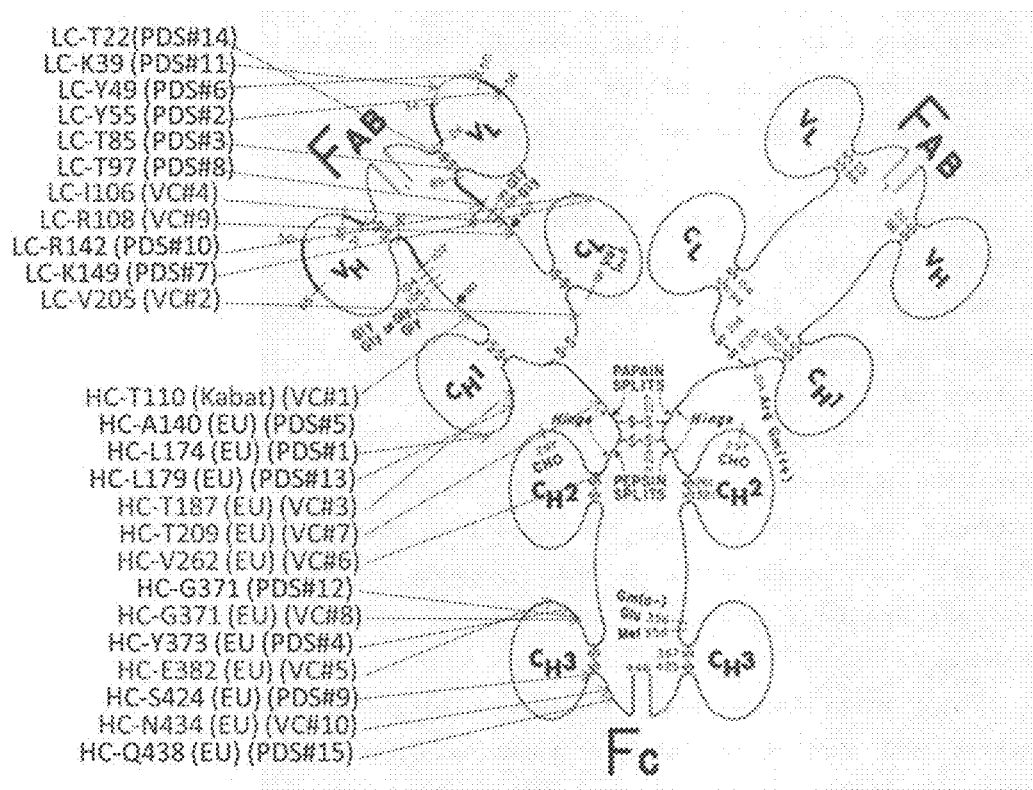
FIG. 21 shows the preferred HC and LC cysteine mutations for PDS and -vc linkers mapped to the diagram of an antibody.

In preferred embodiments, the THIOMAB™ antibodies comprise one or more of the heavy chain mutations according to EU numbering in FIG. 21. Specifically, the heavy chain cysteine mutation in the cysteine engineered antibody is selected from the group of sites consisting of HC-T110C, HC-A140C, HC-L174C, HC-L179C, HC-T187C, HC-T209C, HC-V262C, HC-G371C, HC-Y373C, HC-E382C, HC-S242C, HC-N434C, and Q438C according to EU numbering. In preferred embodiments, the THIOMAB™ antibodies comprises a cysteine engineered antibody that is conjugated to a drug moiety by a PDS linker at an engineered cysteine selected from the group consisting of HC-A140C, HC-L174C, HC-L179C, HC-G371C, HC-Y373C, HC-S424C, and HC-Q438C according to EU numbering. In preferred embodiments, the THIOMAB™ antibodies comprises a cysteine engineered antibody that is conjugated to a drug moiety by a vc-(i.e., maleimide) linker at an engineered cysteine selected from the group consisting of HC-T110C, HC-T187C, HC-T209C, HC-V262C, HC-G371C, HC-E382C, and HC-N434C.

In certain embodiments, the THIOMAB™ antibodies comprise one or more of the heavy chain mutations according to Kabat numbering in Table 3. In certain embodiments, the THIOMAB™ antibodies comprise an engineered cysteine at the equivalent position as those listed in Table 3 according to the 4D5 sequence. For example, if an antibody comprises a native alanine (A) at position 5 according to Kabat numbering in its heavy chain (as compared to the native valine (V) in 4D5), the alanine can be mutated to a cysteine to yield a HC-A5C THIOMAB™ antibody. In certain embodiments, the engineered cysteines identified in Table 3, or the positional equivalent engineered cysteine, in the THIOMAB™ antibodies is a free cysteine.

TABLE 3

Heavy Chain Cysteine Mutations According to Kabat Numbering.

| HC Mutant | Sequence | SEQ ID NO |
|---|---|---|
| V2C | ECQLVESGGGL | SEQ ID NO: 20 |
| L4C | EVQCVESGGGL | SEQ ID NO: 21 |
| V5C | EVQLCESGGGL | SEQ ID NO: 22 |
| L11C | ESGGGCVQPGG | SEQ ID NO: 23 |
| R19C | PGGSLCLSCAA | SEQ ID NO: 24 |
| F27C | CAASGCNIKDT | SEQ ID NO: 25 |
| I29C | ASGFNCKDTYI | SEQ ID NO: 26 |
| T32C | FNIKDCYIHWV | SEQ ID NO: 27 |
| Y33C | NIKDTCIHWVR | SEQ ID NO: 28 |
| Q39C | IHWVRCAPGKG | SEQ ID NO: 29 |

TABLE 3-continued

Heavy Chain Cysteine Mutations According to Kabat Numbering.

| HC Mutant | Sequence | SEQ ID NO |
|---|---|---|
| A40C | HWVRQCPGKGL | SEQ ID NO: 30 |
| K43C | RQAPGCGLEWV | SEQ ID NO: 31 |
| L45C | APGKGCEWVAR | SEQ ID NO: 32 |
| E46C | GKGLCWVARI | SEQ ID NO: 33 |
| T53C | ARIYPCNGYTR | SEQ ID NO: 34 |
| G55C | IYPTNCYTRYA | SEQ ID NO: 35 |
| T57C | PTNGYCRYADS | SEQ ID NO: 36 |
| R58C | TNGYTCYADSV | SEQ ID NO: 37 |
| Y59C | NGYTRCADSVK | SEQ ID NO: 38 |
| A60C | GYTRYCDSVKG | SEQ ID NO: 39 |
| T68C | VKGRFCISADT | SEQ ID NO: 40 |
| N76N | ADTSKCTAYLQ | SEQ ID NO: 41 |
| Y79C | SKNTACLQMNS | SEQ ID NO: 42 |
| Q81C | NTAYLCMNSLR | SEQ ID NO: 43 |
| W95C | YYCSRCGGDGF | SEQ ID NO: 44 |
| G96C | YCSRWCGDGFY | SEQ ID NO: 45 |
| D101C | GFYAMCYWGQG | SEQ ID NO: 46 |
| W103C | YAMDYCGQGTL | SEQ ID NO: 47 |
| T116C | VASASCKGPSV | SEQ ID NO: 48 |
| K117C | SSASTCGPSVF | SEQ ID NO: 49 |
| T135C | STSGGCAALGC | SEQ ID NO: 50 |
| N155C | VTVSWCSGALT | SEQ ID NO: 51 |
| A158C | SWNSGCLTSGV | SEQ ID NO: 52 |
| G162C | GALTSCVHTFP | SEQ ID NO: 53 |
| G174C | VLQSSCLYSLS | SEQ ID NO: 54 |
| L175C | LQSSGCYSLSS | SEQ ID NO: 55 |
| T183C | LSSVVCVPSSS | SEQ ID NO: 56 |
| V184C | SSVVTCPSSSL | SEQ ID NO: 57 |
| I195C | GTQTYCCNVNH | SEQ ID NO: 58 |
| N199C | YICNVCHKPSN | SEQ ID NO: 59 |
| S203C | VNHKPCNTKVD | SEQ ID NO: 60 |
| F239C | PSVFLCPPKPK | SEQ ID NO: 61 |
| M248C | PKDTLCISRTP | SEQ ID NO: 62 |
| E254C | ISRTPCVTCVV | SEQ ID NO: 63 |
| V258C | PEVTCCVVDVS | SEQ ID NO: 64 |
| N272C | PEVKFCWYVDG | SEQ ID NO: 65 |
| V278C | WYVDGCEVHNA | SEQ ID NO: 66 |
| L305C | SVLTVCHQDWL | SEQ ID NO: 67 |
| T331C | APIEKCISKAK | SEQ ID NO: 68 |
| S333C | IEKTICKAKGQ | SEQ ID NO: 69 |
| R340C | AKGQPCEPQVY | SEQ ID NO: 70 |
| Q343C | QPREPCVYTLP | SEQ ID NO: 71 |
| K356C | RDELTCNQVSL | SEQ ID NO: 72 |
| E384C | SNGQPCNNYKT | SEQ ID NO: 73 |
| S399C | LDSDGCFFLYS | SEQ ID NO: 74 |
| K410C | KLTVDCSRWQQ | SEQ ID NO: 75 |
| Q414C | DKSRWCQGNVF | SEQ ID NO: 76 |
| G416C | SRWQQCNVFSC | SEQ ID NO: 77 |
| N417C | RWQQGCVFSCS | SEQ ID NO: 78 |
| Y432C | ALHNHCTQKSL | SEQ ID NO: 79 |
| T433C | LHNHYCQKSLS | SEQ ID NO: 80 |
| K435C | NHYTQCSLSLS | SEQ ID NO: 81 |
| S438 | TQKSLCLSPGK | SEQ ID NO: 82 |
| L439C | QKSLSCSPGK | SEQ ID NO: 83 |
| M100cC | DGFYACDYWGQ | SEQ ID NO: 84 |
| N82aC | AYLQMCSLRAE | SEQ ID NO: 85 |

In certain embodiments, the THIOMAB™ antibodies comprise a sequence listed in Table 3. In certain embodiments, the THIOMAB™ antibodies with mutations and/or sequences listed in Table 3 comprise a PDS linker. In certain embodiments, the THIOMAB™ antibodies with mutations and/or sequences listed in Table 3 comprise a maleimide (e.g. –vc) linker. In specific embodiments, a heavy chain site (according to Kabat numbering) is mutated to a cysteine, selected from the following group, to form a cysteine engineered antibody and linked to a drug using a PDS linker: V2C, T29C, Y30C, A37C, E43C, Y77C, W96C, G97C, D105C, T139C, N159C, A162C, G166C, G178C, L179C, V188C, I199C, N203C, S207C, E388C, K414C, Q418C, S242C, Y436C, T437C, Q438C, L443C, and M104C. In specific embodiments, a heavy chain site (according to Kabat numbering) is mutated to a cysteine, selected from the following group, to form a cysteine engineered antibody and linked to a drug using a –vc (i.e., maleimide) linker: V2C, L1C, V2C, LBC, R16C, F24C, I26C, Y30C, Q36C, A37C, K40C, L42C, E43C, T51C, G53C, T55C, R56C, Y57C, A58C, T66C, N74C, Q79C, W107C, T120C, K121C, A140C, G166C, G178C, T187C, I199C, T209C, F243C, M252C, E258C, V262C, N276C, V282C, L309C, T335C, S337C, R344C, Q347C, K360C, G371C, E382C, P387C, E388C, S403C, K414C, Q418C, G420C, N421C, S424C, N434C, Y436C, T437C, Q438C, K439C, S442C, L443C, M104C, and N81C.

In specific embodiments, the cysteine engineered antibodies that comprise a heavy chain cysteine mutation selected from the mutations listed in Table 2 have an average DAR between 1.0 and 2.0 using the Affinity-Capture LC-MS Assays for Stability Determination Assay described herein (see Examples 12 and 13). In specific embodiments, the cysteine engineered antibodies that comprise a heavy chain cysteine mutation selected from the mutations listed in Table 2 have an average DAR between 1.1 and 1.3. In specific embodiments, the cysteine engineered antibodies that comprise a heavy chain cysteine mutation selected from the mutations listed in Table 2 have an average DAR between 1.3 and 1.5. In specific embodiments, the THIOMAB™ antibodies with a cysteine mutation selected from the list in Table 1 has an average DAR between 1.5 and 1.8. In specific embodiments, the cysteine engineered antibodies that comprise a heavy chain cysteine mutation selected from the mutations listed in Table 2 have an average DAR between 1.8 and 2.0.

In a preferred embodiment, the cysteine engineered antibodies comprise one or more of the heavy chain mutations according to Kabat numbering in Table 2. In a preferred embodiment, the cysteine engineered antibodies comprise an engineered cysteine at the equivalent position as those listed in Table 2 according to the 4D5 sequence. For example, if an antibody comprises a native lysine (K) at position 19 according to Kabat numbering in its heavy chain (as compared to the native arginine (R) in 4D5), the lysine can be mutated to a cysteine to yield a K19C THIOMAB™ antibody. In a preferred embodiment, the engineered cysteines identified in Table 2, or the positional equivalent engineered cysteine, in the THIOMAB™ antibodies is a free cysteine.

TABLE 4

Light Chain Cysteine Mutations According to Kabat Numbering.

| LC Mutant | Sequence | SEQ ID NO: |
|---|---|---|
| S12C | SPSSLCASVGD | SEQ ID NO: 86 |
| S14C | SSLSACVGDRV | SEQ ID NO: 87 |
| G16C | LSASVCDRVTI | SEQ ID NO: 88 |
| R18C | ASVGDCVTITC | SEQ ID NO: 89 |
| T22C | DRVTICCRASQ | SEQ ID NO: 90 |
| R24C | VTITCCASQDV | SEQ ID NO: 91 |
| Q27C | TCRASCDVNTA | SEQ ID NO: 92 |
| T31C | SQDVNCAVAWY | SEQ ID NO: 93 |
| A32C | QDVNTCVAWYQ | SEQ ID NO: 94 |
| Q38C | VAWYQCKPGKA | SEQ ID NO: 95 |
| K39C | AWYQQCPGKAP | SEQ ID NO: 96 |
| G41C | YQQKPCKAPKL | SEQ ID NO: 97 |
| K42C | QQKPGCAPKLL | SEQ ID NO: 98 |
| P44C | KPGKACKLLIY | SEQ ID NO: 99 |
| Y49C | PKLLICSASFL | SEQ ID NO: 100 |
| S50C | KLLIYCASFLY | SEQ ID NO: 101 |
| S52C | LIYSACFLYSG | SEQ ID NO: 102 |
| F53C | IYSASCLYSGV | SEQ ID NO: 103 |

TABLE 4-continued

Light Chain Cysteine Mutations According to Kabat Numbering.

| LC Mutant | Sequence | SEQ ID NO: |
|---|---|---|
| L54C | YSASFCYSGVP | SEQ ID NO: 104 |
| Y55C | SASFLCSGVPS | SEQ ID NO: 105 |
| S63C | VPSRFCGSRSG | SEQ ID NO: 106 |
| G64C | PSRFSCSRSGT | SEQ ID NO: 107 |
| R66C | RFSGSCSGTDF | SEQ ID NO: 108 |
| D70C | SRSGTCFTLTI | SEQ ID NO: 109 |
| T72C | SGTDFCLTISS | SEQ ID NO: 110 |
| T74C | TDFTLCISSLQ | SEQ ID NO: 111 |
| S76C | FTLTICSLQPE | SEQ ID NO: 112 |
| Q79C | TISSLCPEDFA | SEQ ID NO: 113 |
| T85C | PEDFACYYCQQ | SEQ ID NO: 114 |
| H91C | YYCQQCYTTPP | SEQ ID NO: 115 |
| Y92C | YCQQHCTTPPT | SEQ ID NO: 116 |
| P95C | QHYTTCPTFGQ | SEQ ID NO: 117 |
| T97C | YTTPPCFGQGT | SEQ ID NO: 118 |
| F98C | TTPPTCGQGTK | SEQ ID NO: 119 |
| K103C | FGQGTCVEIKR | SEQ ID NO: 120 |
| E105C | QGTKVCIKRTV | SEQ ID NO: 121 |
| K107C | TKVEICRTVAA | SEQ ID NO: 122 |
| P119C | SVFIFCPSDEQ | SEQ ID NO: 123 |
| K126C | SDEQLCSGTAS | SEQ ID NO: 124 |
| T129C | QLKSGCASVVC | SEQ ID NO: 125 |
| S131C | KSGTACVVCLL | SEQ ID NO: 126 |
| Q147C | REAKVCWKVDN | SEQ ID NO: 127 |
| W148C | EAKVQCKVDNA | SEQ ID NO: 128 |
| A153C | WKVDNCLQSGN | SEQ ID NO: 129 |
| Q155C | VDNALCSGNSQ | SEQ ID NO: 130 |
| S156C | DNALQCGNSQE | SEQ ID NO: 131 |
| S159C | LQSGNCQESVT | SEQ ID NO: 132 |
| Q160C | QSGNSCESVTE | SEQ ID NO: 133 |
| S162C | GNSQECVTEQD | SEQ ID NO: 134 |
| Q166C | ESVTECDSKDS | SEQ ID NO: 135 |
| T172C | DSKDSCYSLSS | SEQ ID NO: 136 |
| T180C | LSSTLCLSKAD | SEQ ID NO: 137 |
| V191C | YEKHKCYACEV | SEQ ID NO: 138 |
| A193C | KHKVYCCEVTH | SEQ ID NO: 139 |
| E195C | KVYACCVTHQG | SEQ ID NO: 140 |
| V205C | GLSSPCTKSFN | SEQ ID NO: 141 |

TABLE 4-continued

Light Chain Cysteine Mutations According to Kabat Numbering.

| LC Mutant | Sequence | SEQ ID NO: |
|---|---|---|
| T206C | LSSPVCKSFNR | SEQ ID NO: 142 |
| N210C | PVTKSFCRGEC | SEQ ID NO: 143 |

In a preferred embodiment, the THIOMAB™ antibodies comprise one or more of the light chain mutations according to Kabat numbering in Table 1. In a preferred embodiment, the THIOMAB™ antibodies comprise an engineered cysteine at the equivalent position as those listed in Table 1 according to the 4D5 sequence. In a preferred embodiment, the engineered cysteines identified in Table 1, or the positional equivalent engineered cysteine, in the THIOMAB™ antibodies is a free cysteine. In a preferred embodiment, the THIOMAB™ antibody comprises an engineered cysteine at position LC-K149C according to Kabat numbering (see Examples 2 and 7). In preferred embodiment the LC-K149C antibody is conjugated to a drug moiety via a PDS linker. In preferred embodiment the LC-K149C antibody is conjugated to a drug moiety via a –vc (i.e., maleimide) linker.

In certain embodiments, the THIOMAB™ antibodies comprise one or more of the light chain mutations according to Kabat numbering in FIG. 21. Specifically, the light chain cysteine mutation in the cysteine engineered antibody is selected from the group of sites consisting of LC-T22C, LC-K39C, LC-Y49C, LC-Y55C, LC-T85C, LC-T97C, LC-I106C, LC-R108C, LC-R142C, LC-K149C, and LC-V205C according to Kabat numbering. In preferred embodiments, the THIOMAB™ antibodies comprises a cysteine engineered antibody that is conjugated to a drug moiety by a PDS linker at an engineered cysteine selected from the group consisting of LC-I106C, LC-R108C, and LC-V205C according to Kabat numbering. In preferred embodiments, the THIOMAB™ antibodies comprises a cysteine engineered antibody that is conjugated to a drug moiety by a vc- (i.e., maleimide) linker at an engineered cysteine selected from the group consisting of LC-T22C, LC-K39C, LC-Y49C, LC-Y55C, LC-T85C, LC-T97C, LC-R142C, and LC-K149C according to Kabat numbering.

In specific embodiments, the cysteine engineered antibodies that comprise a light chain cysteine mutation selected from the mutations listed in Table 1 have an average DAR between 1.0 and 2.0 using the Affinity-Capture LC-MS Assays for Stability Determination Assay described herein (see Examples 12 and 13). In specific embodiments, the cysteine engineered antibodies that comprise a light chain cysteine mutation selected from the mutations listed in Table 1 have an average DAR between 1.1 and 1.3. In specific embodiments, the cysteine engineered antibodies that comprise a light chain cysteine mutation selected from the mutations listed in Table 1 have an average DAR between 1.3 and 1.5. In specific embodiments, the cysteine engineered antibodies with a cysteine mutation selected from the list in Table 1 has an average DAR between 1.5 and 1.8. In specific embodiments, the cysteine engineered antibodies that comprise a heavy chain cysteine mutation selected from the mutations listed in Table 1 have an average DAR between 1.8 and 2.0. In specific embodiments, the cysteine engineered antibodies that comprise a heavy chain cysteine mutation selected from the mutations listed in Table 1 have an average DAR between 0.8 and 1.4.

In preferred embodiments, the THIOMAB™ antibodies comprise a sequence listed in Table 1. In preferred embodiments, the THIOMAB™ antibodies with mutations and/or sequences listed in Table 1 comprise a PDS linker. In preferred embodiments, the THIOMAB™ antibodies with mutations and/or sequences listed in Table 1 comprise a –vc linker.

In certain embodiments, the THIOMAB™ antibodies comprise a sequence listed in Table 4. In certain embodiments, the THIOMAB™ antibodies with mutations and/or sequences listed in Table 4 comprise a PDS linker. In certain embodiments, the THIOMAB™ antibodies with mutations and/or sequences listed in Table 4 comprise a –vc linker.

In certain embodiments, the cysteine engineered antibodies that comprise a light chain cysteine mutation selected from the mutations listed in Table 4 have an average DAR between 1.0 and 2.0 using the Affinity-Capture LC-MS Assays for Stability Determination Assay described herein (see Examples 12 and 13). In specific embodiments, the THIOMAB™ antibodies with a cysteine mutation selected from the list in Table 4 has an average DAR between 1.3 and 1.9. In specific embodiments, the THIOMAB™ antibodies with a cysteine mutation selected from the list in Table 4 has an average DAR between 1.3 and 1.8. In specific embodiments, the THIOMAB™ antibodies with a cysteine mutation selected from the list in Table 4 has an average DAR between 1.5 and 1.9. In specific embodiments, the THIOMAB™ antibodies with a cysteine mutation selected from the list in Table 4 has an average DAR between 0.8 and 1.0.

In preferred embodiments, the THIOMAB™ antibodies comprise one or more of the light chain mutations according to EU numbering in FIG. 21. Specifically, the light chain cysteine mutation in the cysteine engineered antibody is selected from the group of sites consisting of LC-T22C, LC-K39C, LC-Y49C, LC-Y55C, LC-T85C, LC-T97C, LC-I106C, LC-R108C, LC-R142C, LC-K149C, and LC-V205C according to EU numbering. In preferred embodiments, the THIOMAB™ antibodies comprises a cysteine engineered antibody that is conjugated to a drug moiety by a PDS linker at an engineered cysteine selected from the group consisting of LC-T22C, LC-K39C, LC-Y49C, LC-Y55C, LC-T85C, LC-T97C, LC-R142C, and LC-K149C according to EU numbering. In preferred embodiments, the THIOMAB™ antibodies comprises a cysteine engineered antibody that is conjugated to a drug moiety by a vc-(i.e., maleimide) linker at an engineered cysteine selected from the group consisting of LC-I106C, LC-R108C, and LC-V205C.

In a certain embodiments, the THIOMAB™ antibodies comprise a sequence listed in Table 5. In a certain embodiment, the THIOMAB™ antibodies comprise an engineered cysteine at the equivalent position as those listed in Table 5 according to the 4D5 sequence. For example, if an antibody comprises a native serine (S) at position 40 according to Kabat numbering in its heavy chain (as compared to the native Alanine (A) in 4D5), the serine can be mutated to a cysteine to yield a S40C THIOMAB™ antibody. In a certain embodiment, the engineered cysteines identified in Table 5, or the positional equivalent engineered cysteine, in the THIOMAB™ antibodies are free cysteines.

TABLE 5

Heavy Chain and Light Chain Cysteine Mutations According to Kabat Numbering.

| Mutant | Sequence | SEQ ID NO |
|---|---|---|
| HC-I195C | GTQTYCCNVNH | SEQ ID NO: 58 |
| HC-S420C | QGNVFCCSVMH | SEQ ID NO: 15 |
| HC-Y432C | ALHNHCTQKSL | SEQ ID NO: 79 |
| LC-G64C | PSRFSCSRSGT | SEQ ID NO: 107 |

In certain embodiments, the THIOMAB™ antibodies comprise a sequence listed in Table 5. In certain embodiments, the THIOMAB™ antibodies with mutations and/or sequences listed in Table 5 comprise a –vc or PDS linker.

In specific embodiments, the THIOMAB™ antibodies with a cysteine mutation selected from the list in Table 5 has an average DAR between 1.0 and 2.0. In specific embodiments, the THIOMAB™ antibodies with a cysteine mutation selected from the list in Table 5 has an average DAR between 1.3 and 1.9. In specific embodiments, the THIOMAB™ antibodies with a cysteine mutation selected from the list in Table 5 has an average DAR between 1.3 and 1.8. In specific embodiments, the THIOMAB™ antibodies with a cysteine mutation selected from the list in Table 5 has an average DAR between 1.5 and 1.9.

According to another embodiment, the THIOMAB™ antibodies comprise an engineered cysteine identified in any one of Tables 1-5. In the preferred embodiment, the THIOMAB™ antibodies comprise an engineered cysteine identified in any one of Tables 1 and 2. According to another embodiment, the THIOMAB™ antibodies can be designed for any target antigen.

THIOMAB™ Antibody Design and Engineering

Single cysteine substitutions were introduced into each position of the heavy chain and light chain of the anti-HER2 hu4D5 antibody (i.e., a total of 648 antibodies with PDS linkers and a total of 648 antibodies with –vc linkers were made) (Example 1). Single cysteine substitutions were also introduced into select positions of anti-CD33 antibodies, anti-STEAP1 antibodies, anti-MUC16 antibodies, anti-NaPi2b antibodies, anti-Ly6E antibodies, anti-CD22 antibodies, anti-CD79b antibodies, anti-B7H4 antibodies, and additional anti-HER2 antibodies. All of the heavy chain mutants and light chain mutants were prepared according to the methods described herein. Heavy chain and light chain sequences are numbered according to the Kabat numbering system. The positional equivalent according to sequential numbering and EU numbering of each Kabat position is provided in FIGS. 1A and 1B. In the light chain, both Kabat, Sequential, and EU numbering denotes same numbers.

The heavy and light chain 4D5 THIOMAB™ antibodies were conjugated to a drug via a PDS or a vc linker (i.e., a total of 648 antibodies with PDS linkers and a total of 648 antibodies with –vc linkers were made). Each THIOMAB™ antibody was screened for average drug-antibody ratio (DAR), concentration (mg/mL), aggregation (% total), and stability (Example 2). Accordingly, each THIOMAB™ antibody had DAR, concentration, aggregation, and stability measurements for the PDS and vc conjugates. The PDS conjugates and measurements are provided in the tables provided herein and the vc conjugates and measurements are provided in the tables provided herein.

TABLE 6

Average DAR, concentration, aggregation, and stability (ELISA Rat Plasma Stability) of the cysteine engineered antibodies of Tables 3 and 4 conjugated with a PDS-linker

| Cysteine Mutation (HC/LC) | Residue | Kabat Mutation Site # | Average DAR | Source Conc. (mg/mL) | % Aggregation | Stability n = 1 | Stability n = 2 | Average Stability |
|---|---|---|---|---|---|---|---|---|
| HC | V | 5 | 1.5 | 1.99 | 12.5 | 84.41 | 94.37 | 89.39 |
| HC | V | 5 | 1.6 | 1.97 | 12.0 | 82.32 | 71.05 | 76.68 |
| HC | V | 5 | 1.6 | 3.1 | 11.6 | 79.19 | 88.69 | 83.94 |
| HC | T | 32 | 1.0 | 2.70 | 9.7 | 93.02 | 93.14 | 93.08 |
| HC | Y | 33 | 1.6 | 3.25 | 11 | 98.70 | 99.68 | 99.19 |
| HC | A | 40 | 1.8 | 3.15 | 11.8 | 81.27 | 89.31 | 85.29 |
| HC | E | 46 | 1.5 | 2.23 | 12.7 | 73.60 | 75.15 | 74.38 |
| HC | Y | 79 | 1.2 | 3.92 | 11.8 | 96.74 | 96.98 | 96.86 |
| HC | Y | 79 | 1.8 | 2.53 | 22.2 | 87.47 | 98.94 | 93.20 |
| HC | W | 95 | 1.5 | 1.75 | 12.3 | 71.34 | 104.21 | 87.77 |
| HC | G | 96 | 1.8 | 1.91 | 29.9 | 96.44 | 107.22 | 101.83 |
| HC | D | 101 | 1.7 | 2.22 | 10.2 | 108.58 | 109.95 | 109.26 |
| HC | T | 135 | 1.7 | 1.48 | 27 | 73.48 | 89.94 | 81.71 |
| HC | A | 136 | 1.3 | 1.23 | 5.2 | 80.27 | 76.38 | 78.33 |
| HC | N | 155 | 1.3 | 2.19 | 13.8 | 79.61 | 78.51 | 79.06 |
| HC | A | 158 | 1.3 | 0.99 | 16.9 | 9.97 | 3.49 | 6.73 |
| HC | G | 162 | 1.8 | 2.07 | 10.7 | 95.76 | 77.92 | 86.84 |
| HC | L | 170 | 1.5 | 1.50 | 9.2 | 86.56 | 75.80 | 81.18 |
| HC | G | 174 | 1.9 | 1.55 | 6.5 | 82.85 | 90.34 | 86.60 |
| HC | L | 175 | 1.8 | 2.20 | 8.4 | 95.31 | 87.15 | 91.23 |
| HC | V | 184 | 1.4 | 2.62 | 7.2 | 92.11 | 95.77 | 93.94 |
| HC | I | 195 | 1.4 | 1.3 | 8.9 | 114.73 | 125.84 | 120.28 |
| HC | N | 199 | 1.4 | 1.6703 | 14.2 | 74.08 | 91.72 | 82.90 |
| HC | S | 203 | 1.5 | 1.67 | 22.5 | 77.40 | 102.58 | 89.99 |
| HC | T | 205 | 1.3 | 2.6 | 12.9 | 92.25 | 85.88 | 89.06 |
| HC | G | 367 | 1.3 | 2.60 | 22.9 | 73.82 | 94.73 | 84.28 |
| HC | Y | 369 | 1.4 | 2.56 | 21.7 | 96.19 | 86.04 | 91.11 |
| HC | E | 384 | 1.1 | 2.03 | 10.7 | 130.85 | 101.76 | 116.30 |
| HC | K | 410 | 1.2 | 1.98 | 30.1 | 93.74 | 86.50 | 90.12 |
| HC | K | 410 | 1.1 | 2.44 | 30.1 | 97.37 | 111.22 | 104.30 |
| HC | Q | 414 | 1.5 | 1.30 | 18.9 | 89.83 | 65.18 | 77.50 |

TABLE 6-continued

Average DAR, concentration, aggregation, and stability (ELISA Rat Plasma Stability) of the cysteine engineered antibodies of Tables 3 and 4 conjugated with a PDS-linker

| Cysteine Mutation (HC/LC) | Residue | Kabat Mutation Site # | Average DAR | Source Conc. (mg/mL) | % Aggregation | Stability n = 1 | Stability n = 2 | Average Stability |
|---|---|---|---|---|---|---|---|---|
| HC | S | 420 | 1.0 | 3.81 | 12.3 | 123.15 | 104.60 | 113.87 |
| HC | Y | 432 | 1.6 | 2.52 | 12.9 | 119.35 | 95.87 | 107.61 |
| HC | T | 433 | 1.2 | 1.49 | 8.7 | 96.98 | 83.67 | 90.33 |
| HC | Q | 434 | 1.5 | 1.05 | 15.3 | 123.91 | 99.85 | 111.88 |
| HC | L | 439 | 1.2 | 1.61 | 12.4 | 88.71 | 89.02 | 88.86 |
| HC | M | 100C | 1.7 | 2.35 | 12.3 | 170.78 | 204.19 | 187.49 |
| LC | S | 12 | 1.5 | 1.5 | 5.8 | 94.75 | 86.30 | 90.52 |
| LC | T | 22 | 1.7 | 1.3 | 8.9 | 125.21 | 101.52 | 113.37 |
| LC | R | 24 | 1.3 | 1.9 | 12.4 | 63.01 | 75.67 | 69.34 |
| LC | A | 32 | 1.8 | 2.3 | 8.9 | 274.10 | 259.77 | 266.94 |
| LC | Q | 38 |  | 1.7 | 6.1 | 77.11 | 62.89 | 70.00 |
| LC | K | 39 | 1.3 | 2.6 | 3.3 | 109.23 | 113.47 | 111.35 |
| LC | G | 41 | 1.6 | 2.9 | 7.2 | 65.85 | 75.39 | 70.62 |
| LC | K | 42 |  | 1.3 | 11.4 | 141.46 | 95.69 | 118.58 |
| LC | K | 42 | 1.4 | 2.2 | 6.5 | 89.87 | 94.81 | 92.34 |
| LC | P | 44 |  | 1.4 | 3.7 | 264.11 | 195.14 | 229.63 |
| LC | Y | 49 | 1.8 | 1.9 | 5.2 | 100.72 | 160.34 | 130.53 |
| LC | S | 50 | 1.7 | 1.3 | 23.1 | 399.27 | 359.73 | 379.50 |
| LC | F | 53 | 1.6 | 3.04 | 22.2 | 88.94 | 95.53 | 92.23 |
| LC | Y | 55 | 1.1 | 1.8 | 6.8 | 88.98 | 100.53 | 94.75 |
| LC | G | 64 | 1.2 | 1.74 | 5 | 113.57 | 92.47 | 103.02 |
| LC | T | 72 | 1.6 | 3.15 | 8.2 | 107.26 | 112.28 | 109.77 |
| LC | T | 74 | 1.6 | 1.77 | 5.8 | 82.49 | 101.90 | 92.20 |
| LC | Q | 79 | 1.5 | 1.51 | 9.3 | 111.51 | 78.50 | 95.01 |
| LC | T | 85 | 1.4 | 3.12 | 3.3 | 88.64 | 96.98 | 92.81 |
| LC | Y | 92 |  | 1.3 | 5.4 | 89.08 | 65.80 | 77.44 |
| LC | Y | 92 | 1.6 | 1.8 | 13.3 | 91.23 | 109.13 | 100.18 |
| LC | T | 97 | 1.6 | 1.54 | 5.6 | 85.23 | 121.61 | 103.42 |
| LC | K | 103 | 1.5 | 1.64 | 3.5 | 90.88 | 104.15 | 97.51 |
| LC | E | 105 | 1.6 | 1.68 | 3.9 | 100.07 | 94.60 | 97.34 |
| LC | T | 129 | 1.7 | 3.30 | 6.9 | 84.25 | 91.76 | 88.01 |
| LC | S | 131 |  | 1.7 | 47.2 | 159.03 | 98.79 | 128.91 |
| LC | R | 142 | 1.3 | 2.15 | 4.2 | 107.21 | 106.06 | 106.64 |
| LC | Q | 147 | 1.5 | 1.73 | 5 | 113.44 | 119.40 | 116.42 |
| LC | K | 149 | 0.8 | 2.5385 | 8.8 | 103.50 | 93.64 | 98.57 |
| LC | K | 149 | 0.8 | 2.8358 | 9.5 | 81.74 | 102.87 | 92.30 |
| LC | Q | 155 | 1.6 | 1.71 | 7.3 | 103.00 | 114.55 | 108.78 |
| LC | S | 159 | 1.3 | 2.06 | 5.3 | 93.50 | 98.33 | 95.92 |
| LC | Q | 160 | 1.6 | 1.71 | 5.7 | 87.04 | 69.93 | 78.48 |
| LC | Q | 166 | 1.3 | 1.58 | 6.2 | 82.32 | 98.19 | 90.25 |
| LC | T | 172 | 1.3 | 1.44 | 3.6 | 85.21 | 99.12 | 92.16 |
| LC | T | 180 | 1.6 | 2.90 | 8 | 80.46 | 81.38 | 80.92 |
| LC | V | 191 | 1.3 | 1.55 | 4.5 | 70.97 | 84.90 | 77.93 |
| LC | A | 193 | 1.7 | 1.52 | 4.2 | 76.67 | 75.64 | 76.16 |
| LC | E | 195 | 1.4 | 1.82 | 4.5 | 94.41 | 94.46 | 94.44 |
| LC | V | 205 | 1.6 | 2.31 | 5.1 | 94.20 | 93.69 | 93.94 |
| LC | V | 205 | 1.6 | 2.00 | 5.4 | 85.61 | 101.00 | 93.30 |
| LC | V | 205 | 1.4 | 2.80 | 3.3 | 102.06 | 93.59 | 97.83 |
| LC | V | 205 | 1.5 | 2.10 | 3.5 | 102.25 | 109.87 | 106.06 |
| LC | V | 205 | 1.6 | 2.33 | 3.9 | 93.82 | 106.76 | 100.29 |
| LC | V | 205 | 1.5 | 1.40 | 3.8 | 87.50 | 97.07 | 92.29 |
| LC | V | 205 | 1.5 | 1.95 | 3.8 | 85.21 | 92.34 | 88.78 |
| LC | V | 205 | 1.5 | 2.06 | 2.3 | 130.35 | 113.50 | 121.93 |
| LC | V | 205 | 1.2 | 2.06 | 19.8 | 101.78 | 111.46 | 106.62 |
| LC | V | 205 | 1.4 | 1.85 | 3.2 | 98.53 | 84.81 | 91.67 |
| LC | V | 205 | 1.6 | 2.4 | 4.6 | 104.46 | 108.69 | 106.58 |
| LC | V | 205 | 0.9 | 2.4714 | 4.4 | 104.63 | 109.96 | 107.30 |
| LC | T | 206 | 1.1 | 1.78 | 5.6 | 90.29 | 117.35 | 103.82 |
| LC | N | 210 |  | 1.87 |  | 100.95 | 100.00 | 100.47 |

TABLE 7

Average DAR, concentration, aggregation, and stability (Mass Spec Rat Plasma Stability)
of the cysteine engineered antibodies of Tables 3 and 4 conjugated with a PDS-linker

| Cysteine Mutation (HC/LC) | Residue | Kabat Mutation Site # | Calculated DAR at 0 hrs (BCP) | Calculated DAR at 48 hrs (BCP) | Calculated DAR at 96 hrs (BCP) | % DAR @ 96 hr relative to Assigned DAR | % DAR @ 96 hrs relative to DAR @ 0 hr |
|---|---|---|---|---|---|---|---|
| HC | V | 5 | 1.84 | 1.55 | 1.45 | 94.45 | 78.96 |
| HC | V | 5 | 1.89 | 1.43 | 1.23 | 75.97 | 65.16 |
| HC | V | 5 | 1.73 | 1.55 | 1.31 | 82.41 | 75.63 |
| HC | T | 32 | 0.54 | 0.71 | 0.70 | 70.42 | 131.06 |
| HC | Y | 33 | 1.55 | 1.35 | 0.63 | 38.16 | 40.49 |
| HC | A | 40 | 1.80 | 1.60 | 1.28 | 72.19 | 70.83 |
| HC | E | 46 | 1.58 | 0.87 | 0.62 | 41.25 | 39.21 |
| HC | Y | 79 | n/a | 1.43 | 0.90 | 75.16 | n/a |
| HC | Y | 79 | 1.80 | 1.23 | 0.69 | 39.70 | 38.60 |
| HC | W | 95 | 0.58 | 0.59 | 0.75 | 49.34 | |
| HC | G | 96 | 1.89 | 1.56 | 0.93 | 52.14 | 49.41 |
| HC | D | 101 | 1.69 | 1.75 | 1.60 | 92.49 | 94.88 |
| HC | T | 135 | 1.67 | 1.48 | 1.17 | 70.71 | 70.00 |
| HC | A | 136 | 1.50 | 1.79 | 1.71 | 132.89 | 114.29 |
| HC | N | 155 | 1.42 | 1.10 | 0.93 | 69.82 | 65.55 |
| HC | A | 158 | 1.57 | 0.00 | 0.00 | 0.00 | 0.00 |
| HC | G | 162 | 1.77 | 1.51 | 1.22 | 68.37 | 69.24 |
| HC | L | 170 | 1.46 | 1.43 | 1.26 | 83.25 | 86.02 |
| HC | G | 174 | 1.93 | 1.70 | 1.43 | 76.10 | 74.12 |
| HC | L | 175 | 1.84 | 1.58 | 1.41 | 77.76 | 76.40 |
| HC | V | 184 | 1.19 | 1.38 | 1.01 | 71.09 | 84.95 |
| HC | I | 195 | 1.48 | 1.71 | 1.65 | 118.01 | 111.63 |
| HC | N | 199 | 1.78 | 1.44 | 0.84 | 59.41 | 47.28 |
| HC | S | 203 | 1.58 | 1.16 | 1.08 | 73.44 | 68.18 |
| HC | T | 205 | 1.34 | 1.47 | 1.38 | 107.76 | 102.74 |
| HC | G | 367 | 1.46 | 1.46 | 1.33 | 103.64 | 90.76 |
| HC | Y | 369 | 1.38 | 1.40 | 1.35 | 97.89 | 98.12 |
| HC | E | 384 | 1.50 | 1.31 | 1.22 | 106.69 | 81.08 |
| HC | K | 410 | 1.29 | 1.50 | 1.41 | 122.94 | 109.25 |
| HC | K | 410 | 1.52 | 1.50 | 1.22 | 108.89 | 80.14 |
| HC | Q | 414 | 1.87 | 1.33 | 0.93 | 62.85 | 49.76 |
| HC | S | 420 | 1.27 | 1.33 | 1.33 | 134.68 | 105.26 |
| HC | Y | 432 | 0.85 | 0.89 | 0.67 | 42.31 | 78.43 |
| HC | T | 433 | 1.36 | 1.22 | 1.15 | 96.64 | 84.74 |
| HC | Q | 434 | 1.80 | 1.54 | 1.44 | 94.57 | 79.86 |
| HC | L | 439 | 1.30 | 1.34 | 1.10 | 94.70 | 84.41 |
| HC | M | 100C | n/a | 1.13 | 0.84 | 50.00 | n/a |
| LC | S | 12 | 1.44 | 1.20 | 1.14 | 75.69 | 79.37 |
| LC | T | 22 | 1.77 | 1.69 | 1.67 | 97.47 | 94.29 |
| LC | R | 24 | 1.35 | 0.82 | 0.72 | 54.75 | 53.62 |
| LC | A | 32 | 0.71 | 0.73 | 0.73 | 40.83 | 102.97 |
| LC | Q | 38 | 0.00 | 0.00 | 0.00 | | |
| LC | K | 39 | 1.50 | 1.39 | 1.39 | 104.73 | 92.86 |
| LC | G | 41 | 1.79 | 1.70 | 1.45 | 91.11 | 81.13 |
| LC | K | 42 | 1.80 | 1.28 | 1.27 | | 70.46 |
| LC | K | 42 | 1.32 | 1.42 | 1.32 | 97.52 | 99.62 |
| LC | P | 44 | 0.00 | 0.00 | 0.00 | | |
| LC | Y | 49 | 1.64 | 1.84 | 1.80 | 100.56 | 110.06 |
| LC | S | 50 | 1.09 | 1.04 | 1.04 | 61.00 | 95.06 |
| LC | F | 53 | 1.78 | 0.89 | 0.60 | 38.71 | 33.79 |
| LC | Y | 55 | 0.83 | 0.96 | 0.89 | 83.07 | 107.02 |
| LC | G | 64 | 0.89 | 1.22 | 0.56 | 45.73 | 63.28 |
| LC | T | 72 | 1.67 | 1.67 | 1.48 | 94.87 | 88.64 |
| LC | T | 74 | 1.69 | 1.39 | 1.04 | 63.48 | 61.78 |
| LC | Q | 79 | 1.69 | 1.38 | 1.16 | 76.10 | 68.80 |
| LC | T | 85 | 1.29 | 1.38 | 1.18 | 87.08 | 91.43 |
| LC | Y | 92 | 1.45 | 1.15 | 1.15 | #DIV/0! | 79.51 |
| LC | Y | 92 | 1.65 | 1.44 | 1.35 | 86.54 | 81.69 |
| LC | T | 97 | 1.19 | 1.12 | 0.91 | 58.59 | 76.97 |
| LC | K | 103 | 1.50 | 1.44 | 1.28 | 86.34 | 85.19 |
| LC | E | 105 | 1.74 | 1.45 | 1.11 | 67.86 | 63.57 |
| LC | T | 129 | 1.78 | 1.56 | 1.32 | 76.13 | 73.81 |
| LC | S | 131 | 0.89 | 0.74 | 0.63 | #DIV/0! | 70.72 |
| LC | R | 142 | 1.64 | 1.60 | 1.46 | 116.67 | 88.84 |
| LC | Q | 147 | 1.72 | 1.33 | 1.02 | 67.91 | 59.28 |
| LC | K | 149 | 0.88 | 1.04 | 0.93 | 117.97 | 106.12 |
| LC | K | 149 | 0.91 | 1.02 | 0.94 | 120.41 | 103.40 |
| LC | Q | 155 | 1.74 | 1.53 | 1.10 | 70.06 | 63.22 |
| LC | S | 159 | 1.23 | 0.94 | 0.58 | 42.94 | 46.94 |
| LC | Q | 160 | 1.77 | 1.28 | 1.01 | 62.64 | 57.40 |
| LC | Q | 166 | 1.38 | 0.96 | 0.62 | 49.62 | 44.91 |

TABLE 7-continued

Average DAR, concentration, aggregation, and stability (Mass Spec Rat Plasma Stability) of the cysteine engineered antibodies of Tables 3 and 4 conjugated with a PDS-linker

| Cysteine Mutation (HC/LC) | Residue | Kabat Mutation Site # | Calculated DAR at 0 hrs (BCP) | Calculated DAR at 48 hrs (BCP) | Calculated DAR at 96 hrs (BCP) | % DAR @ 96 hr relative to Assigned DAR | % DAR @ 96 hrs relative to DAR @ 0 hr |
|---|---|---|---|---|---|---|---|
| LC | T | 172 | 0.88 | 1.21 | 1.06 | 79.47 | 120.50 |
| LC | T | 180 | 1.77 | 1.37 | 0.94 | 59.57 | 53.20 |
| LC | V | 191 | 1.65 | 1.40 | 1.07 | 84.57 | 65.13 |
| LC | A | 193 | 1.72 | 1.47 | 0.88 | 52.67 | 51.15 |
| LC | E | 195 | 1.69 | 1.61 | 1.51 | 105.55 | 89.57 |
| LC | V | 205 | n/a | 1.49 | 1.33 | 82.30 | n/a |
| LC | V | 205 |  | 1.55 | 1.34 | 85.02 |  |
| LC | V | 205 | n/a | 1.64 | 1.39 | 96.92 | n/a |
| LC | V | 205 | n/a | 1.58 | 1.48 | 97.55 |  |
| LC | V | 205 | n/a | 1.52 | 1.46 | 92.37 | n/a |
| LC | V | 205 | 1.64 | 1.50 | 1.30 | 87.74 | 79.35 |
| LC | V | 205 | n/a | 1.64 | 1.37 | 91.62 | n/a |
| LC | V | 205 | 1.59 | 1.51 | 1.48 | 99.43 | 93.43 |
| LC | V | 205 | 1.18 | 1.20 | 1.12 | 97.56 | 95.37 |
| LC | V | 205 | 1.50 | 1.34 | 1.28 | 90.29 | 85.47 |
| LC | V | 205 | 1.45 | 1.56 | 1.44 | 92.98 | 99.28 |
| LC | V | 205 | 0.85 | 0.90 | 0.76 | 81.25 | 88.48 |
| LC | T | 206 | 1.51 | 1.31 | 1.17 | 102.26 | 77.29 |
| LC | N | 210 | 1.08 | 0.41 | 0.00 | n/a | 0.00 |

TABLE 8

Average DAR, concentration, aggregation, and stability (ELISA Rat Plasma Stability) of the cysteine engineered antibodies of Tables 3 and 4 conjugated with a -vc linker

| Cysteine Mutation (HC/LC) | Residue | Kabat Mutation Site # | Average DAR | Source Conc. (mg/mL) | % Aggregation | Stability n = 1 | Stability n = 2 | Average Stability |
|---|---|---|---|---|---|---|---|---|
| HC | V | 2 | 1.3 | 1.6 | 13.5 | 98.23 | 80.46 | 89.35 |
| HC | L | 4 | 1.3 | 1.7 | 46.6 | 85.51 | 89.22 | 87.36 |
| HC | V | 5 | 1.5 | 2.68 | 11.3 | 73.22 | 95.18 | 84.20 |
| HC | L | 11 | 1.3 | 1.5 | 7.8 | 85.30 | 69.88 | 77.59 |
| HC | R | 19 | 1.0 | 2.79 | 17.0 | 96.24 | 95.42 | 95.83 |
| HC | F | 27 | 1.4 | 2.29 | 11.5 | 93.75 | 112.45 | 103.10 |
| HC | I | 29 | 1.6 | 2.00 | 29.5 | 83.10 | 90.49 | 86.80 |
| HC | Y | 33 | 1.2 | 2.65 | 13.0 | 220.20 | 215.88 | 218.04 |
| HC | Q | 39 | 1.3 | 1.85 | 8.7 | 125.15 | 126.26 | 125.70 |
| HC | A | 40 | 1.4 | 2.46 | 11.9 | 93.21 | 112.45 | 102.83 |
| HC | K | 43 | 1.4 | 1.76 | 9.0 | 85.83 | 91.44 | 88.64 |
| HC | L | 45 | 1.0 | 2.24 | 12.9 | 88.64 | 140.29 | 114.47 |
| HC | E | 46 | 1.7 | 1.44 | 12.7 | 91.19 | 102.51 | 96.85 |
| HC | T | 53 | 1.8 | 2.88 | 25.1 | 91.44 | 96.89 | 94.17 |
| HC | G | 55 | 1.7 | 2.51 | 30.4 | 89.83 | 92.37 | 91.10 |
| HC | T | 57 | 1.1 | 2.01 | 12.5 | 104.44 | 116.30 | 110.37 |
| HC | R | 58 | 1.5 | 1.52 | 30.2 | 164.60 | 176.86 | 170.73 |
| HC | Y | 59 | 1.1 | 3.23 | 16.2 | 92.06 | 99.12 | 95.59 |
| HC | A | 60 | 1.2 | 1.8118 | 17.1 | 105.84 | 115.48 | 110.66 |
| HC | T | 68 | 1.6 | 2.81 | 23.1 | 92.99 | 80.23 | 86.61 |
| HC | N | 76 | 1.9 | 4.18 | 21.7 | 88.36 | 85.25 | 86.81 |
| HC | Q | 81 | 1.6 | 2.21 | 36.9 | 119.84 | 123.33 | 121.59 |
| HC | W | 103 | 1.1 | 1.94 | 20.4 | 162.14 | 149.40 | 155.77 |
| HC | T | 110 | 1.2 | 2.22 | 6.6 | 119.49 | 84.61 | 102.05 |
| HC | T | 116 | 1.3 | 1.74 | 15.1 | 85.08 | 85.88 | 85.48 |
| HC | K | 117 | 1.2 | 1.9 | 9.1 | 112.11 | 74.68 | 93.40 |
| HC | A | 136 | 1.2 | 1.36 | 5.5 | 78.31 | 89.68 | 83.99 |
| HC | G | 162 | 1.2 | 1.81 | 10.8 | 90.10 | 95.89 | 93.00 |
| HC | G | 174 | 1.8 | 1.37 | 6.9 | 97.31 | 92.85 | 95.08 |
| HC | T | 183 | 1.6 | 1.04 | 8.3 | 109.77 | 102.24 | 106.00 |
| HC | I | 195 | 1.6 | 2.0 | 9.0 | 125.06 | 87.13 | 106.10 |
| HC | T | 205 | 1.3 | 3.7 | 12.7 | 102.73 | 72.95 | 87.84 |
| HC | F | 239 |  | 1.9 | 10.4 | 79.64 | 106.13 | 92.88 |
| HC | M | 248 | 1.7 | 1.7 | 17.4 | 81.26 | 59.52 | 70.39 |
| HC | E | 254 | 1.6 | 1.36 | 13.4 | 116.08 | 94.55 | 105.32 |
| HC | V | 258 | 1.4 | 2.55 | 7.2 | 89.56 | 103.24 | 96.40 |
| HC | N | 272 | 1.3 | 1.55 | 21.9 | 83.69 | 82.97 | 83.33 |
| HC | V | 278 |  | 1.48 | 10.4 | 72.24 | 107.60 | 89.92 |
| HC | L | 305 | 1.6 | 2.0 | 27.2 | 89.65 | 83.24 | 86.45 |

TABLE 8-continued

Average DAR, concentration, aggregation, and stability (ELISA Rat Plasma Stability)
of the cysteine engineered antibodies of Tables 3 and 4 conjugated with a -vc linker

| Cysteine Mutation (HC/LC) | Residue | Kabat Mutation Site # | Average DAR | Source Conc. (mg/mL) | % Aggregation | Stability n = 1 | Stability n = 2 | Average Stability |
|---|---|---|---|---|---|---|---|---|
| HC | T | 331 | 1.5 | 2.0732 | 14.5 | 81.30 | 86.99 | 84.14 |
| HC | S | 333 | 1.2 | 2.46 | 14.0 | 108.18 | 99.31 | 103.74 |
| HC | R | 340 | 1.1 | 1.97 | 7.3 | 85.33 | 96.85 | 91.09 |
| HC | Q | 343 | 1.2 | 2.2497 | 12.5 | 86.29 | 100.03 | 93.16 |
| HC | K | 356 | 1.7 | 1.9358 | 16.2 | 74.14 | 80.15 | 77.14 |
| HC | G | 367 | 1.3 | 1.92 | 22.8 | 106.33 | 93.19 | 99.76 |
| HC | E | 378 | 1.4 | 1.52 | 7.9 | 109.03 | 110.21 | 109.62 |
| HC | P | 383 | 1.9 | 1.74 | 13.3 | 85.17 | 87.85 | 86.51 |
| HC | E | 384 | 1.4 | 3.16 | 12.1 | 83.38 | 95.03 | 89.20 |
| HC | E | 384 | 1.3 | 2.25 | 9.9 | 110.71 | 95.13 | 102.92 |
| HC | S | 399 | 1.1 | 1.89 | 12.4 | 89.14 | 87.67 | 88.40 |
| HC | K | 410 | 1.3 | 2.78 | 19.0 | 90.59 | 108.20 | 99.40 |
| HC | K | 410 | 1.5 | 2.38 | 19.0 | 68.86 | 88.22 | 78.54 |
| HC | Q | 414 | 1.5 | 2.35 | 14.7 | 86.64 | 83.88 | 85.26 |
| HC | Q | 414 | 1.5 | 1.92 | 14.7 | 75.28 | 104.41 | 89.84 |
| HC | G | 416 | 1.5 | 4.06 | 17.4 | 72.34 | 86.56 | 79.45 |
| HC | N | 417 | 1.4 | 2.28 | 11.9 | 90.00 | 152.01 | 121.01 |
| HC | S | 420 | 1.4 | 2.09 | 11.8 | 104.31 | 97.46 | 100.89 |
| HC | N | 430 | 1.6 | 1.95 | 17.1 | 83.42 | 114.03 | 98.72 |
| HC | Y | 432 | 1.5 | 1.67 | 7.9 | 95.25 | 96.20 | 95.72 |
| HC | T | 433 | 1.3 | 1.42 | 9.1 | 78.24 | 107.70 | 92.97 |
| HC | Q | 434 | 1.6 | 0.97 | 8.9 | 90.29 | 112.01 | 101.15 |
| HC | K | 435 | 1.3 | 3.44 | 12.5 | 80.36 | 91.29 | 85.82 |
| HC | S | 438 | 1.3 | 3.38 | 10.8 | 61.24 | 98.10 | 79.67 |
| HC | L | 439 | 1.2 | 1.59 | 10.3 | 96.69 | 92.26 | 94.47 |
| HC | M | 100C | 1.5 | 1.87 | 13.1 | 115.29 | 101.84 | 108.57 |
| HC | N | 82A | 1.7 | 2.71 | 25.5 | 96.58 | 102.86 | 99.72 |
| LC | S | 14 | 1.4 | 2.4 | 9.6 | 77.96 | 99.41 | 88.68 |
| LC | G | 16 | 1.0 | 2.1 | 35.4 | 101.03 | 90.52 | 95.77 |
| LC | R | 18 | 1.7 | 2.3112 | 19.9 | 79.37 | 100.64 | 90.01 |
| LC | T | 22 | 1.9 | 2.7 | 8.0 | 97.25 | 88.09 | 92.67 |
| LC | R | 24 | 1.4 | 1.6 | 12.1 | 90.74 | 83.07 | 86.91 |
| LC | Q | 27 | 1.8 | 1.4 | 31.9 | 84.73 | 59.27 | 72.00 |
| LC | T | 31 | 1.9 | 3.33 | 20.4 | 101.90 | 116.63 | 109.26 |
| LC | A | 32 | 1.6 | 1.2 | 9.5 | 218.53 | 225.87 | 222.20 |
| LC | Q | 38 | | 1.8 | 6.7 | 207.34 | 125.78 | 166.56 |
| LC | K | 39 | 1.4 | 4.2 | 2.8 | 92.02 | 87.13 | 89.57 |
| LC | K | 42 | | 1.4 | 12.2 | 140.35 | 155.65 | 148.00 |
| LC | K | 42 | 1.3 | 1.7 | 6.9 | 93.56 | 63.12 | 78.34 |
| LC | P | 44 | | 1.5 | 4.1 | 63.27 | 182.10 | 122.68 |
| LC | Y | 49 | 1.3 | 2.0 | 4.3 | 157.80 | 128.47 | 143.14 |
| LC | S | 50 | 1.6 | 1.1 | 24.4 | 371.08 | 327.56 | 349.32 |
| LC | S | 52 | 1.5 | 1.68 | 13.3 | 100.36 | 101.21 | 100.78 |
| LC | L | 54 | 1.0 | 1.89 | 7.1 | 86.65 | 96.53 | 91.59 |
| LC | S | 63 | 1.8 | 1.91 | 10.1 | 89.90 | 85.62 | 87.76 |
| LC | G | 64 | 1.3 | 2.05 | 3.8 | 98.58 | 98.16 | 98.37 |
| LC | R | 66 | 1.4 | 1.94 | 5.5 | 101.37 | 98.21 | 99.79 |
| LC | D | 70 | 1.6 | 3.5 | 17.4 | 86.34 | 70.73 | 78.54 |
| LC | S | 76 | | 2.0 | 15.4 | 101.44 | 92.90 | 97.17 |
| LC | T | 85 | 1.2 | 2.53 | 3.2 | 86.76 | 89.30 | 88.03 |
| LC | H | 91 | | 1.8 | 6.1 | 105.08 | 86.37 | 95.72 |
| LC | H | 91 | 1.1 | 1.6 | 6.3 | 99.73 | 63.59 | 81.66 |
| LC | Y | 92 | | 1.5 | 5.9 | 94.79 | 94.91 | 94.85 |
| LC | P | 95 | 1.1 | 2.1265 | 11.0 | 98.48 | 89.11 | 93.80 |
| LC | P | 95 | 1.0 | 1.7878 | 10.4 | 105.00 | 95.69 | 100.34 |
| LC | F | 98 | 1.2 | 3.12 | 5.4 | 87.16 | 90.52 | 88.84 |
| LC | E | 105 | 1.8 | 2.54 | 3.6 | 98.50 | 94.72 | 96.61 |
| LC | I | 106 | 1.1 | 2.64 | 3.4 | 100.79 | 87.24 | 94.01 |
| LC | K | 107 | 1.7 | 1.71 | 7.3 | 105.14 | 82.06 | 93.60 |
| LC | R | 108 | 1.5 | 1.69 | 5.3 | 92.05 | 94.91 | 93.48 |
| LC | P | 119 | | 2.8 | 8.2 | 128.42 | 129.74 | 129.08 |
| LC | K | 126 | 1.4 | 1.92 | 4.5 | 93.54 | 107.58 | 100.56 |
| LC | T | 129 | 1.7 | 3.28 | 6.2 | 85.32 | 85.73 | 85.53 |
| LC | S | 131 | | 1.0 | 48.2 | 121.78 | 133.73 | 127.75 |
| LC | R | 142 | 1.2 | 3.01 | 3.9 | 101.76 | 118.88 | 110.32 |
| LC | K | 149 | 1.4 | 2.3798 | 8.2 | 82.17 | 96.00 | 89.09 |
| LC | K | 149 | 1.3 | 1.6385 | 8.3 | 80.02 | 101.63 | 90.83 |
| LC | A | 153 | 1.9 | 1.49 | 11.2 | 83.42 | 85.60 | 84.51 |
| LC | Q | 155 | 1.5 | 1.92 | 5.9 | 89.73 | 159.47 | 124.60 |
| LC | S | 156 | 1.7 | 1.13 | 36.4 | 90.95 | 90.22 | 90.59 |
| LC | Q | 160 | 1.5 | 1.91 | 5.1 | 49.46 | 48.36 | 48.91 |
| LC | S | 162 | 1.0 | 2.66 | 4.9 | 98.35 | 86.31 | 92.33 |
| LC | A | 193 | 1.5 | 2.10 | 4.7 | 152.79 | 93.78 | 123.29 |

TABLE 8-continued

Average DAR, concentration, aggregation, and stability (ELISA Rat Plasma Stability) of the cysteine engineered antibodies of Tables 3 and 4 conjugated with a -vc linker

| Cysteine Mutation (HC/LC) | Residue | Kabat Mutation Site # | Average DAR | Source Conc. (mg/mL) | % Aggregation | Stability n = 1 | Stability n = 2 | Average Stability |
|---|---|---|---|---|---|---|---|---|
| LC | E | 195 | 1.6 | 1.7974 | 5.0 | 91.54 | 126.55 | 109.04 |
| LC | V | 205 | 2.0 | 3.11 | 5.0 | 102.31 | 81.18 | 91.74 |
| LC | V | 205 | 1.6 | 2.68 | 5.5 | 89.97 | 96.86 | 93.42 |
| LC | V | 205 | 1.6 | 2.05 | 3.9 | 95.93 | 91.20 | 93.57 |
| LC | V | 205 | 1.5 | 2.94 | 3.0 | 103.18 | 106.42 | 104.80 |
| LC | V | 205 | 1.7 | 1.69 | 0.0 | 106.69 | 97.53 | 102.11 |
| LC | V | 205 | 1.8 | 1.97 | 0.0 | 91.51 | 104.20 | 97.86 |
| LC | V | 205 | 1.3 | 1.4 | 2.4 | 108.64 | 89.50 | 99.07 |
| LC | V | 205 | 1.5 | 3.01 | 17.0 | 87.68 | 95.62 | 91.65 |
| LC | V | 205 | 1.5 | 1.83 | 3.3 | 120.79 | 130.76 | 125.78 |
| LC | V | 205 | 1.4 | 2.1 | 4.5 | 100.74 | 104.30 | 102.52 |
| LC | V | 205 | 1.4 | 1.8346 | 5.6 | 58.12 | 108.51 | 83.31 |
| LC | T | 206 | 1.7 | 2.13 | 4.7 | 116.21 | 89.01 | 102.61 |

TABLE 9

Average DAR/stability (Mass Spec Rat Plasma Stability) of the cysteine engineered antibodies of Tables 3 and 4 conjugated with a -vc linker

| Cysteine Mutation (HC/LC) | Residue | Kabat Mutation Site # | Calculated DAR at 0 hrs (BCP) | Calculated DAR at 48 hrs (BCP) | Calculated DAR at 96 hrs (BCP) | % DAR @ 96 hr relative to Assigned DAR | % DAR @ 96 hrs relative to DAR @ 0 hr |
|---|---|---|---|---|---|---|---|
| HC | V | 2 | 1.64 | 1.48 | 1.44 | 113.43 | 87.82 |
| HC | L | 4 | 1.26 | 0.88 | 0.90 | 70.21 | 71.53 |
| HC | V | 5 | 1.80 | 1.34 | 1.26 | 86.04 | 69.79 |
| HC | L | 11 | 1.29 | 1.11 | 1.17 | 93.74 | 90.54 |
| HC | R | 19 | 1.55 | 1.33 | 1.09 | 104.63 | 70.41 |
| HC | F | 27 | 1.30 | 1.00 | 1.26 | 89.16 | 96.81 |
| HC | I | 29 | n/a | 1.09 | 1.01 | 63.72 | n/a |
| HC | Y | 33 | n/a | 1.00 | 0.82 | 66.95 | n/a |
| HC | Q | 39 | n/a | 1.35 | 1.34 | 105.77 | n/a |
| HC | A | 40 | n/a | 1.20 | 1.09 | 80.81 | n/a |
| HC | K | 43 | n/a | 1.41 | 1.28 | 90.84 | n/a |
| HC | L | 45 | n/a | 1.00 | 0.62 | 63.82 | n/a |
| HC | E | 46 | n/a | 1.36 | 0.78 | 47.14 | n/a |
| HC | T | 53 | 1.91 | 1.51 | 1.46 | 83.60 | 76.63 |
| HC | G | 55 | n/a | 1.45 | 0.81 | 48.88 | n/a |
| HC | T | 57 | n/a | 1.31 | 1.12 | 100.31 | n/a |
| HC | R | 58 | n/a | 0.92 | 1.01 | 67.15 | n/a |
| HC | Y | 59 | 1.39 | 1.08 | 0.84 | 74.64 | 60.79 |
| HC | A | 60 | 1.44 | 0.96 | 0.72 | 62.32 | 50.29 |
| HC | T | 68 | 1.60 | 1.32 | 1.37 | 84.98 | 85.69 |
| HC | N | 76 | 1.69 | 1.52 | 1.62 | 85.54 | 95.87 |
| HC | Q | 81 | n/a | 0.91 | 0.95 | 58.30 | n/a |
| HC | W | 103 | n/a | 1.07 | 1.05 | 97.13 | n/a |
| HC | T | 110 | n/a | 1.50 | 1.70 | 139.34 | n/a |
| HC | T | 116 | n/a | 1.10 | 1.12 | 84.41 | n/a |
| HC | K | 117 | 0.99 | 1.37 | 1.30 | 111.31 | 131.31 |
| HC | A | 136 | 1.61 | 1.73 | 1.31 | 113.15 | 81.75 |
| HC | G | 162 | n/a | 1.29 | 1.30 | 107.06 | n/a |
| HC | G | 174 | n/a | 1.61 | 1.62 | 91.99 | n/a |
| HC | T | 183 | n/a | 1.54 | 1.65 | 104.39 | n/a |
| HC | I | 195 | 1.65 | 1.58 | 1.64 | 104.33 | 99.14 |
| HC | T | 205 | 1.53 | 1.62 | 1.57 | 124.22 | 102.15 |
| HC | F | 239 | 1.88 | 1.19 | 1.19 | #DIV/0! | 63.49 |
| HC | M | 248 | 1.79 | 0.71 | 0.72 | 43.43 | 40.29 |
| HC | E | 254 | n/a | 1.67 | 1.50 | 93.75 | n/a |
| HC | V | 258 | 1.73 | 1.81 | 1.81 | 128.26 | 104.81 |
| HC | N | 272 | n/a | 1.13 | 1.13 | 86.11 | n/a |
| HC | V | 278 | 0.84 | 0.95 | 1.07 | #DIV/0! | 127.44 |
| HC | L | 305 | 1.70 | 1.24 | 1.19 | 76.31 | 70.07 |
| HC | T | 331 | 1.69 | 1.53 | 1.50 | 100.67 | 88.78 |
| HC | S | 333 | 1.48 | 1.45 | 1.44 | 123.92 | 96.88 |
| HC | R | 340 | 1.55 | 1.45 | 1.27 | 115.82 | 82.00 |
| HC | Q | 343 | 1.41 | 1.18 | 1.20 | 103.29 | 85.05 |
| HC | K | 356 | 1.85 | 1.51 | 1.42 | 81.53 | 76.64 |
| HC | G | 367 | 1.38 | 1.39 | 1.41 | 111.20 | 101.99 |

TABLE 9-continued

Average DAR/stability (Mass Spec Rat Plasma Stability) of the cysteine
engineered antibodies of Tables 3 and 4 conjugated with a -vc linker

| Cysteine Mutation (HC/LC) | Residue | Kabat Mutation Site # | Calculated DAR at 0 hrs (BCP) | Calculated DAR at 48 hrs (BCP) | Calculated DAR at 96 hrs (BCP) | % DAR @ 96 hr relative to Assigned DAR | % DAR @ 96 hrs relative to DAR @ 0 hr |
|---|---|---|---|---|---|---|---|
| HC | E | 378 | n/a | 1.53 | 1.50 | 104.17 | n/a |
| HC | P | 383 | n/a | 1.30 | 1.32 | 69.75 | n/a |
| HC | E | 384 | 1.33 | 1.32 | 1.33 | 94.26 | 100.14 |
| HC | E | 384 | 1.53 | 1.40 | 1.35 | 101.98 | 87.85 |
| HC | S | 399 | 0.98 | 1.11 | 0.90 | 79.29 | 91.20 |
| HC | K | 410 | 1.34 | 1.44 | 1.29 | 100.32 | 96.37 |
| HC | K | 410 | 1.64 | 1.38 | 1.33 | 91.95 | 81.40 |
| HC | Q | 414 | 1.95 | 1.75 | 1.58 | 108.45 | 81.10 |
| HC | Q | 414 | 1.91 | 1.73 | 1.61 | 105.14 | 84.27 |
| HC | G | 416 | 1.98 | 1.61 | 1.47 | 95.92 | 74.29 |
| HC | N | 417 | 1.84 | 1.70 | 1.70 | 118.31 | 92.49 |
| HC | S | 420 | 1.77 | 1.76 | 1.74 | 127.01 | 98.26 |
| HC | N | 430 | 1.76 | 1.75 | 1.75 | 109.67 | 99.70 |
| HC | Y | 432 | 1.50 | 1.41 | 1.32 | 86.89 | 88.30 |
| HC | T | 433 | 1.61 | 1.29 | 1.27 | 94.61 | 78.60 |
| HC | Q | 434 | 1.67 | 1.48 | 1.45 | 92.87 | 86.92 |
| HC | K | 435 | 1.38 | 1.19 | 1.07 | 82.29 | 77.80 |
| HC | S | 438 | 1.46 | 1.10 | 1.06 | 84.89 | 72.65 |
| HC | L | 439 | 1.24 | 1.23 | 1.20 | 96.47 | 96.13 |
| HC | M | 100C | n/a | 0.95 | 0.97 | 62.70 | n/a |
| HC | N | 82A | n/a | 1.28 | 1.19 | 70.50 | n/a |
| LC | S | 14 | 1.80 | 1.41 | 1.38 | 96.15 | 76.39 |
| LC | G | 16 | 1.48 | 1.38 | 1.28 | 134.50 | 86.44 |
| LC | R | 18 | 1.92 | 1.40 | 1.45 | 83.82 | 75.54 |
| LC | T | 22 | 1.81 | 1.33 | 1.33 | 70.55 | 73.56 |
| LC | R | 24 | 1.61 | 1.40 | 1.32 | 93.29 | 82.11 |
| LC | Q | 27 | 1.91 | 1.31 | 1.17 | 67.04 | 61.45 |
| LC | T | 31 | 1.89 | 1.08 | 0.95 | 50.13 | 50.15 |
| LC | A | 32 | 0.43 | 0.67 | 0.57 | 35.49 | 133.33 |
| LC | Q | 38 | 0.29 | 0.20 | 0.18 | #DIV/0! | 61.34 |
| LC | K | 39 | 1.48 | 1.20 | 1.16 | 81.78 | 78.39 |
| LC | K | 42 | 1.68 | 1.50 | 1.44 | #DIV/0! | 85.65 |
| LC | K | 42 | 1.42 | 1.32 | 1.35 | 105.47 | 95.29 |
| LC | P | 44 | 0.09 | 0.22 | 0.24 | #DIV/0! | 261.90 |
| LC | Y | 49 | 1.20 | 1.14 | 1.13 | 89.72 | 93.88 |
| LC | S | 50 | 0.78 | 0.95 | 0.74 | 46.01 | 94.81 |
| LC | S | 52 | 1.67 | 1.26 | 1.28 | 86.46 | 76.77 |
| LC | L | 54 | n/a | 1.27 | 1.11 | 109.21 | n/a |
| LC | S | 63 | n/a | 1.30 | 1.20 | 65.38 | n/a |
| LC | G | 64 | n/a | 1.12 | 0.91 | 69.76 | n/a |
| LC | R | 66 | n/a | 1.34 | 1.20 | 86.33 | n/a |
| LC | D | 70 | 1.87 | 1.44 | 1.38 | 86.16 | 73.74 |
| LC | S | 76 | 1.91 | 1.45 | 1.44 | #DIV/0! | 75.30 |
| LC | T | 85 | n/a | 1.46 | 1.23 | 99.46 | n/a |
| LC | H | 91 | 0.46 | 0.39 | 0.39 | #DIV/0! | 85.06 |
| LC | H | 91 | 0.14 | 0.20 | 0.33 | 30.03 | 238.46 |
| LC | Y | 92 | 1.38 | 1.26 | 1.29 | #DIV/0! | 93.40 |
| LC | P | 95 | 1.31 | 1.02 | 1.10 | 99.74 | 83.89 |
| LC | P | 95 | 0.97 | 1.03 | 1.02 | 99.58 | 105.09 |
| LC | F | 98 | n/a | 0.84 | 0.77 | 66.05 | n/a |
| LC | E | 105 | 1.50 | 1.33 | 1.25 | 70.22 | 83.33 |
| LC | I | 106 | n/a | 1.32 | 1.17 | 104.37 | n/a |
| LC | K | 107 | n/a | 1.45 | 1.27 | 77.06 | n/a |
| LC | R | 108 | n/a | 1.41 | 1.23 | 80.76 | n/a |
| LC | P | 119 | 0.61 | 0.55 | 0.55 | #DIV/0! | 90.54 |
| LC | K | 126 | n/a | 0.64 | 0.64 | 46.11 | n/a |
| LC | T | 129 | 1.65 | 1.38 | 1.39 | 82.29 | 84.08 |
| LC | S | 131 | 0.55 | #DIV/0! | #DIV/0! | #DIV/0! | #DIV/0! |
| LC | R | 142 | 1.54 | 1.41 | 1.41 | 117.28 | 91.65 |
| LC | K | 149 | 1.65 | 1.53 | 1.29 | 90.91 | 78.38 |
| LC | K | 149 | 1.50 | 1.42 | 1.24 | 93.58 | 82.35 |
| LC | A | 153 | n/a | 1.29 | 1.21 | 63.38 | n/a |
| LC | Q | 155 | n/a | 1.60 | 1.29 | 86.27 | n/a |
| LC | S | 156 | n/a | 0.97 | 0.98 | 57.07 | n/a |
| LC | Q | 160 | 1.80 | 0.83 | 0.74 | 49.87 | 41.28 |
| LC | S | 162 | 1.18 | 1.25 | 0.73 | 70.85 | n/a |
| LC | A | 193 | n/a | 1.43 | 1.51 | 101.24 | n/a |
| LC | E | 195 | n/a | 1.62 | 1.48 | 93.43 | n/a |
| LC | V | 205 | 1.31 | 1.23 | 1.47 | 75.41 | 112.46 |
| LC | V | 205 | n/a | 1.29 | 1.50 | 94.94 | n/a |
| LC | V | 205 | n/a | 1.19 | 1.20 | 76.92 | n/a |

TABLE 9-continued

Average DAR/stability (Mass Spec Rat Plasma Stability) of the cysteine
engineered antibodies of Tables 3 and 4 conjugated with a -vc linker

| Cysteine Mutation (HC/LC) | Residue | Kabat Mutation Site # | Calculated DAR at 0 hrs (BCP) | Calculated DAR at 48 hrs (BCP) | Calculated DAR at 96 hrs (BCP) | % DAR @ 96 hr relative to Assigned DAR | % DAR @ 96 hrs relative to DAR @ 0 hr |
|---|---|---|---|---|---|---|---|
| LC | V | 205 | n/a  | 1.32 | 1.14 | 76.80  | n/a   |
| LC | V | 205 | n/a  | 1.68 | 1.58 | 91.80  | n/a   |
| LC | V | 205 | n/a  | 1.23 | 1.20 | 67.42  | n/a   |
| LC | V | 205 | 1.70 | 1.64 | 1.58 | 118.16 | 93.19 |
| LC | V | 205 | 1.79 | 1.64 | 1.59 | 109.12 | 89.03 |
| LC | V | 205 | 1.91 | 1.68 | 1.65 | 112.95 | 86.38 |
| LC | V | 205 | 1.73 | 1.61 | 1.54 | 109.55 | 89.52 |
| LC | V | 205 | 1.70 | 1.55 | 1.49 | 106.94 | 87.62 |
| LC | T | 206 | n/a  | 1.59 | 1.20 | 69.58  | n/a   |

The PDS-MMAE THIOMAB™ antibodies identified in Tables 6 and 7 were analyzed with a starting concentration of ≥1 mg/mL of source material (i.e., the PDS-MMAE THIOMAB™ antibody). The DAR calculations for the PDS-MMAE THIOMAB™ antibodies identified in Tables 6 and 7 were all ≥DAR1. All of the PDS-MMAE THIOMAB™ antibodies identified in Tables 6 and 7 had ≤50% aggregation, reoxidized. The PDS-MMAE THIOMAB™ antibodies identified in Table 6 exhibited at least ≥77% stability in rat matrix over time for ELISA replicates. The same samples analyzed in Table 6 were used in the experiments performed for Table 7. Table 7 shows the LCSM confirmation of the ELISA stability results of Table 6.

The MC-VC-MMAE THIOMAB™ antibodies identified in Tables 8 and 9 were analyzed with a starting concentration of ≥1 mg/mL of source material (i.e., the MC-VC-MMAE THIOMAB™ antibody). The DAR calculations for the MC-VC-MMAE THIOMAB™ antibodies identified in Tables 8 and 9 were all ≥DAR1. All of the MC-VC-MMAE THIOMAB™ antibodies identified in Tables 8 and 9 had ≤50% aggregation, reoxidized. The MC-VC-MMAE THIOMAB™ antibodies identified in Table 8 exhibited at least ≥77% stability in rat matrix over time for ELISA replicates. Table 9 shows the LCSM confirmation of the ELISA stability results of Table 8.

TABLE 10

Average DAR, concentration, and aggregation of the preferred cysteine engineered antibodies of Tables 1 and 2 (Same samples as those shown in Tables 11 and 12)

| Linker | Cysteine Mutation (HC/LC) | Residue | EU Mutation Site # | Kabat Mutation Site # | Average DAR | Source Conc. (mg/mL) | % Aggregation |
|---|---|---|---|---|---|---|---|
| PDS | HC | V | 2 | 5 | 3.1 | 11.6 | 1.6 |
| PDS | HC | D | 105 | 101 | 2.22 | 10.2 | 1.7 |
| PDS | HC | A | 140 | 136 | 1.23 | 5.2 | 1.3 |
| PDS | HC | G | 166 | 162 | 2.07 | 10.7 | 1.8 |
| PDS | HC | L | 174 | 170 | 1.50 | 9.2 | 1.5 |
| PDS | HC | G | 178 | 174 | 1.55 | 6.5 | 1.9 |
| PDS | HC | L | 179 | 175 | 2.20 | 8.4 | 1.8 |
| PDS | HC | I | 199 | 195 | 1.3 | 8.9 | 1.4 |
| PDS | HC | S | 207 | 203 | 1.67 | 22.5 | 1.5 |
| PDS | HC | T | 209 | 205 | 2.6 | 12.9 | 1.3 |
| PDS | HC | G | 371 | 367 | 2.60 | 22.9 | 1.3 |
| PDS | HC | Y | 373 | 369 | 2.56 | 21.7 | 1.4 |
| PDS | HC | K | 414 | 410 | 1.98 | 30.1 | 1.2 |
| PDS | HC | S | 424 | 420 | 3.81 | 12.3 | 1.0 |
| PDS | HC | T | 437 | 433 | 1.49 | 8.7 | 1.2 |
| PDS | HC | Q | 438 | 434 | 1.05 | 15.3 | 1.5 |
| PDS | HC | L | 443 | 439 | 1.61 | 12.4 | 1.2 |
| PDS | LC | T | 22 | 22 | 1.3 | 8.9 | 1.7 |
| PDS | LC | K | 39 | 39 | 2.6 | 3.3 | 1.3 |
| PDS | LC | G | 41 | 41 | 2.9 | 7.2 | 1.6 |
| PDS | LC | K | 42 | 42 | 2.2 | 6.5 | 1.4 |
| PDS | LC | Y | 49 | 49 | 1.9 | 5.2 | 1.8 |
| PDS | LC | Y | 55 | 55 | 1.8 | 6.8 | 1.1 |
| PDS | LC | T | 72 | 72 | 3.15 | 8.2 | 1.6 |
| PDS | LC | Q | 79 | 79 | 1.51 | 9.3 | 1.5 |
| PDS | LC | T | 85 | 85 | 3.12 | 3.3 | 1.4 |
| PDS | LC | Y | 92 | 92 | 1.8 | 13.3 | 1.6 |
| PDS | LC | T | 97 | 97 | 1.54 | 5.6 | 1.6 |
| PDS | LC | K | 103 | 103 | 1.64 | 3.5 | 1.5 |
| PDS | LC | T | 129 | 129 | 3.30 | 6.9 | 1.7 |
| PDS | LC | R | 142 | 142 | 2.15 | 4.2 | 1.3 |
| PDS | LC | K | 149 | 149 | 2.8358 | 9.5 | 0.8 |
| vc | LC | Q | 160 | 160 | 1.91 | 5.1 | 1.5 |

TABLE 10-continued

Average DAR, concentration, and aggregation of the preferred cysteine engineered antibodies of Tables 1 and 2 (Same samples as those shown in Tables 11 and 12)

| Linker | Cysteine Mutation (HC/LC) | Residue | EU Mutation Site # | Kabat Mutation Site # | Average DAR | Source Conc. (mg/mL) | % Aggregation |
|---|---|---|---|---|---|---|---|
| vc | LC | E | 195 | 195 | 1.7974 | 5.0 | 1.6 |
| vc | LC | V | 205 | 205 | 1.69 | 0.0 | 1.7 |
| vc | LC | T | 206 | 206 | 2.13 | 4.7 | 1.7 |

TABLE 11

ELISA and MS stability results of the preferred cysteine engineered antibodies of Tables 1 and 2 (Same samples as those shown in Tables 10 and 12)

| | | | | ELISA Rat Plasma Stability | | | MS Rat Plasma Stability | | | | |
|---|---|---|---|---|---|---|---|---|---|---|---|
| Linker | Cysteine Mutation (HC/LC) | Residue | Kabat Site # | % Conjugated @ 48 hrs (Duplicate 1) | % Conjugated @ 48 hrs (Duplicate 2) | % Conjugated @ 48 hrs (Average) | Calculated DAR at 0 hrs (BCP) | Calculated DAR at 48 hrs (BCP) | Calculated DAR at 96 hrs (BCP) | % DAR @ 96 hr relative to Assigned DAR | % DAR @ 96 hrs relative to DAR @ 0 hr |
| PDS | HC | V | 5 | 79.19 | 88.69 | 83.94 | 1.73 | 1.55 | 1.31 | 82.41 | 75.63 |
| PDS | HC | D | 101 | 108.58 | 109.95 | 109.26 | 1.69 | 1.75 | 1.60 | 92.49 | 94.88 |
| PDS | HC | A | 136 | 80.27 | 76.38 | 78.33 | 1.50 | 1.79 | 1.71 | 132.89 | 114.29 |
| PDS | HC | G | 162 | 95.76 | 77.92 | 86.84 | 1.77 | 1.51 | 1.22 | 68.37 | 69.24 |
| PDS | HC | L | 170 | 86.56 | 75.80 | 81.18 | 1.46 | 1.43 | 1.26 | 83.25 | 86.02 |
| PDS | HC | G | 174 | 82.85 | 90.34 | 86.60 | 1.93 | 1.70 | 1.43 | 76.10 | 74.12 |
| PDS | HC | L | 175 | 95.31 | 87.15 | 91.23 | 1.84 | 1.58 | 1.41 | 77.76 | 76.40 |
| PDS | HC | I | 195 | 114.73 | 125.84 | 120.28 | 1.48 | 1.71 | 1.65 | 118.01 | 111.63 |
| PDS | HC | S | 203 | 77.40 | 102.58 | 89.99 | 1.58 | 1.16 | 1.08 | 73.44 | 68.18 |
| PDS | HC | T | 205 | 92.25 | 85.88 | 89.06 | 1.34 | 1.47 | 1.38 | 107.76 | 102.74 |
| PDS | HC | G | 367 | 73.82 | 94.73 | 84.28 | 1.46 | 1.46 | 1.33 | 103.64 | 90.76 |
| PDS | HC | Y | 369 | 96.19 | 86.04 | 91.11 | 1.38 | 1.40 | 1.35 | 97.89 | 98.12 |
| PDS | HC | K | 410 | 93.74 | 86.50 | 90.12 | 1.29 | 1.50 | 1.41 | 122.94 | 109.25 |
| PDS | HC | S | 420 | 123.15 | 104.60 | 113.87 | 1.27 | 1.33 | 1.33 | 134.68 | 105.26 |
| PDS | HC | T | 433 | 96.98 | 83.67 | 90.33 | 1.36 | 1.22 | 1.15 | 96.64 | 84.74 |
| PDS | HC | Q | 434 | 123.91 | 99.85 | 111.88 | 1.80 | 1.54 | 1.44 | 94.57 | 79.86 |
| PDS | HC | L | 439 | 88.71 | 89.02 | 88.86 | 1.30 | 1.34 | 1.10 | 94.70 | 84.41 |
| PDS | LC | T | 22 | 125.21 | 101.52 | 113.37 | 1.77 | 1.69 | 1.67 | 97.47 | 94.29 |
| PDS | LC | K | 39 | 109.23 | 113.47 | 111.35 | 1.50 | 1.39 | 1.39 | 104.73 | 92.86 |
| PDS | LC | G | 41 | 65.85 | 75.39 | 70.62 | 1.79 | 1.70 | 1.45 | 91.11 | 81.13 |
| PDS | LC | K | 42 | 89.87 | 94.81 | 92.34 | 1.32 | 1.42 | 1.32 | 97.52 | 99.62 |
| PDS | LC | Y | 49 | 100.72 | 160.34 | 130.53 | 1.64 | 1.84 | 1.80 | 100.56 | 110.06 |
| PDS | LC | Y | 55 | 88.98 | 100.53 | 94.75 | 0.83 | 0.96 | 0.89 | 83.07 | 107.02 |
| PDS | LC | T | 72 | 107.26 | 112.28 | 109.77 | 1.67 | 1.67 | 1.48 | 94.87 | 88.64 |
| PDS | LC | Q | 79 | 111.51 | 78.50 | 95.01 | 1.69 | 1.38 | 1.16 | 76.10 | 68.80 |
| PDS | LC | T | 85 | 88.64 | 96.98 | 92.81 | 1.29 | 1.38 | 1.18 | 87.08 | 91.43 |
| PDS | LC | Y | 92 | 91.23 | 109.13 | 100.18 | 1.65 | 1.44 | 1.35 | 86.54 | 81.69 |
| PDS | LC | T | 97 | 85.23 | 121.61 | 103.42 | 1.19 | 1.12 | 0.91 | 58.59 | 76.97 |
| PDS | LC | K | 103 | 90.88 | 104.15 | 97.51 | 1.50 | 1.44 | 1.28 | 86.34 | 85.19 |
| PDS | LC | T | 129 | 84.25 | 91.76 | 88.01 | 1.78 | 1.56 | 1.32 | 76.13 | 73.81 |
| PDS | LC | R | 142 | 107.21 | 106.06 | 106.64 | 1.64 | 1.60 | 1.46 | 116.67 | 88.84 |
| PDS | LC | K | 149 | 81.74 | 102.87 | 92.30 | 0.91 | 1.02 | 0.94 | 120.41 | 103.40 |
| vc | LC | Q | 160 | 49.46 | 48.36 | 48.91 | 1.80 | 0.83 | 0.74 | 49.87 | 41.28 |
| vc | LC | E | 195 | 91.54 | 126.55 | 109.04 | n/a | 1.62 | 1.48 | 93.43 | n/a |
| vc | LC | V | 205 | 106.69 | 97.53 | 102.11 | n/a | 1.68 | 1.58 | 91.80 | n/a |
| vc | LC | T | 206 | 116.21 | 89.01 | 102.61 | n/a | 1.59 | 1.20 | 69.58 | n/a |

TABLE 12

Cysteine reduction assay results of the preferred cysteine engineered antibodies of Tables 1 and 2 (Same samples as those shown in Tables 10 and 11)

| | | | | Cysteine Reduction Results | | | Cysteine Reduction Confirmation | | | Cysteine Reduction Stability at Higher Concentration | |
|---|---|---|---|---|---|---|---|---|---|---|---|
| | | | | | | % DAR | | | % DAR | | |
| Linker | Cysteine Mutation (HC/LC) | Residue | Kabat Site # | DAR with 0 uM Cysteine | DAR with 50 uM Cysteine | Change from 0 uM to 50 uM | DAR with 0 uM Cysteine | DAR with 50 uM Cysteine | Change from 0 uM to 50 uM | DAR with 250 uM Cysteine | % DAR Change from 0 uM to 250 uM |
| PDS | HC | V | 5 | 1.8742 | 0 | 100 | n/a | n/a | n/a | n/a | n/a |
| PDS | HC | D | 101 | 1.7004 | 0.4544 | 73.27688 | n/a | n/a | n/a | n/a | n/a |
| PDS | HC | A | 136 | 1.6769 | 1.2591 | 24.91502 | 1.66 | 1.05 | 36.75 | 0.24 | 85.54 |
| PDS | HC | G | 162 | 1.6762 | 0 | 100 | n/a | n/a | n/a | n/a | n/a |
| PDS | HC | L | 170 | 1.6681 | 1.5586 | 6.564355 | 1.77 | 1.56 | 11.86 | 1.13 | 36.16 |
| PDS | HC | G | 174 | 1.95743 | 0.119 | 93.9206 | n/a | n/a | n/a | n/a | n/a |
| PDS | HC | L | 175 | 1.6635 | 0.5454 | 67.21371 | 1.71 | 0.6 | 64.91 | 0 | 100 |
| PDS | HC | I | 195 | 1.8582 | 0.05876 | 96.8378 | n/a | n/a | n/a | n/a | n/a |
| PDS | HC | S | 203 | 1.71344 | 0.2683 | 84.34144 | n/a | n/a | n/a | n/a | n/a |
| PDS | HC | T | 205 | 1.4654 | 0.07159 | 95.11464 | n/a | n/a | n/a | n/a | n/a |
| PDS | HC | G | 367 | 1.6468 | 0.6658 | 59.57008 | 1.6 | 0.62 | 61.25 | 0 | 100 |
| PDS | HC | Y | 369 | 1.735 | 1.3773 | 20.61671 | 1.87 | 1.27 | 32.09 | 0.33 | 82.35 |
| PDS | HC | K | 410 | 1.2231 | 0.2401 | 80.36955 | n/a | n/a | n/a | n/a | n/a |
| PDS | HC | S | 420 | 1.5446 | 0.8361 | 45.86948 | 1.59 | 0.81 | 49.06 | 0 | 100 |
| PDS | HC | T | 433 | 1.3657 | 0.05475 | 95.99107 | n/a | n/a | n/a | n/a | n/a |
| PDS | HC | Q | 434 | 1.91452 | 0.6531 | 65.88701 | 1.93 | 0.56 | 70.98 | 0 | 100 |
| PDS | HC | L | 439 | 1.46 | 0.359 | 75.41096 | n/a | n/a | n/a | n/a | n/a |
| PDS | LC | T | 22 | 1.8431 | 0.6782 | 63.2033 | 1.92 | 0.57 | 70.31 | 0 | 100 |
| PDS | LC | K | 39 | 1.6652 | 0.8724 | 47.6099 | 1.75 | 0.66 | 62.29 | 0 | 100 |
| PDS | LC | G | 41 | 1.85 | 0 | 100 | n/a | n/a | n/a | n/a | n/a |
| PDS | LC | K | 42 | 1.5105 | 0.34604 | 77.09103 | n/a | n/a | n/a | n/a | n/a |
| PDS | LC | Y | 49 | 1.7923 | 1.4371 | 19.81811 | 1.89 | 1.33 | 29.63 | 0.23 | 87.83 |
| PDS | LC | Y | 55 | 0.8656 | 0.8344 | 3.604436 | 0.89 | 0.75 | 15.73 | 0.56 | 37.08 |
| PDS | LC | T | 72 | 1.8279 | 0.35698 | 80.47049 | n/a | n/a | n/a | n/a | n/a |
| PDS | LC | Q | 79 | 1.783 | 0.29954 | 83.20022 | n/a | n/a | n/a | n/a | n/a |
| PDS | LC | T | 85 | 1.577 | 1.4823 | 6.005073 | 1.69 | 1.66 | 1.77 | 0.8 | 52.66 |
| PDS | LC | Y | 92 | 1.8244 | 0.0913 | 94.99562 | n/a | n/a | n/a | n/a | n/a |
| PDS | LC | T | 97 | 1.4234 | 0.7754 | 45.5248 | 1.49 | 0.84 | 43.62 | 0 | 100 |
| PDS | LC | K | 103 | 1.6749 | 0.4446 | 73.45513 | n/a | n/a | n/a | n/a | n/a |
| PDS | LC | T | 129 | 1.8214 | 0 | 100 | n/a | n/a | n/a | n/a | n/a |
| PDS | LC | R | 142 | 1.7244 | 0.9902 | 42.57713 | 1.77 | 0.69 | 61.02 | 0 | 100 |
| PDS | LC | K | 149 | 1.1712 | 0.824 | 29.64481 | 1.23 | 0.68 | 44.72 | 0.009 | 99.27 |
| vc | LC | Q | 160 | 1.6781 | 0 | 100 | n/a | n/a | n/a | n/a | n/a |
| vc | LC | E | 195 | 1.7655 | 0 | 100 | n/a | n/a | n/a | n/a | n/a |
| vc | LC | V | 205 | 1.6923 | 0.1614 | 90.46268 | n/a | n/a | n/a | n/a | n/a |
| vc | LC | T | 206 | 1.642 | 0 | 100 | n/a | n/a | n/a | n/a | n/a |

The DAR calculations for the PDS-MMAE and –vc-MMAE THIOMAB™ antibodies identified in Tables 8-10 were all >DAR0. The PDS-MMAE THIOMAB™ antibodies identified in Table 8 exhibited at least ≥80% stability in rat matrix over time for at least one of the two ELISA replicates.

Interestingly, the DAR, concentration, aggregation, and stability were not the same for the vc- and PDS-conjugated cysteine engineered antibodies (i.e., THIOMAB™ antibodies). For example, the preferred cysteine engineered antibodies of Tables 6 and 7 (PDS linker) and Tables 8 and 9 (vc linker) were not identical. For example, the top stable sites preferred for PDS linker conjugation to a drug moiety are LC-T22C, LC-K39C, LC-Y49C, LC-Y55C, LC-T85C, LC-T97C, LC-R142C, LC-K149C, HC-A140C, HC-L174C, HC-L179C, HC-G371C, HC-Y373C, and HC-S424C while the top stable sites preferred for –vc linker conjugation to a drug moiety are LC-I106C, LC-R108C, LC-V205C, HC-T110C (Kabat numbering), HC-T187C, HC-T209C, HC-V262C, HC-G371C, HC-E382C, HC-N434C according to EU numbering (see FIG. 21). Thus, only HC-G371C was a top site for PDS and –vc in the screen. Accordingly, determining which sites worked best for stability when conjugating a drug moiety to a cysteine engineered antibody with either a PDS or –vc linker could not be predicted and required extensive experimentation.

Thiol Reactivity of THIOMAB™ Antibodies

The thiol reactivity of full length, IgG cysteine engineered antibodies (THIOMAB™ antibodies) can be measured by biotinylation and streptavidin binding as described in U.S. Pat. No. 7,521,541 which is incorporated by reference in its entirety. Specifically, a western blot assay was can be set up to screen the THIOMAB™ antibody that is specifically conjugated with biotin-maleimide. In this assay, the antibodies can be analyzed on reducing SDS-PAGE and the presence of biotin is specifically probed by incubating with streptavidin-HRP. The streptavidin-HRP interaction can either be observed in heavy chain or light chain depending on which engineered cys variant is being used and the binding can be compared to the biotin-streptavidin interaction of a wild type IgG without an engineered cysteine, thereby indicating which THIOMAB™ antibodies specifically conjugate the biotin as compared to any background binding of the wild type antibody.

Antibody-Drug Conjugates

The cysteine engineered antibodies of the invention may be conjugated with any therapeutic agent, i.e. drug moiety, which can be covalently attached to the antibody through a reactive cysteine thiol group. For exemplary purposes, the cysteine engineered antibodies disclosed in the tables provided herein were conjugated to a maytansinoid drug, specifically MMAE.

An exemplary embodiment of an antibody-drug conjugate (ADC) compound comprises a cysteine engineered antibody (Ab), and a drug moiety (D) wherein the antibody has one or more free cysteine amino acids, and the antibody is attached through the one or more free cysteine amino acids by a linker moiety (L) to D; the composition having Formula I:

$$Ab\text{-}(L\text{-}D)_p \qquad\qquad I$$

where p is 1, 2, 3, or 4. The number of drug moieties which may be conjugated via a thiol reactive linker moiety to an antibody molecule is limited by the number of cysteine residues which are introduced by the methods described herein. Exemplary ADC of Formula I therefore comprise antibodies which have 1, 2, 3, or 4 engineered cysteine amino acids.

Another exemplary embodiment of an antibody-drug conjugate compound (ADC) comprises a cysteine engineered antibody (Ab), an albumin-binding peptide (ABP) and a drug moiety (D) wherein the antibody is attached to the drug moiety by a linker moiety (L) and the antibody is attached to the albumin-binding peptide by an amide bond or a second linker moiety; the composition having Formula Ia:

$$ABP\text{-}Ab\text{-}(L\text{-}D)_p \qquad\qquad Ia$$

where p is 1, 2, 3, or 4.

The ADC compounds of the invention include those with utility for anticancer activity. In particular, the compounds include a cysteine-engineered antibody conjugated, i.e. covalently attached by a linker, to a drug moiety, i.e. toxin. When the drug is not conjugated to an antibody, the drug has a cytotoxic or cytostatic effect. The biological activity of the drug moiety is thus modulated by conjugation to an antibody. The antibody-drug conjugates (ADC) of the invention selectively deliver an effective dose of a cytotoxic agent to tumor tissue whereby greater selectivity, i.e. a lower efficacious dose, may be achieved.

Drug Moieties

The drug moiety (D) of the antibody-drug conjugates (ADC) includes any compound, moiety or group which has a cytotoxic or cytostatic effect. Drug moieties include: (i) chemotherapeutic agents, which may function as microtubulin inhibitors, mitosis inhibitors, topoisomerase inhibitors, or DNA intercalators; (ii) protein toxins, which may function enzymatically; and (iii) radioisotopes.

Exemplary drug moieties include, but are not limited to, a maytansinoid, an auristatin, a dolastatin, a trichothecene, CC1065, a calicheamicin and other enediyne antibiotics, a taxane, a pyrrolobenzodiazepine (PBD), a 1-(Chloromethyl)-2,3-dihydro-1H-benzo[e]indole (CBI) dimer, a CBI-PBD heterodimer, an anthracycline, and stereoisomers, isosteres, analogs or derivatives thereof.

Maytansine compounds suitable for use as maytansinoid drug moieties are well known in the art, and can be isolated from natural sources according to known methods, produced using genetic engineering techniques (see Yu et al (2002) PROC. NAT. ACAD. SCI. (USA) 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/–C-19-dechloro (U.S. Pat. Nos. 4,361,650 and 4,307,016) (prepared by demethylation using Streptomyces or Actinomyces or dechlorination using LAH); and C-20-demethoxy, C-20-acyloxy (—OCOR, +/–dechloro (U.S. Pat. No. 4,294,757) (prepared by acylation using acyl chlorides). and those having modifications at other positions Exemplary maytansinoid drug moieties also include those having modifications such as: C-9-SH (U.S. Pat. No. 4,424,219) (prepared by the reaction of maytansinol with $H_2S$ or $P_2S_5$); C-14-alkoxymethyl(demethoxy/$CH_2$ OR) (U.S. Pat. No. 4,331,598); C-14-hydroxymethyl or acyloxymethyl ($CH_2OH$ or $CH_2OAc$) (U.S. Pat. No. 4,450,254) (prepared from Nocardia); C-15-hydroxy/acyloxy (U.S. Pat. No. 4,364,866) (prepared by the conversion of maytansinol by Streptomyces); C-15-methoxy (U.S. Pat. Nos. 4,313,946 and 4,315,929) (isolated from Trewia nudlflora); C-18-N-demethyl (U.S. Pat. Nos. 4,362,663 and 4,322,348) (prepared by the demethylation of maytansinol by Streptomyces); and 4,5-deoxy (U.S. Pat. No. 4,371,533) (prepared by the titanium trichloride/LAH reduction of maytansinol). Many positions on maytansine compounds are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable.

The drug moiety (D) of the antibody-drug conjugates (ADC) of Formula I include maytansinoids having the structure:

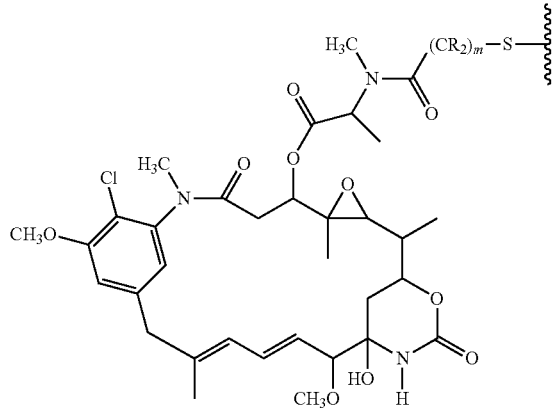

where the wavy line indicates the covalent attachment of the sulfur atom of D to a linker (L) of an antibody-drug conjugate (ADC). R may independently be H or a $C_1$-$C_6$ alkyl selected from methyl, ethyl, 1-propyl, 2-propyl, 1-butyl, 2-methyl-1-propyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl. The alkylene chain attaching the amide group to the sulfur atom may be methanyl, ethanyl, or propyl, i.e. m is 1, 2, or 3.

Maytansine compounds inhibit cell proliferation by inhibiting the formation of microtubules during mitosis through inhibition of polymerization of the microtubulin protein, tubulin (Remillard et al (1975) Science 189:1002-1005). Maytansine and maytansinoids are highly cytotoxic but their clinical use in cancer therapy has been greatly limited by their severe systemic side-effects primarily attributed to their poor selectivity for tumors. Clinical trials with maytansine had been discontinued due to serious adverse effects on the central nervous system and gastrointestinal system (Issel et al (1978) Can. Treatment. Rev. 5:199-207).

Maytansinoid drug moieties are attractive drug moieties in antibody-drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines (US 2005/0169933; WO 2005/037992; U.S. Pat. No. 5,208,020).

As with other drug moieties, all stereoisomers of the maytansinoid drug moiety are contemplated for the compounds of the invention, i.e. any combination of R and S configurations at the chiral carbons of D. In one embodiment, the maytansinoid drug moiety (D) will have the following stereochemistry:

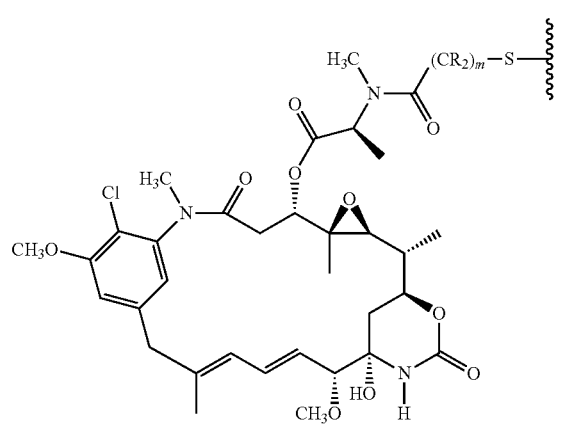

Exemplary embodiments of maytansinoid drug moieties include: DM1, $(CR_2)_m=CH_2CH_2$; DM3, $(CR_2)_m=CH_2CH_2CH(CH_3)$; and DM4, $(CR_2)_m=CH_2CH_2C(CH_3)_2$, having the structures:

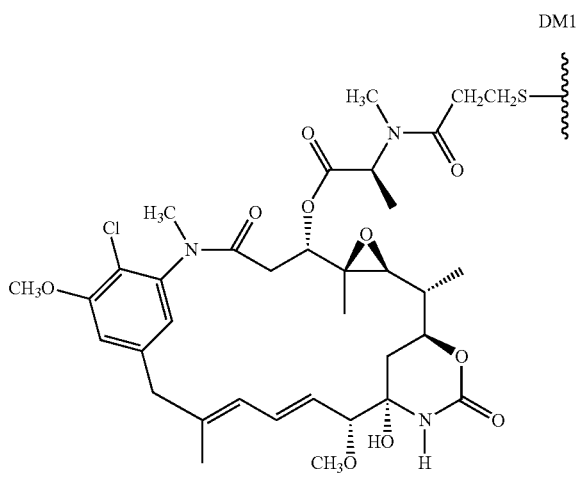

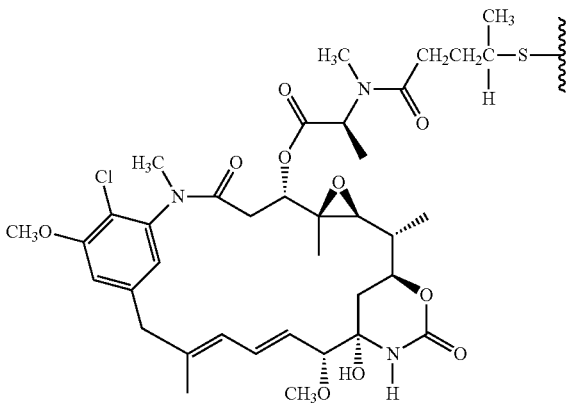

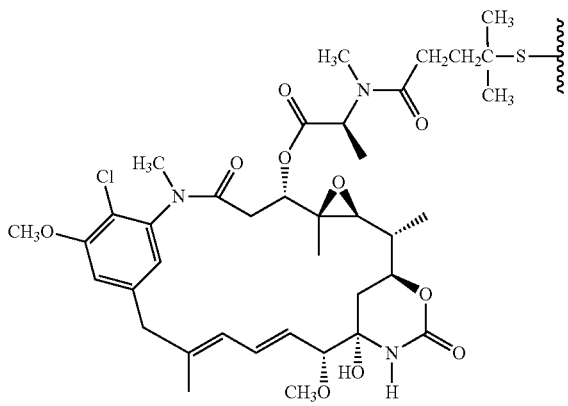

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

The drug moiety (D) of the antibody-drug conjugates (ADC) of Formula I also include dolastatins and their peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). Various forms of a dolastatin or auristatin drug moiety may be covalently attached to an antibody through the N (amino) terminus or the C (carboxyl) terminus of the peptidic drug moiety (WO 02/088172; Doronina et al (2003) Nature Biotechnology 21(7):778-784; Francisco et al (2003) Blood 102(4):1458-1465).

Drug moieties include dolastatins, auristatins (U.S. Pat. No. 5,635,483; U.S. Pat. No. 5,780,588; U.S. Pat. No. 5,767,237; U.S. Pat. No. 6,124,431), and analogs and derivatives thereof. Dolastatins and auristatins have been shown to interfere with microtubule dynamics, GTP hydrolysis, and nuclear and cellular division (Woyke et al (2001)

Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in U.S. Pat. No. 7,498,298 and U.S. Pat. No. 7,659,241, the disclosure of each which is expressly incorporated by reference in their entirety.

The drug moiety (D) of the antibody-drug conjugates (ADC) of Formula I include the monomethylauristatin drug moieties MMAE and MMAF linked through the N-terminus to the antibody, and having the structures:

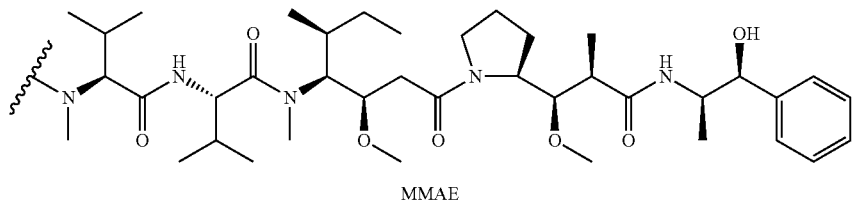

MMAE

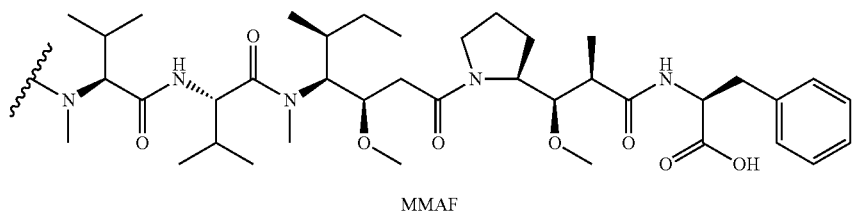

MMAF

Figure 11:
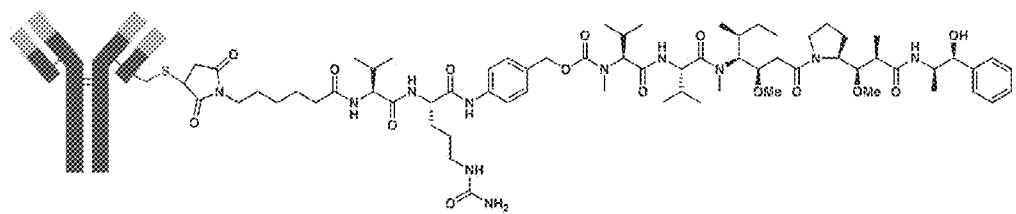
FIG. 11 shows a drawing (not to scale) of a MC-vc-MMAE THIOMAB™ antibody.

Exemplary MMAE ADC are shown in FIGS. 11 and 12. Typically, peptide-based drug moieties can be prepared by forming a peptide bond between two or more amino acids and/or peptide fragments. Such peptide bonds can be prepared, for example, according to the liquid phase synthesis method (see E. Schröder and K. Lüke, "The Peptides", volume 1, pp 76-136, 1965, Academic Press) that is well known in the field of peptide chemistry.

The drug moiety includes calicheamicin, and analogs and derivatives thereof. The calicheamicin family of antibiotics are capable of producing double-stranded DNA breaks at sub-picomolar concentrations. For the preparation of conjugates of the calicheamicin family, see U.S. Pat. No. 5,712,374; U.S. Pat. No. 5,714,586; U.S. Pat. No. 5,739,116; U.S. Pat. No. 5,767,285; U.S. Pat. No. 5,770,701, U.S. Pat. No. 5,770,710; U.S. Pat. No. 5,773,001; U.S. Pat. No. 5,877,296. Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al Cancer Research 53:3336-3342 (1993), Lode et al Cancer Research 58:2925-2928 (1998).

In some embodiments, an ADC comprises a pyrrolobenzodiazepine (PBD). In some embodiments, PDB dimers recognize and bind to specific DNA sequences. The natural product anthramycin, a PBD, was first reported in 1965 (Leimgruber, et al., (1965) J. Am. Chem. Soc., 87:5793-5795; Leimgruber, et al., (1965) J. Am. Chem. Soc., 87:5791-5793). Since then, a number of PBDs, both naturally-occurring and analogues, have been reported (Thurston, et al., (1994) Chem. Rev. 1994, 433-465 including dimers of the tricyclic PBD scaffold (U.S. Pat. No. 6,884, 799; U.S. Pat. No. 7,049,311; U.S. Pat. No. 7,067,511; U.S. Pat. No. 7,265,105; U.S. Pat. No. 7,511,032; U.S. Pat. No. 7,528,126; U.S. Pat. No. 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) Acc. Chem. Res., 19:230-237). Dimeric PBD compounds bearing C2 aryl substituents have been shown to be useful as cytotoxic agents (Hartley et al (2010) Cancer Res. 70(17):6849-6858; Antonow (2010) J. Med. Chem. 53(7):2927-2941; Howard et al (2009) Bioorganic and Med. Chem. Letters 19(22):6463-6466).

In some embodiments, PBD compounds can be employed as prodrugs by protecting them at the N10 position with a nitrogen protecting group which is removable in vivo (WO 00/12507; WO 2005/023814).

In some embodiments, the immunoconjugate comprises an antibody conjugated to one or more calicheamicin molecules. The calicheamicin family of antibiotics, and analogues thereof, are capable of producing double-stranded DNA breaks at sub-picomolar concentrations (Hinman et al., (1993) Cancer Research 53:3336-3342; Lode et al., (1998) Cancer Research 58:2925-2928). Calicheamicin has intracellular sites of action but, in certain instances, does not readily cross the plasma membrane. Therefore, cellular uptake of these agents through antibody-mediated internalization may, in some embodiments, greatly enhances their cytotoxic effects. Nonlimiting exemplary methods of preparing antibody-drug conjugates with a calicheamicin drug moiety are described, for example, in U.S. Pat. No. 5,712, 374; U.S. Pat. No. 5,714,586; U.S. Pat. No. 5,739,116; and U.S. Pat. No. 5,767,285.

In some embodiments, the calicheamicin drug moiety conjugated to the antibody is a compound having the formula:

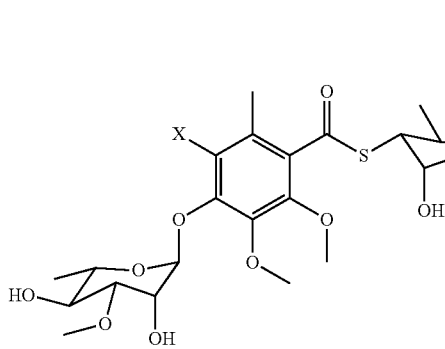
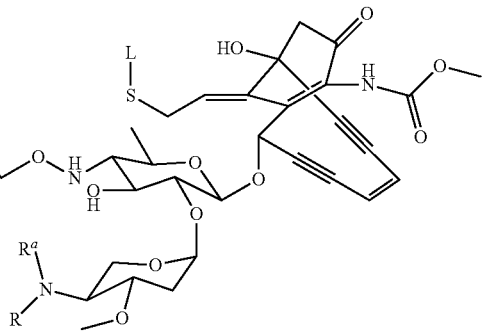

wherein X is Br or I;

L is a linker; R is hydrogen, $C_{1-6}$alkyl, or —C(=O) $C_{1-6}$alkyl; and $R^a$ is hydrogen or $C_{1-6}$alkyl.

In some embodiments, X is Br, $R^a$ is hydrogen and R is isopropyl.

In other embodiments, X is Br, $R^a$ is hydrogen and R is ethyl.

In other embodiments, X is I, $R^a$ is hydrogen and R is isopropyl.

In other embodiments, X is I, $R^a$ is hydrogen and R is ethyl.

In some embodiments, X is Br, $R^a$ is hydrogen and R—C(=O)CH$_3$.

In other embodiments, X is I, $R^a$ is hydrogen and R is —C(=O)CH$_3$.

In other embodiments, X is I, $R^a$ is ethyl and R is —C(=O)CH$_3$.

In other embodiments, X is Br, Ra is ethyl and R is —C(=O)CH$_3$.

PBD dimers have been conjugated to antibodies and the resulting ADC shown to have anti-cancer properties (US 2010/0203007). Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598).

In some embodiments, an ADC comprises a pyrrolobenzodiazepine (PBD). In some embodiments, PDB dimers recognize and bind to specific DNA sequences. The natural product anthramycin, a PBD, was first reported in 1965 (Leimgruber, et al., (1965) J. Am. Chem. Soc., 87:5793-5795; Leimgruber, et al., (1965) J. Am. Chem. Soc., 87:5791-5793). Since then, a number of PBDs, both naturally-occurring and analogues, have been reported (Thurston, et al., (1994) Chem. Rev. 1994, 433-465 including dimers of the tricyclic PBD scaffold (U.S. Pat. No. 6,884, 799; U.S. Pat. No. 7,049,311; U.S. Pat. No. 7,067,511; U.S. Pat. No. 7,265,105; U.S. Pat. No. 7,511,032; U.S. Pat. No. 7,528,126; U.S. Pat. No. 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) Acc. Chem. Res., 19:230-237). Dimeric PBD compounds bearing C2 aryl substituents have been shown to be useful as cytotoxic agents (Hartley et al (2010) Cancer Res. 70(17):6849-6858; Antonow (2010) J. Med. Chem. 53(7):2927-2941; Howard et al (2009) Bioorganic and Med. Chem. Letters 19(22):6463-6466).

In some embodiments, PBD compounds can be employed as prodrugs by protecting them at the N10 position with a nitrogen protecting group which is removable in vivo (WO 00/12507; WO 2005/023814).

PBD dimers have been conjugated to antibodies and the resulting ADC shown to have anti-cancer properties (US 2010/0203007). Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598).

Nonlimiting exemplary PBD dimer components of ADCs are of Formula A:

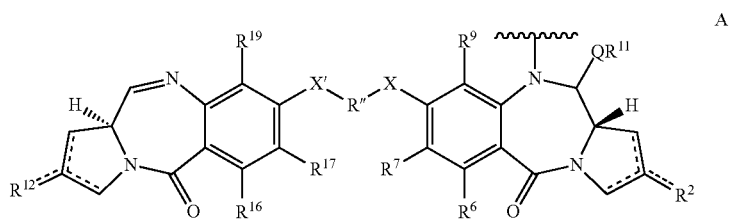

A and salts and solvates thereof, wherein:
the wavy line indicates the covalent attachment site to the linker;
the dotted lines indicate the optional presence of a double bond between C1 and C2 or C2 and C3;
$R^2$ is independently selected from H, OH, =O, =CH$_2$, CN, R, OR, =CH—$R^D$, =C($R^D$)$_2$, O—SO$_2$—R, CO$_2$R and COR, and optionally further selected from halo or dihalo, wherein $R^D$ is independently selected from R, CO$_2$R, COR, CHO, CO$_2$H, and halo;
$R^6$ and $R^9$ are independently selected from H, R, OH, OR, SH, SR, NH$_2$, NHR, NRR', NO$_2$, Me$_3$Sn and halo;

R$^7$ is independently selected from H, R, OH, OR, SH, SR, NH$_2$, NHR, NRR', NO$_2$, Me$_3$Sn and halo;

Q is independently selected from O, S and NH;

R$^{11}$ is either H, or R or, where Q is O, SO$_3$M, where M is a metal cation;

R and R' are each independently selected from optionally substituted C$_{1-8}$ alkyl, C$_{1-12}$ alkyl, C$_{3-8}$ heterocyclyl, C$_{3-20}$ heterocycle, and C$_{5-20}$ aryl groups, and optionally in relation to the group NRR', R and R' together with the nitrogen atom to which they are attached form an optionally substituted 4-, 5-, 6- or 7-membered heterocyclic ring;

R$^{12}$, R$^{16}$, R$^{19}$ and R$^{17}$ are as defined for R$^2$, R$^6$, R$^9$ and R$^7$ respectively;

R" is a C$_{3-12}$ alkylene group, which chain may be interrupted by one or more heteroatoms, e.g. O, S, N(H), NMe and/or aromatic rings, e.g. benzene or pyridine, which rings are optionally substituted; and X and X' are independently selected from O, S and N(H).

In some embodiments, R and R' are each independently selected from optionally substituted C$_{1-12}$ alkyl, C$_{3-20}$ heterocycle, and C$_{5-20}$ aryl groups, and optionally in relation to the group NRR', R and R' together with the nitrogen atom to which they are attached form an optionally substituted 4-, 5-, 6- or 7-membered heterocyclic ring.

In some embodiments, R$^9$ and R$^{19}$ are H.

In some embodiments, R$^6$ and R$^{16}$ are H.

In some embodiments, R$^7$ are R$^{17}$ are both OR$^{7A}$, where R$^{7A}$ is optionally substituted C$_{1-4}$ alkyl. In some embodiments, R$^{7A}$ is Me. In some embodiments, R$^{7A}$ is is Ch$_2$Ph, where Ph is a phenyl group.

In some embodiments, X is O.

In some embodiments, R$^{11}$ is H.

In some embodiments, there is a double bond between C2 and C3 in each monomer unit.

In some embodiments, R$^2$ and R$^{12}$ are independently selected from H and R. In some embodiments, R$^2$ and R$^{12}$ are independently R. In some embodiments, R$^2$ and R$^{12}$ are independently optionally substituted C$_{5-20}$ aryl or C$_{5-7}$ aryl or C$_{8-10}$ aryl. In some embodiments, R$^2$ and R$^{12}$ are independently optionally substituted phenyl, thienyl, napthyl, pyridyl, quinolinyl, or isoquinolinyl. In some embodiments, R$^2$ and R$^{12}$ are independently selected from =O, =CH$_2$, =CH—R$^D$, and =C(R$^D$)$_2$. In some embodiments, R$^2$ and R$^{12}$ are each =CH$_2$. In some embodiments, R$^2$ and R$^{12}$ are each H. In some embodiments, R$^2$ and R$^{12}$ are each =O. In some embodiments, R$^2$ and R$^{12}$ are each =CF$_2$. In some embodiments, R$^2$ and/or R$^{12}$ are independently =C(R$^D$)$_2$. In some embodiments, R$^2$ and/or R$^{12}$ are independently =CH—R$^D$.

In some embodiments, when R$^2$ and/or R$^{12}$ is =CH—R$^D$, each group may independently have either configuration shown below:

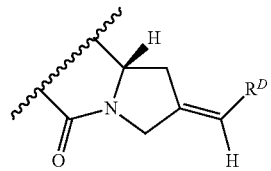

(I)

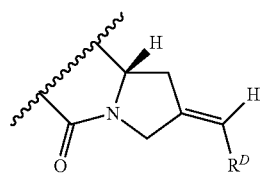

(II)

In some embodiments, a =CH—R$^D$ is in configuration (I).

In some embodiments, R" is a C$_3$ alkylene group or a C$_5$ alkylene group.

In some embodiments, an exemplary PBD dimer component of an ADC has the structure of Formula A(I):

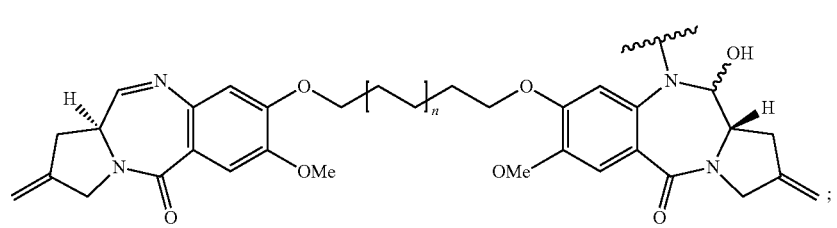

A(I)

wherein n is 0 or 1.

In some embodiments, an exemplary PBD dimer component of an ADC has the structure of Formula A(II):

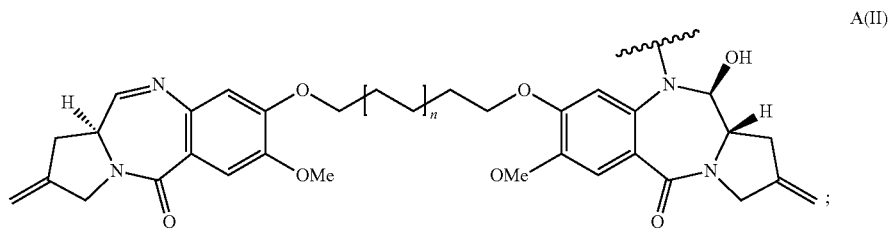

A(II)

wherein n is 0 or 1.

In some embodiments, an exemplary PBD dimer component of an ADC has the structure of Formula A(III):

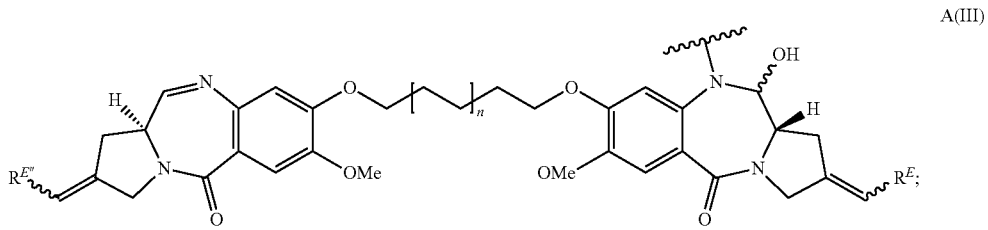

A(III)

wherein $R^E$ and $R^{E''}$ are each independently selected from H or $R^D$, wherein $R^D$ is defined as above; and
wherein n is 0 or 1.

In some embodiments, n is 0. In some embodiments, n is 1. In some embodiments, $R^E$ and/or $R^{E''}$ is H. In some embodiments, $R^E$ and $R^{E''}$ are H. In some embodiments, $R^E$ and/or $R^{E''}$ is $R^D$, wherein $R^D$ is optionally substituted $C_{1-12}$ alkyl. In some embodiments, $R^E$ and/or $R^{E''}$ is $R^D$, wherein $R^D$ is methyl.

In some embodiments, an exemplary PBD dimer component of an ADC has the structure of Formula A(IV):

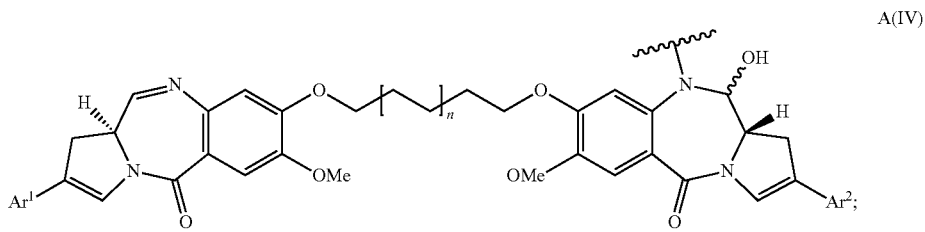

A(IV)

wherein $Ar^1$ and $Ar^2$ are each independently optionally substituted $C_{5-20}$ aryl; wherein $Ar^1$ and $Ar^2$ may be the same or different; and
wherein n is 0 or 1.

In some embodiments, an exemplary PBD dimer component of an ADC has the structure of Formula A(V):

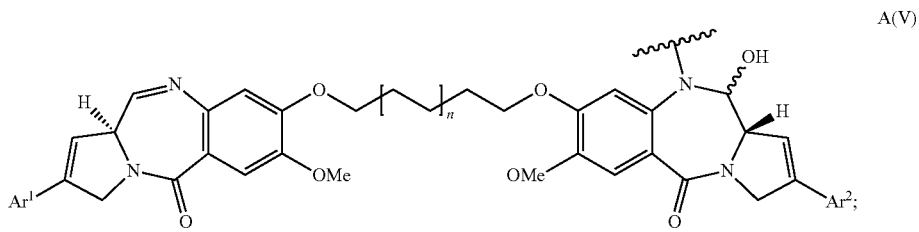

A(V)

wherein $Ar^1$ and $Ar^2$ are each independently optionally substituted $C_{5-20}$ aryl; wherein $Ar^1$ and $Ar^2$ may be the same or different; and
wherein n is 0 or 1.

In some embodiments, $Ar^1$ and $Ar^2$ are each independently selected from optionally substituted phenyl, furanyl, thiophenyl and pyridyl. In some embodiments, $Ar^1$ and $Ar^2$ are each independently optionally substituted phenyl. In some embodiments, $Ar^1$ and $Ar^2$ are each independently optionally substituted thien-2-yl or thien-3-yl. In some embodiments, $Ar^1$ and $Ar^2$ are each independently optionally substituted quinolinyl or isoquinolinyl. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. In some embodiments, the quinolinyl is selected from quinolin-3-yl and quinolin-6-yl. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. In some embodiments, the isoquinolinyl is selected from isoquinolin-3-yl and isoquinolin-6-yl.

Further nonlimiting exemplary PBD dimer components of ADCs are of Formula B:

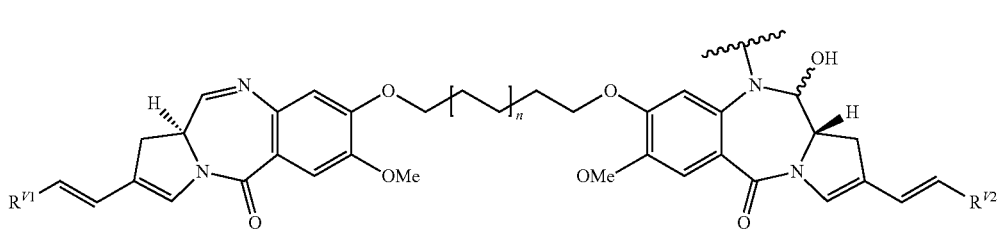

and salts and solvates thereof, wherein:
the wavy line indicates the covalent attachment site to the linker;
the wavy line connected to the OH indicates the S or R configuration;
$R^{V1}$ and $R^{V2}$ are independently selected from H, methyl, ethyl and phenyl (which phenyl may be optionally substituted with fluoro, particularly in the 4 position) and $C_{5-6}$ heterocyclyl; wherein $R^{V1}$ and $R^{V2}$ may be the same or different; and
n is 0 or 1.

In some embodiments, $R^{V1}$ and $R^{V2}$ are independently selected from H, phenyl, and 4-fluorophenyl.

In some embodiments, a linker may be attached at one of various sites of the PBD dimer drug moiety, including the N10 imine of the B ring, the C-2 endo/exo position of the C ring, or the tether unit linking the A rings (see structures C(I) and C(II) below).

Nonlimiting exemplary PBD dimer components of ADCs include Formulas C(I) and C(II):

Formulas C(I) and C(II) are shown in their N10-C11 imine form. Exemplary PBD drug moieties also include the carbinolamine and protected carbinolamine forms as well, as shown in the table below:

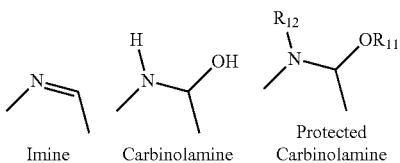

wherein:
X is $CH_2$ (n=1 to 5), N, or O;
Z and Z' are independently selected from OR and $NR_2$, where R is a primary, secondary or tertiary alkyl chain containing 1 to 5 carbon atoms;
$R_1$, $R'_1$, $R_2$ and $R'_2$ are each independently selected from H, $C_1$-$C_8$ alkyl, $C_2$-$C_8$ alkenyl, $C_2$-$C_8$ alkynyl, $C_{5-20}$ aryl (including substituted aryls), $C_{5-20}$ heteroaryl groups, —$NH_2$, —NHMe, —OH, and —SH, where, in some embodiments, alkyl, alkenyl and alkynyl chains comprise up to 5 carbon atoms;
$R_3$ and $R'_3$ are independently selected from H, OR, NHR, and $NR_2$, where R is a primary, secondary or tertiary alkyl chain containing 1 to 5 carbon atoms;

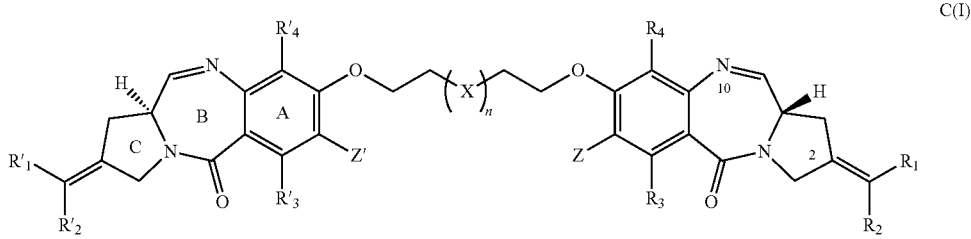

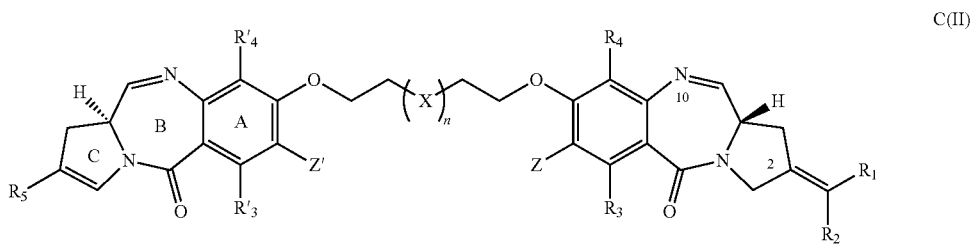

$R_4$ and $R'_4$ are independently selected from H, Me, and OMe;

$R_5$ is selected from $C_1$-$C_8$ alkyl, $C_2$-$C_8$ alkenyl, $C_2$-$C_8$ alkynyl, $C_{5-20}$ aryl (including aryls substituted by halo, nitro, cyano, alkoxy, alkyl, heterocyclyl) and $C_{5-20}$ heteroaryl groups, where, in some embodiments, alkyl, alkenyl and alkynyl chains comprise up to 5 carbon atoms;

$R_{11}$ is H, $C_1$-$C_8$ alkyl, or a protecting group (such as acetyl, trifluoroacetyl, t-butoxycarbonyl (BOC), benzyloxycarbonyl (CBZ), 9-fluorenylmethylenoxycarbonyl (Fmoc), or a moiety comprising a self-immolating unit such as valine-citrulline-PAB);

$R_{12}$ is is H, $C_1$-$C_8$ alkyl, or a protecting group;

wherein a hydrogen of one of $R_1$, $R'_1$, $R_2$, $R'_2$, $R_5$, or $R_{12}$ or a hydrogen of the —$OCH_2CH_2(X)_nCH_2CH_2O$— spacer between the A rings is replaced with a bond connected to the linker of the ADC.

Exemplary PDB dimer portions of ADC include, but are not limited to (the wavy line indicates the site of covalent attachment to the linker):

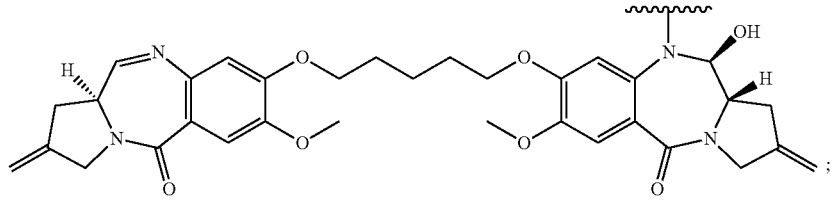

PBD dimer

Nonlimiting exemplary embodiments of ADCs comprising PBD dimers have the following structures:

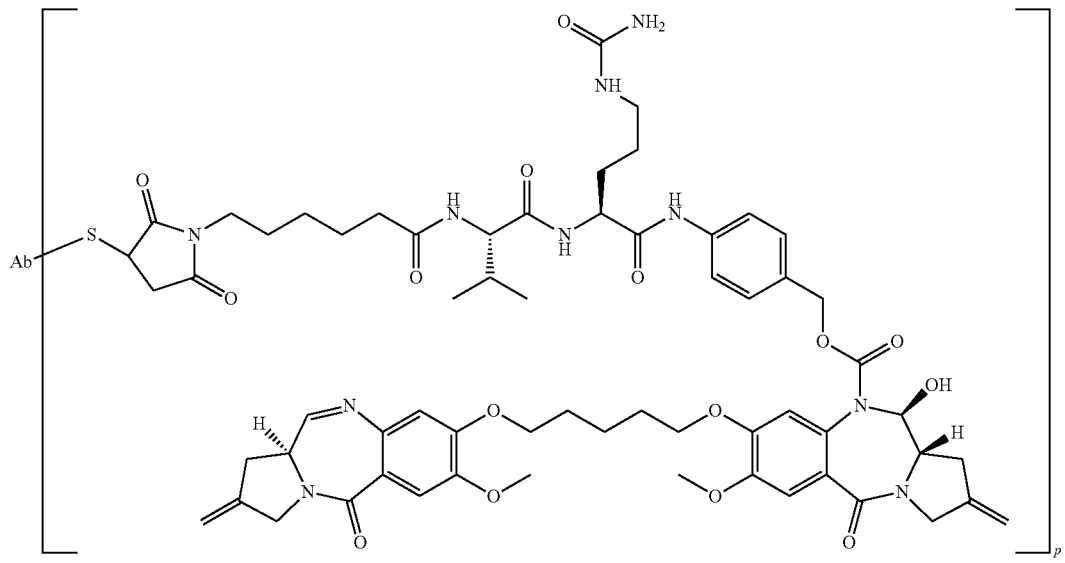

PBD dimer-val-cit-PAB-Ab;

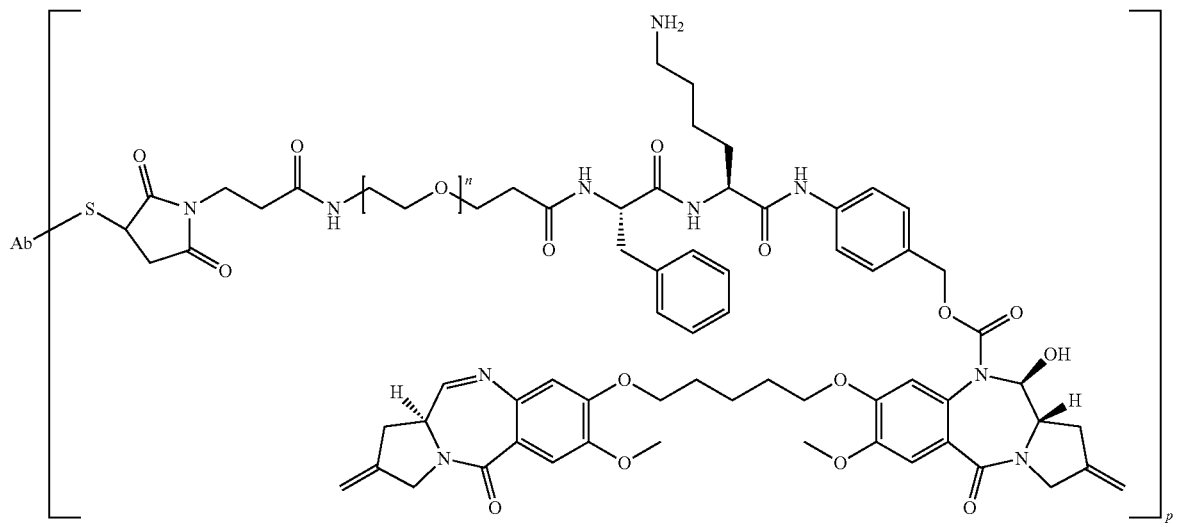

PBD dimer-Phe-Lys-PAB-Ab, wherein:
n is 0 to 12. In some embodiments, n is 2 to 10. In some embodiments, n is 4 to 8. In some embodiments, n is selected from 4, 5, 6, 7, and 8.

In some embodiments, an ADC comprising a PBD dimer described herein may be made by conjugating a linker-drug intermediate including a pyridine leaving group via a sulfur atom with a cysteine thiol of an antibody to form a disulfide linkage. Further, in some embodiments, an ADC comprising a PBD dimer described herein may be made by conjugating a linker-drug intermediate including a thiopyridyl leaving group, wherein the pyridine ring is substituted with one or more nitro groups. In some embodiments, the pyridyl ring is monosubstituted with —$NO_2$. In some embodiments, the —$NO_2$ monosubstitution is para relative to the disulfide. In some embodiments, the PBD dimer is connected through the N10 position. For example, non-limiting exemplary ADC comprising a PBD dimer may be made by conjugating a monomethylethyl pyridyl disulfide, N10-linked PBD linker intermediate (shown below) to an antibody:

daunorubicin and doxorubicin have been prepared and studied (Kratz et al (2006) *Current Med. Chem.* 13:477-523; Jeffrey et al (2006) *Bioorganic & Med. Chem. Letters* 16:358-362; Torgov et al (2005) *Bioconj. Chem.* 16:717-721; Nagy et al (2000) *Proc. Natl. Acad. Sci. USA* 97:829-834; Dubowchik et al (2002) *Bioorg. & Med. Chem. Letters* 12:1529-1532; King et al (2002) *J Med. Chem.* 45:4336-4343; EP 0328147; U.S. Pat. No. 6,630,579). The antibody-drug conjugate BR96-doxorubicin reacts specifically with the tumor-associated antigen Lewis-Y and has been evaluated in phase I and II studies (Saleh et al (2000) *J. Clin. Oncology* 18:2282-2292; Ajani et al (2000) *Cancer Jour.* 6:78-81; Tolcher et al (1999) *J. Clin. Oncology* 17:478-484).

PNU-159682 is a potent metabolite (or derivative) of nemorubicin (Quintieri, et al. (2005) *Clinical Cancer Research* 11(4):1608-1617). Nemorubicin is a semisynthetic analog of doxorubicin with a 2-methoxymorpholino group on the glycoside amino of doxorubicin and has been under clinical evaluation (Grandi et al (1990) *Cancer Treat. Rev.* 17:133; Ripamonti et al (1992) *Brit. J. Cancer* 65:703),

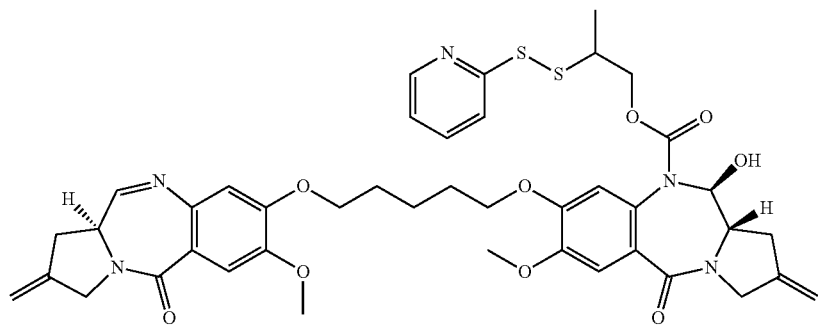

The linkers of PBD dimer-val-cit-PAB-Ab and the PBD dimer-Phe-Lys-PAB-Ab are protease cleavable, while the linker of PBD dimer-maleimide-acetal is acid-labile.

PBD dimers and ADC comprising PBD dimers may be prepared according to methods known in the art. See, e.g., WO 2009/016516; US 2009/304710; US 2010/047257; US 2009/036431; US 2011/0256157; WO 2011/130598; WO 2013/055987.

In some embodiments, an ADC comprising anthracycline. Anthracyclines are antibiotic compounds that exhibit cytotoxic activity. While not intending to be bound by any particular theory, studies have indicated that anthracyclines may operate to kill cells by a number of different mechanisms, including: 1) intercalation of the drug molecules into the DNA of the cell thereby inhibiting DNA-dependent nucleic acid synthesis; 2) production by the drug of free radicals which then react with cellular macromolecules to cause damage to the cells, and/or 3) interactions of the drug molecules with the cell membrane (see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102). Because of their cytotoxic potential anthracyclines have been used in the treatment of numerous cancers such as leukemia, breast carcinoma, lung carcinoma, ovarian adenocarcinoma and sarcomas (see e.g., P. H-Wiernik, in *Anthracycline: Current Status And New Developments* p 11).

Nonlimiting exemplary anthracyclines include doxorubicin, epirubicin, idarubicin, daunomycin, nemorubicin, and derivatives thereof. Immunoconjugates and prodrugs of including phase II/III trials for hepatocellular carcinoma (Sun et al (2003) *Proceedings of the American Society for Clinical Oncology* 22, Abs1448; Quintieri (2003) *Proceedings of the American Association of Cancer Research*, 44:1st Ed, Abs 4649; Pacciarini et al (2006) *Jour. Clin. Oncology* 24:14116).

A nonlimiting exemplary ADC comprising nemorubicin or nemorubicin derivatives is shown in Formula Ia:

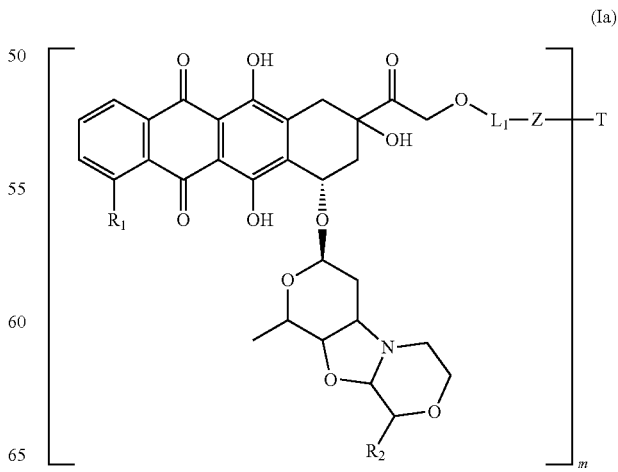

(Ia)

wherein $R_1$ is hydrogen atom, hydroxy or methoxy group and $R_2$ is a $C_1$-$C_5$ alkoxy group, or a pharmaceutically acceptable salt thereof;

$L_1$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

A further nonlimiting exemplary ADC comprising nemorubicin or nemorubicin derivatives is shown in Formula Ib:

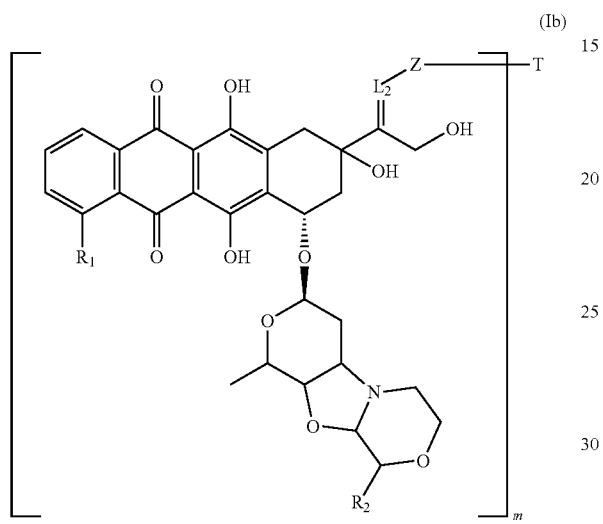

wherein $R_1$ is hydrogen atom, hydroxy or methoxy group and $R_2$ is a $C_1$-$C_5$ alkoxy group, or a pharmaceutically acceptable salt thereof;

L2 and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

In some embodiments, the nemorubicin component of a nemorubicin-containing ADC is PNU-159682. In some such embodiments, the drug portion of the ADC may have one of the following structures:

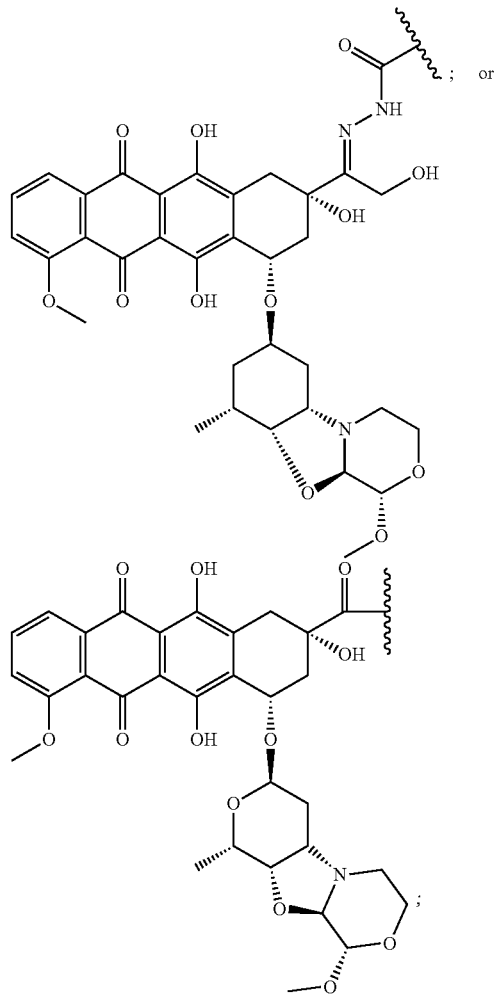

wherein the wavy line indicates the attachment to the linker (L).

Anthracyclines, including PNU-159682, may be conjugated to antibodies through several linkage sites and a variety of linkers (US 2011/0076287; WO2009/099741; US 2010/0034837; WO 2010/009124), including the linkers described herein.

Exemplary ADCs comprising a nemorubicin and linker include, but are not limited to:

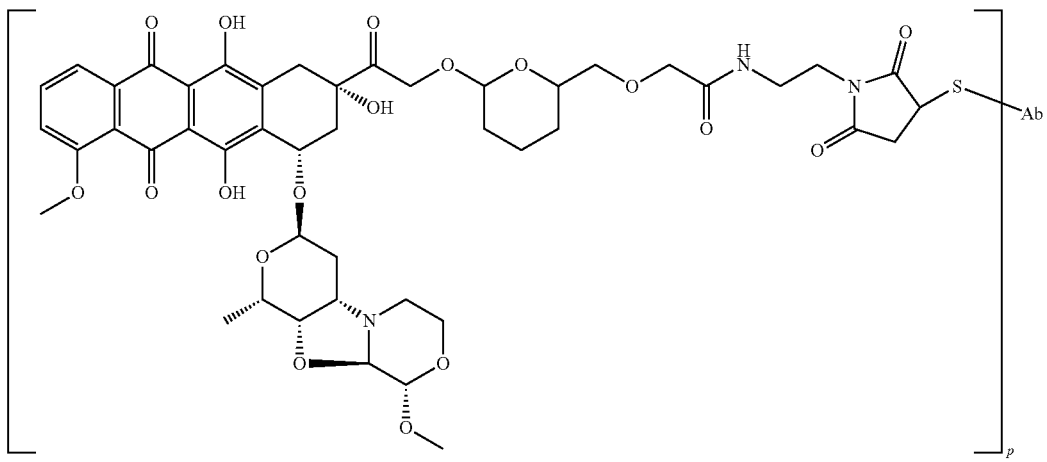

PNU-159682 maleimide acetal-Ab;

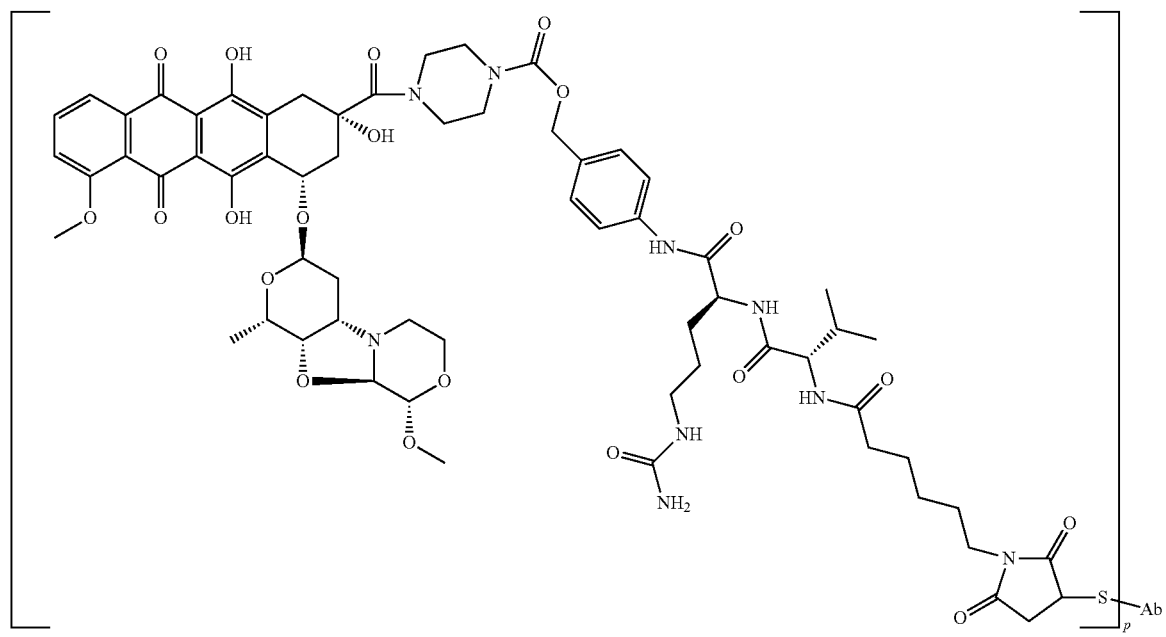
PNU-159682-val-cit-PAB-Ab;
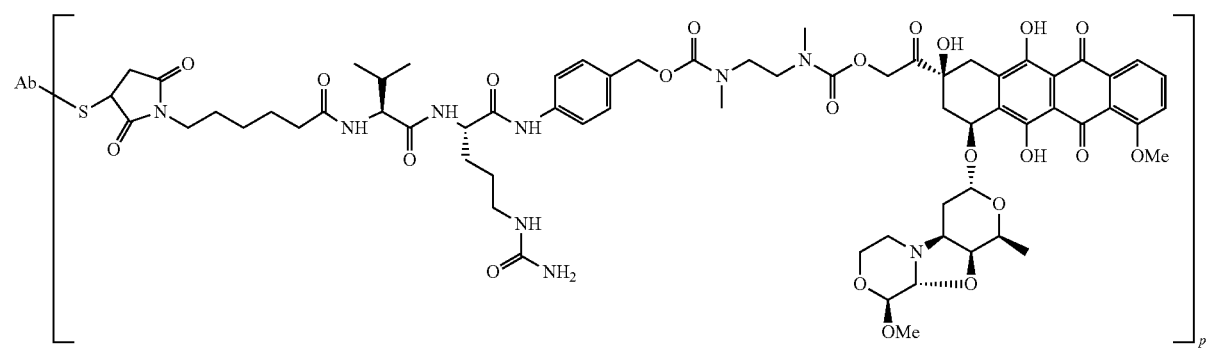
PNU-159682-val-cit-PAB-spacer-Ab;

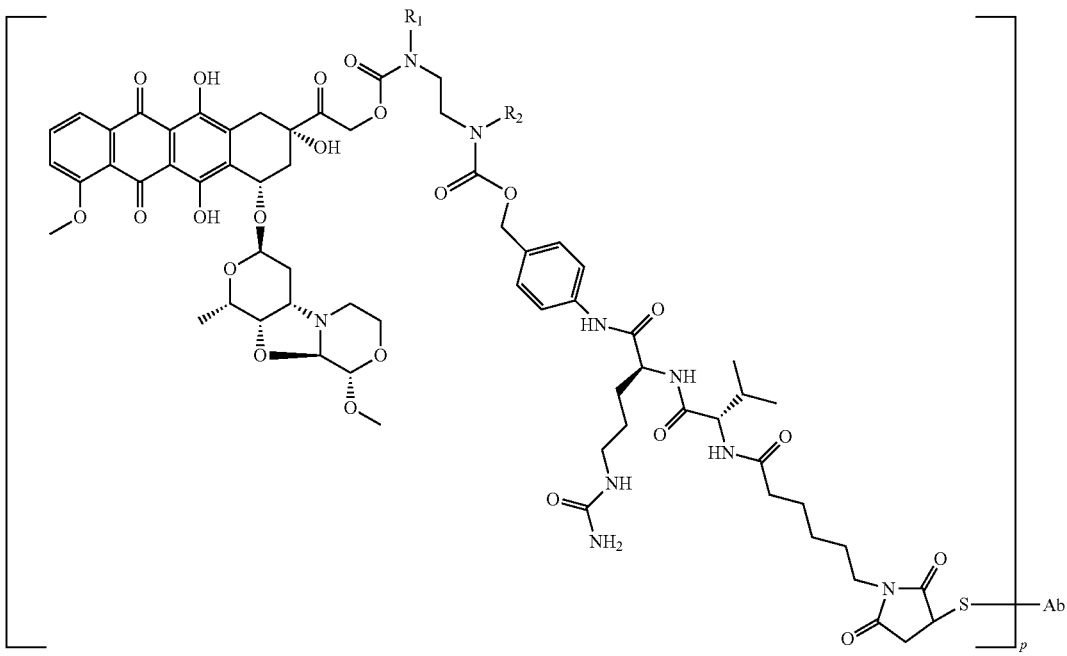

PNU-159682-val-cit-PAB-spacer($R^1R^2$)-Ab, wherein:
$R_1$ and $R_2$ are independently selected from H and $C_1$-$C_6$ alkyl; and

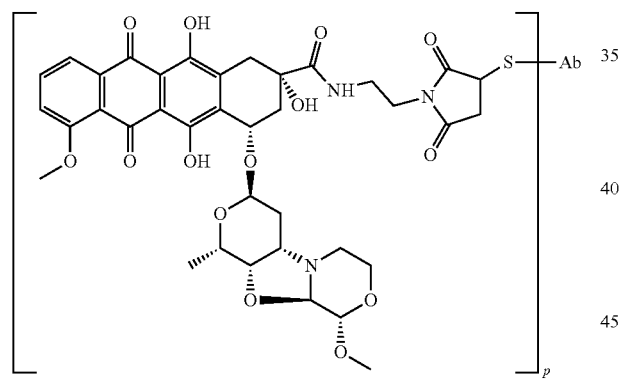

PNU-159682-maleimide-Ab.

The linker of PNU-159682 maleimide acetal-Ab is acid-labile, while the linkers of PNU-159682-val-cit-PAB-Ab, PNU-159682-val-cit-PAB-spacer-Ab, and PNU-159682-val-cit-PAB-spacer($R^1R^2$)-Ab are protease cleavable.

Figure 10A:
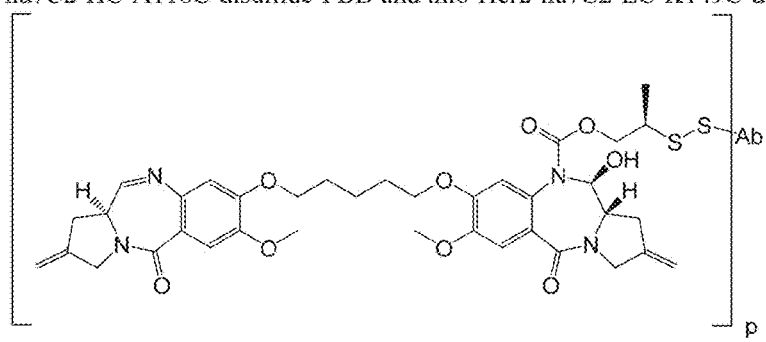
FIGS. 10A-E show exemplary THIOMAB™ antibody structures.
Figure 10B:
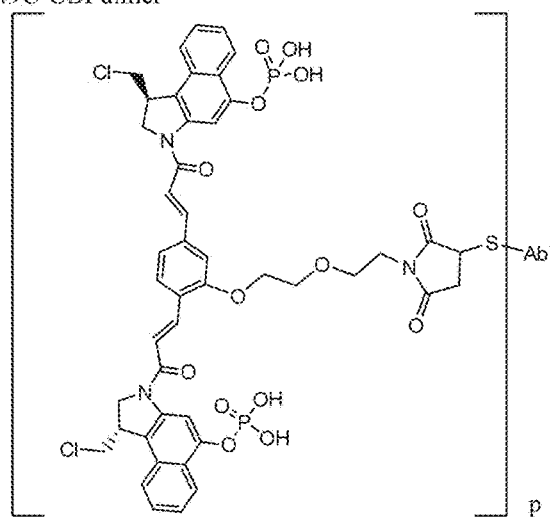
Figure 10C:
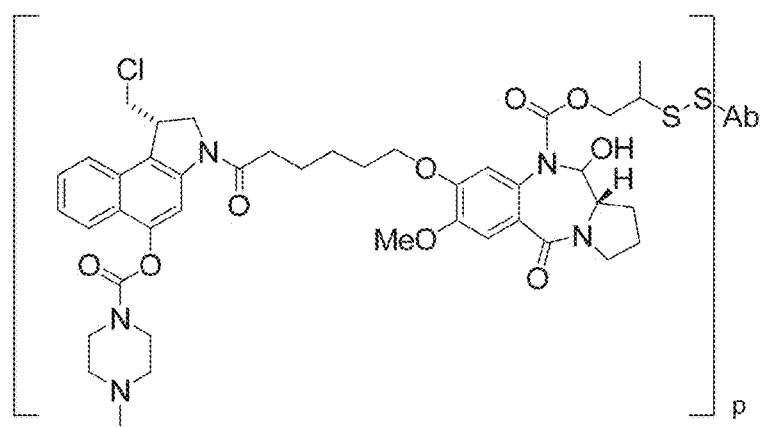
Figure 10D:
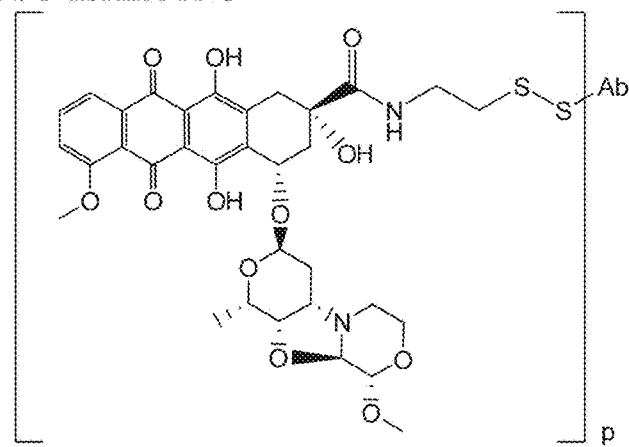
Figure 10E:
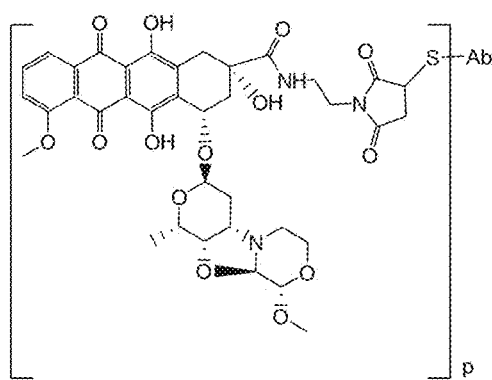

Exemplary PNU ADC are shown in FIGS. 10D and 10E.

In some embodiments, an ADC comprises 1-(chloromethyl)-2,3-dihydro-1H-benzo[e]indole (CBI). The 5-amino-1-(chloromethyl)-1,2-dihydro-3H-benz[e]indole (amino CBI) class of DNA minor groove alkylators are potent cytotoxins (Atwell, et al (1999) J. Med. Chem., 42:3400), and have been utilized as effector units in a number of classes of prodrugs designed for cancer therapy. These have included antibody conjugates, (Jeffrey, et al. (2005) J. Med. Chem., 48:1344), prodrugs for gene therapy based on nitrobenzyl carbamates (Hay, et al (2003) J. Med. Chem. 46:2456) and the corresponding nitro-CBI derivatives as hypoxia-activated prodrugs (Tercel, et al (2011) Angew. Chem., Int. Ed., 50:2606-2609). The CBI and pyrrolo[2,1-c][1,4]benzodiazepine (PBD) pharmacophores have been linked together by an alkyl chain (Tercel et al (2003) J. Med. Chem 46:2132-2151).

In some embodiments, an ADC comprises a 1-(chloromethyl)-2,3-dihydro-1H-benzo[e]indole (CBI) dimer (WO 2015/023355).

An exemplary CBI dimer ADC is shown in FIG. 10B.

In some such embodiments, the dimer is a heterodimer wherein one half of the dimer is a CBI moiety and the other half of the dimer is a PBD moiety.

An exemplary CBI-PBD heterodimer ADC is shown in FIG. 10C.

In some embodiments, a CBI dimer comprises the formula:

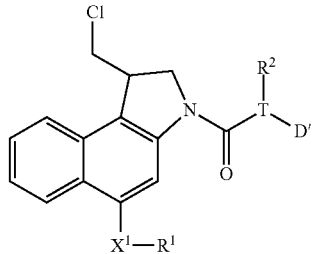

where
$R^1$ is selected from H, $P(O)_3H_2$, $C(O)NR^aR^b$, or a bond to a linker (L); $R^2$ is selected from H, $P(O)_3H_2$, $C(O)NR^aR^b$, or a bond to a linker (L);
$R^a$ and $R^b$ are independently selected from H and $C_1$-$C_6$ alkyl optionally substituted with one or more F, or $R^a$ and $R^b$ form a five or six membered heterocyclyl group;
T is a tether group selected from $C_3$-$C_{12}$ alkylene, Y, ($C_1$-$C_6$ alkylene)-Y—($C_1$-$C_6$ alkylene), ($C_1$-$C_6$ alkylene)-Y—($C_1$-$C_6$ alkylene)-Y—($C_1$-$C_6$ alkylene), ($C_2$-$C_6$ alkenylene)-Y—($C_2$-$C_6$ alkenylene), and ($C_2$-$C_6$ alkynylene)-Y—($C_2$-$C_6$ alkynylene);

where Y is independently selected from O, S, NR$^1$, aryl, and heteroaryl;
where alkylene, alkenylene, aryl, and heteroaryl are independently and optionally substituted with F, OH, O(C$_1$-C$_6$ alkyl), NH$_2$, NHCH$_3$, N(CH$_3$)$_2$, OP(O)$_3$H$_2$, and C$_1$-C$_6$ alkyl, where alkyl is optionally substituted with one or more F;
or alkylene, alkenylene, aryl, and heteroaryl are independently and optionally substituted with a bond to L;
D' is a drug moiety selected from:

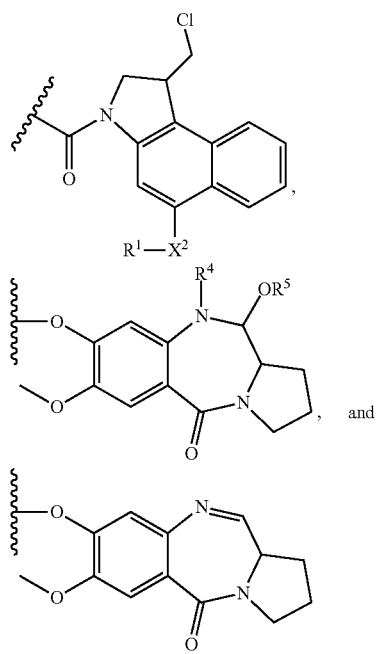

, and where the wavy line indicates the site of attachment to T;
X$^1$ and X$^2$ are independently selected from O and NR$^3$, where R$^3$ is selected from H and C$_1$-C$_6$ alkyl optionally substituted with one or more F; R$^4$ is H, CO$_2$R, or a bond to a linker (L), where R is C$_1$-C$_6$ alkyl or benzyl; and R$^5$ is H or C$_1$-C$_6$ alkyl.

In some embodiments, the immunoconjugate comprises an antibody conjugated to one or more amatoxin molecules. Amatoxins are cyclic peptides composed of 8 amino acids. They can be isolated from *Amanita phalloides* mushrooms or prepared synthetically. Amatoxins specifically inhibit the DNA-dependent RNA polymerase II of mammalian cells, and thereby also the transcription and protein biosynthesis of the affected cells. Inhibition of transcription in a cell causes stop of growth and proliferation. See e.g., Moldenhauer et al. JNCI 104:1-13 (2012), WO2010115629, WO2012041504, WO2012119787, WO2014043403, WO2014135282, and WO2012119787, which are hereby incorporated by reference in its entirety. In some embodiments, the one or more amatoxin molecules are one or more α-amanitin molecules.

Other drug moieties include, protein toxins such as: diphtheria A chain, nonbinding active fragments of diphtheria toxin, exotoxin A chain (from *Pseudomonas aeruginosa*), ricin A chain (Vitetta et al (1987) Science, 238:1098), abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes (WO 93/21232).

It is to be understood that where more than one nucleophilic group reacts with a drug-linker intermediate or linker reagent, then the resulting product is a mixture of ADC compounds with a distribution of one or more drug moieties attached to an antibody. The average number of drugs per antibody (DAR) may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) *Prot. Engr. Design & Selection* 19(7):299-307; Hamblett et al (2004) *Clin. Cancer Res.* 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

Antibody drug conjugates 51-58 of Table 18 (see, Example 16) may be prepared by coupling a drug moiety with a linker reagent, and according to the procedures of WO 2013/055987; WO 2015/023355; WO 2010/009124; WO 2015/095227, and conjugated with any of the antibodies, including cysteine engineered antibodies, described herein. Specific antibody-drug conjugates are recited in Table 19 (see, Example 16).

Drug moieties also include compounds with nucleolytic activity (e.g., a ribonuclease or a DNA endonuclease).

Therapeutic radioisotopes include: $^{32}P$, $^{33}P$, $^{90}Y$, $^{125}I$, $^{131}I$, $^{131}In$, $^{153}Sm$, $^{186}Re$, $^{188}Re$, $^{211}At$, $^{212}Bi$, $^{212}Pb$, and radioactive isotopes of Lu.

The radioisotope or other labels may be incorporated in the conjugate in known ways (Fraker et al (1978) Biochem. Biophys. Res. Commun. 80: 49-57; "Monoclonal Antibodies in Immunoscintigraphy" Chatal, CRC Press 1989). Carbon-14-labeled 1-isothiocyanatobenzyl-3-methyldiethylene triaminepentaacetic acid (MX-DTPA) is an exemplary chelating agent for conjugation of a radionuclide to the antibody (WO 94/11026).

Specific examples of additional ADCs are presented in Example 16.

Linkers

A "Linker" (L) is a bifunctional or multifunctional moiety that can be used to link one or more drug moieties (D) to an antibody (Ab) to form an antibody-drug conjugate (ADC) of Formula I. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio)pentanoate ("SPP"), and 4-(N-maleimidomethyl)cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

In certain embodiments, a linker has the following Formula II:

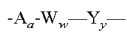

wherein A is a "stretcher unit", and a is an integer from 0 to 1; W is an "amino acid unit", and w is an integer from 0 to 12; Y is a "spacer unit", and y is 0, 1, or 2; and Ab, D, and p are defined as above for Formula I. Exemplary embodiments of such linkers are described in U.S. Pat. No. 7,498,298, which is expressly incorporated herein by reference.

In some embodiments, a linker component comprises a "stretcher unit" that links an antibody to another linker component or to a drug moiety. Nonlimiting exemplary stretcher units are shown below (wherein the wavy line indicates sites of covalent attachment to an antibody, drug, or additional linker components):

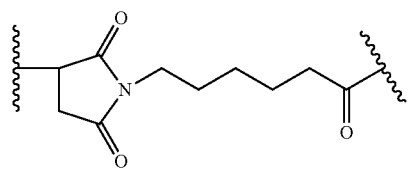

MC

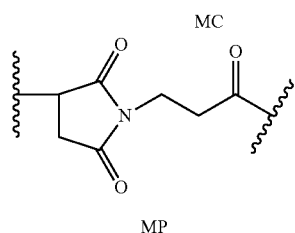

MP

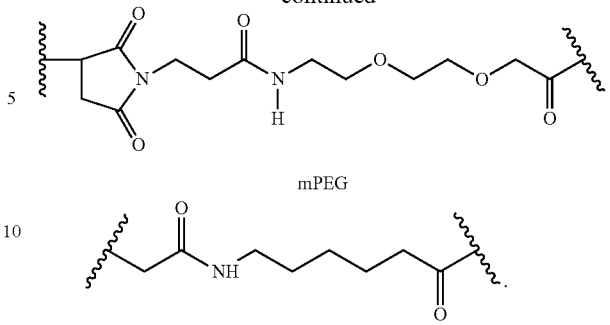

mPEG

In some embodiments, the linker may be a peptidomimetic linker such as those described in WO2015/095227, WO2015/095124 or WO2015/095223, which documents are hereby incorporated by reference in their entirety.

In one aspect, a Linker has a reactive site which has an electrophilic group that is reactive to a nucleophilic cysteine present on an antibody. The cysteine thiol of the antibody is reactive with an electrophilic group on a Linker and forms a covalent bond to a Linker. Useful electrophilic groups include, but are not limited to, maleimide and haloacetamide groups.

Cysteine engineered antibodies react with linker reagents or drug-linker intermediates, with electrophilic functional groups such as maleimide or α-halo carbonyl, according to the conjugation method at page 766 of Klussman, et al (2004), Bioconjugate Chemistry 15(4):765-773, and according to the protocol of Example 4.

In yet another embodiment, the reactive group of a linker reagent or drug-linker intermediate contains a thiol-reactive functional group that can form a bond with a free cysteine thiol of an antibody. Examples of thiol-reaction functional groups include, but are not limited to, maleimide, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates.

In another embodiment, the linker may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768; King (2002) Tetrahedron Letters 43:1987-1990). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker.

The linker may comprise amino acid residues which links the antibody (Ab) to the drug moiety (D) of the cysteine engineered antibody-drug conjugate (ADC) of the invention. The amino acid residues may form a dipeptide, tripeptide, tetrapeptide, pentapeptide, hexapeptide, heptapeptide, octapeptide, nonapeptide, decapeptide, undecapeptide or dodecapeptide unit. Amino acid residues include those occurring naturally, as well as minor amino acids and non-naturally occurring amino acid analogs, such as citrulline.

Useful amino acid residue units can be designed and optimized in their selectivity for enzymatic cleavage by a particular enzymes, for example, a tumor-associated protease to liberate an active drug moiety. In one embodiment, an amino acid residue unit, such as valine-citrulline (vc or val-cit), is that whose cleavage is catalyzed by cathepsin B, C and D, or a plasmin protease.

A linker unit may be of the self-immolative type such as a p-aminobenzylcarbamoyl (PAB) unit where the ADC has the exemplary structure:

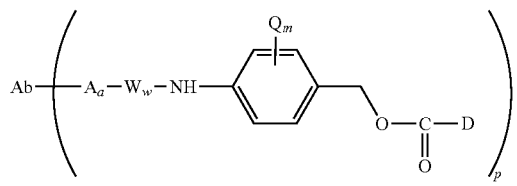

wherein Q is —$C_1$-$C_8$ alkyl, —O—($C_1$-$C_8$ alkyl), -halogen, -nitro or -cyano; m is an integer ranging from 0-4; and p ranges from 1 to 4.

Other examples of self-immolative spacers include, but are not limited to, aromatic compounds that are electronically similar to the PAB group such as 2-aminoimidazol-5-methanol derivatives (U.S. Pat. No. 7,375,078; Hay et al. (1999) Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Elimination of amine-containing drugs that are substituted at glycine (Kingsbury et al (1984) J. Med. Chem. 27:1447) are also examples of self-immolative spacer useful in ADCs.

In another embodiment, linker L may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker (WO 2004/01993; Szalai et al (2003) J. Amer. Chem. Soc. 125:15688-15689; Shamis et al (2004) J. Amer. Chem. Soc. 126:1726-1731; Amir et al (2003) Angew. Chem. Int. Ed. 42:4494-4499).

Embodiments of the Formula Ia antibody-drug conjugate compounds include (val-cit), (MC-val-cit), and (MC-val-cit-PAB):

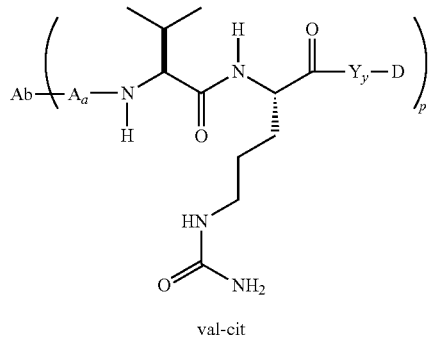

val-cit

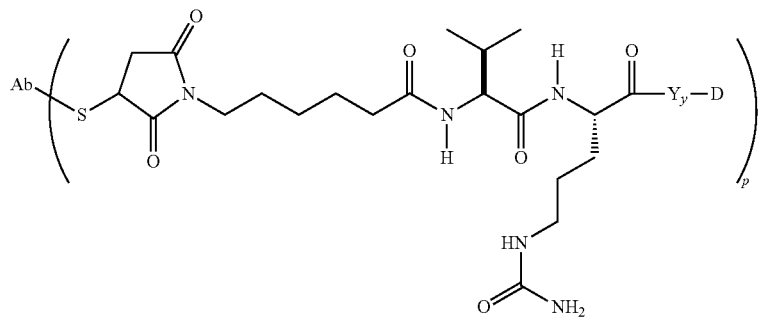

MC-val-cit

-continued

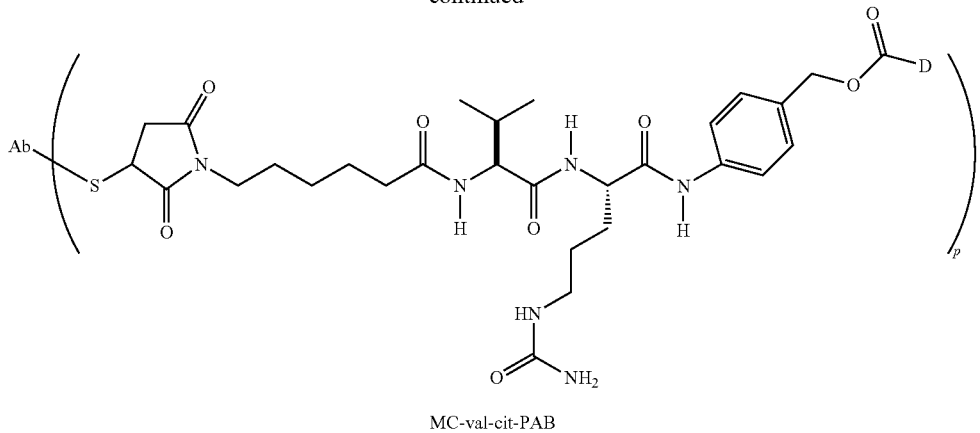

MC-val-cit-PAB

Other exemplary embodiments of the Formula Ia antibody-drug conjugate compounds include the structures:

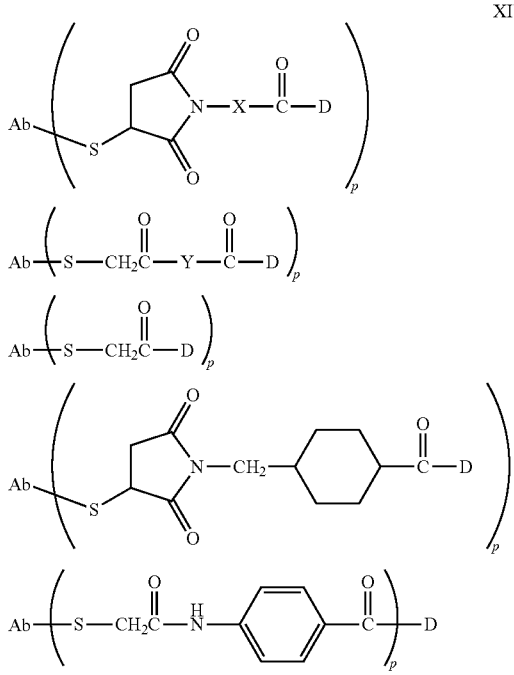

XIVd where X is:

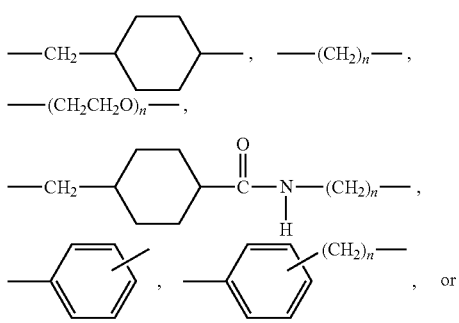

$$—(CH_2)_n—\overset{O}{\underset{}{C}}—\underset{H}{N}—(CH_2)_n—;$$

Y is:

$$—\underset{R}{N}—\underset{}{\underset{}{\bigcirc}}— \quad \text{or} \quad —\underset{R}{N}—(CH_2)_n—;$$

and R is independently H or $C_1$-$C_6$ alkyl; and n is 1 to 12.

In another embodiment, a Linker has a reactive functional group which has a nucleophilic group that is reactive to an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Typically, peptide-type Linkers can be prepared by forming a peptide bond between two or more amino acids and/or peptide fragments. Such peptide bonds can be prepared, for example, according to the liquid phase synthesis method (E. Schröder and K. Lübke (1965) "The Peptides", volume 1, pp 76-136, Academic Press) which is well known in the field of peptide chemistry.

In another embodiment, the Linker may be substituted with groups which modulated solubility or reactivity. For example, a charged substituent such as sulfonate (—$SO_3$—) or ammonium, may increase water solubility of the reagent and facilitate the coupling reaction of the linker reagent with the antibody or the drug moiety, or facilitate the coupling reaction of Ab-L (antibody-linker intermediate) with D, or D-L (drug-linker intermediate) with Ab, depending on the synthetic route employed to prepare the ADC.

The compounds of the invention expressly contemplate, but are not limited to, ADC prepared with linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents: DTME, BMB, BMDB, BMH, BMOE, BM(PEO)$_3$, and BM(PEO)$_4$, which are commercially available from Pierce Biotechnology, Inc., Customer Service Department, P.O. Box 117, Rockford, Ill. 61105 U.S.A, 1-800-874-3723, International +815-968-0747. See pages 467-498, 2003-2004 Applications Handbook and Catalog. Bis-maleimide reagents allow the attachment of the thiol group of a cysteine engineered antibody to a thiol-containing drug moiety, label, or linker intermediate, in a sequential or concurrent fashion. Other functional groups besides maleimide, which are reactive with a thiol group of a cysteine engineered antibody, drug moiety, label, or linker intermediate include iodoacetamide, bromoacetamide, vinyl pyridine, disulfide, pyridyl disulfide, isocyanate, and isothiocyanate.

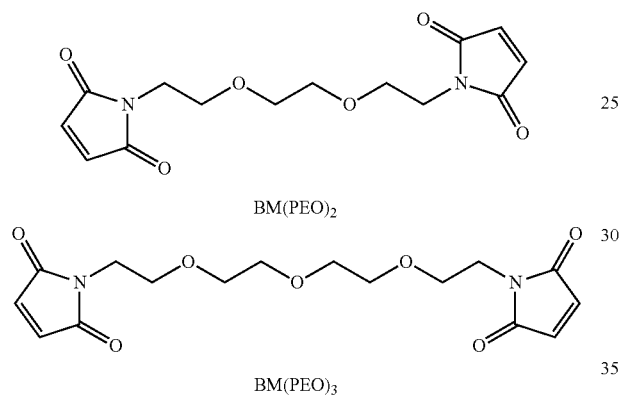

BM(PEO)$_2$

BM(PEO)$_3$

Useful linker reagents can also be obtained via other commercial sources, such as Molecular Biosciences Inc. (Boulder, Colo.), or synthesized in accordance with procedures described in Toki et al (2002) J. Org. Chem. 67:1866-1872; Walker, M. A. (1995) J. Org. Chem. 60:5352-5355; Frisch et al (1996) Bioconjugate Chem. 7:180-186; U.S. Pat. No. 6,214,345; WO 02/088172; US 2003130189; US2003096743; WO 03/026577; WO 03/043583; and WO 04/032828.

An exemplary valine-citrulline (val-cit or vc) dipeptide linker reagent having a maleimide Stretcher and a para-aminobenzylcarbamoyl (PAB) self-immolative Spacer has the structure:

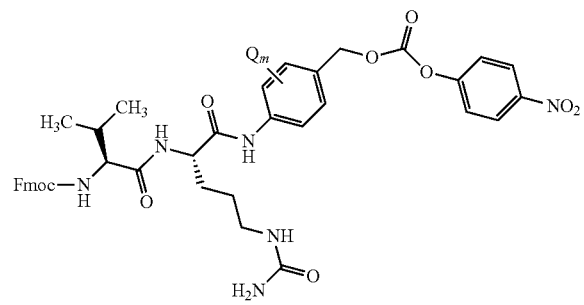

where Q is —C$_1$-C$_8$ alkyl, —O—(C$_1$-C$_8$ alkyl), -halogen, -nitro or -cyano; and m is an integer ranging from 0-4.

An exemplary phe-lys(Mtr) dipeptide linker reagent having a maleimide Stretcher unit and a p-aminobenzyl self-immolative Spacer unit can be prepared according to Dubowchik, et al. (1997) Tetrahedron Letters, 38:5257-60, and has the structure:

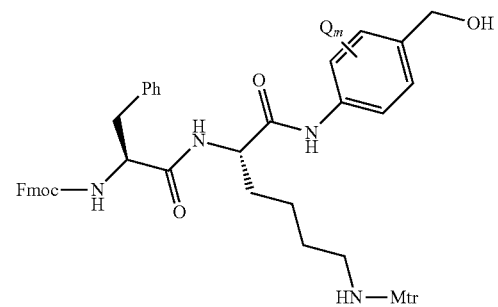

where Mtr is mono-4-methoxytrityl, Q is —C$_1$-C$_8$ alkyl, —O—(C$_1$-C$_8$ alkyl), -halogen, -nitro or -cyano; and m is an integer ranging from 0-4.

Exemplary antibody-drug conjugate compounds of the invention include:

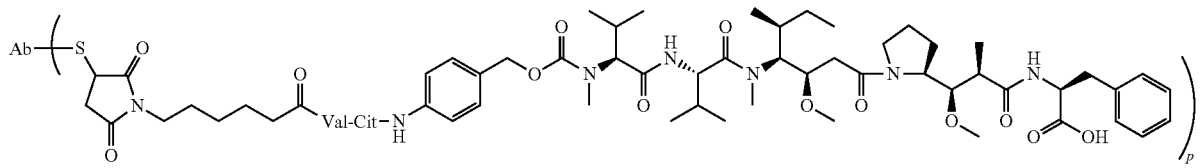

Ab-MC-vc-PAB-MMAF

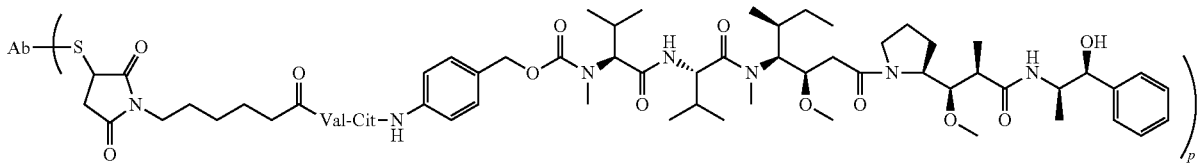

Ab-MC-vc-PAB-MMAE

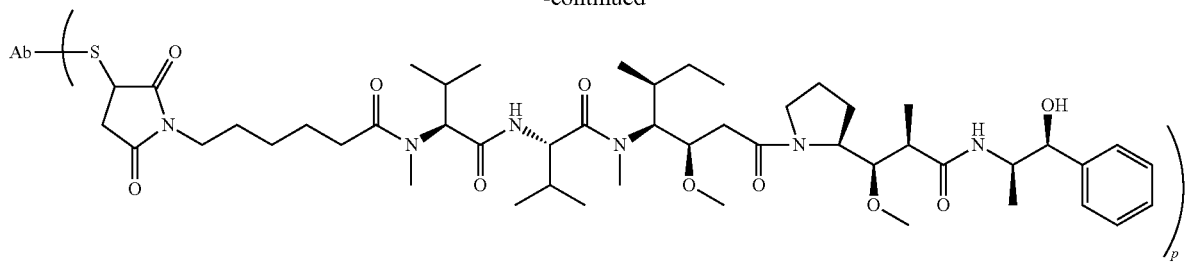

Ab-MC-MMAE

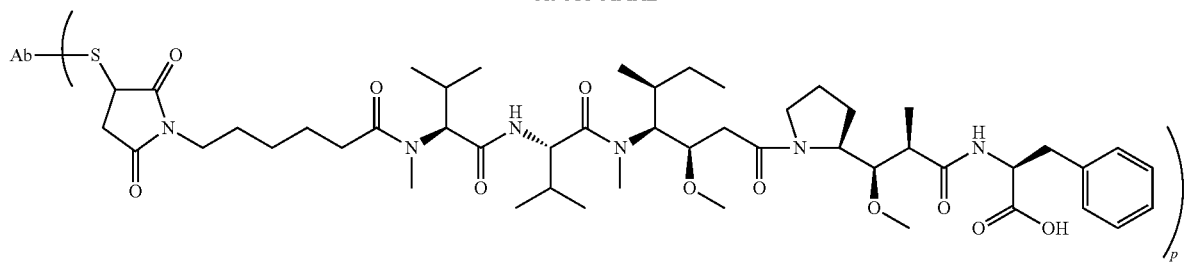

Ab-MC-MMAF where Val is valine; Cit is citrulline; p is 1, 2, 3, or 4; and Ab is a cysteine engineered antibody. Other exemplary antibody drug conjugates where maytansinoid drug moiety DM1 is linked through a BMPEO linker to a thiol group of trastuzumab have the structure:

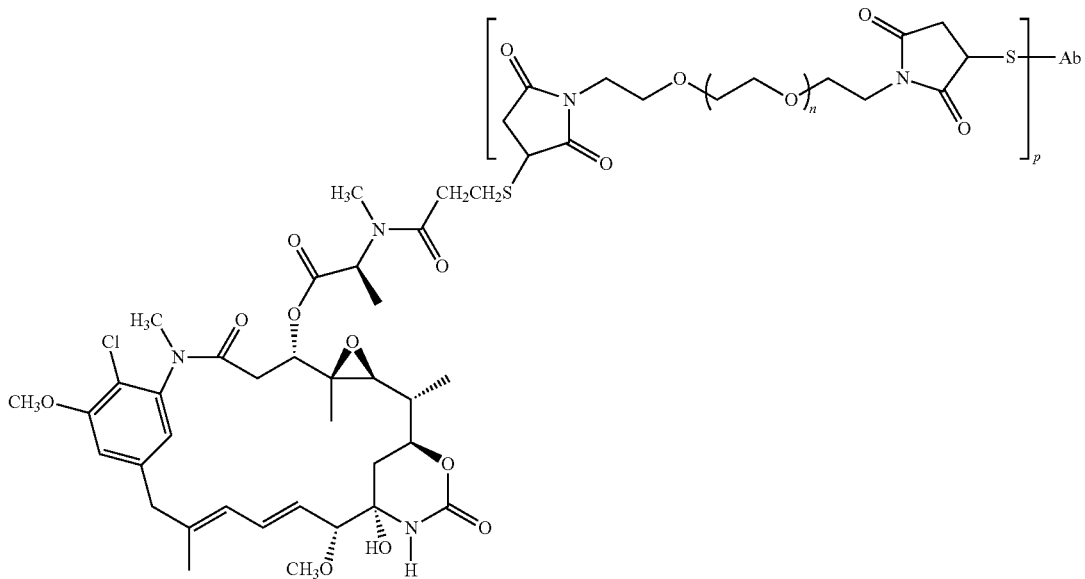

where Ab is a cysteine engineered antibody; n is 0, 1, or 2; and p is 1, 2, 3, or 4.

Preparation of Antibody-Drug Conjugates

The ADC of Formula I may be prepared by several routes, employing organic chemistry reactions, conditions, and reagents known to those skilled in the art, including: (1) reaction of a cysteine group of a cysteine engineered antibody with a linker reagent, to form antibody-linker intermediate Ab-L, via a covalent bond, followed by reaction with an activated drug moiety D; and (2) reaction of a nucleophilic group of a drug moiety with a linker reagent, to form drug-linker intermediate D-L, via a covalent bond, followed by reaction with a cysteine group of a cysteine engineered antibody. Conjugation methods (1) and (2) may be employed with a variety of cysteine engineered antibodies, drug moieties, and linkers to prepare the antibody-drug conjugates of Formula I.

Antibody cysteine thiol groups are nucleophilic and capable of reacting to form covalent bonds with electrophilic groups on linker reagents and drug-linker intermediates including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Maytansine may, for example, be converted to May-SSCH$_3$, which can be reduced to the free thiol, May-SH, and reacted with a modified antibody (Chari et al (1992) Cancer Research 52:127-131) to generate a maytansinoid-antibody immunoconjugate with a disulfide linker. Antibody-maytansinoid conjugates with disulfide linkers have been reported (WO 04/016801; U.S. Pat. No. 6,884,874; US 2004/039176 A1; WO 03/068144; US 2004/001838 A1; U.S. Pat. Nos. 6,441,163, 5,208,020, 5,416,064; WO 01/024763). The disulfide linker SPP is constructed with linker reagent N-succinimidyl 4-(2-pyridylthio)pentanoate.

Under certain conditions, the cysteine engineered antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Full length, cysteine engineered monoclonal antibodies (THIOMAB™ antibodies) expressed in CHO cells were reduced with about a 50 fold excess of TCEP for 3 hrs at 37° C. to reduce disulfide bonds which may form between the newly introduced cysteine residues and the cysteine present in the culture media. The reduced THIOMAB™ antibodies were diluted and loaded onto HiTrap S column in 10 mM sodium acetate, pH 5, and eluted with PBS containing 0.3M sodium chloride. Disulfide bonds were reestablished between cysteine residues present in the parent Mab with dilute (200 nM) aqueous copper sulfate (CuSO$_4$) at room temperature, overnight. Other oxidants, i.e. oxidizing agents, and oxidizing conditions, which are known in the art may be used. Ambient air oxidation is also effective. This mild, partial reoxidation step forms intrachain disulfides efficiently with high fidelity. An approximate 10 fold excess of drug-linker intermediate, e.g. BM(PEO)$_4$-DM1 was added, mixed, and let stand for about an hour at room temperature to effect conjugation and form the antibody-drug conjugate (i.e., a conjugated THIOMAB™ antibodies). The conjugation mixture was gel filtered and loaded and eluted through a HiTrap S column to remove excess drug-linker intermediate and other impurities.

For example, U.S. Pat. Pub. No. 20110301334, which is incorporated by reference in its entirety, shows the general process to prepare a cysteine engineered antibody expressed from cell culture for conjugation. Cysteine adducts, presumably along with various interchain disulfide bonds, are reductively cleaved to give a reduced form of the antibody. The interchain disulfide bonds between paired cysteine residues are reformed under partial oxidation conditions, such as exposure to ambient oxygen. The newly introduced, engineered, and unpaired cysteine residues remain available for reaction with linker reagents or drug-linker intermediates to form the antibody conjugates of the invention. The THIOMAB™ antibodies expressed in mammalian cell lines result in externally conjugated Cys adduct to an engineered Cys through —S—S— bond formation. Hence the purified THIOMAB™ antibodies have to be treated with reduction and oxidation procedures to produce reactive THIOMAB™ antibodies. These THIOMAB™ antibodies are used to conjugate with maleimide containing cytotoxic drugs, fluorophores, and other labels.

Exemplary THIOMAB™ antibodies conjugates were prepared and can be found in the tables provided herein.

In Vitro Cell Proliferation Assays

Generally, the cytotoxic or cytostatic activity of an antibody-drug conjugate (ADC) is measured by: exposing mammalian cells having receptor proteins, e.g. HER2, to the antibody of the ADC in a cell culture medium; culturing the cells for a period from about 6 hours to about 5 days; and measuring cell viability. Cell-based in vitro assays were used to measure viability (proliferation), cytotoxicity, and induction of apoptosis (caspase activation) of the ADC of the invention.

The in vitro potency of antibody-drug conjugates can be measured by a cell proliferation assay. For example, the CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713 and 5,700,670). This cell proliferation assay determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay is conducted in 96 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

In Vivo Efficacy

The in vivo efficacy of the THIOMAB™ antibodies described herein can be measured by a high expressing transgenic explant mouse model (e.g., the THIOMAB™ antibodies of the tables provided herein made from the anti-HER2 4D5 antibody can be measured by a high expressing HER2 transgenic explant mouse model). An allograft can be propagated, for example, from the Fo5 mmtv transgenic mouse which does not respond to, or responds poorly to, HERCEPTIN® therapy. Subjects can be treated once with a anti-HER2 4D5 THIOMAB™ antibody and a placebo PBS buffer control (Vehicle) and can be monitored over 3 weeks to measure the time to tumor doubling, log cell kill, and tumor shrinkage.

Administration of Antibody-Drug Conjugates

The antibody-drug conjugates (ADC) of the invention may be administered by any route appropriate to the condition to be treated. The ADC will typically be administered parenterally, i.e. infusion, subcutaneous, intramuscular, intravenous, intradermal, intrathecal and epidural.

Pharmaceutical Formulations

Pharmaceutical formulations of therapeutic antibody-drug conjugates (ADC) of the invention are typically prepared for parenteral administration, i.e. bolus, intravenous, intratumor injection with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

Pharmaceutical formulations of the cysteine engineered antibodies described herein can be prepared by mixing such antibody (i.e. a THIOMAB™ antibody) having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody and immunoconjugate formulations are described in U.S. Pat. No. 6,267,958 which is incorporated herein in its entirety. Aqueous antibody or immunoconjugate formulations include those described in U.S. Pat. No. 6,171,586 and WO2006/044908, the latter formulations including a histidine-acetate buffer, both of which are incorporated herein in their entirities.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

Antibody-Drug Conjugate Therapeutic Methods and Compositions

It is contemplated that the antibody-drug conjugates (ADC) of the present invention may be used to treat various diseases or disorders, e.g. characterized by the overexpression of a tumor antigen. Exemplary conditions are hyperproliferative disorders which include benign or malignant tumors and leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight.

For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of an anti-ErbB2 antibody. Other dosage regimens may be useful. The progress of this therapy is easily monitored by conventional techniques and assays.

In one aspect, a THIOMAB™ antibody provided herein can be used in a method of inhibiting cellular proliferation. For example, an anti-HER2 THIOMAB™ antibody can be used to inhibit the cellular proliferation of a HER2-positive cell. By way of a second example, an anti-CD33 THIOMAB™ antibody can be used to inhibit the cellular proliferation of a CD33-positive cell. Accordingly, an antibody can be made against any polypeptide expressed on a tumor cell and that antibody can be engineered to include a non-native cysteine for drug conjugation (i.e., the antibody can be engineered into a THIOMAB™ antibody). Once the THIOMAB™ antibody is made, the method of inhibiting cellular proliferation comprises exposing the cell to the THIOMAB™ antibody (e.g., an anti-HER2 THIOMAB™ antibody) under conditions permissive for binding of the THIOMAB™ antibody to the target (e.g., HER2) on the surface of the cell, thereby inhibiting the proliferation of the cell. In certain embodiments, the method is an in vitro or an in vivo method.

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) *J. Immunol. Meth.* 160:81-88, U.S. Pat. No. 6,602,677. The assay may be conducted in 96- or 384-well format, making it amenable to automated high-throughput screening (HTS). See Cree et al. (1995) *AntiCancer Drugs* 6:398-404. The assay procedure involves adding a single reagent (Cell-Titer-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, a THIOMAB™ antibody for use as a medicament is provided (e.g., an anti-HER2 THIOMAB™ antibody). In further aspects, THIOMAB™ antibody for use in a method of treatment is provided. In a non-limiting embodiment, an anti-HER2 THIOMAB™ antibody for use in treating HER2-positive cancer is provided. In certain embodiments, the invention provides an anti-HER2 THIOMAB™ antibody for use in a method of treating an individual having a HER2-positive cancer, the method comprising administering to the individual an effective amount of the anti-THIOMAB™ antibody. In one such embodiment, the method further comprises administering to the individual an effective amount of at least one additional therapeutic agent, e.g., as described below. In a non-limiting embodiment, an anti-CD33 THIOMAB™ antibody for use in treating CD33-positive cancer is provided. In certain embodiments, the invention provides an anti-CD33 THIOMAB™ antibody for use in a method of treating an individual having a CD33-positive cancer, the method comprising administering to the individual an effective amount of the anti-THIOMAB™ antibody. In one such embodiment, the method further comprises administering to the individual an effective amount of at least one additional therapeutic agent, e.g., as described below.

In a further aspect, the invention provides for the use of a THIOMAB™ antibody in the manufacture or preparation of a medicament (e.g., an anti-HER2 THIOMAB™ antibody). For example, an anti-HER2 THIOMAB™ antibody medicament is for use in a method of treating HER2-positive cancer, the method comprising administering to an individual having HER2-positive cancer an effective amount of the medicament. In one such embodiment, the method further comprises administering to the individual an effective amount of at least one additional therapeutic agent, e.g., as described below.

In a further aspect, the invention provides for the use of a THIOMAB™ antibody in the manufacture or preparation of a medicament (e.g., an anti-MUC16 THIOMAB™ antibody). For example, an anti-MUC16 THIOMAB™ antibody medicament is for use in a method of treating MUC16-positive cancer, the method comprising administering to an individual having MUC16-positive cancer an effective amount of the medicament. In one such embodiment, the method further comprises administering to the individual an effective amount of at least one additional therapeutic agent, e.g., as described below.

In a further aspect, the invention provides for the use of a THIOMAB™ antibody in the manufacture or preparation of a medicament (e.g., an anti-STEAP1 THIOMAB™ antibody). For example, an anti-STEAP1 THIOMAB™ antibody medicament is for use in a method of treating STEAP1-positive cancer, the method comprising administering to an individual having STEAP1-positive cancer an effective amount of the medicament. In one such embodiment, the method further comprises administering to the individual an effective amount of at least one additional therapeutic agent, e.g., as described below.

In a further aspect, the invention provides for the use of a THIOMAB™ antibody in the manufacture or preparation of a medicament (e.g., an anti-NAPI2B THIOMAB™ antibody). For example, an anti-NAPI2B THIOMAB™ antibody medicament is for use in a method of treating NAPI2B-positive cancer, the method comprising administering to an individual having NAPI2B-positive cancer an effective amount of the medicament. In one such embodiment, the method further comprises administering to the individual an effective amount of at least one additional therapeutic agent, e.g., as described below.

In a further aspect, the invention provides for the use of a THIOMAB™ antibody in the manufacture or preparation of a medicament (e.g., an anti-LY6E THIOMAB™ antibody). For example, an anti-LY6E THIOMAB™ antibody medicament is for use in a method of treating LY6E-positive cancer, the method comprising administering to an individual having LY6E-positive cancer an effective amount of the medicament. In one such embodiment, the method further comprises administering to the individual an effective amount of at least one additional therapeutic agent, e.g., as described below.

In a further aspect, the invention provides for the use of a THIOMAB™ antibody in the manufacture or preparation of a medicament (e.g., an anti-B7H4 THIOMAB™ antibody). For example, an anti-B7H4 THIOMAB™ antibody medicament is for use in a method of treating B7H4-positive cancer, the method comprising administering to an individual having B7H4-positive cancer an effective amount of the medicament. In one such embodiment, the method further comprises administering to the individual an effective amount of at least one additional therapeutic agent, e.g., as described below.

In a further aspect, the invention provides for the use of a THIOMAB™ antibody in the manufacture or preparation of a medicament (e.g., an anti-CD79B THIOMAB™ antibody). For example, an anti-CD79B THIOMAB™ antibody medicament is for use in a method of treating CD79B-positive cancer, the method comprising administering to an individual having CD79B-positive cancer an effective amount of the medicament. In one such embodiment, the method further comprises administering to the individual an effective amount of at least one additional therapeutic agent, e.g., as described below.

In a further aspect, the invention provides for the use of a THIOMAB™ antibody in the manufacture or preparation of a medicament (e.g., an anti-CD22 THIOMAB™ antibody). For example, an anti-CD22 THIOMAB™ antibody medicament is for use in a method of treating CD22-positive cancer, the method comprising administering to an individual having CD22-positive cancer an effective amount of the medicament. In one such embodiment, the method further comprises administering to the individual an effective amount of at least one additional therapeutic agent, e.g., as described below.

In a further aspect, the invention provides a method for cancer by administering a THIOMAB™ antibody or a medicament thereof. In specific embodiments, the THIOMAB™ antibody or a medicament thereof prevents proliferation of the cancer cells. In specific embodiments, the THIOMAB™ antibody or a medicament thereof promotes apoptosis of the cancer cells. In specific embodiments, the THIOMAB™ antibody or a medicament thereof reduces tumor volume of the cancer cells. In one such embodiment, the method further comprises administering to the individual an effective amount of at least one additional therapeutic agent, e.g., as described below.

The THIOMAB™ antibodies of the invention can be used either alone or in combination with other agents in a therapy. For instance, an antibody or immunoconjugate of the invention may be co-administered with at least one additional therapeutic agent. For example, the additional therapeutic agent can be a second THIOMAB™ antibody or a chemotherapeutic agent as defined herein.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

The THIOMAB™ antibodies of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

The THIOMAB™ antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. THIOMAB™ antibodies need not be, but are optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a THIOMAB™ antibody of the invention (when used alone or in combination with one or more other additional therapeutic agents) will depend on the type of disease to be treated, the type of antibody or immunoconjugate, the severity and course of the disease, whether the THIOMAB™ antibody is administered for preventive or therapeutic purposes, previous therapy, the patient's clinical history and response to the THIOMAB™ antibody, and the discretion of the attending physician. The THIOMAB™ antibody is suitably administered to the patient at one time or over a series of treatments. Depending on the type and severity of the disease, about 1 µg/kg to 15 mg/kg (e.g. 0.1 mg/kg-10 mg/kg) of the THIOMAB™ antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the THIOMAB™ antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both a THIOMAB™ antibody of the invention and second chemotherapeutic agent as defined herein.

Labelled Antibody Imaging Methods

In another embodiment of the invention, cysteine engineered antibodies may be labelled through the cysteine thiol with radionuclides, fluorescent dyes, bioluminescence-triggering substrate moieties, chemiluminescence-triggering substrate moieties, enzymes, and other detection labels for imaging experiments with diagnostic, pharmacodynamic, and therapeutic applications. Generally, the labelled cysteine engineered antibody, i.e. "biomarker" or "probe", is administered by injection, perfusion, or oral ingestion to a living organism, e.g. human, rodent, or other small animal, a perfused organ, or tissue sample. The distribution of the probe is detected over a time course and represented by an image.

Articles of Manufacture

In another embodiment of the invention, an article of manufacture, or "kit", containing materials useful for the treatment of the disorders described above is provided. The article of manufacture comprises a container and a label or package insert on or associated with the container. Suitable containers include, for example, bottles, vials, syringes, blister pack, etc. The containers may be formed from a variety of materials such as glass or plastic. The container holds a THIOMAB™ antibody of this invention which is effective for treating the condition and may have a sterile access port (for example the container may be an intravenous solution bag or a vial having a stopper pierceable by a hypodermic injection needle). At least one active agent in the composition is a THIOMAB™ antibody. The label or package insert indicates that the composition is used for treating the condition of choice, such as cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

Example 1—Preparation of the THIOMAB™ Antibodies

THIOMAB™ antibodies were generated using hu4D5 plasmid as double stranded DNA template. PCR based site-directed mutagenesis was performed using Quick Change II XL kit from Agilent Technologies.

The methods were used to for the site directed mutagenesis to make the THIOMAB™ antibodies: 1) the Hu4D5 plasmid DNA (50-100 ng) was used, 2) forward and reverse primers (1 μM each) containing the desired mutation were used, 3) dNTP (0.4 mM) and PfuUltra HF DNA polymerase (2.5 units) were added to a 25 μl reaction mixture, 4) samples were incubated in a thermal cycler (Applied Biosystems, Foster City, Calif.) for initial denaturation (4 min at 94° C.) followed by 20 cycles with 0.5 min denaturation (94° C.), 0.5 min annealing (52° C.) and 10 min chain elongation (68° C.), 5) PCR amplified DNA samples were incubated with DpnI restriction enzyme for 4 h at 37° C., 6) competent cells (Novablue Singles, 50 μl) were transformed with DpnI treated PCR sample (2 μl), 7) Single colonies were picked from transformed plates and grown in 5 ml 2YT medium containing carbenicillin (50 ug/ml), and 8) plasmid DNA was purified and clones obtained were screened by DNA sequencing to identify the cysteine substitution and the absence of non-specific mutations in the light and heavy chain region of the antibody sequence.

The cysteine engineered hu4D5 plasmids were stably transfected into a mammalian cell line for protein production. The 293T cell line used for this study was a suspension adapted HEK293 cell line that was stably transfected with the SV40 large T-antigen. Cells were cultivated as a seed train in shake flasks under conditions of 37° C., 5%, and 150 rpm agitation speed at a 25 mm throw diameter in an 80% humidified incubator before transient transfection. Gibco Freestyle 293 expression medium (Life Sciences, Carlsbad Calif.) supplemented with 1% ultra-low IgG serum (Sigma, St. Louis, Mo.) was used as the seed train and production medium, Unless otherwise specified, all transient transfections were carried out in 50 mL tubespins (Stealer et al., 2007) with a 30 mL final working volume and processed in batches of 96. A Biomek FX$^P$ liquid handling robot was used to bulk dispense cells into the 96 tubespins for efficiency. Post-transfection, cells were cultured for 7 days at 37° C., 5% $CO_2$ and 225 rpm agitation speed at a 50 mm throw diameter in an 80% humidified Kuhner ISF1-X incubator.

For the transfection, cells were seeded at 1.0e6cells/mL and incubated at 37° C., 5% $CO_2$ for 2 h prior to transfection. Valproic acid was added to the production culture at a concentration of 75 mM, at the time of seeding. Plasmid DNA encoding a selected THIOMAB™ hu IgG1 antibody was purified at the maxi prep scale (Sigma, St. Louis, Mo.). Utilizing the standard transient transfection process, 30 ug of DNA was diluted in a DMEM-based medium to a final volume of 3 mL. Then 60 ul of 7.5 mM 25 kDa linear PEI was added to the DNA solution, mixed and incubated at room temperature for 10 mins before being added to the cells.

Example 2—Conjugation of the THIOMAB™ Antibodies

Each cysteine engineered antibody (THIOMAB™ antibody) made according to Example 1 was separately conjugated to two linker drugs: MC-vc-PAB-MMAE and PDS-MMAE. For example, the 4D5 LC-K149C cysteine engineered antibody was made into two different THIOMAB™ antibodies: 1) 4D5 LC-K149C-MC-vc-PAB-MMAE and 2) 4D5 LC-K149C-PDS-MMAE. Additional examples of the preferred conjugations can be found in Tables 1 and 2 and in the description herein and include, but are not limited to 4D5 HC-A140C-MC-vc-PAB-MMAE and 4D5 HC-A140C-PDS-MMAE according to EU numbering and 4D5 HC-L174C-MC-vc-PAB-MMAE and 4D5

HC-L174C-PDS-MMAE according to EU numbering. Other examples of the top stable conjugates identified in the fully antibody screen can be found in Table 3 and 4. See FIG. 21 for the preferred sites for -vc and PDS conjugation.

Conjugation of the THIOMAB™ antibodies was performed in 96 well filter plates (volume 2 ml, PolyProplyene 0.45 um filter from EK Scientific). The plates allowed aqueous buffer to flow through only upon centrifugation at 500×g for 2 min. 450 µl of MabSelect SuRe resin (GE Healthcare) was added to each well in the form of a50% slurry in 20% ethanol. The resin was washed 3 times and equilibrated in 50 mM Tris pH 8.0, 150 mM NaCl, 2 mM EDTA (buffer A). 1.5 mg of each THIOMAB™ antibody was added to each well and allowed to bind to resin for 30 min on a plate shaker at 600 RPM at RT. After 30 min the plates were centrifuged to remove excess buffer. The THIOMAB™ antibodies were then reduced in the presence of 0.9 ml of 2 mM dithiothreitol (DTT) in buffer A overnight with agitation at RT. The reducing agent (i.e., the DTT) and any cysteine or glutathione blocks were removed by two washes with buffer A.

The plates were then washed three times with 1 ml of 1 mM dehydroascorbic acid (DHAA) in buffer A to saturate the plates with oxidizing agent. After the last addition of 0.9 ml of 1 mM DHAA in buffer A the THIOMAB™ antibodies were allow to reoxidize for 3 hrs on a plate shaker at RT. Oxidizing agent was removed by centrifugation.

A two-fold molar excess (over available thiol groups) of the linker drug (MC-vc-PAB-MMAE or PDS-MMAE) dissolved in 10% DMA in buffer A was added and incubated for 2 hrs on a plate shaker at RT with THIOMAB™ antibodies. The excess linker drug was removed by washing the plates 6 times with equilibration buffer (buffer A).

The THIOMAB™ antibodies were eluted with 0.1 M glycine buffer, pH 2.7 for 30 min on a plate shaker at RT. The THIOMAB™ antibodies were then neutralized immediately with 15% of 0.5M Tris, pH 8.0. The number of drugs conjugated per THIOMAB™ antibody was quantified by LC/MS analysis. Aggregation of the conjugate was assessed by size exclusion chromatography.

Example 3—Mass Spectrometric Analysis of the THIOMAB™ Antibodies

The Drug-Antibody Ratio (DAR) of each THIOMAB™ antibody was determined using mass spectrometric analysis (i.e., LC/MS analysis).

LC/MS analysis was performed on a 6224 Mass Time-of-Flight (TOF) LC/MS machine (Agilent Technologies). Samples were chromatographed on a PRLP-S column, 1000 Å, 8 µm (50 mm×2.1 mm, Agilent Technologies) heated to 80° C. A linear gradient from 34-42% B in 3 minutes at 0.7 ml/min flow rate (solvent A, 0.05% TFA in water; solvent B, 0.04% TFA in acetonitrile) was used and the eluent was directly ionized using the electrospray source. Data was collected and deconvoluted using the Agilent Mass Hunter qualitative analysis software. The drug DAR was calculated using the abundance of the deconvoluted peaks present in LC/MS chromatogram. The DAR calculations can be found, for example, in Tables 6-12 above.

Furthermore, LC/MS analysis were performed on 4D5 cysteine engineered antibodies that contain a single engineered cysteine mutation at every position in the antibody. The blank cells in Tables 13-16 represent inconclusive experiments, not a 0 DAR.

TABLE 13

DAR of PDS-linked THIOMAB™ antibodies with Heavy Chain cysteine substitutions.

| Residue | Kabat # | Avg. DAR | Residue | Kabat # | Avg. DAR | Residue | Kabat # | Avg. DAR | Residue | Kabat # | Avg. DAR |
|---|---|---|---|---|---|---|---|---|---|---|---|
| V | 5 | 1.54 | A | 71 | 0.11 | Y | 315 | | C | 92 | 0 |
| T | 32 | 1 | T | 77 | 0.15 | K | 316 | 0.09 | S | 93 | 0 |
| Y | 33 | 1.64 | A | 78 | 0 | S | 320 | 1.6 | G | 97 | 1.75 |
| A | 40 | 1.77 | L | 80 | 0.03 | N | 321 | 1.49 | D | 98 | 1.44 |
| Y | 79 | 1.2 | L | 82C | 0.05 | I | 328 | 1.39 | G | 99 | 1.86 |
| G | 96 | 1.79 | T | 87 | 1.62 | E | 329 | | S | 112 | 1.75 |
| D | 101 | 1.73 | A | 88 | 0.12 | T | 331 | 0.8 | S | 113 | 1.73 |
| G | 162 | 1.79 | Y | 90 | 0 | I | 332 | 0.1 | S | 115 | 1.58 |
| G | 174 | 1.88 | Y | 91 | 0 | S | 333 | 0.52 | G | 118 | 1.4 |
| L | 175 | 1.81 | R | 94 | 0 | K | 334 | 0.2 | P | 119 | 0.2 |
| V | 184 | 1.42 | F | 100 | 1.94 | P | 339 | 1.31 | A | 125 | 0.14 |
| I | 195 | 1.4 | Y | 100A | 1.75 | E | 341 | 1.47 | P | 126 | 0.42 |
| T | 205 | 1.3 | A | 100B | 1.1 | P | 342 | 0 | S | 127 | 0.45 |
| Y | 369 | 1.38 | Y | 102 | 0 | V | 344 | 0.21 | S | 128 | 0.46 |
| E | 384 | 1.78 | G | 104 | 0.37 | Y | 345 | 0.1 | K | 129 | 0.45 |
| K | 410 | 1.15 | Q | 105 | 1.67 | T | 346 | 0 | S | 130 | 0.12 |
| S | 420 | 1.42 | T | 107 | 0.28 | L | 347 | 0 | T | 131 | 0.42 |
| Y | 432 | 1.58 | L | 108 | 1.9 | P | 348 | 0.67 | S | 132 | 0.44 |
| T | 433 | 1.19 | T | 110 | 1.64 | P | 349 | 0 | G | 133 | 0.31 |
| Q | 434 | 1.52 | V | 111 | 0.05 | M | 354 | 1.81 | K | 143 | 0.1 |
| L | 439 | 1.16 | A | 114 | 1.77 | K | 356 | 1.0 | E | 148 | 1.82 |
| V | 5 | 1.54 | T | 116 | 1.43 | Q | 358 | 1.69 | V | 152 | 0.05 |
| L | 11 | 0.9 | S | 120 | 1.7 | V | 359 | 0.0 | S | 156 | 1.28 |
| R | 19 | 1.33 | V | 121 | | S | 360 | 0 | T | 160 | 1.63 |
| S | 21 | 1.43 | F | 122 | | L | 361 | 0 | S | 161 | 1.21 |
| T | 32 | 1 | P | 123 | 0.17 | L | 364 | 0.1 | Q | 171 | 0.6 |
| Y | 33 | 1.64 | L | 124 | 0 | V | 365 | 0 | S | 172 | 1.41 |
| A | 40 | 1.77 | G | 134 | 0 | K | 366 | 0 | S | 173 | 0.3 |
| R | 50 | 0.36 | A | 137 | 0 | F | 368 | 0.07 | V | 181 | 0 |
| Y | 52 | 1.75 | L | 138 | 0 | A | 374 | 1.4 | P | 185 | 1.09 |
| Y | 79 | 1.2 | G | 139 | 0.02 | W | 377 | 0 | S | 186 | 1.84 |
| D | 86 | 0.52 | L | 141 | 0.07 | P | 383 | 1.57 | S | 187 | 0.1 |

TABLE 13-continued

DAR of PDS-linked THIOMAB ™ antibodies with Heavy Chain cysteine substitutions.

| Residue | Kabat # | Avg. DAR | Residue | Kabat # | Avg. DAR | Residue | Kabat # | Avg. DAR | Residue | Kabat # | Avg. DAR |
|---|---|---|---|---|---|---|---|---|---|---|---|
| W | 95 | 1.52 | V | 142 | 0 | N | 386 | 2 | L | 189 | |
| G | 96 | 1.79 | D | 144 | 1.63 | Y | 387 | 0.2 | G | 190 | |
| M | 100C | 1.68 | F | 146 | 0 | K | 388 | 0.55 | T | 191 | 0.7 |
| D | 101 | 1.73 | P | 147 | 0.98 | T | 389 | 0.4 | T | 193 | 1.38 |
| W | 103 | 0.59 | P | 149 | 1.4 | T | 390 | 0.1 | N | 204 | 1.8 |
| K | 117 | 0.5 | V | 150 | 0 | P | 391 | 0 | D | 208 | 0.9 |
| T | 135 | 1.65 | T | 151 | 1.72 | P | 392 | 0.95 | S | 215 | 0.3 |
| A | 136 | 1.29 | S | 153 | 1.62 | F | 400 | 0 | H | 220 | 0.16 |
| C | 140 | 0.63 | W | 154 | 0 | F | 401 | 0 | P | 223 | 0 |
| Y | 145 | 0.2 | N | 155 | 1.33 | L | 402 | 1.84 | P | 226 | 0 |
| G | 162 | 1.79 | A | 158 | | Y | 403 | 0.63 | L | 231 | 0.07 |
| L | 170 | 1.51 | L | 159 | 1.36 | S | 404 | 0 | G | 233 | 0.1 |
| G | 174 | 1.88 | V | 163 | 0.83 | K | 405 | 0.19 | S | 235 | 1 |
| L | 175 | 1.81 | H | 164 | 0 | L | 406 | 1.74 | F | 237 | 1.33 |
| T | 183 | 0.66 | T | 165 | | V | 408 | 0 | K | 242 | 1.67 |
| V | 184 | 1.42 | F | 166 | 0.062 | D | 409 | 1.4 | P | 243 | 1.51 |
| I | 195 | 1.4 | P | 167 | 1.31 | W | 413 | 1.49 | K | 244 | 1.4 |
| N | 197 | 0.71 | A | 168 | 0.67 | V | 418 | 1.78 | T | 246 | 0.18 |
| N | 199 | 1.4 | V | 169 | 1.57 | F | 419 | 0.9 | M | 248 | 1.8 |
| S | 203 | 1.47 | Y | 176 | 0 | S | 422 | 0.24 | I | 249 | 0.64 |
| T | 205 | 1.3 | S | 177 | 0 | V | 423 | 0 | S | 250 | 0.72 |
| T | 219 | 0.05 | L | 178 | 0 | M | 424 | 0 | R | 251 | 0.17 |
| P | 240 | 0.5 | S | 179 | 0 | H | 425 | 1.54 | S | 263 | 1.82 |
| E | 254 | 1.21 | S | 180 | 0.03 | E | 426 | 1.74 | H | 264 | 1.6 |
| T | 256 | 1.49 | V | 182 | 0.04 | L | 428 | 0.09 | E | 265 | 1.34 |
| F | 271 | 0.5 | S | 188 | | H | 431 | 0 | E | 268 | 1.8 |
| K | 318 | 0.58 | Q | 192 | 1.54 | L | 437 | 0.43 | D | 276 | |
| R | 340 | 0.67 | Y | 194 | 0.1 | G | 438 | 1.6 | G | 277 | 1.47 |
| Q | 343 | 0.4 | V | 198 | 0.1 | P | 441 | 0.2 | E | 279 | 1.6 |
| T | 362 | 0.2 | H | 200 | | G | 442 | 0 | H | 281 | 1.4 |
| G | 367 | 1.28 | K | 201 | 0.3 | E | 1 | 1.0 | N | 282 | 1.3 |
| Y | 369 | 1.38 | K | 206 | 1.64 | L | 4 | 1.4 | A | 283 | 1.6 |
| E | 378 | 1.84 | V | 207 | 0 | S | 7 | 0.8 | K | 284 | 1.45 |
| S | 379 | 0.2 | K | 209 | | G | 8 | 1.7 | P | 287 | |
| E | 384 | 1.78 | K | 210 | | G | 9 | 1.5 | E | 289 | 0 |
| S | 399 | 0.75 | E | 212 | 0.84 | G | 10 | 1.5 | E | 290 | 0 |
| T | 407 | 0.7 | P | 213 | | Q | 13 | 1.5 | Q | 291 | 0 |
| K | 410 | 1.15 | K | 214 | 1.01 | P | 14 | 1.4 | Y | 292 | 1.31 |
| S | 411 | 1.06 | C | 216 | 0 | G | 15 | 1.4 | G | 293 | 1.0 |
| R | 412 | 2 | D | 217 | 0 | G | 16 | 1.5 | L | 305 | 1.5 |
| Q | 414 | 1.48 | K | 218 | 0 | S | 17 | 1.2 | K | 322 | 1.51 |
| N | 417 | 1.84 | T | 221 | 0 | A | 24 | 0 | A | 323 | 1.54 |
| S | 420 | 1.42 | P | 224 | 0.32 | S | 25 | 1.67 | L | 324 | 1.55 |
| A | 427 | 0.07 | A | 227 | 0 | G | 26 | 1.32 | V | 325 | 0.88 |
| Y | 432 | 1.58 | P | 228 | 0 | F | 27 | 1.35 | A | 326 | 1.62 |
| T | 433 | 1.19 | E | 229 | 0.49 | N | 28 | 1.8 | P | 327 | 1.41 |
| Q | 434 | 1.52 | L | 230 | 0.02 | I | 29 | 1.69 | K | 330 | 1.06 |
| K | 435 | 0.26 | G | 232 | 0.08 | R | 38 | 0.11 | A | 335 | 1.83 |
| L | 439 | 1.16 | P | 234 | 0 | Q | 39 | 1.68 | K | 336 | 1.87 |
| V | 2 | 1.6 | V | 236 | 0 | P | 41 | 1.77 | G | 337 | 1.86 |
| Q | 3 | 1.5 | L | 238 | 0.31 | G | 42 | 1.93 | Q | 338 | 1.9 |
| E | 6 | 0.3 | F | 239 | 1.4 | K | 43 | 0 | S | 350 | 0.52 |
| V | 12 | 0.4 | P | 241 | | V | 48 | 0 | R | 351 | 1.67 |
| L | 18 | 0.2 | D | 245 | 0 | T | 53 | 1.54 | E | 352 | 1.25 |
| L | 20 | 0.05 | L | 247 | 0.4 | N | 54 | 1.9 | E | 353 | 0.5 |
| C | 22 | 0 | T | 252 | 1.48 | G | 55 | 1.55 | T | 355 | 1.6 |
| A | 23 | 1.68 | P | 253 | 1.58 | Y | 59 | 1.1 | N | 357 | 0.9 |
| K | 30 | 1.59 | V | 255 | 0.11 | A | 60 | 1.12 | P | 370 | 0.69 |
| D | 31 | 0.55 | V | 258 | 1.66 | D | 61 | 1.31 | S | 371 | 1.77 |
| I | 34 | 0 | V | 259 | 0.1 | S | 62 | 1.45 | I | 373 | 0 |
| H | 35 | 0.34 | V | 260 | 1.36 | K | 64 | 1.64 | N | 380 | 1.5 |
| W | 36 | 0 | A | 261 | 1.86 | T | 68 | 1.8 | G | 381 | 1.6 |
| V | 37 | | V | 262 | 1.7 | I | 69 | 0.13 | Q | 382 | 2 |
| G | 44 | 1.84 | D | 266 | 1.44 | S | 70 | 1.42 | N | 385 | 1.8 |
| L | 45 | 1.3 | P | 267 | 1.64 | D | 72 | 0.74 | V | 393 | 0.95 |
| E | 46 | 1.5 | V | 269 | 0.2 | T | 73 | 1.38 | L | 394 | 1.65 |
| W | 47 | 0.85 | K | 270 | 1.52 | S | 74 | 1.46 | D | 395 | 1.21 |
| A | 49 | 0 | N | 272 | 1.25 | K | 75 | 1.66 | S | 396 | 1.71 |
| I | 51 | 0.3 | Y | 274 | 0.7 | N | 76 | 1.89 | D | 397 | 1 |
| P | 52A | 0.38 | V | 278 | | Q | 81 | 1.64 | G | 398 | 2 |
| Y | 56 | 1.34 | V | 280 | 1.3 | M | 82 | 0.04 | Q | 415 | 1.84 |
| T | 57 | 1.27 | K | 286 | 1.88 | N | 82A | 1.5 | G | 416 | 1.8 |
| R | 58 | 1.62 | R | 288 | 1.7 | S | 82B | 1.61 | H | 429 | 1.88 |
| V | 63 | 0.27 | S | 294 | 0.0 | R | 83 | 1.5 | N | 430 | 1.71 |

TABLE 13-continued

DAR of PDS-linked THIOMAB™ antibodies with Heavy Chain cysteine substitutions.

| Residue | Kabat # | Avg. DAR | Residue | Kabat # | Avg. DAR | Residue | Kabat # | Avg. DAR | Residue | Kabat # | Avg. DAR |
|---|---|---|---|---|---|---|---|---|---|---|---|
| G | 65 |  | V | 298 |  | A | 84 | 1.67 | S | 436 | 1.8 |
| R | 66 |  | T | 303 |  | E | 85 | 1.14 | S | 440 | 1.78 |
| F | 67 | 0 | E | 314 | 1.61 | V | 89 | 0.69 | K | 443 | 0 |

TABLE 14

DAR of PDS-linked THIOMAB™ antibodies with Light Chain cysteine substitutions.

| Residue | Kabat # | Avg. DAR | Residue | Kabat # | Avg. DAR | Residue | Kabat # | Avg. DAR | Residue | Kabat # | Avg. DAR |
|---|---|---|---|---|---|---|---|---|---|---|---|
| S | 12 | 1.51 | Q | 147 | 1.5 | F | 116 | 0.07 | V | 15 | 1.78 |
| T | 22 | 1.71 | W | 148 | 2 | I | 117 | 0 | G | 16 | 0.77 |
| K | 39 | 1.33 | K | 149 | 0.8 | P | 120 | 0 | D | 17 | 1.09 |
| K | 42 | 1.4 | Q | 155 | 1.57 | D | 122 | 0 | R | 18 | 1.1 |
| Y | 49 | 1.79 | S | 159 | 1.34 | S | 127 | 1.61 | S | 26 | 1.39 |
| F | 53 | 1.55 | Q | 160 | 1.62 | A | 130 | 0 | Q | 27 | 1.8 |
| Y | 55 | 1.1 | V | 163 | 1.18 | S | 131 |  | V | 29 | 0.24 |
| G | 64 | 1.23 | Q | 166 | 1.25 | V | 132 | 0.09 | T | 31 | 1.5 |
| T | 72 | 1.56 | S | 171 | 0.94 | L | 135 | 0.02 | A | 34 | 0.2 |
| T | 74 | 1.64 | T | 172 | 1.33 | L | 136 | 0.04 | L | 46 | 0.2 |
| Q | 79 | 1.53 | T | 180 | 1.58 | N | 137 | 0.12 | L | 54 | 1.11 |
| T | 85 | 1.35 | V | 191 | 1.27 | F | 139 | 0.1 | S | 56 | 1.51 |
| Y | 92 | 1.6 | E | 195 | 1.43 | A | 144 | 0.54 | G | 57 | 1.69 |
| T | 97 | 1.56 | H | 198 | 0.99 | K | 145 | 1.73 | V | 58 | 1.35 |
| K | 103 | 1.48 | V | 205 | 1.48 | V | 146 | 0.05 | P | 59 | 0.7 |
| E | 105 | 1.63 | T | 206 | 1.14 | V | 150 | 0.08 | V | 60 | 0.75 |
| T | 129 | 1.73 | M | 4 | 0.1 | D | 151 | 0 | R | 61 | 1.8 |
| R | 142 | 1.25 | S | 10 | 1.73 | G | 157 | 1.06 | F | 62 | 1.09 |
| Q | 147 | 1.5 | A | 13 | 0 | N | 158 | 1.85 | S | 65 | 1.67 |
| W | 148 | 2 | S | 14 | 1.46 | E | 161 | 1.3 | S | 67 | 1.68 |
| K | 149 | 0.8 | V | 19 | 0 | S | 162 | 0.16 | T | 69 | 1.51 |
| Q | 155 | 1.57 | T | 20 | 0 | E | 165 | 1.59 | S | 76 | 1.7 |
| S | 159 | 1.34 | I | 21 | 0 | S | 168 | 1.52 | S | 77 | 1.79 |
| Q | 166 | 1.25 | R | 24 | 1.3 | D | 170 | 1.63 | E | 81 | 1.4 |
| T | 172 | 1.33 | A | 25 | 0 | Y | 173 | 0 | F | 83 | 0.1 |
| T | 180 | 1.58 | D | 28 | 0 | S | 174 | 0 | Y | 87 | 0 |
| E | 195 | 1.43 | N | 30 |  | L | 175 | 0 | C | 88 | 0 |
| V | 205 | 1.48 | V | 33 | 0 | S | 176 | 0 | T | 93 | 1.7 |
| T | 206 | 1.14 | W | 35 | 0 | S | 177 | 0 | T | 94 | 1.2 |
| L | 11 | 0.8 | Y | 36 | 1.5 | T | 178 | 0 | Q | 100 | 1.53 |
| S | 12 | 1.51 | Q | 37 | 0 | L | 179 | 0 | T | 102 | 0 |
| T | 22 | 1.71 | Q | 38 | 0.7 | L | 181 |  | V | 104 | 0 |
| A | 32 | 1.79 | P | 40 | 0 | K | 183 | 1.07 | T | 109 | 0.3 |
| K | 39 | 1.33 | G | 41 | 1.6 | A | 184 | 0 | V | 110 | 1.56 |
| K | 42 | 1.4 | A | 43 | 0.65 | D | 185 | 1.08 | P | 113 | 1.27 |
| I | 48 | 0.6 | P | 44 | 1.1 | Y | 186 | 0 | F | 118 | 0 |
| Y | 49 | 1.79 | K | 45 | 0 | E | 187 | 0.74 | Y | 119 |  |
| S | 50 | 1.7 | L | 47 | 0.1 | K | 188 | 0.63 | S | 121 | 1.15 |
| A | 51 | 0.82 | S | 52 | 1.24 | H | 189 | 0 | E | 123 | 0.64 |
| F | 53 | 1.55 | S | 63 | 1.55 | K | 190 |  | Q | 124 | 0.82 |
| Y | 55 | 1.1 | G | 68 | 1.15 | Y | 192 | 0 | L | 125 | 1.4 |
| G | 64 | 1.23 | D | 70 | 1.7 | A | 193 | 1.67 | K | 126 | 1.09 |
| R | 66 | 0.86 | F | 71 | 0 | V | 196 | 0 | G | 128 | 0.86 |
| T | 72 | 1.56 | L | 73 | 0.14 | T | 197 | 1.88 | V | 133 | 0.03 |
| T | 74 | 1.64 | I | 75 | 0.07 | P | 204 | 1.58 | V | 141 | 0.8 |
| Q | 79 | 1.53 | L | 78 | 0.04 | K | 207 |  | E | 143 | 0.89 |
| T | 85 | 1.35 | P | 80 | 1.72 | S | 208 | 1.25 | N | 152 | 0.68 |
| Q | 89 | 0.65 | D | 82 | 0.72 | F | 209 |  | A | 153 | 1.66 |
| H | 91 | 0.9 | A | 84 | 0.1 | N | 210 | 0 | L | 154 | 1.56 |
| Y | 92 | 1.6 | Y | 86 | 0 | R | 211 | 0 | S | 156 | 1.71 |
| P | 95 | 0.6 | Q | 90 | 0.11 | G | 212 |  | T | 164 | 0.26 |
| T | 97 | 1.56 | P | 96 | 0.3 | C | 214 | 0.17 | D | 167 | 1.55 |
| K | 103 | 1.48 | F | 98 | 1.16 | D | 1 | 0.5 | K | 169 | 1.58 |
| E | 105 | 1.63 | G | 99 | 1.3 | I | 2 | 0.57 | S | 182 | 1.28 |
| I | 106 | 0.87 | G | 101 | 1.51 | Q | 3 | 1.77 | Q | 199 | 1.72 |
| A | 111 | 0.42 | K | 107 | 1.63 | T | 5 | 1.75 | G | 200 | 1.56 |
| T | 129 | 1.73 | R | 108 | 1.67 | Q | 6 | 0.25 | L | 201 | 1.29 |
| N | 138 | 0.93 | A | 112 | 0.73 | S | 7 | 1.49 | S | 202 | 0.86 |

TABLE 14-continued

DAR of PDS-linked THIOMAB™ antibodies with Light Chain cysteine substitutions.

| Residue | Kabat # | Avg. DAR | Residue | Kabat # | Avg. DAR | Residue | Kabat # | Avg. DAR | Residue | Kabat # | Avg. DAR |
|---|---|---|---|---|---|---|---|---|---|---|---|
| Y | 140 | 0.22 | S | 114 | 1.72 | P | 8 | 1.76 | S | 203 | 1.26 |
| R | 142 | 1.25 | V | 115 | 0.04 | S | 9 | 1.7 | E | 213 | |

TABLE 15

DAR of vc-linked THIOMAB™ antibodies with Heavy Chain cysteine substitutions.

| Residue | Kabat # | Avg. DAR | Residue | Kabat # | Avg. DAR | Residue | Kabat # | Avg. DAR | Residue | Kabat # | Avg. DAR |
|---|---|---|---|---|---|---|---|---|---|---|---|
| R | 19 | 1.04 | K | 318 | 0.7 | S | 113 | 2 | V | 262 | 1.85 |
| F | 27 | 1.41 | T | 331 | 1.5 | A | 114 | 1.67 | S | 263 | 1.85 |
| Q | 39 | 1.27 | I | 332 | 0.8 | S | 115 | 1.81 | H | 264 | 1.88 |
| A | 40 | 1.35 | S | 333 | 1.16 | G | 118 | 1.3 | E | 265 | 1.77 |
| K | 43 | 1.41 | R | 340 | 1.1 | P | 119 | 0.3 | D | 266 | 1.42 |
| E | 46 | 1.65 | E | 341 | 1.53 | S | 120 | 1.6 | P | 267 | 1.8 |
| T | 53 | 1.75 | Q | 343 | 1.2 | V | 121 | | E | 268 | 1.68 |
| T | 57 | 1.12 | K | 356 | 1.7 | F | 122 | | V | 269 | 0.5 |
| Y | 59 | 1.13 | G | 367 | 1.27 | L | 124 | 0.17 | F | 271 | 0 |
| A | 60 | 1.16 | Y | 369 | 1.47 | P | 126 | 1.2 | Y | 274 | 1.4 |
| Q | 81 | 1.63 | E | 378 | 1.44 | S | 127 | 0.67 | D | 276 | |
| N | 82A | 1.69 | S | 379 | 0.76 | S | 128 | 0.5 | G | 277 | 1.76 |
| M | 100C | 1.54 | P | 383 | 1.89 | K | 129 | 0.46 | V | 278 | |
| W | 103 | 1.08 | E | 384 | 1.32 | S | 130 | 0 | E | 279 | 1.7 |
| T | 110 | 1.22 | T | 389 | 0.6 | T | 131 | 0.31 | H | 281 | 1.6 |
| G | 162 | 1.21 | D | 395 | 1.42 | S | 132 | 0.57 | N | 282 | 1.2 |
| G | 174 | 1.76 | S | 399 | 1.13 | G | 133 | 0.28 | A | 283 | 1.7 |
| T | 183 | 1.58 | T | 407 | 0.61 | G | 134 | 0.26 | K | 284 | 1.67 |
| I | 195 | 1.57 | D | 409 | 1.21 | A | 137 | 0 | K | 286 | 1.89 |
| E | 254 | 1.6 | K | 410 | 1.29 | C | 140 | 0.67 | P | 287 | |
| V | 258 | 1.44 | S | 411 | 0.92 | V | 142 | 0 | R | 288 | 1.7 |
| S | 333 | 1.16 | Q | 414 | 1.46 | D | 144 | 0.7 | E | 289 | 2 |
| Q | 343 | 1.2 | G | 416 | 1.53 | Y | 145 | 0 | E | 290 | 0 |
| G | 367 | 1.27 | N | 417 | 2 | P | 147 | 0.97 | Q | 291 | 0 |
| E | 378 | 1.44 | F | 419 | 0.99 | E | 148 | 1.61 | Y | 292 | 1.27 |
| D | 395 | 1.42 | S | 420 | 1.37 | P | 149 | 1.47 | G | 293 | 1.3 |
| K | 410 | 1.29 | M | 424 | 1.47 | V | 150 | 0.06 | S | 294 | 0.0 |
| S | 420 | 1.37 | H | 425 | 1.39 | T | 151 | 1.29 | V | 298 | |
| H | 425 | 1.39 | E | 426 | 1.67 | V | 152 | 0 | T | 303 | |
| N | 430 | 1.6 | A | 427 | 1.58 | E | 153 | 1.54 | E | 314 | 1.64 |
| Y | 432 | 1.52 | N | 430 | 1.6 | Y | 154 | 0 | Y | 315 | |
| S | 436 | 1.47 | H | 431 | 0.21 | K | 155 | 0.99 | K | 316 | 0.96 |
| L | 439 | 1.24 | Y | 432 | 0.8 | S | 156 | 1.14 | S | 320 | 1.62 |
| V | 2 | 1.3 | T | 433 | 1.4 | N | 158 | 1.41 | N | 321 | 1.58 |
| L | 4 | 1.3 | Q | 434 | 1.56 | K | 159 | 1.35 | K | 322 | 1.8 |
| V | 5 | 1.46 | K | 435 | 1.3 | A | 160 | 1.41 | A | 323 | 1.62 |
| L | 11 | 1.3 | S | 436 | 1.47 | L | 161 | 1.18 | L | 324 | 1.51 |
| V | 12 | 0.5 | L | 437 | 0.58 | P | 164 | 0 | P | 325 | 0.87 |
| G | 15 | 1.6 | S | 438 | 1.4 | A | 165 | 1.67 | T | 326 | 1.7 |
| R | 19 | 1.04 | L | 439 | 1.24 | P | 166 | 0 | F | 327 | 1.15 |
| A | 23 | 1.72 | E | 1 | 1.0 | I | 167 | 1.12 | I | 328 | 1.52 |
| F | 27 | 1.41 | Q | 3 | 1.4 | E | 171 | 0.7 | E | 329 | |
| I | 29 | 1.58 | E | 6 | 0.4 | S | 172 | 1.15 | G | 330 | 1.47 |
| T | 32 | 0.76 | S | 7 | 1.6 | K | 173 | 0.66 | K | 334 | 0.3 |
| Y | 33 | 1.23 | G | 8 | 1.6 | A | 175 | 1.44 | A | 335 | 1.84 |
| H | 35 | 0.61 | G | 9 | 1.5 | K | 176 | 0 | K | 336 | 2 |
| W | 36 | 0.1 | G | 10 | 1.4 | G | 178 | 0 | G | 337 | 1.86 |
| Q | 39 | 1.27 | Q | 13 | 1.4 | Q | 179 | 0.068 | Q | 338 | 1.84 |
| A | 40 | 1.35 | P | 14 | 1.3 | P | 180 | 0 | P | 339 | 1.58 |
| K | 43 | 1.41 | G | 16 | 1.4 | P | 181 | 0 | P | 342 | 0 |
| L | 45 | 0.97 | S | 17 | 1.4 | V | 182 | 0 | V | 344 | 0 |
| E | 46 | 1.65 | L | 18 | 0.7 | Y | 185 | 0.63 | Y | 345 | 0.4 |
| R | 50 | 0.13 | L | 20 | 0 | T | 186 | 0 | T | 346 | 0 |
| Y | 52 | 1.42 | S | 21 | 1.65 | L | 187 | 0.1 | L | 347 | 0 |
| T | 53 | 1.75 | C | 22 | 0 | P | 188 | | P | 348 | 0.67 |
| G | 55 | 1.65 | A | 24 | 0 | P | 189 | | P | 349 | 0 |
| Y | 56 | 1.32 | S | 25 | 1.54 | S | 190 | | S | 350 | 0.7 |
| T | 57 | 1.12 | G | 26 | 1.57 | R | 191 | 0.8 | R | 351 | 1.78 |
| R | 58 | 1.51 | N | 28 | 1.49 | E | 192 | 1.76 | E | 352 | 0.93 |
| Y | 59 | 1.13 | K | 30 | 1.57 | E | 193 | 1.31 | E | 353 | 0.6 |

TABLE 15-continued

DAR of vc-linked THIOMAB™ antibodies with Heavy Chain cysteine substitutions.

| Residue | Kabat # | Avg. DAR | Residue | Kabat # | Avg. DAR | Residue | Kabat # | Avg. DAR | Residue | Kabat # | Avg. DAR |
|---|---|---|---|---|---|---|---|---|---|---|---|
| A | 60 | 1.16 | D | 31 | 0.6 | Y | 194 | 0.0 | M | 354 | 1.31 |
| V | 63 | 0.46 | I | 34 | 0 | N | 197 |  | T | 355 | 1.7 |
| G | 65 | 0.82 | V | 37 |  | V | 198 | 0.0 | N | 357 | 1.0 |
| T | 68 | 1.67 | R | 38 | 0 | N | 199 | 1.6 | Q | 358 | 1.56 |
| N | 76 | 1.89 | P | 41 | 1.67 | H | 200 |  | V | 359 | 0.0 |
| T | 77 | 0.27 | G | 42 | 1.67 | S | 203 | 1.67 | S | 360 | 0 |
| A | 78 | 0.2 | K | 44 | 1.4 | L | 206 | 1.79 | L | 361 | 0 |
| Q | 81 | 1.63 | W | 47 | 0.74 | D | 208 | 0.8 | T | 362 | 0.1 |
| N | 82A | 1.69 | V | 48 | 0 | L | 209 |  | L | 364 | 0.4 |
| E | 85 | 0.94 | A | 49 | 0 | V | 210 |  | V | 365 | 0 |
| G | 99 | 1.82 | I | 51 | 0.11 | K | 212 |  | K | 366 | 0 |
| F | 100 | 1.77 | E | 52A | 0.27 | F | 213 |  | F | 368 | 0.08 |
| A | 100B | 0.95 | P | 54 | 1.82 | P | 214 | 1.35 | P | 370 | 1.43 |
| M | 100C | 1.54 | N | 61 | 1.47 | S | 215 | 0.3 | S | 371 | 1.89 |
| Y | 102 | 0.26 | D | 62 | 1.85 | I | 216 | 0 | C | 373 | 0 |
| W | 103 | 1.08 | S | 64 | 1.74 | A | 217 | 0.06 | D | 374 | 1.3 |
| T | 107 | 0.11 | K | 66 | 0 | W | 218 | 0.11 | K | 377 | 0 |
| T | 110 | 1.22 | R | 67 | 0 | N | 219 | 0.1 | T | 380 | 1.7 |
| T | 116 | 1.33 | F | 69 | 0.09 | G | 220 | 0.08 | H | 381 | 1.8 |
| K | 117 | 1.2 | I | 70 | 1.56 | Q | 221 | 0 | Q | 382 | 1.85 |
| P | 123 | 0.55 | S | 71 | 0.18 | N | 223 | 0 | N | 385 | 2 |
| A | 125 | 0.52 | A | 72 | 0.99 | N | 224 | 0 | N | 386 | 2 |
| T | 135 | 1.37 | D | 73 | 1.39 | Y | 226 | 0.13 | P | 387 | 0.6 |
| A | 136 | 1.16 | T | 74 | 1.49 | K | 227 | 0.17 | Y | 388 | 0.84 |
| L | 138 | 0.13 | S | 75 | 1.54 | T | 228 | 0 | K | 390 | 0.1 |
| G | 139 | 0.06 | K | 79 | 1.75 | P | 229 | 0.45 | P | 391 | 0.19 |
| L | 141 | 0.54 | V | 80 | 0 | P | 230 | 0.05 | L | 392 | 0.93 |
| K | 143 | 0.28 | L | 82 | 0 | V | 231 | 0.12 | V | 393 | 0.93 |
| F | 146 | 0.15 | M | 82B | 1.84 | L | 232 | 0.08 | L | 394 | 1.81 |
| G | 162 | 1.21 | S | 82C | 0.08 | S | 233 | 0.41 | G | 396 | 1.67 |
| V | 163 | 1.45 | L | 83 | 1.73 | D | 234 | 0 | S | 397 | 1.6 |
| A | 168 | 0.81 | R | 84 | 1.65 | G | 236 | 1.01 | D | 398 | 1.65 |
| V | 169 | 0.93 | A | 86 | 0.52 | F | 237 | 1.37 | G | 400 | 1.85 |
| L | 170 | 1.15 | D | 87 | 1.67 | F | 238 | 0.89 | F | 401 | 1.7 |
| G | 174 | 1.76 | T | 88 | 0.08 | L | 239 | 1.4 | F | 402 | 1.09 |
| S | 177 | 0.81 | A | 89 | 0.55 | Y | 240 | 0.8 | L | 403 | 0.25 |
| T | 183 | 1.58 | V | 90 | 0 | S | 241 |  | Y | 404 | 1.7 |
| V | 184 | 0.99 | Y | 91 | 0 | K | 242 | 1.67 | S | 405 | 1.61 |
| I | 195 | 1.57 | Y | 92 | 0.18 | L | 243 | 1.47 | K | 406 | 1.63 |
| K | 201 | 0.5 | C | 93 | 0 | V | 244 | 1.5 | L | 408 | 0.16 |
| N | 204 | 1.82 | S | 94 | 0 | R | 245 | 0 | V | 412 | 1.8 |
| T | 205 | 1.3 | R | 95 | 1.38 | W | 246 | 0.29 | R | 413 | 1.57 |
| V | 207 | 0.06 | W | 96 | 1.64 | Q | 247 | 0.4 | W | 415 | 1.77 |
| S | 235 | 1.3 | G | 97 | 1.95 | V | 249 | 1.65 | Q | 418 | 1.53 |
| M | 248 | 1.66 | G | 98 | 1.6 | S | 250 | 0.52 | V | 422 | 0.3 |
| E | 254 | 1.6 | D | 100A | 1.92 | V | 251 | 0.63 | S | 423 | 0 |
| T | 256 | 1.23 | Y | 101 | 1.01 | L | 252 | 1.58 | V | 428 | 0.18 |
| V | 258 | 1.44 | D | 104 | 0.96 | H | 253 | 1.8 | L | 429 | 1.7 |
| K | 270 | 1.8 | G | 105 | 1.79 | S | 255 | 0.13 | H | 440 | 1.67 |
| N | 272 | 1.31 | Q | 108 | 1.73 | P | 259 | 0.11 | S | 441 | 1.13 |
| V | 280 | 1.4 | V | 111 | 0 | G | 260 | 1.58 | P | 442 | 0 |
| L | 305 | 1.56 | S | 112 | 1.58 | K | 261 | 1.71 | G | 443 | 0.18 |

TABLE 16

DAR of vc-linked THIOMAB™ antibodies with Light Chain cysteine substitutions.

| Residue | Kabat # | Avg. DAR | Residue | Kabat # | Avg. DAR | Residue | Kabat # | Avg. DAR | Residue | Kabat # | Avg. DAR |
|---|---|---|---|---|---|---|---|---|---|---|---|
| T | 22 | 1.89 | A | 111 | 0.5 | L | 47 | 0.1 | N | 138 | 1.4 |
| T | 31 | 1.89 | S | 114 | 1.78 | I | 48 | 0.4 | F | 139 | 0.08 |
| Y | 49 | 1.26 | F | 118 | 0.07 | Y | 55 | 0.0 | Y | 140 | 0.27 |
| S | 52 | 1.48 | Q | 124 | 1.22 | S | 56 | 1.53 | P | 141 | 0.53 |
| G | 64 | 1.3 | K | 126 | 1.38 | G | 57 | 1.81 | E | 143 | 1.09 |
| R | 66 | 1.39 | T | 129 | 1.69 | V | 58 | 1.3 | A | 144 | 1.01 |
| P | 95 | 1.1 | V | 133 | 0.07 | A | 59 | 0.57 | K | 145 | 1.66 |
| E | 105 | 1.78 | R | 142 | 1.2 | S | 60 | 0.83 | V | 146 | 0.09 |
| I | 106 | 1.12 | K | 149 | 1.4 | R | 61 | 1.75 | Q | 147 | 1.6 |
| R | 108 | 1.52 | V | 150 | 0.06 | F | 62 | 1.37 | W | 148 | 0 |

TABLE 16-continued

DAR of vc-linked THIOMAB ™ antibodies with Light Chain cysteine substitutions.

| Residue | Kabat # | Avg. DAR | Residue | Kabat # | Avg. DAR | Residue | Kabat # | Avg. DAR | Residue | Kabat # | Avg. DAR |
|---|---|---|---|---|---|---|---|---|---|---|---|
| K | 126 | 1.38 | A | 153 | 1.91 | S | 65 | 1.7 | D | 151 | 0.23 |
| R | 142 | 1.2 | L | 154 | 1.56 | N | 67 | 1.75 | N | 152 | 0.82 |
| Q | 155 | 1.5 | Q | 155 | 1.5 | G | 68 | 1.5 | G | 157 | 1.13 |
| S | 162 | 1.03 | S | 156 | 1.71 | T | 69 | 1.66 | N | 158 | 0 |
| A | 193 | 1.49 | S | 162 | 1.03 | F | 71 | 0 | S | 159 | 1.27 |
| V | 205 | 1.72 | V | 163 | 1.45 | T | 72 | 1.69 | Q | 160 | 1.49 |
| T | 206 | 1.72 | S | 168 | 1.38 | L | 73 | 0.1 | E | 161 | 1.43 |
| L | 11 | 0.62 | S | 171 | 0.71 | S | 76 | 1.6 | T | 164 | 0.51 |
| S | 14 | 1.43 | S | 177 | 0.74 | S | 77 | 1.8 | E | 165 | 1.51 |
| G | 16 | 0.95 | L | 179 | 0.6 | L | 78 | 0 | Q | 166 | 1.24 |
| R | 18 | 1.7 | K | 188 | 0.88 | Q | 79 | 1.73 | D | 167 | 1.6 |
| T | 22 | 1.89 | A | 193 | 1.49 | P | 80 | 1.7 | K | 169 | 1.66 |
| R | 24 | 1.4 | E | 195 | 1.58 | E | 81 | 1.3 | D | 170 | 1.58 |
| Q | 27 | 1.8 | L | 201 | 1.58 | F | 83 | 0.2 | T | 172 | 1.48 |
| T | 31 | 1.89 | V | 205 | 1.72 | A | 84 | 0.2 | Y | 173 | 0 |
| A | 32 | 1.61 | T | 206 | 1.72 | Y | 86 | 0 | S | 174 | 0 |
| Y | 36 | 0.9 | D | 1 | 0.39 | Y | 87 | 0 | L | 175 | 0 |
| K | 39 | 1.42 | I | 2 | 0.99 | C | 88 | 0 | S | 176 | 0 |
| K | 42 | 1.3 | Q | 3 | 1.85 | T | 93 | 1.6 | T | 178 | 0.23 |
| A | 43 | 0.78 | M | 4 | 0.37 | T | 94 | 1.1 | T | 180 | 1.46 |
| P | 44 | 0.9 | T | 5 | 1.74 | T | 97 | 1.39 | L | 181 | |
| Y | 49 | 1.26 | Q | 6 | 0.12 | G | 99 | 1.36 | S | 182 | 1.41 |
| S | 50 | 1.61 | S | 7 | 1.51 | Q | 100 | 1.48 | K | 183 | 1.48 |
| A | 51 | 0.38 | P | 8 | 1.8 | G | 101 | 1.48 | A | 184 | 0.73 |
| S | 52 | 1.48 | S | 9 | 1.63 | T | 102 | 0.1 | D | 185 | 1.01 |
| F | 53 | 0.82 | S | 10 | 1.82 | V | 104 | 0 | Y | 186 | 0 |
| L | 54 | 1.02 | S | 12 | 1.61 | T | 109 | 0.3 | E | 187 | |
| S | 63 | 1.84 | A | 13 | 0 | V | 110 | 1.55 | H | 189 | 0.2 |
| G | 64 | 1.3 | V | 15 | 1.54 | A | 112 | 0.62 | K | 190 | |
| R | 66 | 1.39 | D | 17 | 0.99 | P | 113 | 0.91 | V | 191 | 1.77 |
| D | 70 | 1.6 | V | 19 | 0.06 | V | 115 | 0.11 | Y | 192 | 0 |
| T | 74 | 1.51 | T | 20 | 0 | F | 116 | 1.21 | V | 196 | 0.11 |
| I | 75 | 0.07 | I | 21 | 0 | I | 117 | 0.13 | T | 197 | 1.82 |
| D | 82 | 0.75 | A | 25 | 0 | P | 119 | | H | 198 | 0.85 |
| T | 85 | 1.24 | S | 26 | 1.49 | P | 120 | 0.07 | Q | 199 | 1.8 |
| Q | 89 | 0.8 | D | 28 | 1.52 | S | 121 | 1.17 | G | 200 | 1.64 |
| Q | 90 | 0.17 | V | 29 | 0.59 | D | 122 | 0 | S | 202 | 1.17 |
| H | 91 | 1.1 | N | 30 | | E | 123 | 0.25 | S | 203 | 1.6 |
| Y | 92 | 1.4 | V | 33 | 0 | L | 125 | 1.45 | P | 204 | 1.49 |
| P | 95 | 1.1 | A | 34 | 0.3 | S | 127 | 1.67 | K | 207 | |
| P | 96 | 0.9 | W | 35 | 0 | G | 128 | 0.54 | S | 208 | 1.3 |
| F | 98 | 1.16 | Q | 37 | 0 | A | 130 | 0 | F | 209 | |
| K | 103 | 1.74 | Q | 38 | 0.5 | S | 131 | | N | 210 | |
| E | 105 | 1.78 | P | 40 | 0 | V | 132 | 0.18 | N | 211 | |
| I | 106 | 1.12 | G | 41 | 1.4 | L | 135 | 0.07 | G | 212 | |
| K | 107 | 1.65 | K | 45 | 0 | L | 136 | 0.1 | E | 213 | |
| R | 108 | 1.52 | L | 46 | 0.2 | N | 137 | 0.26 | C | 214 | 0.14 |

Example 4—Aggregation Analysis of the MC-Vc-MMAE and PDS-MMAE THIOMAB™ Antibodies Aggregation analysis was performed via size exclusion assays on each of the THIOMAB™ antibodies presented in Tables 6-10.

Size exclusion chromatography was performed on 1100 series HPLC (Agilent Technologies). Samples were chromatographed on a Shodex KW 802.5 column. An isocratic method using mobile phase of 0.2 M potassium phosphate, 0.25 M potassium chloride, pH 6.2, at 0.75 mL/min for 15 min was used to elute the conjugate. Percent aggregation was calculated from integrated areas of aggregate and monomeric peaks from the UV 280 nm chromatogram. FIG. 3 shows a representative plot of aggregate and monomer peaks used for the aggregation analysis and calculations.

Example 5—Conjugation Analysis of THIOMAB™ Antibodies

Conjugation analysis of the THIOMAB™ antibodies was performed using liquid chromatography-mass spectrometry (LC/MS or LCMS). As shown in FIG. 4A and FIG. 4B, UV280 LC/MS chromatographs of THIOMAB™ antibodies show DAR0 (naked antibody), DAR1, and DAR2 conjugations. LCMS results for the most stable sites of the complete antibody cysteine (wherein 4D5 antibodies with single cysteine mutations at every position within the antibody were made to determine the unpredictable most stable sites within an antibody for the purpose of attaching a linker-drug to make an ADC) screen are shown in Tables 7 and 9.

Example 6—Stability Analysis of the MC-Vc-MMAE and PDS-MMAE THIOMAB™ Antibodies

Stability samples of the PDS-MMAE and MC-vc-MMAE THIOMAB™ antibodies were generated in duplicate for both Rat Plasma at three time points (0 hr, 48 hrs and 96 hrs) and Buffer (0 hour). A flow chart of the experimental procedure for the stability screen is provided in FIG. 5. To create stability samples, 9 µL of each THIOMAB™ antibody (i.e., Source Material) was added to 351 µL of either Rat Plasma or Buffer (1×PBS, 0.5% BSA, 15 PPM Proclin) and then thoroughly mixed. The concentrations of the source materials (Conc.) are provided in, for example, Tables 6, 8, and 10. Once mixed, 120 µL of the Rat Plasma stability samples was aliquoted into three separate sets of tubes for the three different time points. The 0 hr time points for Rat Plasma and Buffer were then placed in a −80° C. freezer, while the 48 hr and 96 hr time points for Rat Plasma were placed on a shaker in a 37° C. incubator. When the 48 hr and 96 hr samples reached the given time points they were also placed in the −80° C. freezer. Representative graphs showing the stability of the MC-vc-MMAE and PDS-MMAE LC-R142C THIOMAB™ antibodies using mass spec analysis at 0 hr, 48 hrs, and 96 hrs is provided in FIGS. 6a and 6b.

ELISA assays were used to determine stability of the PDS-MMAE and MC-vc-MMAE THIOMAB™ antibodies. The concentration of Total Antibody (conjugated and unconjugated THIOMAB™ antibodies) in rat plasma was determined by ELISA using extracellular domain (ECD) of human erb2 as capture and goat anti-human IgG horseradish peroxide (HRP) as detection antibody. The assay had a limit of detection (LOD) of 0.5 mg/mL with a minimum dilution of 800-fold.

The concentration of the conjugated PDS-MMAE and MC-vc-MMAE THIOMAB™ antibodies in rat plasma was determined by ELISA using an anti-drug monoclonal antibody for capture and goat anti-human IgG-HRP for detection. The assay had a limit of detection (LOD) of 0.5 mg/mL with a minimum dilution of 800-fold.

The drug load stability based on conjugation at specific cysteine engineered sites was calculated. The conjugated antibody concentration at 0 hr normalized to total antibody was calculated using the ratio of the conjugated antibody concentration at time 0 hr to the total antibody concentration at 0 hr (as determined by ELISA) such that $[C_0]/[T_0]=nC_0$. The conjugated antibody concentration at 48 hr normalized to total antibody was calculated using the ratio of the conjugated antibody concentration at time 48 hr to the total antibody concentration at 48 hr (as determined by ELISA) such that $[C_{48}]/[T_{48}]=nC_{48}$.

The percent drug load stability was calculated by determining the percent stability by calculating the ratio of conjugated antibody at 48 hr to the conjugated antibody at 0 hr (as determined by ELISA) such that $nC_{48}/nC_0$=percent drug load stability.

FIG. 7 shows a graph of the stability of the preferred PDS-MMAE THIOMAB™ antibodies measured at the 48 hr time point. FIG. 8 shows a graph of the stability of the preferred MC-vc-MMAE THIOMAB™ antibodies measured at the 48 hr time point. The stability of all screened PDS-MMAE and MC-vc-MMAE THIOMAB™ antibodies can be found in the tables provided herein.

Example 7—Preparation of LC-K149C, LC-V205C, and HC-A114C THIOMAB™ Antibodies

LC-K149C, LC-V205C, and HC-A114C THIOMAB™ antibodies were made using anti-CD33 and anti-HER2 antibodies and the stability of those THIOMAB™ antibodies were assessed based on average DAR (FIG. 9). The anti-HER2 LC-K149C THIOMAB™ antibody showed surprising stability in the anti-HER2 antibody compared to HC-A114C and LC-V205C. Specifically, the drug conjugation of the anti-HER2 LC-K149C THIOMAB™ antibody was stable and the THIOMAB™ antibody retained a DAR of 2 for six days post-conjugation. Similarly, the anti-CD33 LC-K149C THIOMAB™ antibody also retained a DAR of 2 for 6 days. In contrast, the anti-HER2 LC-V205C and HC-A114C THIOMAB™ antibodies.

Example 8—Stability of PDS-MMAE THIOMAB™ Antibodies 48 hr and 96 hr after Conjugation A cysteine screen of an antibody was performed to determine which resulting PDS-THIOMAB™ antibodies had ≥1DAR, ≥1 mg/mL source stock concentration, ≤50% aggregation, reoxidized, ≥80% stability for VC variant drug load in rat plasma over 48 hrs based on ELISA (both duplicates), ≥70% stability for PDS variant drug load in rat plasma over 48 hrs based on ELISA (both duplicates), and stability up to 96 hrs confirmed by reliable MS spectra. Specifically, the 4D5 antibody was used for exemplary purposed such that one of skill in the art would know that any antibody can be substituted for the 4D5 antibody.

The screen identified preferred candidates within the light chain and heavy chains (see Tables 1 and 2) and additional stable sites (see Tables 3 and 4) for cysteine engineering and linker-drug attachment to produce stable ADCs. Results of the experiment are provided in Tables 6-12.

Example 9—Stability of MC-Vc-MMAE THIOMAB™ Antibodies 48 hr and 96 hr after Conjugation A cysteine screen of an antibody was performed to determine which resulting MC-vc-THIOMAB™ antibodies had ≥1DAR, ≥1 mg/mL source stock concentration, ≤50% aggregation, reoxidized, ≥80% stability for VC variant drug load in rat plasma over 48 hrs based on ELISA (both duplicates), ≥70% stability for PDS variant drug load in rat plasma over 48 hrs based on ELISA (both duplicates), and stability up to 96 hrs confirmed by reliable MS spectra. Specifically, the 4D5 antibody was used for exemplary purposed such that one of skill in the art would know that any antibody can be substituted for the 4D5 antibody.

The screen identified preferred candidates within the light chain and heavy chains (see Tables 1 and 2) and additional stable sites (see Tables 3 and 4) for cysteine engineering and linker-drug attachment to produce stable ADCs. Results of the experiment are provided in Tables 6-12.

Example 10—In Vitro Cell Proliferation Assay

Efficacy of THIOMAB™ antibodies can be measured by a cell proliferation assay employing the following protocol (CellTiter Glo Luminiscent Cell Viability Assay, Promega Corp. Technical Bulletin TB288; Mendoza et al (2002) Cancer Res. 62:5485-5488):
1. An aliquot of 100 µl of cell culture containing about $10^4$ cells (SKBR-3, BT474, MCF7 or MDA-MB-468) in medium can be deposited in each well of a 96-well, opaque-walled plate.
2. Control wells can be prepared containing medium and without cells.
3. A THIOMAB™ antibody can be added to the experimental wells and incubated for 3-5 days.
4. The plates can be equilibrated to room temperature for approximately 30 minutes.

5. A volume of CellTiter-Glo Reagent equal to the volume of cell culture medium present in each well can be added.
6. The contents can be mixed for 2 minutes on an orbital shaker to induce cell lysis.
7. The plate can be incubated at room temperature for 10 minutes to stabilize the luminescence signal.
8. Luminescence can be recorded and reported in graphs as RLU=relative luminescence units.

Certain cells can be seeded at 1000-2000/well (PC3 lines) or 2000-3000/well (OVCAR-3) in a 96-well plate, 50 uL/well. After one (PC3) or two (OVCAR-3) days, THIO-MAB™ antibodies can be added in 50 μL volumes to final concentration of 9000, 3000, 1000, 333, 111, 37, 12.4, 4.1, or 1.4 ng/mL, with "no ADC" control wells receiving medium alone. Conditions are in duplicate or triplicate After 3 (PC3) or 4-5 (OVCAR-3) days, 100 μL/well Cell TiterGlo II is added (luciferase-based assay; proliferation measured by ATP levels) and cell counts can be determined using a luminometer. Data can be plotted, for example, as the mean of luminescence for each set of replicates, with standard deviation error bars. Alternatively the CellTiter Glo Luminiscent Cell Viability Assay (Promega) may be performed according to Promega's protocol:
1. Plate 1000 cells/well of PC3/Muc16, PC3/neo (in 50 μL/well) of media. Ovcar3 cells should be plated at 2000 cells/well (in 50 μL) of their media (PC3/neo and PC3/MUC16 grow in 50/50/10% FBS/glutamine/250 μg/mL G-418 OVCAR-3 grow in RPMI/20% FBS/glutamine). Allow cells to attach overnight.
2. The THIOMAB™ antibody is serially diluted 1:3 in media beginning at at working concentration 18 μg/ml (this results in a final concentration of 9 μg/ml). 50 μL of diluted ADC is added to the 50 μL of cells and media already in the well.
3. Incubate 72-96 hrs (the standard is 72 hours, but watch the 0 ug/mL concentration to stop assay when the cells are 85-95% confluent).
4. Add 100 μL/well of Promega Cell Titer Glo reagent, shake 3 min and read on a luminometer.

Example 11—Tumor Growth Inhibition, In Vivo Efficacy in High Expressing HER2 Transgenic Explant Mice Animals suitable for transgenic experiments can be obtained from standard commercial sources such as Taconic (Germantown, N.Y.). Many strains are suitable, but FVB female mice are preferred because of their higher susceptibility to tumor formation. FVB males were used for mating and vasectomized CD.1 studs were used to stimulate pseudopregnancy. Vasectomized mice can be obtained from any commercial supplier. Founders were bred with either FVB mice or with 129/BL6xFVB p53 heterozygous mice. The mice with heterozygosity at p53 allele were used to potentially increase tumor formation. However, this has proven unnecessary. Therefore, some F1 tumors are of mixed strain. Founder tumors are FVB only. Six founders were obtained with some developing tumors without having litters.

Animals having tumors (allograft propagated from Fo5 mmtv transgenic mice) were treated with a single or multiple dose by IV injection of ADC. Tumor volume was assessed at various time points after injection.

Tumors arise readily in transgenic mice that express a mutationally activated form of neu, the rat homolog of HER2, but the HER2 that is overexpressed in human breast cancers is not mutated and tumor formation is much less robust in transgenic mice that overexpress nonmutated HER2 (Webster et al (1994) Semin. Cancer Biol. 5:69-76).

To improve tumor formation with nonmutated HER2, transgenic mice were produced using a HER2 cDNA plasmid in which an upstream ATG was deleted in order to prevent initiation of translation at such upstream ATG codons, which would otherwise reduce the frequency of translation initiation from the downstream authentic initiation codon of HER2 (for example, see Child et al (1999) J. Biol. Chem. 274: 24335-24341). Additionally, a chimeric intron was added to the 5' end, which should also enhance the level of expression as reported earlier (Neuberger and Williams (1988) Nucleic Acids Res. 16:6713; Buchman and Berg (1988) Mol. Cell. Biol. 8:4395; Brinster et al (1988) Proc. Natl. Acad. Sci. USA 85:836). The chimeric intron was derived from a Promega vector, Pci-neo mammalian expression vector (bp 890-1022). The cDNA 3'-end is flanked by human growth hormone exons 4 and 5, and polyadenylation sequences. Moreover, FVB mice were used because this strain is more susceptible to tumor development. The promoter from MMTV-LTR was used to ensure tissue-specific HER2 expression in the mammary gland. Animals were fed the AIN 76A diet in order to increase susceptibility to tumor formation (Rao et al (1997) Breast Cancer Res. and Treatment 45:149-158).

Similar in vivo models can be made and studied for additional tumor types. For example, an in vivo model can be made to study the efficacy of anti-CD33 THIOMAB™ antibodies using a CD33 expressing model.

Example 12—Use of HC-A140C to Rescue Linker-Drug Instability

As discussed herein, LC-K149C (according to Kabat numbering) was found to be a preferred site for cysteine substitution because of its stability in retaining the linker drug (i.e., the linker-drug remains bound to the antibody at the engineered LC-K149C position). However, it was unexpectedly discovered that even though the linker remained bound to the cysteine engineered antibody at LC-K149C, certain drugs were subject to enzymatic modification when linked to the cysteine engineered antibody at position LC-K149C. Specifically, it was surprising to find that certain drugs attached to LC-K149C via a linker were subject to enzymatic modifications such as carbamate group loss, acetyl loss (i.e., deacetylation), phosphate loss, sugar loss, and ether cleavage.

After observing modifications of certain drugs (including but not limited to cryptophycin, tubulysin M, taxoid drugs, and a CBI-PBD heterodimer linker-drug intermediate) when attached to a cysteine engineered antibody at LC-K149C, additional sites from Tables 1-4 (including HC-A118C, LC-V205C, HC-S121C, and HC-A140C) were examined to see if their use could reduce and/or eliminate drug modification. Specifically, it was observed that cryptophycin was subject to an amide cleavage, Tubulysin was subject to an acetyl loss (i.e., deacetylation), a CBI-PBD heterodimer linker-drug intermediate was subject to a carbamate loss, and a Taxoid was unstable and showed cleavages when conjugated via a linker to LC-K149C on a cysteine engineered antibody (See FIG. 13).

Figure 14A:
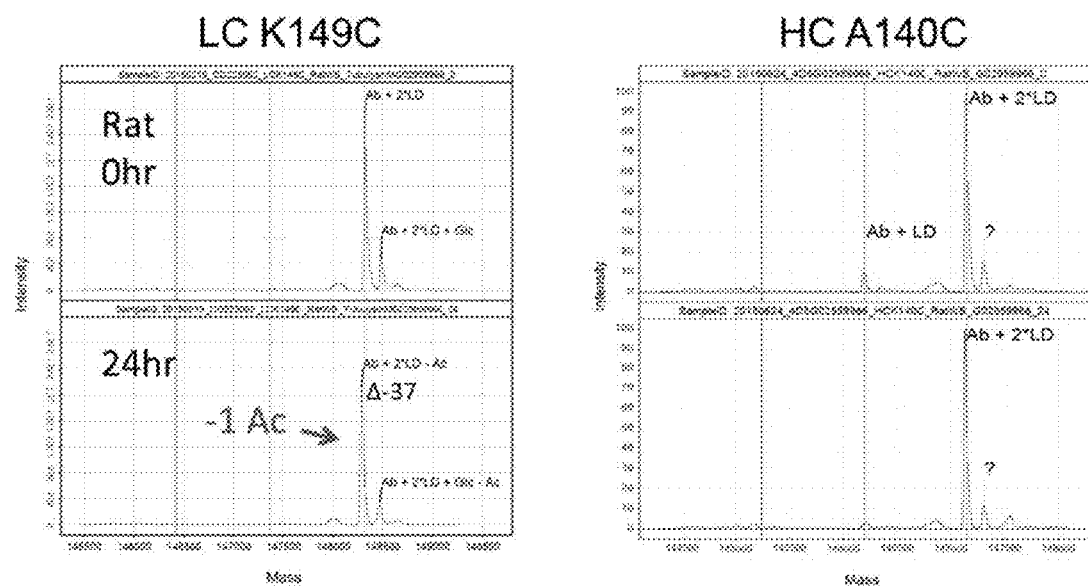
FIG. 14A shows that HC-A140C provides protection of the acetyl group of Tubulysin compared to LC-K149C. Specifically, it was shown using LCMS that there is less degradation of the drug using HC-A140C as the site of attachment than LC-K149C after 24 hrs of incubation.
Figure 14B:
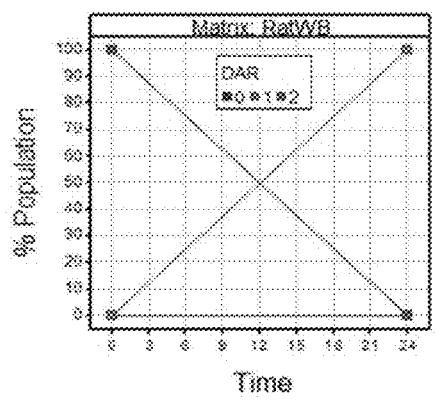
FIGS. 14B and 14C show that HC-A140C was more stable than LC-K149C after 24 hrs of incubation using a novel whole blood assay.
Figure 14C:
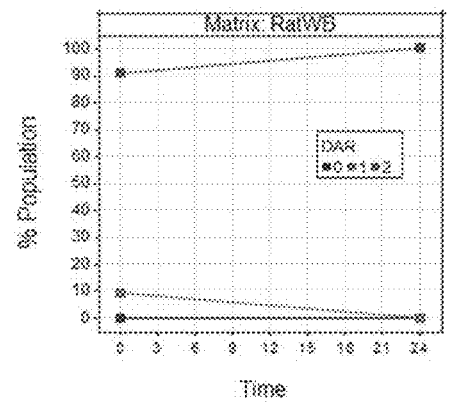

It was unexpectedly discovered that HC-A140C provides protection of the acetyl group of Tubulysin (See FIGS. 14a-14c). Specifically, it was shown using LCMS that there is less degradation of the drug using HC-A140C as the site of attachment than LC-K149C after 24 hrs of incubation (FIG. 14a). HC-A140C was similarly shown to be more stable using a novel whole blood assay.

For the novel whole blood (WB) assay (described herein for the first time) samples were generated in Mouse (CB17 SCID), Rat (Sprague-Dawley), Cynomologus Monkey and/or Human Whole blood Plasma as well as Buffer (0 and 24 hour). Blood was collected by Bioreclamation then shipped cold overnight and samples were created immediately upon arrival of whole blood. To create stability samples, initial dilutions of the source material were made in Buffer (1×PBS, 0.5% BSA, 15 PPM Proclin) so that all molecules were 1 mg/mL in concentration. Then a 1:10× dilution (36 uL of 1 mg/mL initial dilution+324 uL blood or buffer) was performed to generate the stability samples with a final concentration of 100 ug/mL. Once mixed, 150 µL of the Whole Blood/Buffer stability samples was aliquoted into two separate sets of tubes for the two different time points. The 0 hour time points were then placed in a −80° C.

Acetyl loss at HC-A140C and LC-K149C was confirmed in three rounds of WB assays. It was confirmed that HC-A140C rescues acetyl loss modification (FIG. 15).

Figure 16A:
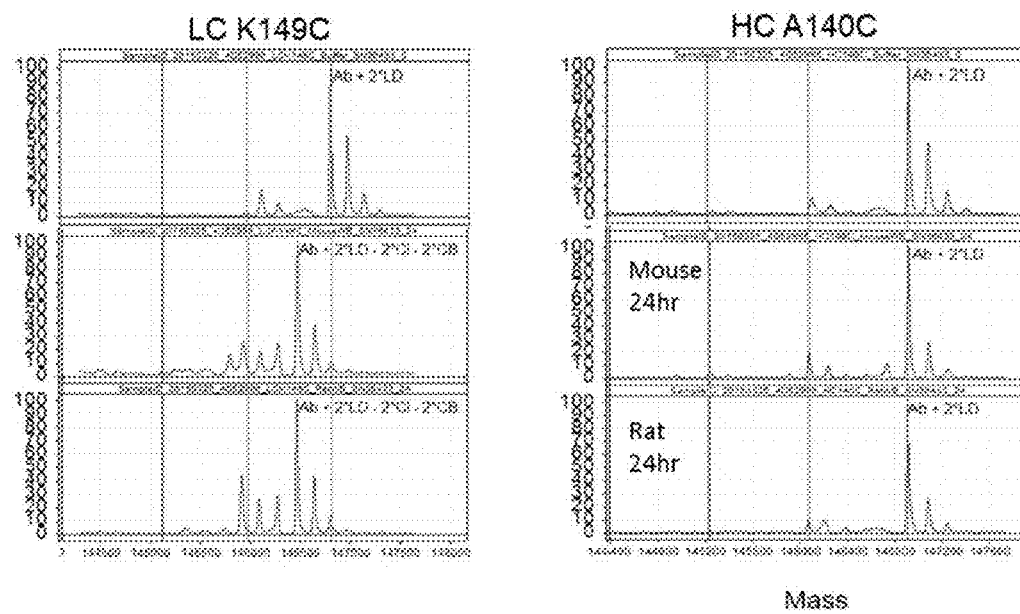
FIG. 16A shows that HC-A140C provides protection of the carbomate group of a CBI-PBD heterodimer linker-drug intermediate. Specifically, it was shown using LCMS that there is less degradation of the drug using HC-A140C as the site of attachment than LC-K149C after 24 hrs of incubation (FIG. 16A).
Figure 16B:
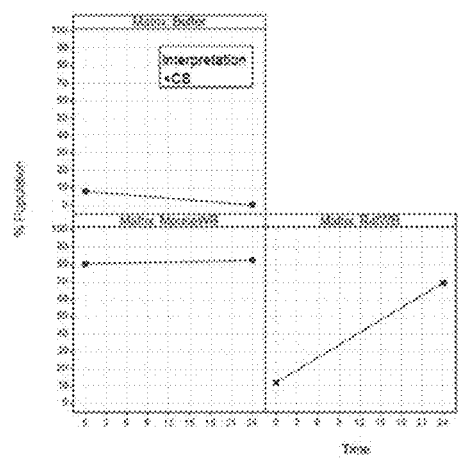
FIGS. 16B and 16C show that HC-A140C was more stable than LC-K149C after 24 hrs of incubation using a novel whole blood assay.
Figure 16C:
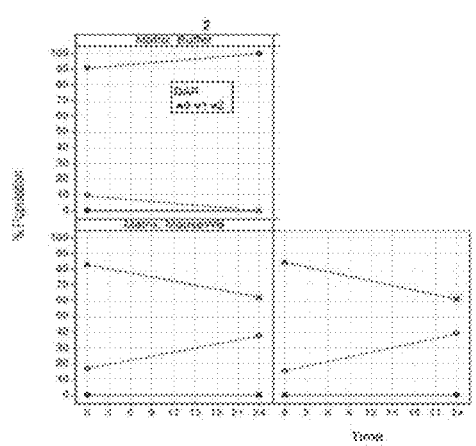

It was unexpectedly discovered that HC-A140C provides protection of the carbomate group of a CBI-PBD heterodimer linker-drug intermediate (See FIGS. 16a-16c). Specifically, it was shown using LCMS that there is less degradation of the drug using HC-A140C as the site of attachment than LC-K149C after 24 hrs of incubation (FIG. 16a). HC-A140C was similarly shown to be more stable using the novel whole blood assay (FIG. 17).

It was also unexpectedly discovered that HC-A140C provides protection from modification of taxoids (See FIGS. 18a-18c). Specifically, it was shown using LCMS that there is less degradation of the drug using HC-A140C as the site of attachment than LC-K149C after 24 hrs of incubation (FIG. 18a). HC-A140C was similarly shown to be more stable (e.g., in terms of protecting taxoid drug loss) using the novel whole blood assay (FIG. 19).

Figure 20:
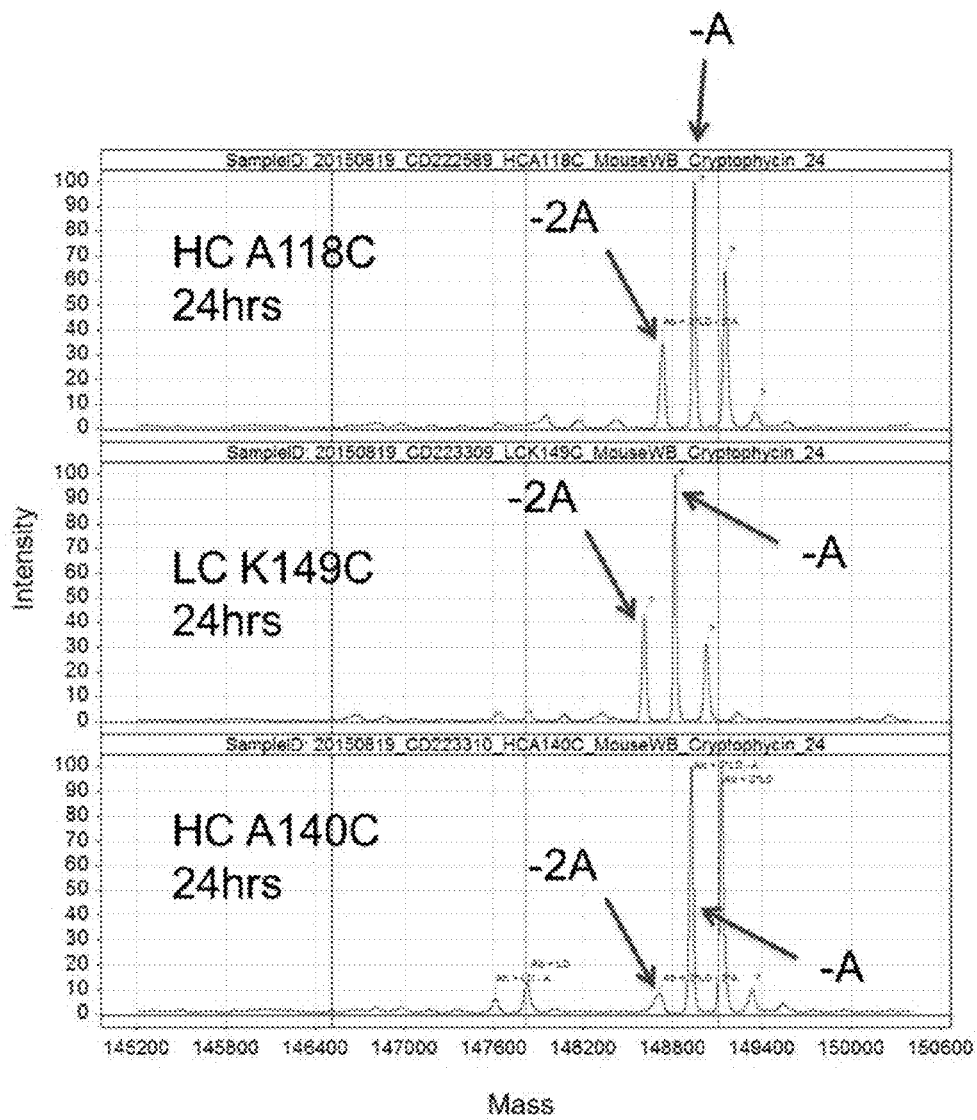
FIG. 20 shows that HC-A140C protects cryptophycin from amide and ester cleavage compared to LC-K149C.

Just as protection was unexpectedly observed for Tubulysin, a CBI-PBD heterodimer linker-drug intermediate, and taxoid drugs by linking the drug to HC-A140C instead of LC-K149C, it was also discovered that HC-A140C protects cryptophycin from amide and ester cleavage (See FIG. 20).

The experiments were performed on anti-HER2 antibodies (specifically 4D5) and/or anti-CD22 antibodies with PDS and/or maleimide (i.e. vc-) linkers.

Example 13—Identification of the Most Stable Sites for PDS Linkage

The top stable variants from the ELISA screen were further evaluated by analyzing the 0, 48 and 96 hr plasma stability samples using an Affinity-Capture LC-MS Assay. First, Streptavidin-coated magnetic beads (Life Technologies Corporation, Grand Island, N.Y.) were washed 2× with HBS-EP buffer (GE Healthcare, Sunnyvale, Calif.), then mixed with biotinylated extracellular domain (ECD) of human erb2 using the KingFisher Flex (Thermo Fisher Scientific, Waltham, Mass.) and incubated for 2 hrs at room temperature with gentle agitation. After the 2 hrs, the SA-bead/Biotin-ECD complex was washed 2× with HBS-EP buffer, mixed with the diluted plasma stability samples and then incubated for 2 hrs at room temperature with gentle agitation. After the 2 hrs, the SA-bead/Biotin-ECD/sample complex was washed 2× with HBS-EP buffer, followed by 2× washes of water (Optima H2O, Fisher Scientific, Pittsburgh, Pa.) and finally 1× wash with 10% acetonitrile. The beads were then placed in 30% acetonitrile/0.1% formic acid for elution where they incubated for 30 mins at room temperature with gentle agitation before the beads were collected. The eluted samples were then loaded on to the LC-MS (Synapt-G2S, Waters, Milford, Mass.) for analysis.

The top stable PDS-MMAE variants were also evaluated using a Cysteine Reduction assay where samples were diluted with water to 100 ug/mL and mixed 1:1 with 100 uM cysteine and 100 mM ammonium bicarbonate buffer for a final concentration of 50 uM cysteine and 50 mM ammonium bicarbonate. Samples were then incubated in dark overnight for 18 hours at room temperature and then equal volume of 60% acetonitrile/0.2% formic acid was added to quench the reaction. Samples were then loaded on to the LC-MS (Synapt-G2S, Waters, Milford, Mass.) for analysis.

The preferred stable PDS-MMAE variants are identified in Tables 1 and 2) and additional stable variants are identified in Tables 3 and 4. Specifically, the top PDS-MMAE variants are clearly identified in FIG. 21 and in Example 2.

Example 14—Identification of the Most Stable Sites for −Vc (i.e., Maleimide) Linkage The top stable variants from the ELISA screen were further evaluated by analyzing the 0, 48 and 96 hr plasma stability samples using an Affinity-Capture LC-MS Assay. First, Streptavidin-coated magnetic beads (Life Technologies Corporation, Grand Island, N.Y.) were washed 2× with HBS-EP buffer (GE Healthcare, Sunnyvale, Calif.), then mixed with biotinylated extracellular domain (ECD) of human erb2 using the KingFisher Flex (Thermo Fisher Scientific, Waltham, Mass.) and incubated for 2 hrs at room temperature with gentle agitation. After the 2 hrs, the SA-bead/Biotin-ECD complex was washed 2× with HBS-EP buffer, mixed with the diluted plasma stability samples and then incubated for 2 hrs at room temperature with gentle agitation. After the 2 hrs, the SA-bead/Biotin-ECD/sample complex was washed 2× with HBS-EP buffer, followed by 2× washes of water (Optima H2O, Fisher Scientific, Pittsburgh, Pa.) and finally 1× wash with 10% acetonitrile. The beads were then placed in 30% acetonitrile/0.1% formic acid for elution where they incubated for 30 mins at room temperature with gentle agitation before the beads were collected. The eluted samples were then loaded on to the LC-MS (Synapt-G2S, Waters, Milford, Mass.) for analysis.

The preferred stable vc-MMAE variants are identified in Tables 1 and 2) and additional stable variants are identified in Tables 3 and 4. Specifically, the top vc-MMAE variants are clearly identified in FIG. 21 and in Example 2.

Example 15—Exemplary Antibodies that can be Engineered to have a Single Cysteine Mutation (i.e., Two Cysteines Per Antibody)

Any antibody can be engineered to have a single cysteine mutation (i.e., two cysteines per antibody). Exemplary antibodies that have been engineered to have a single cysteine mutation (i.e., two cysteines per antibody) using the methods described herein include but are not limited to antibodies against the following antigens: HER2, MUC16, STEAP1, NaPi2b, CD22, Ly6E, CLL-1, B7H4, and CD79.

Certain anti-HER2 antibodies that have been cysteine engineered include 4D5 and 7C2 (see Examples and Figures herein). Similarly, single cysteine mutations have been made in anti-CD33, anti-MUC16, anti-STEAP1, anti-Ly6E, anti-B7H4, anti-CD22, and anti-CD79b antibodies.

An example of an anti-MUC16 antibody that has been engineered to have a single cysteine mutation (i.e., two cysteines per antibody) include the antibody with the following sequences:

| SEQ ID NO: | Description | Sequence |
|---|---|---|
| 149 | Anti-Muc16 antibody HVR-L1 | KASDLIHNWL A |
| 150 | Anti-Muc16 antibody HVR-L2 | YGATSLET |
| 151 | Anti-Muc16 antibody HVR-L3 | QQYWTTPFT |
| 152 | Anti-Muc16 antibody HVR-H1 | GYSITNDYAW N |
| 153 | Anti-Muc16 antibody HVR-H2 | GYISYSGYTT YNPSLKS |
| 154 | Anti-Muc16 antibody HVR-H3 | ARWASGLDY |
| 155 | Anti-Muc16 antibody light chain variable region | DIQMTQSPSS LSASVGDRVT ITCKASDLIH NWLAWYQQKP GKAPKLLIYG ATSLETGVPS RFSGSGSGTD FTLTISSLQP EDFATYYCQQ YWTTPFTFGQ GTKVEIKR |
| 156 | Anti-Muc16 antibody heavy chain variable region | EVQLVESGGG LVQPGGSLRL SCAASGYSIT NDYAWNWVRQ APGKGLEWVG YISYSGYTTY NPSLKSRFTI SRDTSKNTLY LQMNSLRAED TAVYYCARWA SGLDYWGQGT LVTVSS |

An example of an anti-STEAP1 antibody that has been engineered to have a single cysteine mutation (i.e., two cysteines per antibody) include the antibody with the following sequences:

| SEQ ID NO: | Description | Sequence |
|---|---|---|
| 157 | Anti-STEAP-1 HVR-H1 | GYSITSDYAW N |
| 158 | Anti-STEAP-1 HVR-H2 | GYISNSGSTS YNPSLKS |
| 159 | Anti-STEAP-1 HVR-H3 | ERNYDYDDYY YAMDY |
| 160 | Anti-STEAP-1 HVR-L1 | KSSQSLLYRS NQKNYLA |
| 161 | Anti-STEAP-1 HVR-L2 | WASTRES |
| 162 | Anti-STEAP-1 HVR-L3 | QQYYNYPRT |
| 163 | Anti-STEAP1 heavy chain variable region | EVQLVESGGG LVQPGGSLRL SCAVSGYSIT SDYAWNWVRQ APGKGLEWVG YISNSGSTSY NPSLKSRFTI SRDTSKNTLY LQMNSLRAED TAVYYCARER NYDYDDYYA MDYWGQGTLV TVSS |
| 164 | Anti-STEAP1 light chain variable region | DIQMTQSPSS LSASVGDRVT ITCKSSQSLL YRSNQKNYLA WYQQKPGKAP KLLIYWASTR ESGVPSRFSG SGSGTDFTLT ISSLQPEDFA TYYCQQYYNY PRTFGQGTKV EIK |

An example of an anti-NaPi2b antibody that has been engineered to have a single cysteine mutation (i.e., two cysteines per antibody) include the antibody with the following sequences:

| SEQ ID NO: | Description | Sequence |
|---|---|---|
| 165 | Anti-NaPi2b HVR-H1 | GFSFSDFAMS |
| 167 | Anti-NaPi2b HVR-H2 | ATIGRVAFHTYYPDSMKG |

| SEQ ID NO: | Description | Sequence |
|---|---|---|
| 168 | Anti-NaPi2b HVR-H3 | ARHRGFDVGHFDF |
| 169 | Anti-NaPi2b HVR-L1 | RSSETLVHSSGNTYLE |
| 170 | Anti-NaPi2b HVR-L2 | RVSNRFS |
| 171 | Anti-NaPi2b HVR-L3 | FQGSFNPLT |
| 172 | Anti-NaPi2b heavy chain variable region | EVQLVESGGGLVQPGGSLRLSCAASGFSFSDFAMSWV RQAPGKGLEWVATIGRVAFHTYYPDSMKGRFTISRDN SKNTLYLQMNSLRAEDTAVYYCARHRGFDVGHFDFW GQGTLVTVSS |
| 173 | Anti-NaPi2b light chain variable region | DIQMTQSPSSLSASVGDRVTITCRSSETLVHSSGNTYLE WYQQKPGKAPKLLIYRVSNRFSGVPSRFSGSGSGTDFT LTISSLQPEDFATYYCFQGSFNPLTFGQGTKVEIKR |

An example of an anti-Ly6E antibody that has been engineered to have a single cysteine mutation (i.e., two cysteines per antibody) include the antibody with the following sequences:

| SEQ ID NO: | Description | Sequence |
|---|---|---|
| 174 | anti-Ly6E antibody hu9B12 v12 light chain variable region | DIQMTQSPSS LSASVGDRVT ITCSASQGIS NYLNWYQQ GKTVKLLIYY TSNLHSGVPS RFSGSGSGTD YTLTISSLQ EDFATYYCQQ YSELPWTFGQ GTKVEIK |
| 175 | anti-Ly6E antibody hu9B12 v12 heavy chain variable region | EVQLVESGPA LVKPTQTLTL TCTVSGFSLT GYSVNWIRQP PGKALEWLGM IWGDGSTDYN SALKSRLTIS KDTSKNQVVL TMTNMDPVDT ATYYCARDYY FNYASWFAYW GQGTLVTVSS |
| 176 | anti-Ly6E antibody hu9B12 v12 HVR-L1 | SASQGISNYLN |
| 177 | anti-Ly6E antibody hu9B12 v12 HVR-L2 | YTSNLHS |
| 178 | anti-Ly6E antibody hu9B12 v12 HVR-L3 | QQYSELPWT |
| 179 | anti-Ly6E antibody hu9B12 v12 HVR-H1 | GFSLTGYSVN |
| 180 | anti-Ly6E antibody hu9B12 v12 HVR-H2 | MIWGDGSTDY NSALKS |
| 181 | anti-Ly6E antibody hu9B12 v12 HVR-H3 | DYYVNYASWFAY |

| SEQ ID NO: | Description | Sequence |
|---|---|---|
| 182 | anti-Ly6E antibody hu9B12 v12 K149C kappa light chain | DIQMTQSPSS LSASVGDRVT ITCSASQGIS NYLNWYQQKP GKTVKLLIYY TSNLHSGVPS RFSGSGSGTD YTLTISSLQP EDFATYYCQQ YSELPWTFGQ GTKVEIK RTVAAPSVFIF PPSDEQLKSG TASVVCLLNN FYPREAKVQW CVDNALQSGN SQESVTEQDS KDSTYSLSST LTLSKADYEK HKVYACEVTH QGLSSPVTKS FNRGEC |
| 183 | anti-Ly6E antibody hu9B12 v12 IgG1 heavy chain | EVQLVESGPA LVKPTQTLTL TCTVSGFSLT GYSVNWIRQP PGKALEWLGM IWGDGSTDYN SALKSRLTIS KDTSKNQVVL TMTNMDPVDT ATYYCARDYY FNYASWFAYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |

An example of an anti-CD79b antibody that has been engineered to have a single cysteine mutation (i.e., two cysteines per antibody) include the antibody with the following sequences:

| SEQ ID NO: | Description | Sequence |
|---|---|---|
| 184 | huMA79bv28 heavy chain variable region | EVQLVESGGG LVQPGGSLRL SCAASGYTFS SYWIEWVRQA PGKGLEWIGE ILPGGGDTNY NEIFKGRATF SADTSKNTAY LQMNSLRAED TAVYYCTRRV PIRLDYWGQG TLVTVSS |
| 185 | huMA79bv28 light chain variable region | DIQLTQSPSS LSASVGDRVT ITCKASQSVD YEGDSFLNWY QQKPGKAPKL LIYAASNLES GVPSRFSGSG SGTDFTLTIS SLQPEDFATY YCQQSNEDPL TFGQGTKVEI KR |
| 186 | huMA79bv28 HVR H1 | GYTFSSYWIE |
| 187 | huMA79bv28 HVR H2 | GEILPGGGDTNYNEIFKG |
| 188 | huMA79bv28 HVR H3 | TRRVPIRLDY |
| 189 | huMA79bv28 HVR L1 | KASQSVDYEGDSFLN |
| 190 | huMA79bv28 HVR L2 | AASNLES |
| 191 | huMA79bv28 HVR L3 | QQSNEDPLT |

An example of an anti-CD22 antibody that has been engineered to have a single cysteine mutation (i.e., two cysteines per antibody) include the antibody with the following sequences:

| SEQ ID NO: | Description | Sequence |
|---|---|---|
| 192 | Anti-CD22 HVR-H1 | GYEFSRSWMN |
| 193 | Anti-CD22 HVR-H2 | GRIYPGDGDTNYSGKFKG |
| 194 | Anti-CD22 HVR-H3 | DGSSWDWYFDV |
| 195 | Anti-CD22 HVR-L1 | RSSQSIVHSVGNTFLE |
| 196 | Anti-CD22 HVR-L2 | KVSNRFS |
| 197 | Anti-CD22 HVR-L3 | GYEFSRSWMN |

Experiments were performed on the anti-Ly6E, antibody described above that were engineered to have the LC-K149C mutation. Experiments were performed on the anti-NaPi2b, antibody described above that were engineered to have the LC-K149C mutation. Similarly, experiments were performed on the anti-CD22 antibody described above that was engineered to have the LC-K149C mutation.

Furthermore, the anti-CD22 antibody described herein was also engineered to have the HC-L174C mutation according to EU numbering.

Experiments were performed on the anti-CD22, antibody described above that were engineered to have the HC-A140C mutation (according to EU numbering). Experiments were performed on the anti-CD22, antibody described above that were engineered to have the HC-L174C mutation (according to EU numbering).

Certain anti-CLL1 antibodies have been cysteine engineered to include one of the preferred sites in Tables 1 or 2 and can be engineered with one of the stable sites disclosed in Tables 3 and 4. Specifically, anti-CLL1 antibodies were cysteine engineered to include the LC-K149C cysteine mutation.

Certain anti-B7H4 antibodies can be cysteine engineered to include one of the preferred sites in Tables 1 or 2 and can be engineered with one of the stable sites disclosed in Tables 3 and 4.

In addition to the experiments described herein, any of the antibodies described herein can be engineered to have any of the preferred engineered cysteine sites described in Tables 1 or 2 to be made into a cysteine engineered antibody (i.e., a THIOMAB™ antibody). Furthermore, any of the antibodies described herein can be engineered to have any of the stable engineered cysteine sites described in Tables 3 or 4 to be made into a cysteine engineered antibody (i.e., a THIOMAB™ antibody). Specifically, any of the antibodies described herein can be engineered to have the LC-K149C, HC-A140C (according to EU numbering), or HC-L174C (according to EU numbering) and can be conjugated to one of the drugs described herein with a PDS or –vc linker.

Example 16—Exemplary ADCs

Any of the antibodies described herein can be conjugated to any of the classes of drugs described herein using a linker that attaches the drug to the engineered cysteine residue. Examples of such ADCs may be prepared by coupling a drug moiety with a linker reagent, and according to the procedures of WO 2013/055987; WO 2015/023355; WO 2010/009124; WO 2015/095227, and conjugated with any of the cysteine engineered antibodies, described herein.

The following terms and abbreviations are used in the tables below: DAR=drug/antibody ratio average, A118C (heavy chain, EU numbering) (alternatively referred to as A121C according to GNE's sequential numbering (see FIG. 1*b*) and alternatively referred to as A114C according to Kabat numbering), K149C (light chain, Kabat numbering), A140C (EU numbering) of heavy chainWild-type ("WY"), cysteine engineered mutant antibody ("thio"), light chain ("LC"), heavy chain ("HC"), 6-maleimidocaproyl ("MC"), maleimidopropanoyl ("MP"), valine-citrulline ("val-cit" or "vc"), alanine-phenylalanine ("ala-phe"), p-aminobenzyl ("PAB"), p-aminobenzyloxycarbonyl ("PABC"), 1-(chloromethyl)-2,3-dihydro-1H-benzo[e]indole ("CBI"), pyrrolobenzodiazepine ("PBD"), and monomethylauristatin ("MMAE").

Examples of such additional ADCs include, but are not limited to those provided in Table 17 below.

TABLE 17
Structures of exemplary antibody drug conjugates #s 51-69
| ADC No. | Structure |
|---|---|
| 51 | 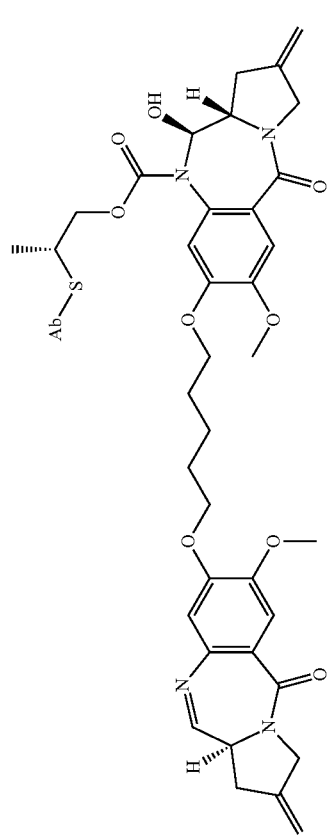 |
| 52 | 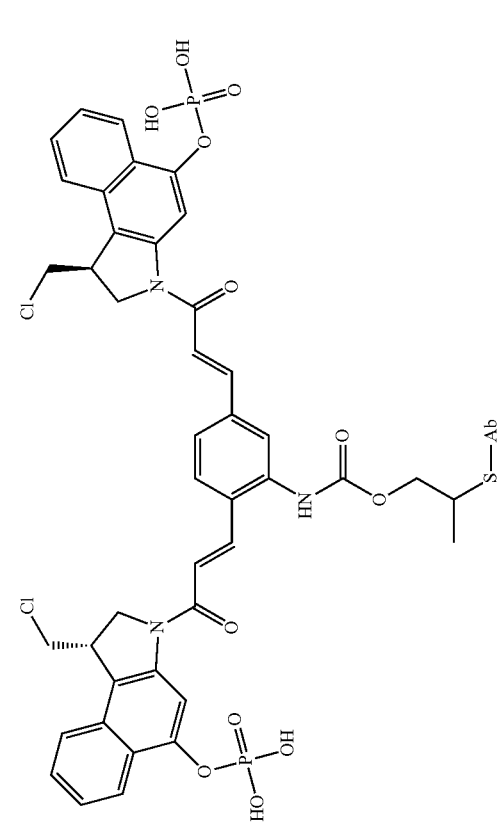 |

TABLE 17-continued
Structures of exemplary antibody drug conjuages #s 51-69
| ADC No. | Structure |
|---|---|
| 53 | 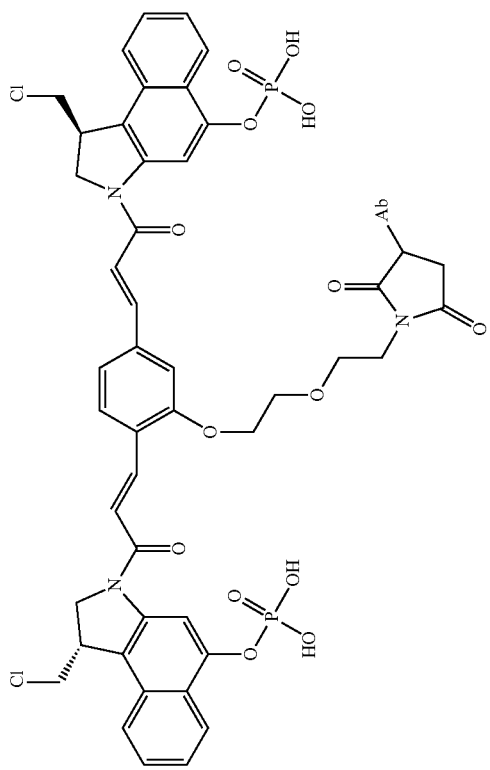 |
| 54 | 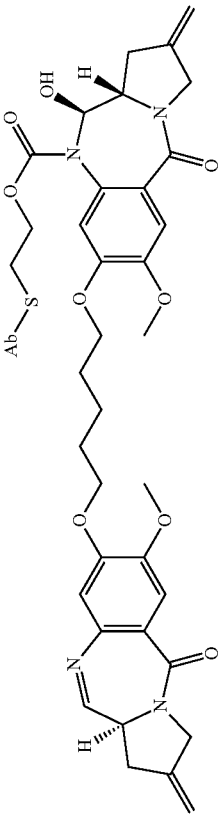 |

TABLE 17-continued
Structures of exemplary antibody drug conjuages #s 51-69
| ADC No. | Structure |
|---|---|
| 55 | 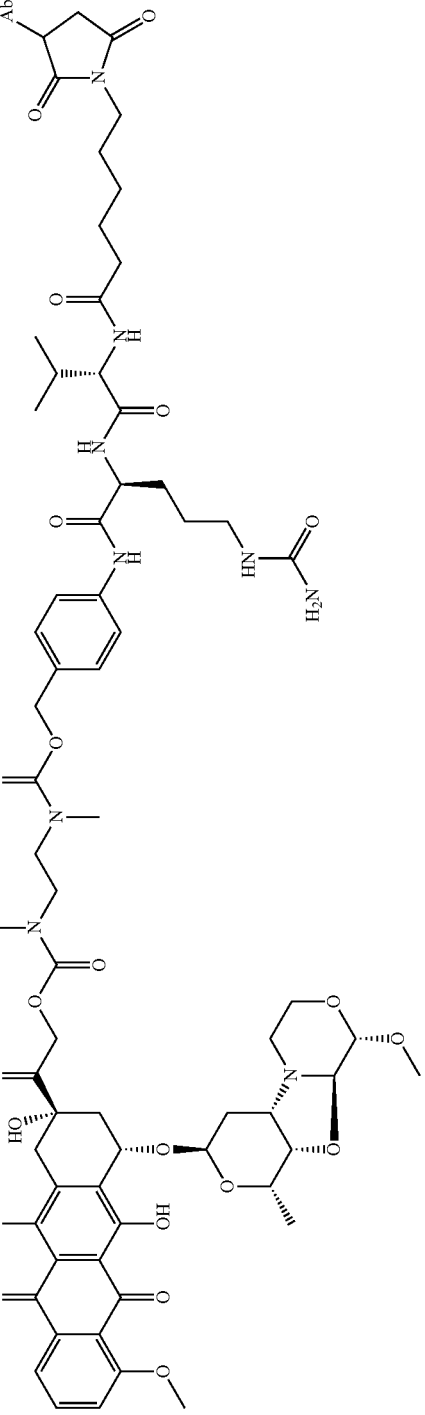 |
| 56 | 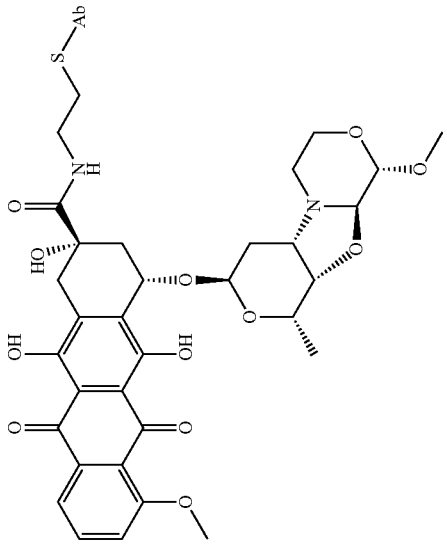 |

TABLE 17-continued

Structures of exemplary antibody drug conjuages #s 51-69

| ADC No. | Structure |
|---|---|
| 57 | 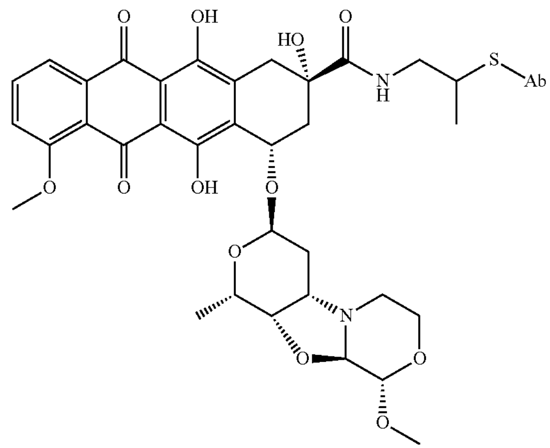 |
| 58 | 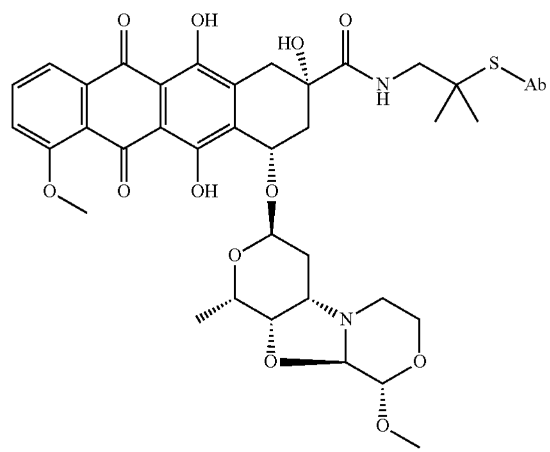 |

TABLE 17-continued
Structures of exemplary antibody drug conjuages #s 51-69
| ADC No. | Structure |
|---|---|
| 59 | 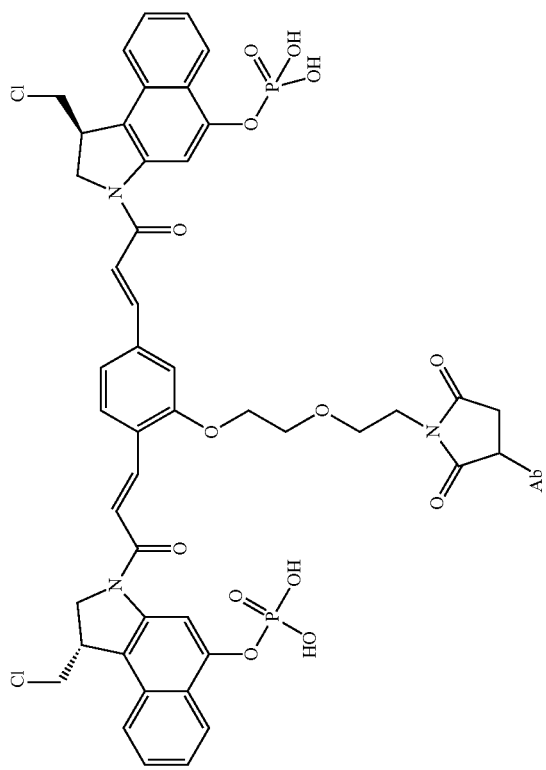 |
| 60 | 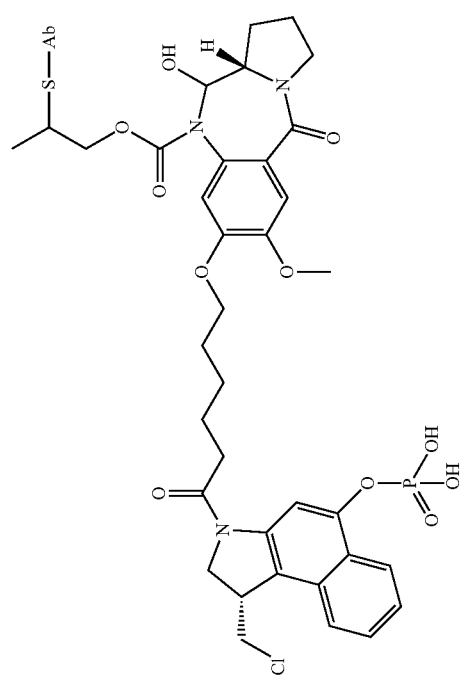 |

TABLE 17-continued
Structures of exemplary antibody drug conjuages #s 51-69
| ADC No. | Structure |
|---|---|
| 61 | 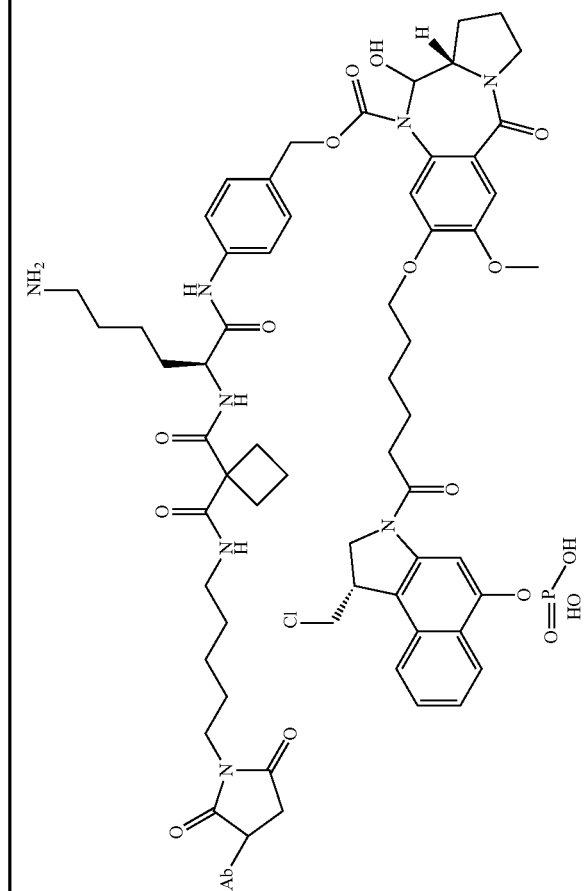 |

TABLE 17-continued
Structures of exemplary antibody drug conjuages #s 51-69
| ADC No. | Structure |
|---|---|
| 62 | 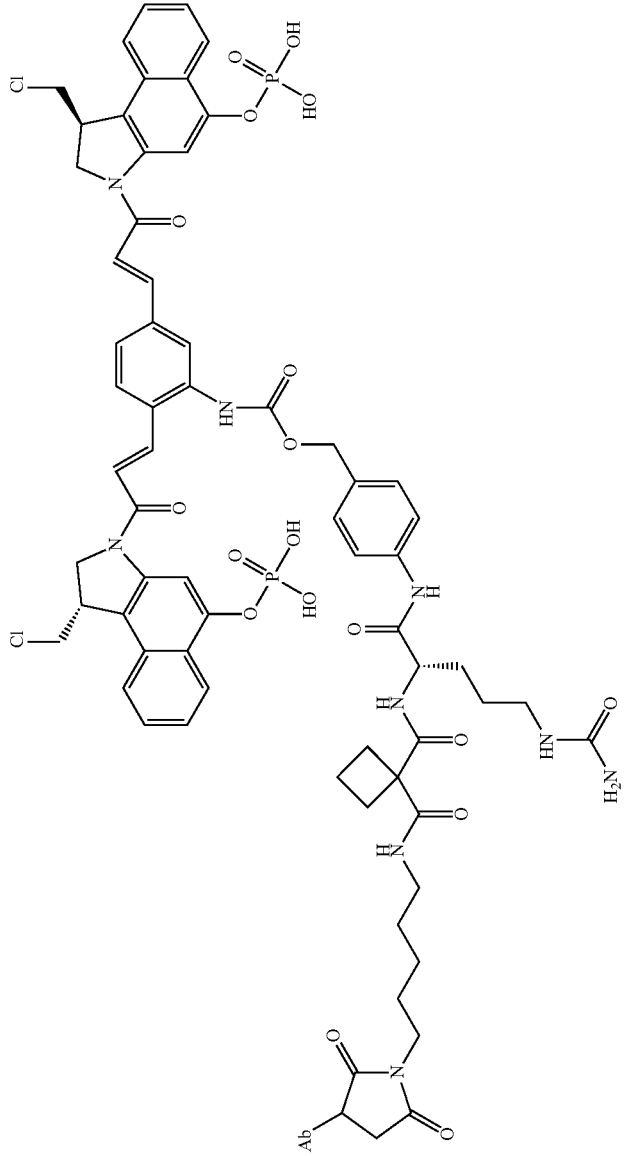 |

TABLE 17-continued
Structures of exemplary antibody drug conjuages #s 51-69
| ADC No. | Structure |
|---|---|
| 63 | 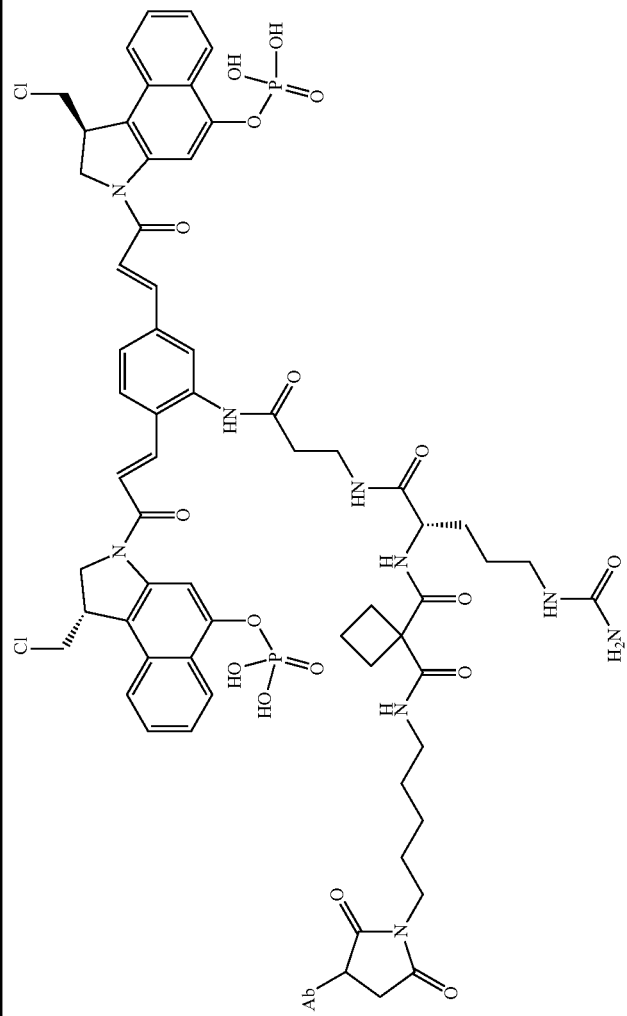 |

TABLE 17-continued
Structures of exemplary antibody drug conjugates #s 51-69
| ADC No. | Structure |
|---|---|
| 64 | 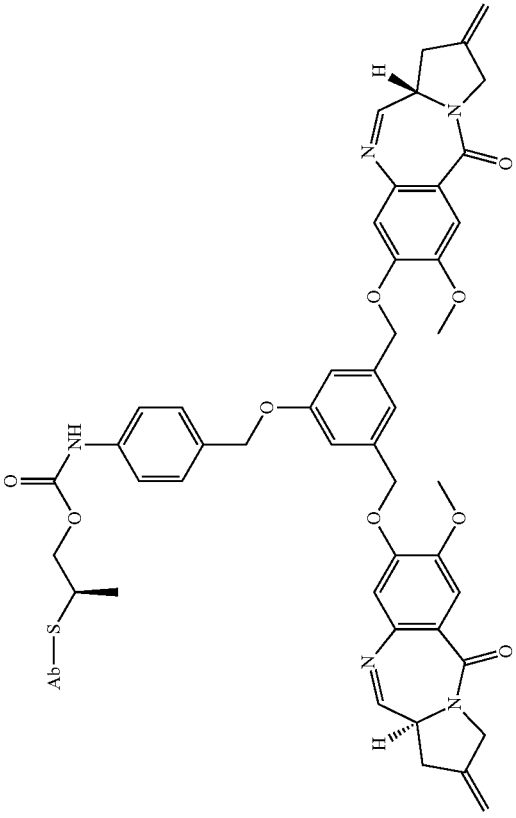 |
| 65 | 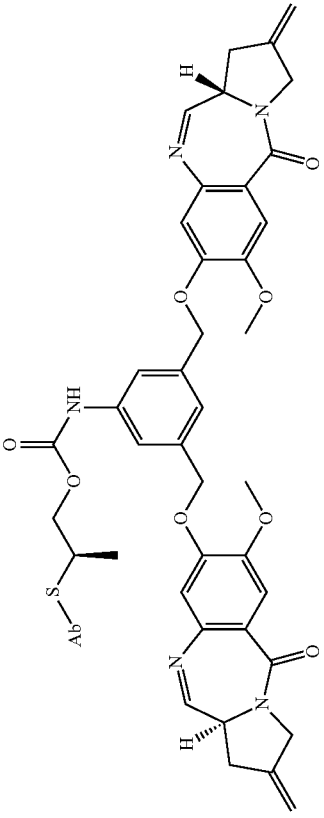 |

TABLE 17-continued

Structures of exemplary antibody drug conjugates #s 51-69

| ADC No. | Structure |
|---|---|
| 66 | 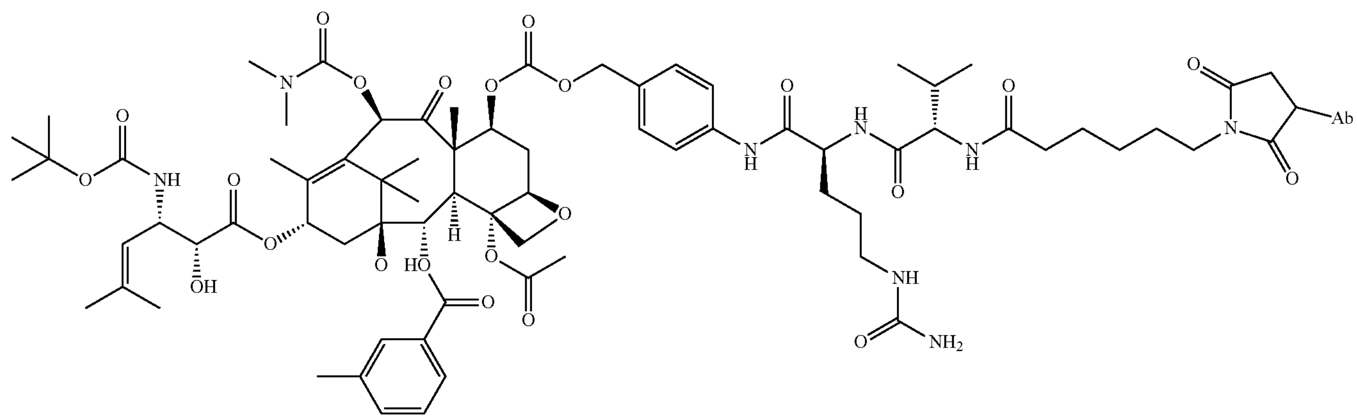 |
| 67 | 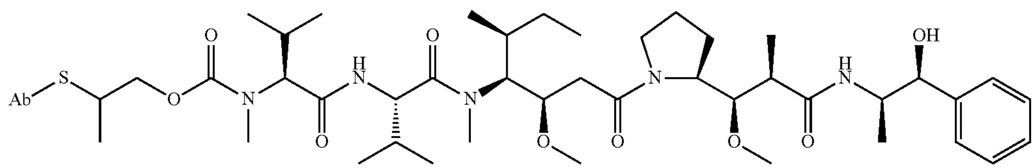 |

TABLE 17-continued
Structures of exemplary antibody drug conjuages #s 51-69
| ADC No. | Structure |
|---|---|
| 68 | 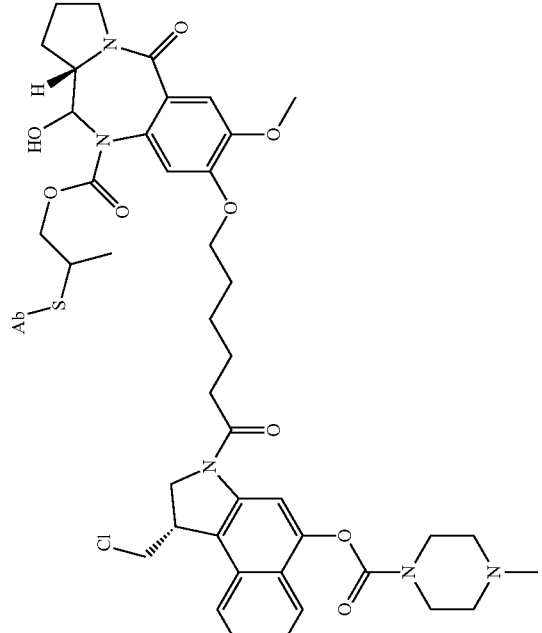 |
| 69 | 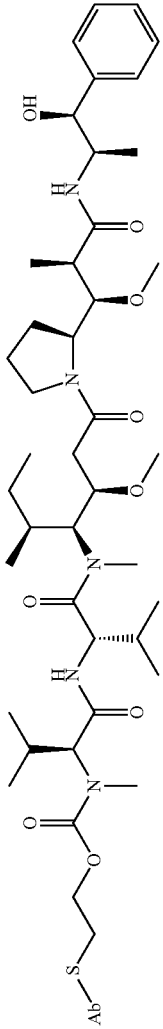 |

It is noted that for simplicity the structures above and those of ADCs 51 to 63 only show one linker-drug group attached to an antibody. As mentioned above, more than one linker-drug group can be attached to an antibody.
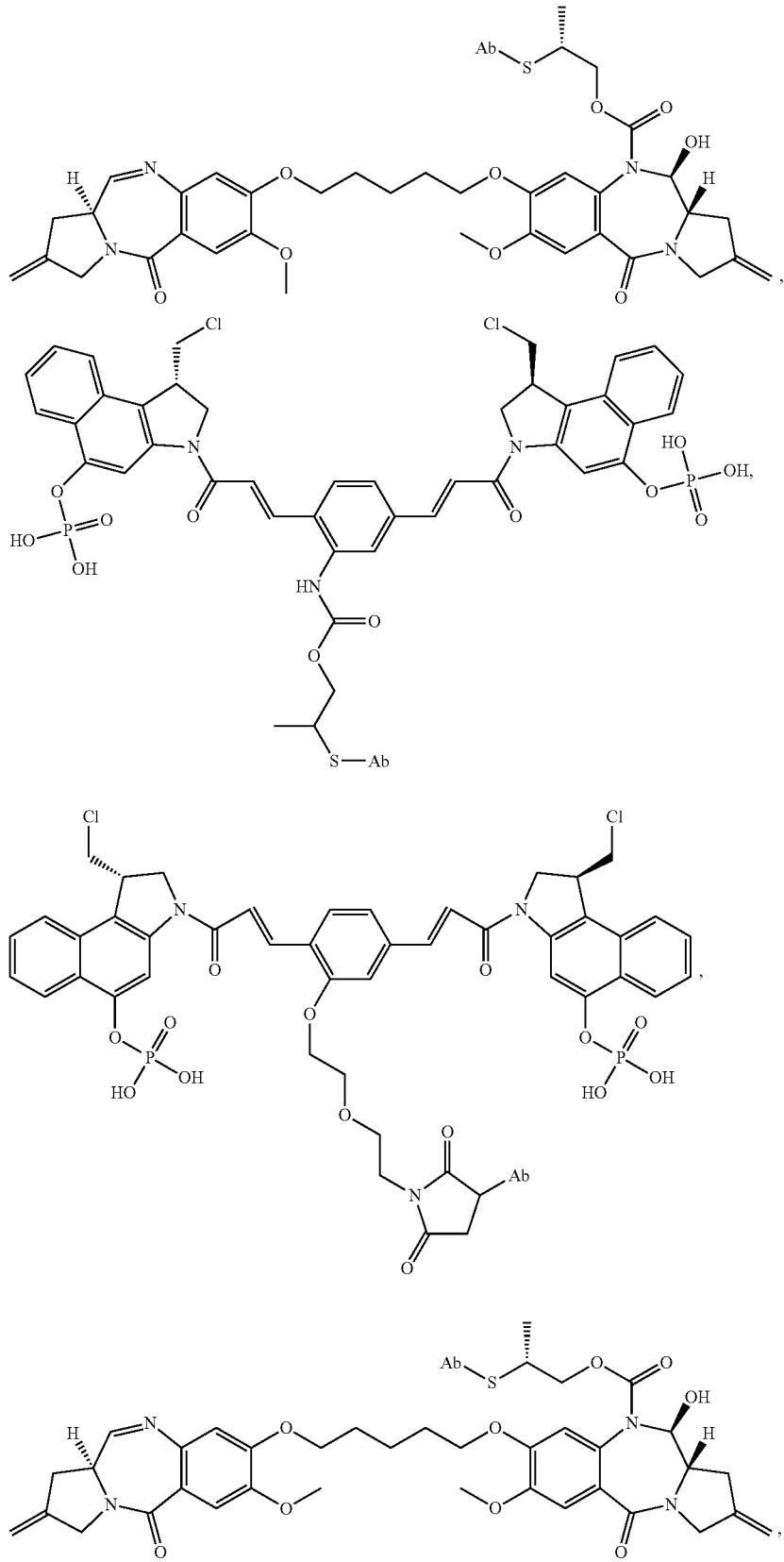

191
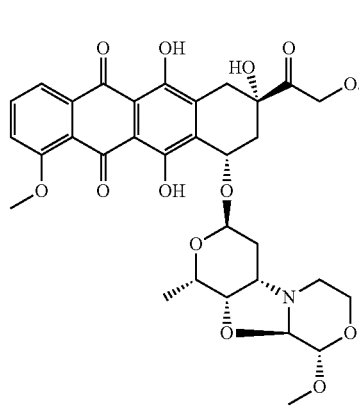
192 -continued
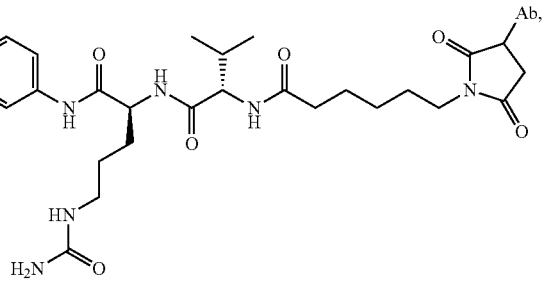
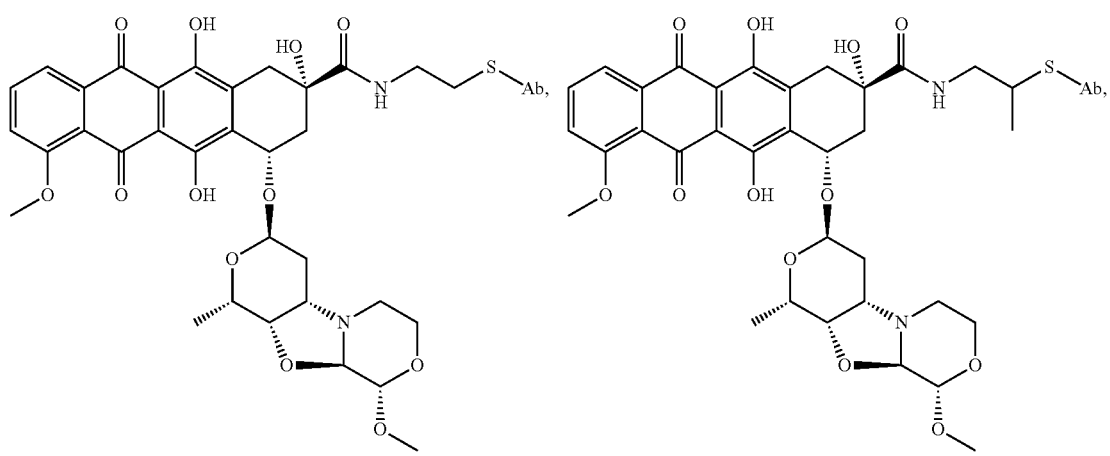
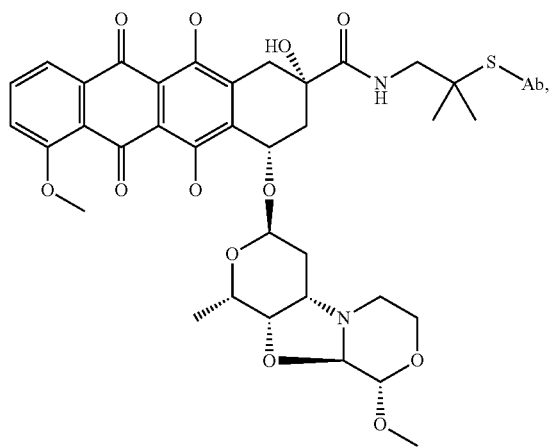

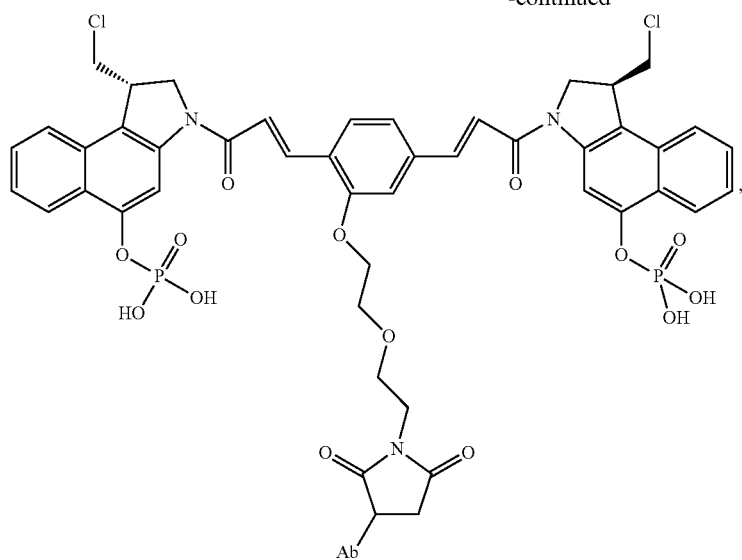
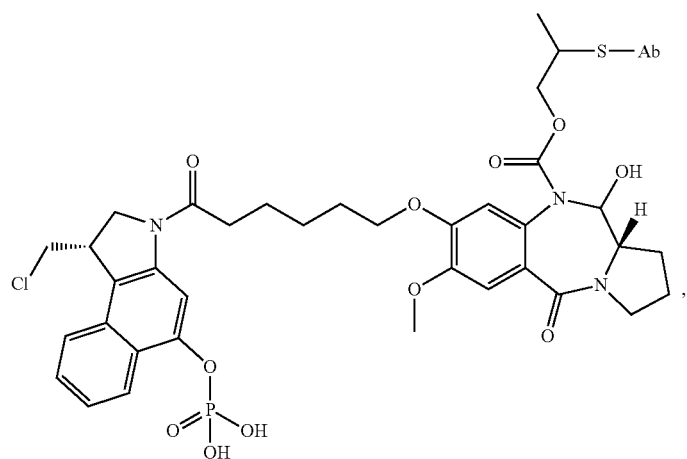
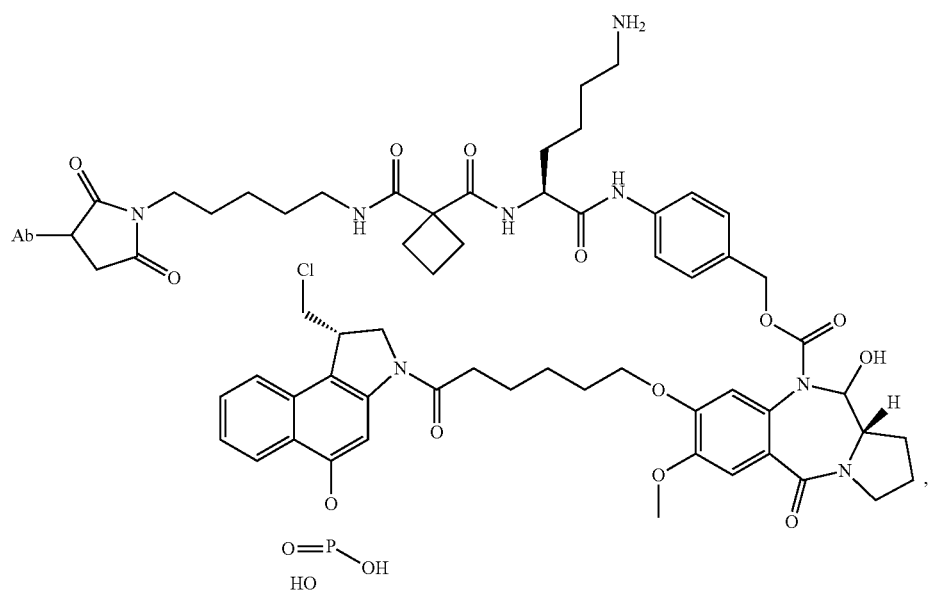

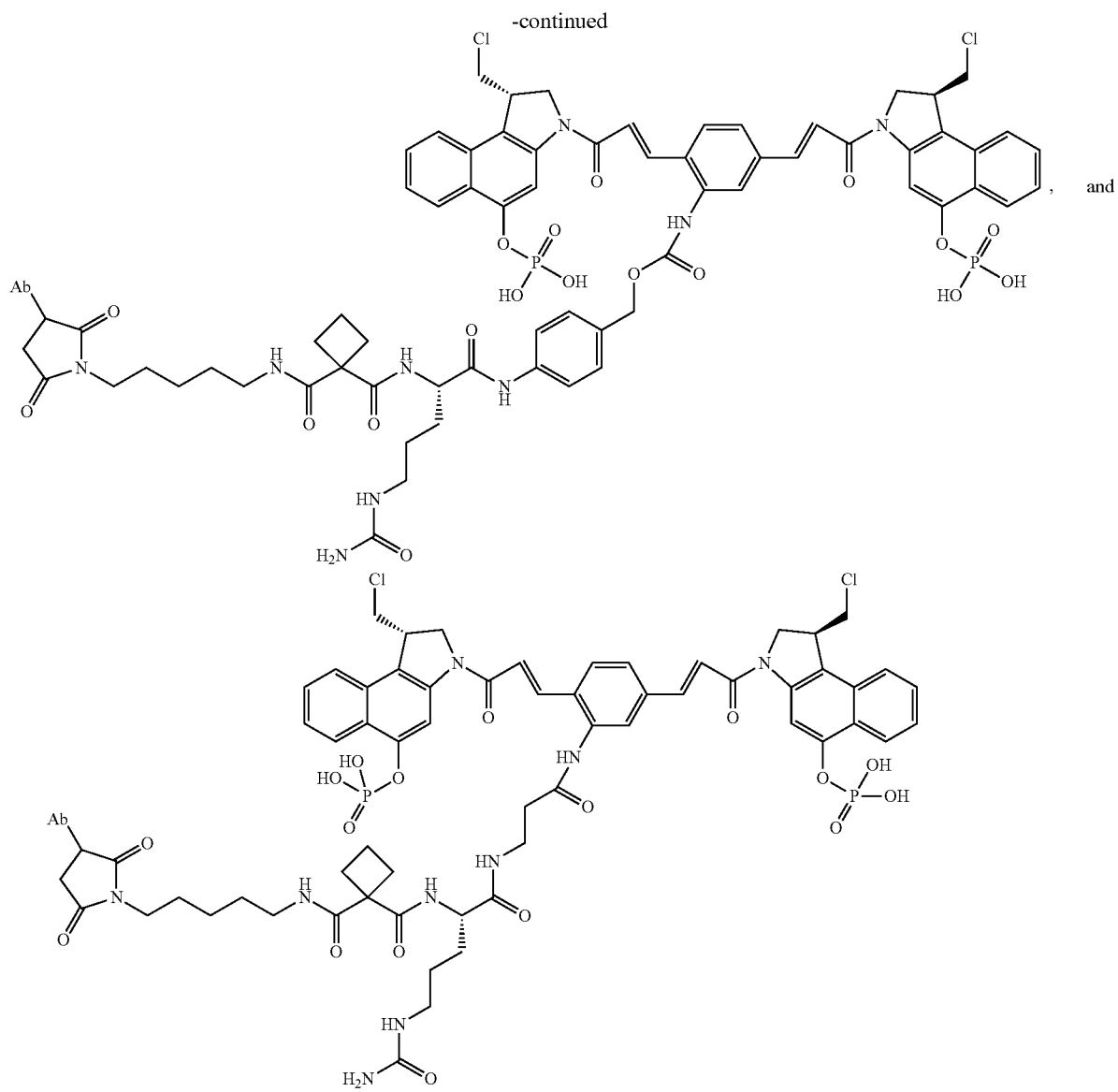

Specific examples of ADCs that have been made are provided in Tables 18 and 19. Table 18 provides examples of ADCs that have been made wherein the L-D is attached to the antibody at cysteine engineered site LC-K149C. Table 19 provides examples of ADCs that have been made wherein the L-D is attached to the antibody at cysteine engineered site HC-A140C.

TABLE 18

Examples of ADCs that have been made wherein the L-D is attached to the antibody at cysteine engineered site LC-K149C

| ADC name | linker-drug group from ADC No. (Table 17) | DAR |
|---|---|---|
| Thio anti-CD22 10F4v3 K149C maleimide CBI dimer | 59 | 2.0 |
| Thio Hu Anti-Ly6E 9B12.v12 LC K149C disulfide CBI-PBD heterodimer | 60 | 2.0 |
| Thio Hu Anti-NaPi2b 10H1.11.4B LC K149C disulfide PBD dimer | 54 | 2.0 |

TABLE 18-continued

Examples of ADCs that have been made wherein the L-D is attached to the antibody at cysteine engineered site LC-K149C

| ADC name | linker-drug group from ADC No. (Table 17) | DAR |
|---|---|---|
| Thio Hu Anti-CD22 10F4v3 LC K149C disulfide PBD dimer | 54 | 2.0 |
| Thio Hu Anti-Napi2b 10H1.11.4B LC K149C YTE methyl disulfide PBD dimer | 51 | 1.8 |
| Thio Hu anti-Her2 7C2 LC K149C disulfide CBI-PBD heterodimer | 60 | 2.0 |
| Thio anti-CD22 10F4v3 K149C cyclobutyl PAB CBI dimer | 62 | 2.1 |
| Thio anti-CD22 10F4v3 K149C cyclobutyl EDA CBI dimer | 63 | 2.0 |
| Thio Hu Anti-CD22 10F4v3 LC K149C disulfide PAB tether PBD dimer | 64 | 1.9 |
| Thio Hu Anti-Ly6E 9B12.v12 LC K149C disulfide PAB tether PBD dimer | 64 | 1.6 |

TABLE 18-continued

Examples of ADCs that have been made wherein the L-D is attached to the antibody at cysteine engineered site LC-K149C

| ADC name | linker-drug group from ADC No. (Table 17) | DAR |
|---|---|---|
| Thio Hu Anti-CD22 10F4v3 LC K149C disulfide bz tether PBD dimer | 65 | 1.9 |
| Thio Hu Anti-Ly6E 9B12.v12 LC K149C disulfide bz tether PBD dimer | 65 | 1.9 |
| Thio Hu-Anti Ly6E 9B12 LC K149C maleimide cyclobutyl PAB CBI-PBD heterodimer | 61 | 2.0 |
| Thio Hu anti-CD22 10F4v3 LC K149C disulfide CBI-PBD heterodimer | 60 | 2.0 |
| Thio Hu Anti-Ly6E 9B12.v12 LC K149C methyl disulfide PBD dimer | 51 | 1.9 |
| Thio Hu anti-Her2 7C2 LC K149C methyl disulfide PBD dimer | 51 | 1.8 |
| Thio Hu anti-CD22 10F4v3 LC K149C methyl disulfide PBD dimer | 51 | 1.8 |
| Thio Hu anti-Her2 7C2 LC K149C maleimide CBI dimer | 59 | 1.9 |
| Thio Hu Anti-Ly6E 9B12.v12 LC K149C maleimide CBI dimer | 59 | 2.0 |
| Thio Hu Anti-Ly6E 9B12.v12 LC K149C cyclobutyl PAB CBI dimer | 62 | 2.0 |
| Thio Hu Anti-Ly6E 9B12.v12 LC K149C cyclobutyl EDA CBI dimer | 63 | 2.0 |
| Thio Hu Anti-Ly6E 9B12.v12 LC K149C disulfide CBI-PBD heterodimer | 60 | 2.0 |
| Thio Hu anti-Her2 7C2 LC K149C disulfide CBI-PBD heterodimer | 60 | 2.0 |
| Thio Hu Anti-NaPi2b 10H1.11.4B LC K149C disulfide CBI-PBD heterodimer | 60 | 2.0 |
| Thio Hu anti-CD22 10F4v3 LC K149C disulfide CBI-PBD heterodimer | 60 | 2.0 |
| Thio Hu anti-Her2 7C2 LC K149C disulfide CBI-PBD heterodimer | 60 | 1.9 |
| Thio Hu anti-CLL-1 6E7.H1eL4.N54A LC K149C maleimide CBI dimer | 59 | 2.0 |
| Thio Hu Anti-Napi2b 10H1.11.4B LC K149C maleimide CBI dimer | 59 | 1.8 |
| Thio Hu anti-CD22 10F4v3 LC K149C disulfide CBI-PBD heterodimer | 60 | 2.0 |

TABLE 19

Examples of ADCs that have been made wherein the L-D is attached to the antibody at cysteine engineered site HC-A140C

| ADC name | linker-drug group from ADC No. (Table 17) | DAR |
|---|---|---|
| Thio Hu Anti-CD22 10F4v3 HC A140C MC vc PAB taxoid | 66 | 1.9 |
| Thio Hu Anti-CD33 15G15.3 HC A140C disulfide PBD dimer | 54 | 1.9 |
| Thio Hu-Anti-Her2 4D5 HC A140C disulfide PBD dimer | 54 | 1.8 |
| Thio Hu-Anti 4D5 HC A140C disulfide PNU | 57 | 1.2 |
| Thio Hu-Anti 4D5 HC A140C mono-methyl MMAE | 67 | 1.9 |
| Thio Hu-Anti 4D5 HC A140C disulfide CBI-PBD dimer | 68 | 1.7 |
| Thio Hu Anti-CD33 15G15.3 HC A140C methyl disulfide PBD dimer | 51 | 1.9 |
| Thio Hu anti-Her2 4D5 HC A140C methyl disulfide PBD dimer | 51 | 1.7 |
| Thio Hu Anti-CD33 GM15.33 HC A140C disulfide PBD dimer | 54 | 1.2 |
| Thio Hu Anti-CD33 GM15.33 HC A140C methyl disulfide PBD dimer | 51 | 1.5 |
| Thio Hu Anti-Her2 4D5 HC A140C disulfide MMAE | 69 | 1.8 |
| Thio Hu Anti-Her2 4D5 HC A140C disulfide PBD dimer | 54 | 1.2 |

In both Tables 18 and 19, the DAR is calculated in a buffered saline.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All patents, patent applications, and references cited throughout the specification are expressly incorporated by reference in their entirety and for all purposes.

What is claimed is:

1. A cysteine engineered antibody comprising an A140C engineered cysteine amino acid in the heavy chain according to EU numbering, and a K149C engineered cysteine amino acid in the light chain according to Kabat numbering.

2. The cysteine engineered antibody of claim 1, wherein the cysteine engineered antibody comprises the sequences:
   HC-A140C TSGGTCALGCL SEQ ID NO.:6 in the heavy chain,
   and
   LC-K149C AKVQWCVDNAL SEQ ID NO.:4 in the light chain.

3. The cysteine engineered antibody of claim 1 prepared by a process comprising:
   (i) mutagenizing a nucleic acid sequence of a parent antibody by replacing one or more amino acid residues by cysteine to encode the cysteine engineered antibody;
   (ii) expressing the cysteine engineered antibody; and
   (iii) isolating the cysteine engineered antibody.

4. The cysteine engineered antibody of claim 1 wherein the cysteine engineered antibody is selected from a monoclonal antibody, an antibody fragment, a bispecific antibody, a chimeric antibody, a human antibody, and a humanized antibody.

5. The cysteine engineered antibody of claim 4, wherein the antibody fragment is a Fab fragment.

6. The cysteine engineered antibody of claim 1, wherein the cysteine engineered antibody is selected from an anti-HER2 antibody, an anti-Ly6E antibody, an anti-CD79b antibody, an anti-MUC16 antibody, an anti-STEAP1 antibody, an anti-NaPi2b antibody, an anti-CD22 antibody.

7. The cysteine engineered antibody of claim 6, wherein the cysteine engineered antibody is an anti-HER2 antibody, and wherein the anti-HER2 antibody is trastuzumab.

8. The cysteine engineered antibody of claim 6, wherein the cysteine engineered antibody is an anti-Ly6E antibody, and wherein the anti-Ly6E antibody comprises
   (i) an HVR-H1 comprising the amino acid sequence of SEQ ID NO: 179, and an HVR-H2 comprising the amino acid sequence of SEQ ID NO: 180; an HVR-H3 comprising the amino acid sequence of SEQ ID NO: 181; an HVR-L1 comprising the amino acid sequence of SEQ ID NO: 176; an HVR-L2 comprising the amino acid sequence of SEQ ID NO: 177; and an HVR-L3 comprising the amino acid sequence of SEQ ID NO: 178; or
   (ii) a heavy chain variable region comprising the amino acid sequence of SEQ ID NO: 175 and a light chain variable region comprising the amino acid sequence of SEQ ID NO: 174.

9. The cysteine engineered antibody of claim 6, wherein the cysteine engineered antibody is an anti-CD79b antibody, and wherein the anti-CD79b antibody comprises
   (i) an HVR-H1 comprising the amino acid sequence of SEQ ID NO: 186, and an HVR-H2 comprising the amino acid sequence of SEQ ID NO: 187; an HVR-H3 comprising the amino acid sequence of SEQ ID NO: 188; an HVR-L1 comprising the amino acid sequence of SEQ ID NO: 189; an HVR-L2 comprising the amino acid sequence of SEQ ID NO: 190; and an HVR-L3 comprising the amino acid sequence of SEQ ID NO: 191; or
   (ii) a heavy chain variable region comprising the amino acid sequence of SEQ ID NO: 184 and a light chain variable region comprising the amino acid sequence of SEQ ID NO: 185.

10. The cysteine engineered antibody of claim 6, wherein the cysteine engineered antibody is an anti-MUC16 antibody, and wherein the anti-MUC16 antibody comprises
    (i) an HVR-H1 comprising the amino acid sequence of SEQ ID NO: 152, and an HVR-H2 comprising the amino acid sequence of SEQ ID NO: 153; an HVR-H3 comprising the amino acid sequence of SEQ ID NO: 154; an HVR-L1 comprising the amino acid sequence of SEQ ID NO: 149; an HVR-L2 comprising the amino acid sequence of SEQ ID NO: 150; and an HVR-L3 comprising the amino acid sequence of SEQ ID NO: 151; or
    (ii) a heavy chain variable region comprising the amino acid sequence of SEQ ID NO: 156 and a light chain variable region comprising the amino acid sequence of SEQ ID NO: 157.

11. The cysteine engineered antibody of claim 6, wherein the cysteine engineered antibody is an anti-STEAP1 antibody, and wherein the anti-STEAP1 antibody comprises
    (i) an HVR-H1 comprising the amino acid sequence of SEQ ID NO: 157, and an HVR-H2 comprising the amino acid sequence of SEQ ID NO: 158; an HVR-H3 comprising the amino acid sequence of SEQ ID NO: 159; an HVR-L1 comprising the amino acid sequence of SEQ ID NO: 160; an HVR-L2 comprising the amino acid sequence of SEQ ID NO: 161; and an HVR-L3 comprising the amino acid sequence of SEQ ID NO: 162; or
    (ii) a heavy chain variable region comprising the amino acid sequence of SEQ ID NO: 163 and a light chain variable region comprising the amino acid sequence of SEQ ID NO: 164.

12. The cysteine engineered antibody of claim 6, wherein the cysteine engineered antibody is an anti-NaPi2b antibody, and wherein the anti-NaPi2b antibody comprises
    (i) an HVR-H1 comprising the amino acid sequence of SEQ ID NO: 165, and an HVR-H2 comprising the amino acid sequence of SEQ ID NO: 167; an HVR-H3 comprising the amino acid sequence of SEQ ID NO: 168; an HVR-L1 comprising the amino acid sequence of SEQ ID NO: 169; an HVR-L2 comprising the amino acid sequence of SEQ ID NO: 170; and an HVR-L3 comprising the amino acid sequence of SEQ ID NO: 171; or
    (ii) a heavy chain variable region comprising the amino acid sequence of SEQ ID NO: 172 and a light chain variable region comprising the amino acid sequence of SEQ ID NO: 173.

13. The cysteine engineered antibody of claim 6, wherein the cysteine engineered antibody is an anti-CD22 antibody, and wherein the anti-CD22 antibody comprises
an HVR-H1 comprising the amino acid sequence of SEQ ID NO: 192, and an HVR-H2 comprising the amino acid sequence of SEQ ID NO: 193; an HVR-H3 comprising the amino acid sequence of SEQ ID NO: 194; an HVR-L1 comprising the amino acid sequence of SEQ ID NO: 195; an HVR-L2 comprising the amino acid sequence of SEQ ID NO: 196; and an HVR-L3 comprising the amino acid sequence of SEQ ID NO: 197.

14. The cysteine engineered antibody of claim 1, wherein the cysteine engineered antibody binds to one or more of receptors (1)-(53):
(1) BMPR1B (bone morphogenetic protein receptor-type IB);
(2) E16 (LAT1, SLC7A5);
(3) STEAP1 (six transmembrane epithelial antigen of prostate);
(4) 0772P (CA125, MUC16);
(5) MPF (MPF, MSLN, SMR, megakaryocyte potentiating factor, mesothelin);
(6) Napi3b (NaPi2b, NAPI-3B, NPTIIb, SLC34A2, solute carrier family 34 (sodium phosphate), member 2, type II sodium-dependent phosphate transporter 3b);
(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);
(8) PSCA h1g (2700050C12Rik, C530008O16Rik, RIKEN cDNA 2700050C12, RIKEN cDNA 2700050C12 gene);
(9) ETBR (Endothelin type B receptor);
(10) MSG783 (RNF124, hypothetical protein FLJ20315);
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);
(12) TrpM4 (BR22450, FLJ20041, TRPM4, TRPM4B, transient receptor potential cation channel, subfamily M, member 4);
(13) CRIPTO (CR, CR1, CRGF, CRIPTO, TDGF1, teratocarcinoma-derived growth factor);
(14) CD21 (CR2 (Complement receptor 2) or C3DR (C3d/Epstein Barr virus receptor) or Hs.73792);
(15) CD79b (CD79B, CD79β, IGb (immunoglobulin-associated beta), B29);
(16) FcRH2 (IFGP4, IRTA4, SPAP1A (SH2 domain containing phosphatase anchor protein 1a), SPAP1B, SPAP1C);
(17) HER2;
(18) NCA;
(19) MDP;
(20) IL20Rα;
(21) Brevican;
(22) EphB2R;
(23) ASLG659;
(24) PSCA;
(25) GEDA;
(26) BAFF-R (B cell-activating factor receptor, BLyS receptor 3, BR3;
(27) CD22 (B-cell receptor CD22-B isoform);
(28) CD79a (CD79A, CD79α, immunoglobulin-associated alpha, a B cell-specific protein);
(29) CXCR5 (Burkitt's lymphoma receptor 1, a G protein-coupled receptor);
(30) HLA-DOB (Beta subunit of MHC class II molecule (Ia antigen);
(31) P2X5 (Purinergic receptor P2X ligand-gated ion channel 5);
(32) CD72 (B-cell differentiation antigen CD72, Lyb-2);
(33) LY64 (Lymphocyte antigen 64 (RP105), type I membrane protein of the leucine rich repeat (LRR) family);
(34) FcRH1 (Fc receptor-like protein 1);
(35) IRTA2 (Immunoglobulin superfamily receptor translocation associated 2);
(36) TENB2 (putative transmembrane proteoglycan);
(37) PMEL17 (silver homolog; SILV; D12S53E; PMEL17; SI; SIL);
(38) TMEFF1 (transmembrane protein with EGF-like and two follistatin-like domains 1; Tomoregulin-1);
(39) GDNF-Ra1 (GDNF family receptor alpha 1; GFRA1; GDNFR; GDNFRA; RETL1; TRNR1; RET1L; GDNFR-alpha1; GFR-ALPHA-1);
(40) Ly6E (lymphocyte antigen 6 complex, locus E; Ly67, RIG-E, SCA-2, TSA-1)
(41) TMEM46 (shisa homolog 2);
(42) Ly6G6D (lymphocyte antigen 6 complex, locus G6D; Ly6-D, MEGT1);
(43) LGR5 (leucine-rich repeat-containing G protein-coupled receptor 5; GPR49, GPR67);
(44) RET (ret proto-oncogene; MEN2A; HSCR1; MEN2B; MTC1; PTC; CDHF12; Hs.168114; RET51; RET-ELE1);
(45) LY6K (lymphocyte antigen 6 complex, locus K; LY6K; HSJ001348; FLJ35226);
(46) GPR19 (G protein-coupled receptor 19; Mm.4787);
(47) GPR54 (KISS1 receptor; KISS1R; GPR54; HOT7T175; AXOR12);
(48) ASPHD1 (aspartate beta-hydroxylase domain containing 1; LOC253982);
(49) Tyrosinase (TYR; OCAIA; OCA1A; tyrosinase; SHEP3);
(50) TMEM118 (ring finger protein, transmembrane 2; RNFT2; FLJ14627);
(51) GPR172A (G protein-coupled receptor 172A; GPCR41; FLJ11856; D15Ertd747e);
(52) CD33; and
(53) CLL-1 (CLEC12A, MICL, and DCAL2).

15. The cysteine engineered antibody of claim 1, wherein the antibody is covalently attached to a capture label, a detection label, a drug moiety, or a solid support.

16. The cysteine engineered antibody of claim 15, wherein the antibody is covalently attached to a biotin capture label.

17. The cysteine engineered antibody of claim 15, wherein the antibody is covalently attached to a fluorescent dye detection label.

18. The cysteine engineered antibody of claim 17, wherein the fluorescent dye is selected from a fluorescein type, a rhodamine type, dansyl, lissamine, a cyanine, a phycoerythrin, and an analog thereof.

19. The cysteine engineered antibody of claim 15, wherein the antibody is covalently attached to a radionuclide detection label selected from $^{3}$H, $^{11}$C, $^{14}$C, $^{18}$F, $^{32}$P, $^{35}$S, $^{64}$Cu, $^{68}$Ga, $^{86}$Y, $^{89}$Zr, $^{99}$Tc, $^{111}$In, $^{123}$I, $^{124}$I, $^{125}$I, $^{131}$I, $^{133}$Xe, $^{177}$Lu, $^{211}$At, and $^{213}$Bi.

20. The cysteine engineered antibody of claim 15, wherein the antibody is covalently attached to a detection label by a chelating ligand.

21. The cysteine engineered antibody of claim 20 wherein the chelating ligand is selected from DOTA, DOTP, DOTMA, DTPA and TETA.

22. An antibody-drug conjugate comprising the cysteine engineered antibody of claim 1, wherein the antibody-drug conjugate has Formula I:

Ab-(L-D)$_p$      I where Ab is the cysteine engineered antibody, L is a linker, D is a drug moiety, and p is 1, 2, 3, or 4, and wherein the drug moiety is conjugated to the engineered cysteine amino acid.

23. The antibody drug conjugate of claim 22, wherein L comprises a group selected from 6-maleimidocaproyl (MC), maleimidopropanoyl (MP), valine-citrulline (val-cit (-vc)), alanine-phenylalanine (ala-phe), and p-aminobenzyloxycarbonyl (PAB).

24. The antibody-drug conjugate of claim 22 prepared from a linker reagent selected from N-Succinimidyl 4-(2-pyridylthio) pentanoate (SPP), N-succinimidyl 4-(N-maleimidomethyl) cyclohexane-1 carboxylate (SMCC), 4-(2-Pyridyldithio)butyric acid-N-hydroxysuccinimide ester (SPDB), and N-Succinimidyl (4-iodo-acetyl) aminobenzoate (SIAB).

25. The antibody-drug conjugate of claim 22, prepared from a linker reagent comprising maleimide, iodoacetamide, bromoacetamide or disulfide.

26. The antibody-drug conjugate of claim 22, wherein L forms a disulfide linker.

27. The antibody-drug conjugate of claim 25, wherein the linker reagent comprises a pyridyl disulfide (PDS).

28. The antibody-drug conjugate of claim 22, wherein the drug moiety (D) is a maytansinoid, an auristatin, a dolastatin, a trichothecene, CC1065, a calicheamicin, enediyne antibiotics, a taxane, a pyrrolobenzodiazepine (PBD) dimer, a 1-(Chloromethyl)-2,3-dihydro-1H-benzo[e]indole (CBI) dimer, a CBI-PBD heterodimer, or an anthracycline.

29. The antibody-drug conjugate of claim 28 wherein D is a monomethylauristatin drug moiety MMAE having the structure:

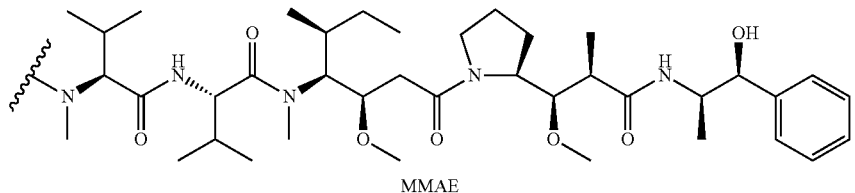 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE wherein the wavy line indicates the covalent attachment site to the linker.

30. The antibody-drug conjugate of claim 28 wherein the antibody-drug conjugate is selected from the structures:

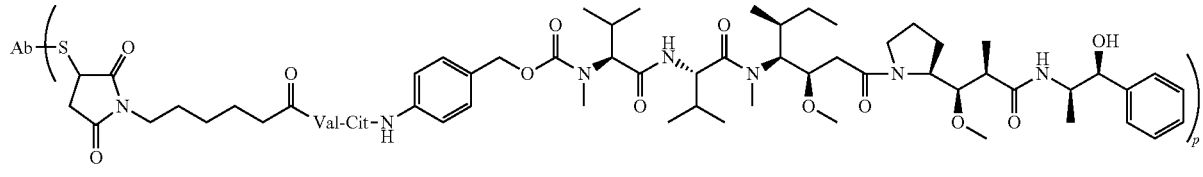

Ab-MC-vc-PAB-MMAE

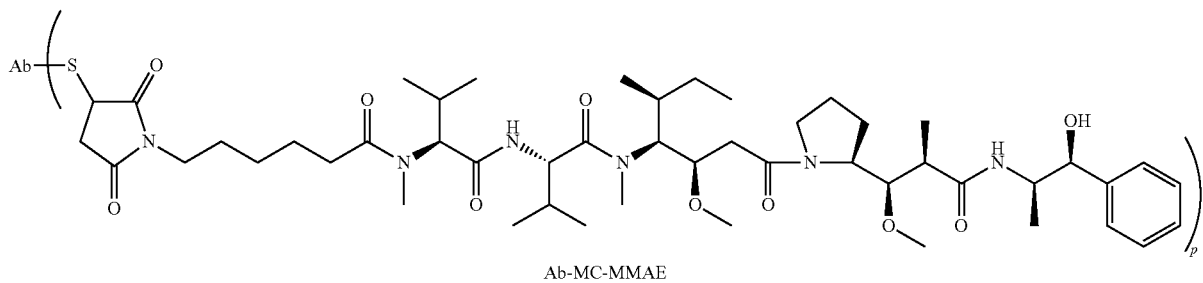

Ab-MC-MMAE where Val is valine; Cit is citrulline; and p is 1, 2, 3, or 4.

31. The antibody drug conjugate of claim 28 wherein D is a PBD dimer drug having the structure:

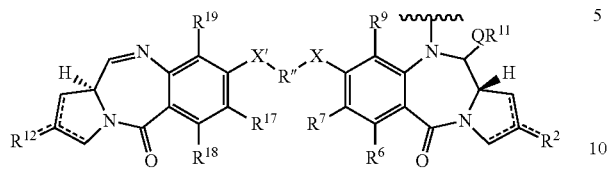

and salts and solvates thereof, wherein:
the wavy line indicates the covalent attachment site to the linker;
the dotted lines indicate the optional presence of a double bond between C1 and C2 or C2 and C3;

$R^2$ is independently selected from H, OH, =O, =CH$_2$, CN, R, OR, =CH—$R^D$, =C($R^D$)$_2$, O—SO$_2$—R, CO$_2$R and COR, and optionally further selected from halo or dihalo, wherein $R^D$ is independently selected from R, CO$_2$R, COR, CHO, CO$_2$H, and halo;

$R^6$ and $R^9$ are independently selected from H, R, OH, OR, SH, SR, NH$_2$, NHR, NRR', NO$_2$, Me$_3$Sn and halo;

$R^7$ is independently selected from H, R, OH, OR, SH, SR, NH$_2$, NHR, NRR', NO$_2$, Me$_3$Sn and halo;

Q is independently selected from O, S and NH;

$R^{11}$ is either H, or R or, where Q is O, SO$_3$M, where M is a metal cation;

R and R' are each independently selected from optionally substituted C$_{1-8}$ alkyl, C$_{1-12}$ alkyl, C$_{3-8}$ heterocyclyl, C$_{3-20}$ heterocycle, and C$_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a C$_{3-12}$ alkylene group, which chain may be interrupted by one or more heteroatom; e.g. O, S, N(H), NMe and/or aromatic rings, e.g. benzene or pyridine, which rings are optionally substituted; and X and X' are independently selected from O, S and N(H).

32. The antibody drug conjugate of claim 31 wherein the structure of the PBD dimer is:

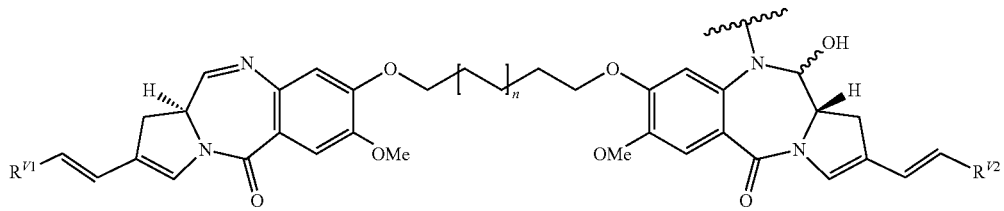

including salts and solvates thereof, wherein
the wavy line indicates the covalent attachment site to the linker; the wavy line connected to the OH indicates the S or R configuration; $R^{V1}$ and $R^{V2}$ are independently selected from H, methyl, ethyl and phenyl (which phenyl may be optionally substituted with fluoro, particularly in the 4 position) and C$_{5-6}$ heterocyclyl; wherein $R^{V1}$ and $R^{V2}$ may be the same or different; and n is 0 or 1.

33. The antibody drug conjugate of claim 31 selected from:

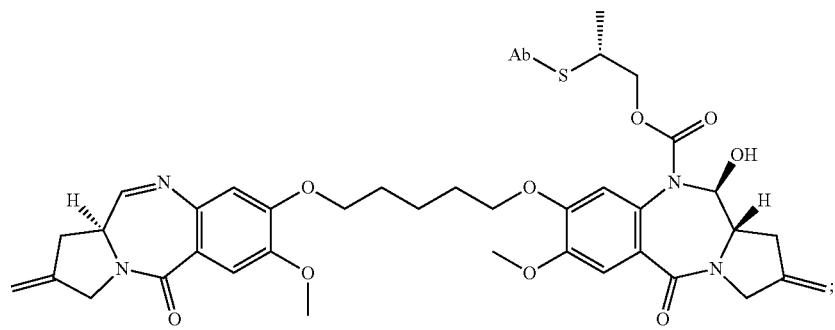

-continued

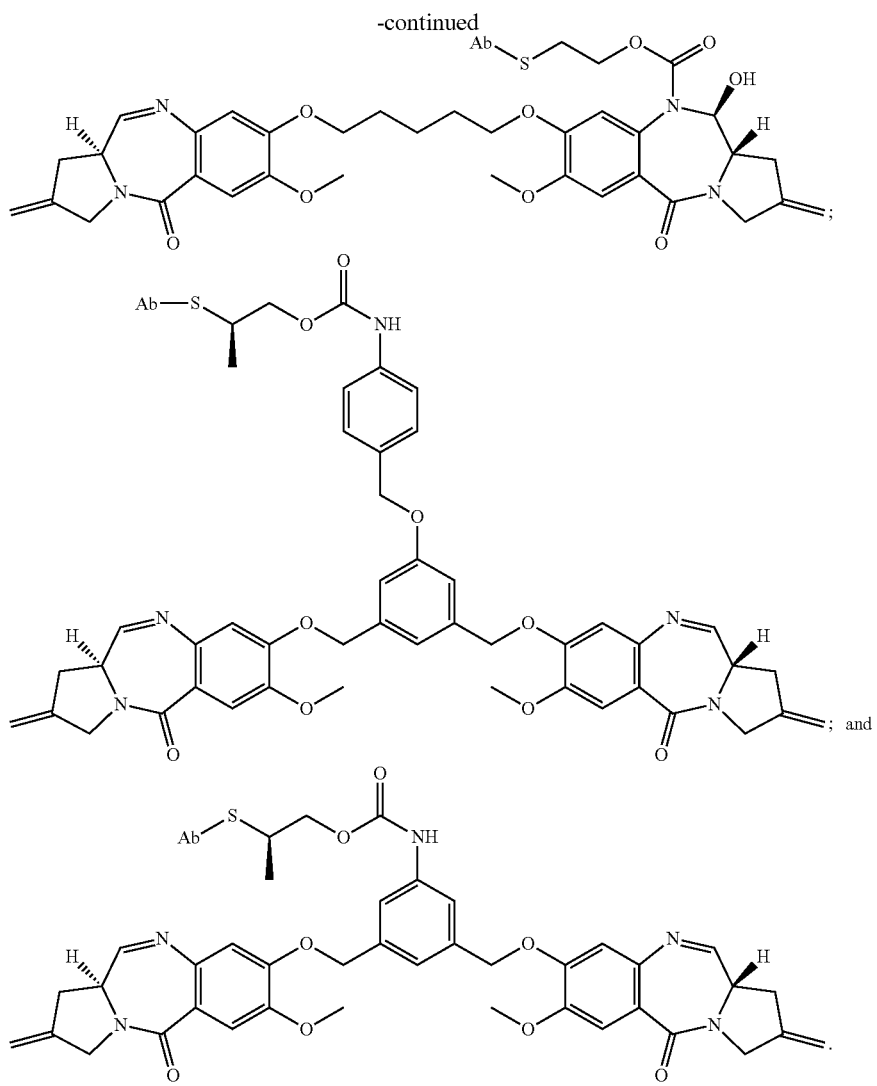

34. The cysteine engineered antibody of claim 28 wherein D is a CBI dimer drug having the structure:

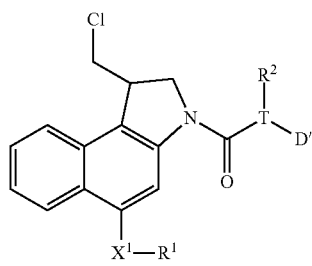

where
R$^1$ is selected from H, P(O)$_3$H$_2$, C(O)NR$^a$R$^b$, or a bond to a linker (L);
R$^2$ is selected from H, P(O)$_3$H$_2$, C(O)NR$^a$R$^b$, or a bond to a linker (L);
R$^a$ and R$^b$ are independently selected from H and C$_1$-C$_6$ alkyl optionally substituted with one or more F, or R$^a$ and R$^b$ form a five or six membered heterocyclyl group;
T is a tether group selected from C$_3$-C$_{12}$ alkylene, Y, (C$_1$-C$_6$ alkylene)-Y—(C$_1$-C$_6$ alkylene), (C$_1$-C$_6$ alkylene)-Y—(C$_1$-C$_6$ alkylene)-Y—(C$_1$-C$_6$ alkylene), (C$_2$-C$_6$ alkenylene)-Y—(C$_2$-C$_6$ alkenylene), and (C$_2$-C$_6$ alkynylene)-Y—(C$_2$-C$_6$ alkynylene);
where Y is independently selected from O, S, NR$^1$, aryl, and heteroaryl;
where alkylene, alkenylene, aryl, and heteroaryl are independently and optionally substituted with F, OH, O(C$_1$-C$_6$ alkyl), NH$_2$, NHCH$_3$, N(CH$_3$)$_2$, OP(O)$_3$H$_2$, and C$_1$-C$_6$ alkyl, where alkyl is optionally substituted with one or more F;
or alkylene, alkenylene, aryl, and heteroaryl are independently and optionally substituted with a bond to L;
D' is a drug moiety selected from:

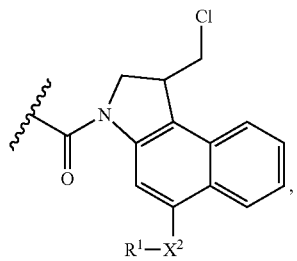

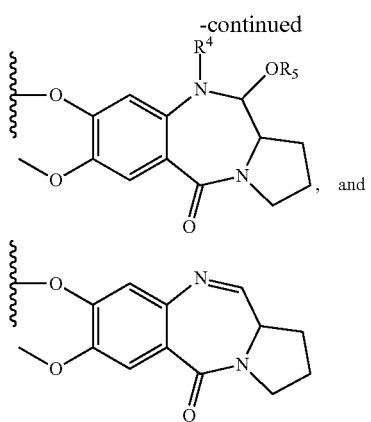
, and
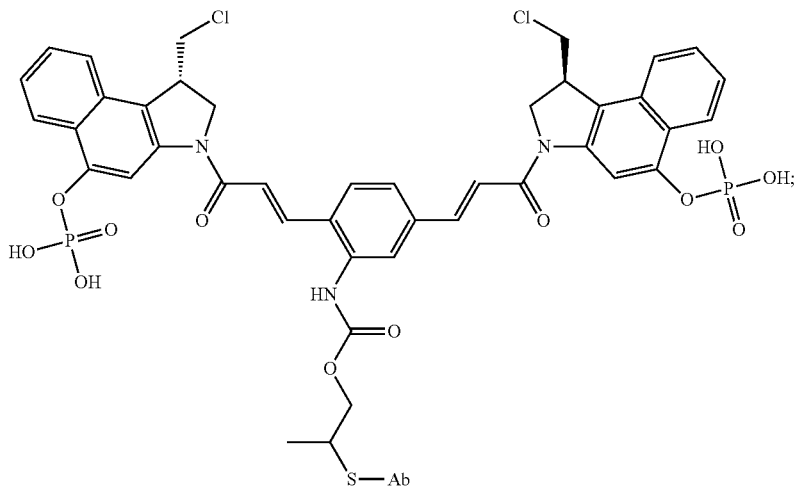
where the wavy line indicates the site of attachment to T;
$X^1$ and $X^2$ are independently selected from O and $NR^3$, where $R^3$ is selected from H and $C_1$-$C_6$ alkyl optionally substituted with one or more F;
$R^4$ is H, $CO_2R$, or a bond to a linker (L), where R is $C_1$-$C_6$ alkyl or benzyl; and
$R^5$ is H or $C_1$-$C_6$ alkyl.
35. The antibody drug conjugate of claim 34 selected from:
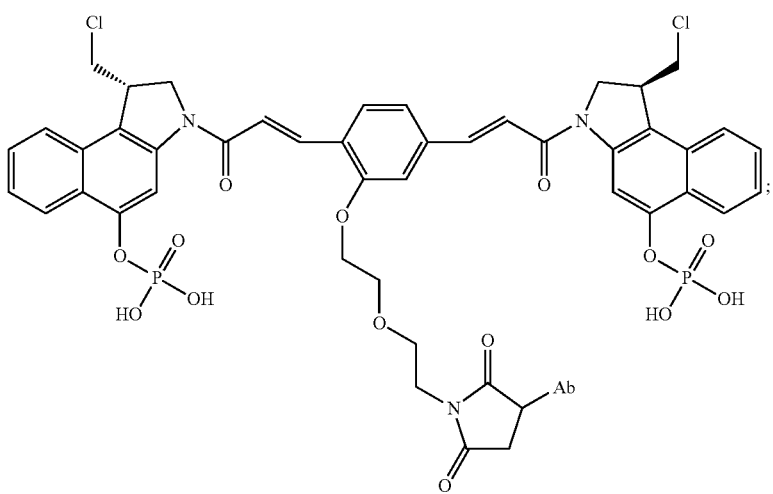

291
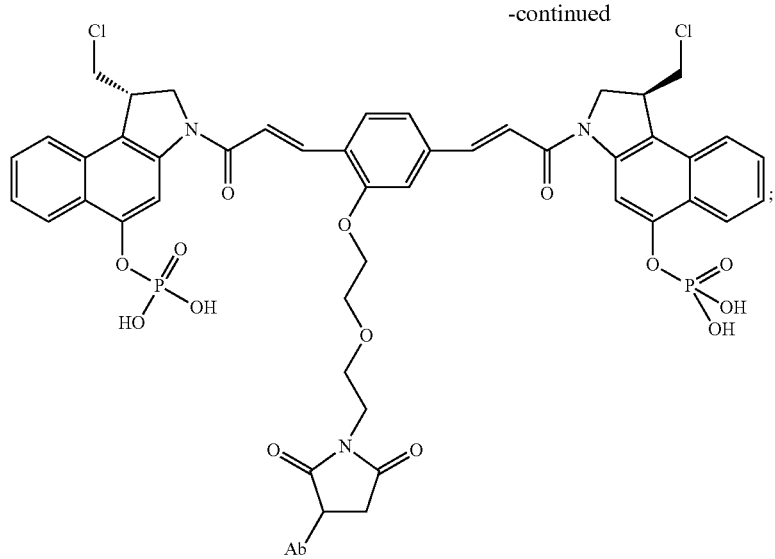
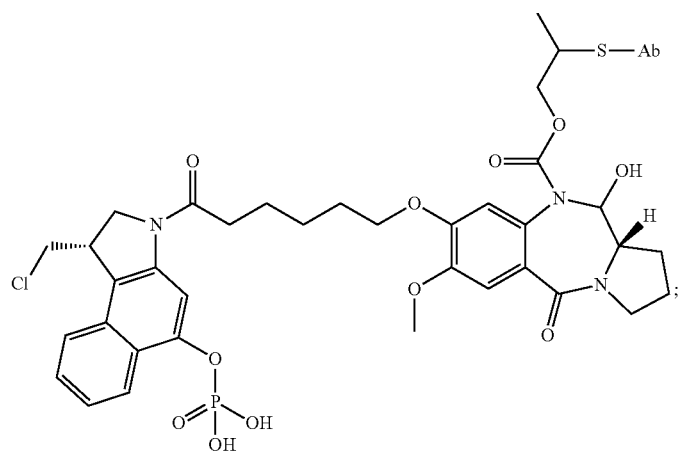
292
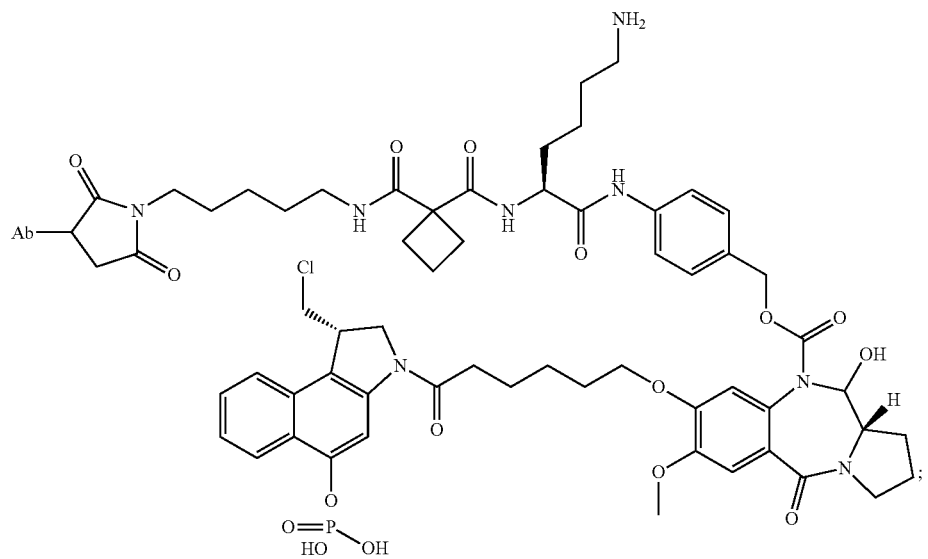

293
294
-continued
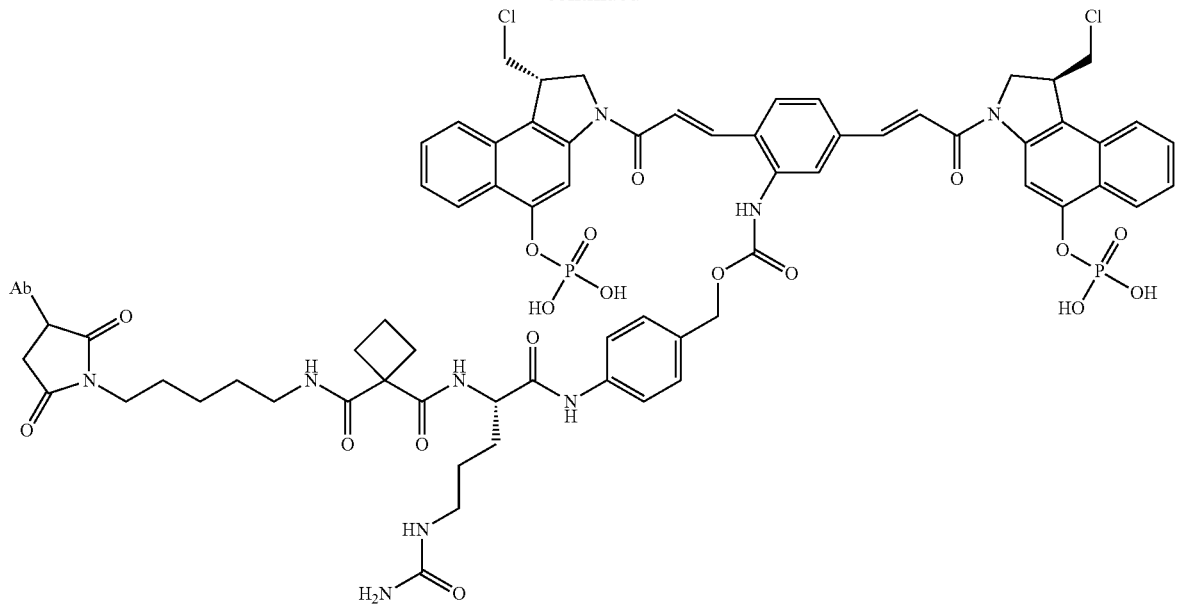
; and

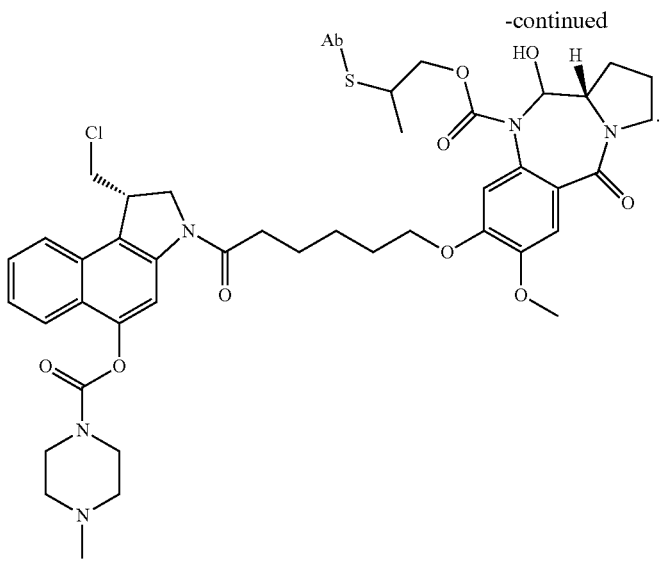

36. A method of preparing an antibody-drug conjugate comprising reacting at least one cysteine of a cysteine engineered antibody (Ab) with a linker-drug intermediate to form an antibody-drug conjugate having Formula I:

$$Ab\text{-}(L\text{-}D)_p \qquad I$$

wherein Ab is the cysteine engineered antibody of claim 1, L is a linker, D is a drug moiety, and p is 1, 2, 3, or 4.

37. The antibody drug conjugate of claim 22 wherein L comprises a pyridyl disulfide (PDS), and D is selected from the group consisting of a CBI-PBD heterodimer, cryptophycin, a taxoid, and tubulysin M.

38. The antibody drug conjugate of claim 22 wherein L comprises a –vc linker, and D is selected from the group consisting of a CBI-PBD heterodimer, cryptophycin, a taxoid, and tubulysin M.

39. The antibody drug conjugate of claim 38 wherein the D is the CBI-PBD heterodimer:

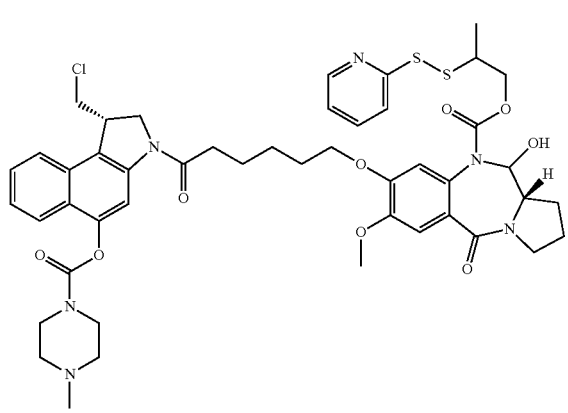

40. The antibody drug conjugate of claim 22 wherein L comprises a pyridyl disulfide (PDS).

41. A pharmaceutical composition comprising an antibody drug conjugate of claim 22.

* * * * *

UNITED STATES PATENT AND TRADEMARK OFFICE
CERTIFICATE OF CORRECTION

PATENT NO. : 10,077,318 B2
APPLICATION NO. : 14/851348
DATED : September 18, 2018
INVENTOR(S) : Bhakta et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 188 days.

Signed and Sealed this
Twenty-fifth Day of June, 2019

Andrei Iancu
*Director of the United States Patent and Trademark Office*